US012168798B2

(12) United States Patent
Eberhart et al.

(10) Patent No.: US 12,168,798 B2
(45) Date of Patent: Dec. 17, 2024

(54) SAMPLE PREPARATION, PROCESSING AND ANALYSIS SYSTEMS

(71) Applicant: Integenx Inc., Pleasanton, CA (US)

(72) Inventors: David Eberhart, Santa Clara, CA (US); Yuan Li, Dublin, CA (US); James Ogg, Sunnyvale, CA (US); Ezra Van Gelder, Palo Alto, CA (US); Stephen J. Williams, San Carlos, CA (US); Timothy Woudenberg, San Francisco, CA (US); Dean S. Burgi, Sunnyvale, CA (US); William D. Nielsen, San Jose, CA (US)

(73) Assignee: INTEGENX. INC., Pleasanton, CA (US)

( * ) Notice: Subject to any disclaimer, the term of this patent is extended or adjusted under 35 U.S.C. 154(b) by 973 days.

(21) Appl. No.: 17/119,874

(22) Filed: Dec. 11, 2020

(65) Prior Publication Data

US 2021/0277445 A1   Sep. 9, 2021

Related U.S. Application Data

(60) Division of application No. 14/381,179, filed as application No. PCT/US2013/028462 on Feb. 28, (Continued)

(51) Int. Cl.
*C12Q 1/686* (2018.01)
*B01L 3/00* (2006.01)
(Continued)

(52) U.S. Cl.
CPC ........ *C12Q 1/686* (2013.01); *B01L 3/502715* (2013.01); *B01L 3/527* (2013.01);
(Continued)

(58) Field of Classification Search
CPC ... C12Q 1/686; B01L 3/502715; B01L 3/527; B01L 7/52; B01L 3/5029;
(Continued)

(56) References Cited

U.S. PATENT DOCUMENTS 3,075,740 A   1/1963   McIntosh
3,352,643 A   11/1967  Noboru et al.
(Continued)

FOREIGN PATENT DOCUMENTS

CN   1109597 A   10/1995
CN   1146017 A   3/1997
(Continued)

OTHER PUBLICATIONS

Promega, "Maxwell 16 Instrument Operating Manual", 2005 (Year: 2005).*
(Continued)

*Primary Examiner* — Jennifer Wecker
*Assistant Examiner* — Ali Husain Faraz
(74) *Attorney, Agent, or Firm* — Jones Robb, PLLC

(57) ABSTRACT

This disclosure provides an integrated and automated sample-to-answer system that, starting from a sample comprising biological material, generates a genetic profile in less than two hours. In certain embodiments, the biological material is DNA and the genetic profile involves determining alleles at one or a plurality of loci (e.g., genetic loci) of a subject, for example, an STR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several
(Continued)

integrated modules, including an analyte preparation module; a detection and analysis module and a control module.

21 Claims, 51 Drawing Sheets

Related U.S. Application Data 2013, now Pat. No. 10,865,440, which is a continuation-in-part of application No. 13/656,503, filed on Oct. 19, 2012, now Pat. No. 8,894,946.

(60) Provisional application No. 61/703,194, filed on Sep. 19, 2012, provisional application No. 61/696,809, filed on Sep. 5, 2012, provisional application No. 61/691,242, filed on Aug. 20, 2012, provisional application No. 61/674,295, filed on Jul. 20, 2012, provisional application No. 61/671,592, filed on Jul. 13, 2012, provisional application No. 61/664,726, filed on Jun. 26, 2012, provisional application No. 61/654,749, filed on Jun. 1, 2012, provisional application No. 61/641,120, filed on May 1, 2012, provisional application No. 61/610,977, filed on Mar. 14, 2012, provisional application No. 61/605,169, filed on Feb. 29, 2012, provisional application No. 61/550,364, filed on Oct. 21, 2011.

(51) Int. Cl.
*B01L 7/00* (2006.01)
*G01N 27/447* (2006.01)
*G01N 35/00* (2006.01)

(52) U.S. Cl.
CPC .............. *B01L 7/52* (2013.01); *B01L 3/5029* (2013.01); *B01L 2200/025* (2013.01); *B01L 2200/028* (2013.01); *B01L 2200/04* (2013.01); *B01L 2200/0647* (2013.01); *B01L 2200/0684* (2013.01); *B01L 2200/143* (2013.01); *B01L 2300/023* (2013.01); *B01L 2300/027* (2013.01); *B01L 2300/0672* (2013.01); *B01L 2300/123* (2013.01); *B01L 2400/0421* (2013.01); *B01L 2400/043* (2013.01); *B01L 2400/0478* (2013.01); *B01L 2400/0616* (2013.01); *G01N 27/44704* (2013.01); *G01N 2035/00158* (2013.01)

(58) Field of Classification Search
CPC ......... B01L 2200/025; B01L 2200/028; B01L 2200/04; B01L 2200/0647; B01L 2200/0684; B01L 2200/143; B01L 2300/023; B01L 2300/027; B01L 2300/0672; B01L 2300/123; B01L 2400/0421; B01L 2400/043; B01L 2400/0478; B01L 2400/0616; G01N 27/44704; G01N 2035/00158; G01N 27/44734

See application file for complete search history.

(56) References Cited

U.S. PATENT DOCUMENTS

| | | |
|---|---|---|
| 3,433,257 A | 3/1969 | Jensen |
| 3,568,692 A | 3/1971 | Metzger et al. |
| 3,662,517 A | 5/1972 | Tascher et al. |
| 4,011,357 A | 3/1977 | Haase |
| 4,113,665 A | 9/1978 | Law et al. |
| 4,390,307 A | 6/1983 | Rice |
| 4,847,120 A | 7/1989 | Gent |
| 4,963,498 A | 10/1990 | Hillman et al. |
| 5,085,757 A | 2/1992 | Karger et al. |
| 5,275,645 A | 1/1994 | Ternoir et al. |
| 5,338,427 A | 8/1994 | Shartle et al. |
| 5,364,759 A | 11/1994 | Caskey et al. |
| 5,376,252 A | 12/1994 | Ekstroem et al. |
| 5,387,505 A | 2/1995 | Wu |
| 5,453,163 A | 9/1995 | Yan |
| 5,482,836 A | 1/1996 | Cantor et al. |
| 5,523,231 A | 6/1996 | Reeve |
| 5,571,410 A | 11/1996 | Swedberg et al. |
| 5,587,128 A | 12/1996 | Wilding et al. |
| 5,589,136 A | 12/1996 | Northrup et al. |
| 5,635,358 A | 6/1997 | Wilding et al. |
| 5,639,428 A | 6/1997 | Cottingham |
| 5,675,155 A | 10/1997 | Pentoney et al. |
| 5,681,946 A | 10/1997 | Reeve |
| 5,705,628 A | 1/1998 | Hawkins |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,776,748 A | 7/1998 | Singhvi et al. |
| 5,830,662 A | 11/1998 | Soares et al. |
| 5,842,787 A | 12/1998 | Kopf-Sill et al. |
| 5,856,174 A | 1/1999 | Lipshutz et al. |
| 5,863,502 A | 1/1999 | Southgate et al. |
| 5,872,010 A | 2/1999 | Karger et al. |
| 5,885,470 A | 3/1999 | Parce et al. |
| 5,898,071 A | 4/1999 | Hawkins |
| 5,908,552 A | 6/1999 | Dittmann et al. |
| 5,922,591 A | 7/1999 | Anderson et al. |
| 5,942,443 A | 8/1999 | Parce et al. |
| 5,948,684 A | 9/1999 | Weigl et al. |
| 5,951,262 A | 9/1999 | Hartman |
| 5,971,158 A | 10/1999 | Yager et al. |
| 5,994,064 A * | 11/1999 | Staub ................... C12Q 1/6876 536/22.1 |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,110,343 A | 8/2000 | Ramsey et al. |
| 6,120,184 A | 9/2000 | Laurence et al. |
| 6,136,212 A | 10/2000 | Mastrangelo et al. |
| 6,153,389 A | 11/2000 | Haarer et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor et al. |
| 6,321,791 B1 | 11/2001 | Chow |
| 6,322,683 B1 | 11/2001 | Wolk et al. |
| 6,326,068 B1 | 12/2001 | Kong et al. |
| 6,340,029 B1 | 1/2002 | Jun |
| 6,342,142 B1 | 1/2002 | Ramsey |
| 6,348,318 B1 | 2/2002 | Valkirs |
| 6,379,929 B1 | 4/2002 | Burns et al. |
| 6,387,234 B1 | 5/2002 | Yeung et al. |
| 6,387,707 B1 | 5/2002 | Seul et al. |
| 6,391,622 B1 | 5/2002 | Knapp et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,191 B2 | 8/2002 | Schutt |
| 6,432,290 B1 | 8/2002 | Harrison et al. |

(56) References Cited

U.S. PATENT DOCUMENTS

| | | |
|---|---|---|
| 6,454,924 B2 | 9/2002 | Jedrzejewski et al. |
| 6,461,492 B1 | 10/2002 | Hayashizaki et al. |
| 6,485,690 B1 | 11/2002 | Pfost et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,527,003 B1 | 3/2003 | Webster |
| 6,531,041 B1 | 3/2003 | Cong et al. |
| 6,531,282 B1 | 3/2003 | Dau et al. |
| 6,532,997 B1 | 3/2003 | Bedingham et al. |
| 6,533,914 B1 | 3/2003 | Liu |
| 6,534,262 B1 | 3/2003 | McKernan et al. |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,554,591 B1 | 4/2003 | Dai et al. |
| 6,581,441 B1 | 6/2003 | Paul |
| 6,581,899 B2 | 6/2003 | Williams |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein et al. |
| 6,620,584 B1 | 9/2003 | Chee et al. |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,660,148 B2 | 12/2003 | Shoji et al. |
| 6,663,833 B1 | 12/2003 | Stave et al. |
| 6,685,442 B2 | 2/2004 | Chinn et al. |
| 6,685,678 B2 | 2/2004 | Evans et al. |
| 6,685,809 B1 | 2/2004 | Jacobson et al. |
| 6,740,219 B2 | 5/2004 | Imai et al. |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,883,774 B2 | 4/2005 | Nielsen et al. |
| 6,885,982 B2 | 4/2005 | Harris et al. |
| 6,899,137 B2 | 5/2005 | Unger et al. |
| 6,921,253 B2 | 7/2005 | Shuler et al. |
| 6,923,907 B2 | 8/2005 | Hobbs et al. |
| 6,929,030 B2 | 8/2005 | Unger et al. |
| 6,929,239 B1 | 8/2005 | Colin et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,052 B2 | 2/2006 | Shimizu et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,081,191 B2 | 7/2006 | Shoji et al. |
| 7,087,380 B2 | 8/2006 | Griffiths et al. |
| 7,097,809 B2 | 8/2006 | Van et al. |
| 7,105,300 B2 | 9/2006 | Parce et al. |
| 7,118,910 B2 | 10/2006 | Unger et al. |
| 7,142,987 B2 | 11/2006 | Eggers |
| 7,157,228 B2 | 1/2007 | Hashmi et al. |
| 7,169,557 B2 | 1/2007 | Rosenblum et al. |
| 7,170,050 B2 | 1/2007 | Turner et al. |
| 7,198,759 B2 | 4/2007 | Bryning et al. |
| 7,211,388 B2 | 5/2007 | Cash et al. |
| 7,217,367 B2 | 5/2007 | Huang et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,244,961 B2 | 7/2007 | Jovanovich et al. |
| 7,258,744 B2 | 8/2007 | Sakurada et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,323,305 B2 | 1/2008 | Leamon et al. |
| 7,329,388 B2 | 2/2008 | Guzman |
| 7,361,471 B2 | 4/2008 | Gerdes et al. |
| 7,419,578 B2 | 9/2008 | Sakai et al. |
| 7,438,856 B2 | 10/2008 | Jedrzejewski et al. |
| 7,445,926 B2 | 11/2008 | Mathies et al. |
| 7,473,342 B2 | 1/2009 | Ugai et al. |
| 7,486,865 B2 | 2/2009 | Foquet et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,531,076 B2 | 5/2009 | Hayashizaki et al. |
| 7,537,886 B1 | 5/2009 | Nazarenko et al. |
| 7,575,865 B2 | 8/2009 | Leamon et al. |
| 7,584,240 B2 | 9/2009 | Eggers |
| 7,589,184 B2 | 9/2009 | Hogan et al. |
| 7,645,580 B2 | 1/2010 | Barber et al. |
| 7,691,614 B2 | 4/2010 | Senapathy |
| 7,704,735 B2 | 4/2010 | Facer et al. |
| 7,718,442 B2 | 5/2010 | Davis et al. |
| 7,744,737 B1 | 6/2010 | James et al. |
| 7,745,207 B2 | 6/2010 | Jovanovich et al. |
| 7,749,365 B2 | 7/2010 | Nguyen et al. |
| 7,749,737 B2 | 7/2010 | McBride et al. |
| 7,763,453 B2 | 7/2010 | Clemmens et al. |
| 7,766,033 B2 | 8/2010 | Mathies et al. |
| 7,785,458 B2 | 8/2010 | Shimizu et al. |
| 7,790,368 B1 | 9/2010 | Fukuzono |
| 7,799,553 B2 | 9/2010 | Mathies et al. |
| 7,803,281 B2 | 9/2010 | Davies |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 | 1/2011 | Nasarabadi |
| 7,885,770 B2 | 2/2011 | Gill et al. |
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,972,561 B2 | 7/2011 | Viovy et al. |
| 7,976,789 B2 | 7/2011 | Kenis et al. |
| 7,976,795 B2 | 7/2011 | Zhou et al. |
| 7,998,708 B2 * | 8/2011 | Handique ........ F16K 99/0001 435/6.1 |
| 8,007,746 B2 | 8/2011 | Unger et al. |
| 8,018,593 B2 | 9/2011 | Tan et al. |
| 8,034,628 B2 | 10/2011 | Harrison et al. |
| 8,053,192 B2 | 11/2011 | Bignell et al. |
| RE43,122 E | 1/2012 | Harrison et al. |
| 8,142,635 B2 | 3/2012 | Shimizu et al. |
| 8,221,990 B2 | 7/2012 | Mori et al. |
| 8,222,023 B2 | 7/2012 | Battrell et al. |
| 8,268,263 B2 | 9/2012 | Campbell et al. |
| 8,283,165 B2 | 10/2012 | Hogan et al. |
| 8,313,941 B2 | 11/2012 | Takayama et al. |
| 8,337,777 B2 | 12/2012 | Nurse et al. |
| 8,388,908 B2 | 3/2013 | Blaga et al. |
| 8,394,642 B2 | 3/2013 | Jovanovich et al. |
| 8,398,642 B2 | 3/2013 | Weekes |
| 8,420,318 B2 | 4/2013 | Mathies et al. |
| 8,431,340 B2 | 4/2013 | Jovanovich et al. |
| 8,431,384 B2 | 4/2013 | Hogan et al. |
| 8,431,390 B2 | 4/2013 | Jovanovich et al. |
| 8,476,063 B2 | 7/2013 | Jovanovich et al. |
| 8,501,305 B2 | 8/2013 | Barlow |
| 8,512,538 B2 | 8/2013 | Majlof et al. |
| 8,551,714 B2 | 10/2013 | Jovanovich et al. |

(56) References Cited

U.S. PATENT DOCUMENTS

| | | | |
|---|---|---|---|
| 8,557,518 B2 | 10/2013 | Jovanovich et al. | |
| 8,562,918 B2 | 10/2013 | Jovanovich et al. | |
| 8,584,703 B2 | 11/2013 | Kobrin et al. | |
| 8,607,490 B1 | 12/2013 | Zinsner | |
| 8,672,532 B2 | 3/2014 | Jovanovich et al. | |
| 8,748,165 B2 | 6/2014 | Vangbo et al. | |
| 8,763,642 B2 | 7/2014 | Vangbo | |
| 8,841,116 B2 | 9/2014 | Mathies et al. | |
| 8,894,946 B2 | 11/2014 | Nielsen et al. | |
| 9,012,236 B2 | 4/2015 | Jovanovich et al. | |
| 9,121,058 B2 | 9/2015 | Stern et al. | |
| 9,291,284 B2 | 3/2016 | Penterman et al. | |
| 9,341,284 B2 | 5/2016 | Vangbo | |
| 9,592,501 B2 | 3/2017 | Jarvius et al. | |
| 9,663,819 B2 | 5/2017 | Jovanovich et al. | |
| 9,731,266 B2 * | 8/2017 | Stern | C12Q 1/6869 |
| 2001/0012612 A1 | 8/2001 | Petersen et al. | |
| 2001/0041357 A1 | 11/2001 | Fouillet et al. | |
| 2002/0003895 A1 | 1/2002 | Some | |
| 2002/0022261 A1 | 2/2002 | Anderson et al. | |
| 2002/0022587 A1 | 2/2002 | Ferguson et al. | |
| 2002/0025529 A1 | 2/2002 | Quake et al. | |
| 2002/0025576 A1 | 2/2002 | Northrup et al. | |
| 2002/0037499 A1 | 3/2002 | Quake et al. | |
| 2002/0042125 A1 | 4/2002 | Petersen et al. | |
| 2002/0047003 A1 | 4/2002 | Bedingham et al. | |
| 2002/0048536 A1 | 4/2002 | Bergh et al. | |
| 2002/0051992 A1 | 5/2002 | Bridgham et al. | |
| 2002/0055167 A1 | 5/2002 | Pourahmadi et al. | |
| 2002/0058332 A1 | 5/2002 | Quake et al. | |
| 2002/0068357 A1 | 6/2002 | Mathies et al. | |
| 2002/0098097 A1 | 7/2002 | Singh | |
| 2002/0110900 A1 | 8/2002 | Jovanovich et al. | |
| 2002/0115201 A1 | 8/2002 | Barenburg et al. | |
| 2002/0119480 A1 | 8/2002 | Weir et al. | |
| 2002/0119482 A1 | 8/2002 | Nelson et al. | |
| 2002/0137039 A1 | 9/2002 | Gessner | |
| 2002/0139084 A1 | 10/2002 | Tobolka | |
| 2002/0151089 A1 | 10/2002 | Chapman et al. | |
| 2002/0157951 A1 | 10/2002 | Foret et al. | |
| 2002/0160361 A1 | 10/2002 | Loehrlein et al. | |
| 2002/0177238 A1 | 11/2002 | Karp et al. | |
| 2002/0187560 A1 | 12/2002 | Pezzuto et al. | |
| 2003/0007077 A1 | 1/2003 | Maggi | |
| 2003/0008308 A1 | 1/2003 | Enzelberger et al. | |
| 2003/0019753 A1 | 1/2003 | Ogle et al. | |
| 2003/0021734 A1 | 1/2003 | Vann et al. | |
| 2003/0029724 A1 | 2/2003 | Derand et al. | |
| 2003/0070677 A1 | 4/2003 | Handique et al. | |
| 2003/0077839 A1 | 4/2003 | Takei | |
| 2003/0087425 A1 | 5/2003 | Eggers | |
| 2003/0087446 A1 | 5/2003 | Eggers | |
| 2003/0087455 A1 | 5/2003 | Eggers et al. | |
| 2003/0088657 A1 | 5/2003 | Eggers | |
| 2003/0095897 A1 | 5/2003 | Grate et al. | |
| 2003/0104466 A1 | 6/2003 | Knapp et al. | |
| 2003/0129755 A1 | 7/2003 | Sadler et al. | |
| 2003/0162304 A1 | 8/2003 | Dority et al. | |
| 2003/0175706 A1 | 9/2003 | Zhang | |
| 2003/0197139 A1 | 10/2003 | Williams | |
| 2003/0198573 A1 | 10/2003 | Forood et al. | |
| 2003/0215369 A1 | 11/2003 | Eggers et al. | |
| 2003/0217923 A1 | 11/2003 | Harrison et al. | |
| 2004/0003997 A1 | 1/2004 | Anazawa et al. | |
| 2004/0013536 A1 | 1/2004 | Hower et al. | |
| 2004/0014091 A1 | 1/2004 | Duck et al. | |
| 2004/0016898 A1 | 1/2004 | Cox et al. | |
| 2004/0018611 A1 | 1/2004 | Ward et al. | |
| 2004/0021068 A1 | 2/2004 | Staats | |
| 2004/0022676 A1 | 2/2004 | Hamilton et al. | |
| 2004/0037739 A1 | 2/2004 | McNeely et al. | |
| 2004/0038385 A1 | 2/2004 | Langlois et al. | |
| 2004/0053290 A1 | 3/2004 | Terbrueggen et al. | |
| 2004/0063217 A1 | 4/2004 | Webster et al. | |
| 2004/0072278 A1 | 4/2004 | Chou et al. | |
| 2004/0086427 A1 | 5/2004 | Childers et al. | |
| 2004/0086870 A1 | 5/2004 | Tyvoll et al. | |
| 2004/0101966 A1 | 5/2004 | Davis et al. | |
| 2004/0132170 A1 | 7/2004 | Storek et al. | |
| 2004/0146452 A1 | 7/2004 | Fujieda et al. | |
| 2004/0151629 A1 | 8/2004 | Pease et al. | |
| 2004/0185484 A1 | 9/2004 | Costa et al. | |
| 2004/0197845 A1 | 10/2004 | Hassibi et al. | |
| 2004/0200724 A1 | 10/2004 | Fujii et al. | |
| 2004/0209354 A1 | 10/2004 | Mathies et al. | |
| 2004/0217004 A1 | 11/2004 | Hayashizaki et al. | |
| 2004/0219533 A1 | 11/2004 | Davis et al. | |
| 2004/0224380 A1 | 11/2004 | Chou et al. | |
| 2005/0019231 A1 | 1/2005 | Kahl | |
| 2005/0026181 A1 | 2/2005 | Davis et al. | |
| 2005/0026300 A1 | 2/2005 | Samper et al. | |
| 2005/0042656 A1 | 2/2005 | Davis et al. | |
| 2005/0047967 A1 | 3/2005 | Chuang et al. | |
| 2005/0053952 A1 | 3/2005 | Hong et al. | |
| 2005/0142663 A1 | 6/2005 | Parthasarathy et al. | |
| 2005/0161326 A1 | 7/2005 | Morita et al. | |
| 2005/0161669 A1 | 7/2005 | Jovanovich et al. | |
| 2005/0181394 A1 | 8/2005 | Steemers et al. | |
| 2005/0201901 A1 | 9/2005 | Grossman et al. | |
| 2005/0221373 A1 | 10/2005 | Enzelberger et al. | |
| 2005/0224134 A1 | 10/2005 | Yin et al. | |
| 2005/0224352 A1 | 10/2005 | Harrison et al. | |
| 2005/0241941 A1 | 11/2005 | Parce et al. | |
| 2005/0250199 A1 | 11/2005 | Anderson et al. | |
| 2005/0255000 A1 | 11/2005 | Yamamoto et al. | |
| 2005/0255003 A1 | 11/2005 | Summersgill et al. | |
| 2005/0255007 A1 | 11/2005 | Yamada et al. | |
| 2005/0266582 A1 | 12/2005 | Modlin et al. | |
| 2005/0287572 A1 | 12/2005 | Mathies et al. | |
| 2006/0011539 A1 | 1/2006 | Lee et al. | |
| 2006/0014177 A1 | 1/2006 | Hogan et al. | |
| 2006/0027456 A1 | 2/2006 | Harrison et al. | |
| 2006/0040300 A1 | 2/2006 | Dapprich et al. | |
| 2006/0057209 A1 | 3/2006 | Chapman et al. | |
| 2006/0073484 A1 | 4/2006 | Mathies et al. | |
| 2006/0076068 A1 | 4/2006 | Young et al. | |
| 2006/0140051 A1 | 6/2006 | Kim et al. | |
| 2006/0163143 A1 | 7/2006 | Chirica et al. | |
| 2006/0166233 A1 | 7/2006 | Wu et al. | |
| 2006/0177832 A1 | 8/2006 | Brenner | |
| 2006/0186043 A1 | 8/2006 | Covey et al. | |
| 2006/0205085 A1 | 9/2006 | Handique et al. | |
| 2006/0210994 A1 | 9/2006 | Joyce | |
| 2006/0210998 A1 | 9/2006 | Kettlitz et al. | |
| 2006/0260941 A1 | 11/2006 | Tan et al. | |
| 2006/0263789 A1 | 11/2006 | Kincaid | |
| 2006/0266645 A1 | 11/2006 | Chen et al. | |
| 2006/0292032 A1 | 12/2006 | Hataoka et al. | |
| 2007/0015179 A1 | 1/2007 | Klapperich et al. | |
| 2007/0017812 A1 | 1/2007 | Bousse | |
| 2007/0020654 A1 | 1/2007 | Blume et al. | |
| 2007/0031865 A1 | 2/2007 | Willoughby | |
| 2007/0034025 A1 | 2/2007 | Pant et al. | |
| 2007/0105163 A1 | 5/2007 | Grate et al. | |
| 2007/0122819 A1 | 5/2007 | Wu et al. | |
| 2007/0175756 A1 | 8/2007 | Nguyen et al. | |
| 2007/0183935 A1 | 8/2007 | Clemmens et al. | |
| 2007/0184463 A1 | 8/2007 | Molho et al. | |
| 2007/0184547 A1 | 8/2007 | Handique et al. | |
| 2007/0202531 A1 | 8/2007 | Grover | |
| 2007/0218485 A1 | 9/2007 | Davis et al. | |
| 2007/0224084 A1 | 9/2007 | Holmes et al. | |
| 2007/0237686 A1 | 10/2007 | Mathies et al. | |
| 2007/0238109 A1 | 10/2007 | Min et al. | |
| 2007/0248958 A1 | 10/2007 | Jovanovich et al. | |
| 2007/0263049 A1 | 11/2007 | Preckel et al. | |
| 2007/0292941 A1 | 12/2007 | Handique et al. | |
| 2007/0297947 A1 | 12/2007 | Sommers et al. | |
| 2008/0014576 A1 | 1/2008 | Jovanovich et al. | |
| 2008/0014589 A1 | 1/2008 | Link et al. | |
| 2008/0047836 A1 | 2/2008 | Strand et al. | |
| 2008/0064610 A1 | 3/2008 | Lipovsek et al. | |
| 2008/0124723 A1 | 5/2008 | Dale et al. | |
| 2008/0131904 A1 | 6/2008 | Parce et al. | |

(56) References Cited

U.S. PATENT DOCUMENTS

| | | |
|---|---|---|
| 2008/0138809 A1 | 6/2008 | Kapur et al. |
| 2008/0160630 A1 | 7/2008 | Liu et al. |
| 2008/0164155 A1 | 7/2008 | Pease et al. |
| 2008/0179255 A1 | 7/2008 | Jung et al. |
| 2008/0179555 A1 | 7/2008 | Landers et al. |
| 2008/0217178 A1 | 9/2008 | Ben-Asouli et al. |
| 2008/0237146 A1 | 10/2008 | Harrison et al. |
| 2008/0241844 A1 | 10/2008 | Kellogg |
| 2008/0242560 A1 | 10/2008 | Gunderson et al. |
| 2008/0257437 A1 | 10/2008 | Fernandes et al. |
| 2008/0262747 A1 | 10/2008 | Kain et al. |
| 2008/0281089 A1* | 11/2008 | Liu .................... C12N 15/1006 536/25.41 |
| 2008/0281090 A1 | 11/2008 | Lee et al. |
| 2008/0287585 A1 | 11/2008 | Brown |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0020427 A1 | 1/2009 | Tan et al. |
| 2009/0023603 A1 | 1/2009 | Selden et al. |
| 2009/0026082 A1 | 1/2009 | Rothberg et al. |
| 2009/0035770 A1 | 2/2009 | Mathies et al. |
| 2009/0053106 A1 | 2/2009 | Wu et al. |
| 2009/0053799 A1 | 2/2009 | Chang-Yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0087850 A1 | 4/2009 | Eid et al. |
| 2009/0092970 A1 | 4/2009 | Williams |
| 2009/0130745 A1 | 5/2009 | Williams et al. |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0155923 A1 | 6/2009 | Bonecker |
| 2009/0178934 A1 | 7/2009 | Jarvius et al. |
| 2009/0181411 A1 | 7/2009 | Battrell et al. |
| 2009/0183990 A1 | 7/2009 | Shoji et al. |
| 2009/0233325 A1 | 9/2009 | Mori et al. |
| 2009/0253181 A1 | 10/2009 | Vangbo et al. |
| 2009/0269504 A1 | 10/2009 | Liao |
| 2009/0286327 A1 | 11/2009 | Cho et al. |
| 2009/0311804 A1 | 12/2009 | McBrady et al. |
| 2009/0314970 A1 | 12/2009 | McAvoy et al. |
| 2009/0314972 A1 | 12/2009 | McAvoy et al. |
| 2009/0325183 A1 | 12/2009 | Lao et al. |
| 2009/0325276 A1 | 12/2009 | Battrell et al. |
| 2010/0010472 A1 | 1/2010 | Moore |
| 2010/0035252 A1 | 2/2010 | Rothberg et al. |
| 2010/0068723 A1 | 3/2010 | Jovanovich et al. |
| 2010/0075858 A1 | 3/2010 | Davis et al. |
| 2010/0092948 A1 | 4/2010 | Davis et al. |
| 2010/0093068 A1 | 4/2010 | Williams |
| 2010/0111770 A1 | 5/2010 | Hwang et al. |
| 2010/0129810 A1 | 5/2010 | Greiner et al. |
| 2010/0137143 A1 | 6/2010 | Rothberg et al. |
| 2010/0165784 A1 | 7/2010 | Jovanovich et al. |
| 2010/0172898 A1 | 7/2010 | Doyle et al. |
| 2010/0173392 A1 | 7/2010 | Davis et al. |
| 2010/0173398 A1 | 7/2010 | Peterman |
| 2010/0178210 A1 | 7/2010 | Hogan et al. |
| 2010/0197507 A1 | 8/2010 | Rothberg et al. |
| 2010/0209957 A1 | 8/2010 | Hogan et al. |
| 2010/0210008 A1 | 8/2010 | Strand et al. |
| 2010/0218623 A1 | 9/2010 | Eggers et al. |
| 2010/0221726 A1 | 9/2010 | Zenhausern et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0248363 A1 | 9/2010 | Hogan et al. |
| 2010/0266432 A1 | 10/2010 | Pirk et al. |
| 2010/0285578 A1 | 11/2010 | Selden et al. |
| 2010/0285606 A1 | 11/2010 | Phillips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0304986 A1 | 12/2010 | Chen et al. |
| 2010/0326826 A1 | 12/2010 | Harrison et al. |
| 2011/0003301 A1 | 1/2011 | Raymond et al. |
| 2011/0005932 A1 | 1/2011 | Jovanovich et al. |
| 2011/0008785 A1 | 1/2011 | Tan et al. |
| 2011/0008813 A1 | 1/2011 | Dilleen et al. |
| 2011/0027913 A1 | 2/2011 | Bau et al. |
| 2011/0038758 A1 | 2/2011 | Akaba et al. |
| 2011/0039303 A1 | 2/2011 | Jovanovich et al. |
| 2011/0041935 A1 | 2/2011 | Zhou et al. |
| 2011/0045505 A1 | 2/2011 | Warthoe et al. |
| 2011/0048945 A1 | 3/2011 | Harrison et al. |
| 2011/0053784 A1 | 3/2011 | Unger et al. |
| 2011/0070578 A1 | 3/2011 | Bell et al. |
| 2011/0070655 A1 | 3/2011 | Horiuchi et al. |
| 2011/0076735 A1 | 3/2011 | Jovanovich et al. |
| 2011/0124049 A1 | 5/2011 | Li et al. |
| 2011/0126910 A1 | 6/2011 | May |
| 2011/0126911 A1 | 6/2011 | Kobrin et al. |
| 2011/0127222 A1 | 6/2011 | Chang-Yen et al. |
| 2011/0136179 A1 | 6/2011 | Bin et al. |
| 2011/0137018 A1 | 6/2011 | Chang-Yen et al. |
| 2011/0171086 A1 | 7/2011 | Prins et al. |
| 2011/0172403 A1 | 7/2011 | Harrold |
| 2011/0186466 A1 | 8/2011 | Kurowski et al. |
| 2011/0189678 A1 | 8/2011 | McBride et al. |
| 2011/0195495 A1 | 8/2011 | Selden et al. |
| 2011/0206576 A1 | 8/2011 | Woudenberg et al. |
| 2011/0207140 A1 | 8/2011 | Handique et al. |
| 2011/0212440 A1 | 9/2011 | Viovy et al. |
| 2011/0212446 A1 | 9/2011 | Wang et al. |
| 2011/0223605 A1 | 9/2011 | Bienvenue et al. |
| 2011/0229897 A1 | 9/2011 | Bell et al. |
| 2011/0229898 A1 | 9/2011 | Bell et al. |
| 2011/0240127 A1 | 10/2011 | Eberhart et al. |
| 2011/0256530 A1 | 10/2011 | Hogan |
| 2011/0290648 A1 | 12/2011 | Majlof et al. |
| 2011/0312614 A1 | 12/2011 | Selden et al. |
| 2012/0055798 A1 | 3/2012 | Selden et al. |
| 2012/0088249 A1 | 4/2012 | Jovanovich et al. |
| 2012/0100522 A1 | 4/2012 | Saghbini et al. |
| 2012/0115189 A1 | 5/2012 | Jovanovich et al. |
| 2012/0135511 A1 | 5/2012 | Battrell et al. |
| 2012/0138833 A1 | 6/2012 | Matteo |
| 2012/0164036 A1 | 6/2012 | Stern et al. |
| 2012/0181460 A1 | 7/2012 | Eberhart et al. |
| 2012/0240127 A1 | 9/2012 | Brittenham et al. |
| 2012/0267247 A1 | 10/2012 | Tan et al. |
| 2012/0279638 A1 | 11/2012 | Zhou et al. |
| 2012/0290648 A1 | 11/2012 | Sharkey |
| 2012/0308987 A1 | 12/2012 | Hogan et al. |
| 2012/0309637 A1 | 12/2012 | Schumm et al. |
| 2012/0315635 A1 | 12/2012 | Vangbo et al. |
| 2012/0322666 A1 | 12/2012 | Pham et al. |
| 2013/0000758 A1 | 1/2013 | Hoen et al. |
| 2013/0029338 A1 | 1/2013 | Jovanovich et al. |
| 2013/0053255 A1 | 2/2013 | Vangbo et al. |
| 2013/0074944 A1 | 3/2013 | Van Gelder |
| 2013/0084565 A1 | 4/2013 | Landers et al. |
| 2013/0105017 A1 | 5/2013 | Zhou et al. |
| 2013/0115607 A1 | 5/2013 | Nielsen et al. |
| 2013/0130262 A1 | 5/2013 | Battrell et al. |
| 2013/0139895 A1 | 6/2013 | Vangbo |
| 2013/0203634 A1* | 8/2013 | Jovanovich ......... F16K 99/0015 506/26 |
| 2013/0210129 A1 | 8/2013 | Selden et al. |
| 2013/0213810 A1 | 8/2013 | Tan et al. |
| 2013/0217026 A1 | 8/2013 | Egan et al. |
| 2013/0224846 A1 | 8/2013 | Jovanovich et al. |
| 2013/0230906 A1 | 9/2013 | Martinelli et al. |
| 2013/0240140 A1 | 9/2013 | Kurowski et al. |
| 2013/0260380 A1 | 10/2013 | Hall et al. |
| 2013/0344475 A1 | 12/2013 | Jovanovich et al. |
| 2014/0045704 A1 | 2/2014 | Jovanovich et al. |
| 2014/0065628 A1 | 3/2014 | Van et al. |
| 2014/0065689 A1 | 3/2014 | Hogan et al. |
| 2014/0073043 A1 | 3/2014 | Holmes |

(56) References Cited

U.S. PATENT DOCUMENTS

| | | | |
|---|---|---|---|
| 2014/0161686 A1 | 6/2014 | Bort et al. |
| 2014/0170645 A1 | 6/2014 | Jovanovich et al. |
| 2014/0246618 A1 | 9/2014 | Zhou et al. |
| 2014/0370519 A1 | 12/2014 | Vangbo et al. |
| 2015/0021502 A1 | 1/2015 | Vangbo |
| 2015/0024436 A1 | 1/2015 | Eberhart et al. |
| 2015/0136602 A1 | 5/2015 | Jovanovich et al. |
| 2015/0136604 A1 | 5/2015 | Nielsen et al. |
| 2016/0016140 A1 | 1/2016 | Jovanovich et al. |
| 2016/0053314 A1 | 2/2016 | Jovanovich et al. |
| 2016/0096176 A1 | 4/2016 | Jarvius et al. |
| 2016/0116439 A1 | 4/2016 | Kindwall et al. |
| 2016/0305972 A1 | 10/2016 | Ogg et al. |
| 2016/0367981 A1 | 12/2016 | Wunderle et al. |
| 2017/0002399 A1 | 1/2017 | Eberhart et al. |
| 2017/0197213 A1 | 7/2017 | Nielsen et al. |

FOREIGN PATENT DOCUMENTS

| | | | |
|---|---|---|---|
| CN | 1354692 A | 6/2002 | |
| CN | 1593338 A | 3/2005 | |
| CN | 101004423 A | 7/2007 | |
| CN | 101098956 A | 1/2008 | |
| CN | 101312759 A | 11/2008 | |
| EP | 0459241 A1 | 12/1991 | |
| EP | 0637999 A1 | 2/1995 | |
| EP | 0527905 B1 | 11/1995 | |
| EP | 1065378 A2 | 1/2001 | |
| EP | 1411340 A2 | 4/2004 | |
| EP | 1658890 A2 | 5/2006 | |
| EP | 2345739 A2 | 7/2011 | |
| GB | 8419819 | 9/1984 | |
| JP | 10-206384 A | 8/1998 | |
| JP | 2003-074462 A | 3/2003 | |
| JP | 2003-536058 A | 12/2003 | |
| JP | 2004-025159 A | 1/2004 | |
| JP | 2004-108285 A | 4/2004 | |
| JP | 2004-180594 A | 7/2004 | |
| JP | 2005-323519 A | 11/2005 | |
| JP | 2005-337415 A | 12/2005 | |
| JP | 2005-345463 A | 12/2005 | |
| JP | 2007-155491 A | 6/2007 | |
| JP | 2007-198765 A | 8/2007 | |
| JP | 2008-513022 A | 5/2008 | |
| UA | 60060 U | 6/2011 | |
| WO | 93/22058 A1 | 11/1993 | |
| WO | 96/04547 A1 | 2/1996 | |
| WO | 96/14934 A1 | 5/1996 | |
| WO | 97/27324 A1 | 7/1997 | |
| WO | 98/52691 A1 | 11/1998 | |
| WO | 98/53300 A2 | 11/1998 | |
| WO | 99/33559 A1 | 7/1999 | |
| WO | 99/36766 A1 | 7/1999 | |
| WO | 99/40174 A1 | 8/1999 | |
| WO | 00/40712 A1 | 7/2000 | |
| WO | 00/60362 A1 | 10/2000 | |
| WO | 00/61198 A1 | 10/2000 | |
| WO | 01/01025 A2 | 1/2001 | |
| WO | 01/38865 A1 | 5/2001 | |
| WO | 01/85341 A1 | 11/2001 | |
| WO | 01/92575 A1 | 12/2001 | |
| WO | 02/24949 A1 | 3/2002 | |
| WO | 02/41995 A1 | 5/2002 | |
| WO | 02/43615 A2 | 6/2002 | |
| WO | 03/44528 A2 | 5/2003 | |
| WO | 03/62462 A2 | 7/2003 | |
| WO | 03/85379 A2 | 10/2003 | |
| WO | 2004/038363 A2 | 5/2004 | |
| WO | 2004/061085 A2 | 7/2004 | |
| WO | 2004/062804 A1 | 7/2004 | |
| WO | 2004/080597 A2 | 9/2004 | |
| WO | 2004/098757 A2 | 11/2004 | |
| WO | 2005/072858 A1 | 8/2005 | |
| WO | 2005/075081 A1 | 8/2005 | |
| WO | 2005/108620 A2 | 11/2005 | |
| WO | 2005/121308 A1 | 12/2005 | |
| WO | 2005/123950 A2 | 12/2005 | |
| WO | 2007/002579 A2 | 1/2007 | |
| WO | 2007/064635 A1 | 6/2007 | |
| WO | 2007/082480 A1 | 7/2007 | |
| WO | 2008/012104 A2 | 1/2008 | |
| WO | 2008/024319 A2 | 2/2008 | |
| WO | 2008/030631 A2 | 3/2008 | |
| WO | 2008/039875 A1 | 4/2008 | |
| WO | 2008/115626 A2 | 9/2008 | |
| WO | 2009/008236 A1 | 1/2009 | |
| WO | 2009/015296 A1 | 1/2009 | |
| WO | 2009/108260 A2 | 9/2009 | |
| WO | 2009/129415 A1 | 10/2009 | |
| WO | 2010/041174 A1 | 4/2010 | |
| WO | 2010/041231 A2 | 4/2010 | |
| WO | 2010/042784 A2 | 4/2010 | |
| WO | 2010/109392 A1 | 9/2010 | |
| WO | 2010/130762 A2 | 11/2010 | |
| WO | 2010/141921 A1 | 12/2010 | |
| WO | 2011/003941 A1 | 1/2011 | |
| WO | 2011/011172 A1 | 1/2011 | |
| WO | 2011/012621 A1 | 2/2011 | |
| WO | 2011/034621 A2 | 3/2011 | |
| WO | 2011/056215 A1 | 5/2011 | |
| WO | 2011/084703 A2 | 7/2011 | |
| WO | WO-2011094577 A2 * | 8/2011 | ......... B01L 3/50273 |
| WO | 2012/024657 A1 | 2/2012 | |
| WO | 2012/024658 A2 | 2/2012 | |
| WO | 2012/136333 A2 | 10/2012 | |
| WO | 2012/136633 A1 | 10/2012 | |
| WO | 2013/130910 A1 | 9/2013 | |
| WO | 2014/014587 A2 | 1/2014 | |
| WO | 2014/055936 A1 | 4/2014 | |

OTHER PUBLICATIONS

Unger, et al. Monolithic Microfabricated Valves and Pumps by Multilayer Soft Lithography. Science. 2000;288:113-116.

Van Der Moolen, et al. A Micromachined Injection Device for CZE: Application to Correlation CZE. Analytical Chemistry. 1997;69(20):4220-4225.

Van Der Moolen, et al. Correlation Capillary Zone Electrophoresis, a Novel Technique to Decrease Detection Limits. Chromatographia. 1995;40(7/8):368-374.

Van Ness, et al. Isothermal Reactions for the Amplification of Oligonucleotides. Proc. Nat. Acad. Sci. USA. 2003;100 (8):4504-4509.

Vazquez, et al. Electrophoretic Injection within Microdevices. Analytical Chemistry. 2002;74:1952-1961.

Veenstra, et al. The design of an in-plane compliance structure for microfluidical systems. Sensors and Actuators. 2002;881:377-383.

Waller, et al. Quantitative Immunocapture PCR Assay for Detection of Campylobacter jejuni in Foods. Applied Environmental Microbiology. 2000; 66(9):4115-4118.

Weimer, et al. Solid-Phase Capture of Proteins, Spores, and Bacteria. Applied Environmental Microbiology. 2001;67(3):1300-1307.

Wen, et al. Microfabricated isoelectric focusing device for direct electrospray ionization-mass spectrometry. Electrophoresis. 2000;21 :191-197.

Wikipedia brochure for defining stocahstic process. Sep. 2, 2009.

Williams, et al. Amplification of complex gene libraries by emulsion PCR. Nature Methods. 2006;3(7):545-50.

Woolley, et al. Functional Integration of PCR Amplification and Capillary Electrophoresis in a Microfabricated DNA Analysis Device. Analytical Chemistry. 1996;68(23):4081-4086.

Wright, et al. Behavior and Use of Nonaqueous Media without Supporting Electrolyte in Capillary Electrophoresis and Capillary Electrochromatography. Analytical Chemistry. 1997;69(16):3251-3259.

Xiang, et al. An Integrated Microfabricated Device for Dual Microdialysis and On-Line ESI-Ion Trap Mass Spectrometry for Analysis of Complex Biological Samples. Analytical Chemistry. 1999;71 (8):1485-1490.

(56) References Cited

OTHER PUBLICATIONS

Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.

Xue, et al. Multichannel Microchip Electrospray Mass Spectrometry. Analytical Chemistry. 1997;69(3):426-430.

Yang, et al. A MEMS thermopneumatic silicone rubber membrane valve. Sensors and Actuators. 1998;A64(1):101-108.

Yu, et al. Preparation of Monolithic Polymers with Controlled Porous Properties for Microfluidic Chip Applications Using Photoinitiated Free Radial Polymerization. Journal of Polymer Science. 2002;40:755-769.

Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.

Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.

Zhang, et al. Microfabricated Devices for Capillary Electrophoresis-Electrospray Mass Spectrometry. Analytical Chemistry. 1999;71(15):3258-3264.

Li, et al. Rapid and sensitive separation of trace level protein digests using microfabricated devices coupled to a quadrupole-time-of-flight mass spectrometer. Electrophoresis. 2000;21:198-210.

Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.

Licklider, et al. A Micromachined Chip-Based Electrospray Source for Mass Spectrometry. Analytical Chemistry. 2000;72(2):367-375.

Lisec, et al. A bistable pneumatic microswitch for driving fluidic components. Sensors and Actuators. 1996;A54:746-749.

Liu P, Seo TS, Beyor N, Shin KJ, Scherer JR, Mathies RA. Integrated portable polymerase chain reaction-capillary electrophoresis microsystem for rapid forensic short tandem repeat typing. Anal Chem. Mar. 1, 2007; 79(5):1881-9. Epub Feb. 2, 2007.

Liu, et al. Automated parallel DNA sequencing on multiple channel microchips. Proc. Natl. Acad. Sci. USA. 2000;97(10):5369-5374.

Liu, et al. Optimization of High-Speed DNA Sequencing on Microfabricated Capillary Electrophoresis Channels. Analytical Chemistry. 1999;71:566-573.

Lund-Olesen, et al. Capture of DNA in microfluidic channel using magnetic beads: Increasing capture efficiency with integrated microfluidic mixer. Journal of Magnetism and Magnetic Materials 311 (2007): 396-400.

Mamanova, et al. FRT-seq: amplification-free, strand-specific transcriptome sequencing. Nat Methods. Feb. 2010;7(2):130-2. doi: 10.1038/nmeth.1417. Epub Jan. 17, 2010.

Mansfield ES, Robertson JM, Vainer M, Isenberg AR, Frazier RR, Ferguson K, Chow S, Harris DW, Barker DL, Gill PD, Budowle B, McCord BR. Analysis of multiplexed short tandem repeat (STR) systems using capillary array electrophoresis. Electrophoresis. Jan. 1998; 19(1):101-7.

McDonald S, Pan T, Ziaie B. A magnetically driven PDMS micropump with microball valves. Conf Proc IEEE Eng Med Biol Soc.2004; 4:2650-3.

Melin, et al. A Passive 2-Dimensional Liquid Sample Micromixer. 7th International Conference on Miniaturized Chemical and Biochemical Analysis Systems. 2003;167-170.

Metzker, M. Sequencing technologies—the next generation. Nat Rev Genet. Jan. 2010;11(1):31-46. doi: 10.1038/nrg2626. Epub Dec. 8, 2009.

MillGat pump user manual, version 2.12, published 2005, pp. 1-28.

Mitra, et al. Digital genotyping and haplotyping with polymerase colonies. Proc Natl Acad Sci USA. 2003.100(10):15926-5931.

Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.

Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.

Ocvirk, et al. High Performance Liquid Chromatography Partially Integrated onto a Silicon Chip. Analytical Methods and Instrumentation. 1995;2:74-82.

Ocvirk, et al. Optimization of confocal epifluorescence microscopy for microchip-based miniaturized total analysis systems. The Analyst. 1998;123:1429-1434.

Oh, et al. A review of microvalves. J. Micromech. Microeng. 2006; 16:R13-R39.

Ohori, et al. Partly disposable three-way mirovalve for a medical micro total analysis system (muTAS). Sensors and Actuators. 1998;A64(1): 57-62.

Oleschuk, et al. Trapping of Bead-Based Reagents within Microfluidic Systems: On-Chip Solid-Phase Extraction and Electrochromatography. Analytical Chemistry. 2000;72:585-590.

Olsen, et al. Immobilization of DNA Hydrogel Plugs In Microfluidic Channels. Analytical Chemistry. 2002;74:1436-1441.

Paegel, et al. High-throughput DNA sequencing with a 96-lane capillary array electrophoresis bioprocessor. Proc Natl Acad Sci USA. 2002;99:574-579.

Paegel, et al. Microchip Bioprocessor for Integrated Nanovolume Sample Purification and DNA Sequencing. Analytical Chemistry. 2002;74(19):5092-5098.

Paegel, et al. Microfluidic devices for DNA sequencing: sample preparation and electrophoretic analysis. Current Opinion in Biotechnology. 2003;14(1):42-50.

Paegel, et al. Turn Geometry for Minimizing Band Broadening in Microfabricated Capillary Electrophoresis Channels. Analytical Chemistry. 2000;72:3030-3037.

PCT Notification of Transmittal of the International Search Report and The Written Opinion of the International Searching Authority, or the Declaration, mailed Jun. 17, 2008, Application No. PCT/US2007/082568.

Peoples, et al. Microfluidic Immunoaffinity Separations for Bioanalysis. J. Chromat. B. 2008;866:14-25 (available online Aug. 30, 2007).

Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.

Qiu X, Liu C, Mauk MG, Hart RW, Chen D, Qiu J, Kientz T, Fiene J, Bau HH. A portable analyzer for pouch-actuated, immunoassay cassettes. Sensors and Actuators B: Chemical. Dec. 15, 2011; 160(11:1529-35. (Year: 2011).

Ramsey, et al. Generating Electrospray from Microchip Devices Using Electroosmotic Pumping. Analytical Chemistry. 1997;69(6):1174-1178.

Rohr, et al. Porous polymer monoliths: Simple and efficient mixers prepared by direct polymerization in the channels of microfluidic chips. Electrophoresis. 2001;22:3959-3967.

Rye, et al. High-sensitivity two-color detection of double-stranded DNA with a confocal fluorescence gel scanner using ethidium homodimer and thiazole orange. Nucleic Acids Research. 1991;19(2):327-333.

Scherer, et al. High-Pressure Gel Loader for Capillary Array Electrophoresis Microchannel Plates. Biotechniques. 2001;31(5):1150-1154.

Schomburg, et al. Design Optimization of Bistable Microdiaphragm Valves. Sensors and Actuators. 1998;A64:259-264.

Seifar, et al. Capillary electrochromatography with 1.8-mum ODS-modified porous silica particles. Journal of Chromatography. 1998; A808:71-77.

Shaikh, et al. A modular microfluidic architecture for integrated biochemical analysis. Proc Natl Acad Sci U S A. Jul. 12, 2005;102(28):9745-50. Epub Jun. 28, 2005.

Shendure, et al. Next-generation DNA sequencing. Nat Biotechnol. Oct. 2008;26(10):1135-45. doi: 10.1038/nbt1486.

(56) References Cited

OTHER PUBLICATIONS

Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Sings, et al. Microfluidic Devices Connected to Fused-Silica Capillaries with Minimal Dead Dead Volume. Analytical Chemistry. 1999;71(15):3292-3296.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Stevens, et al. Bacterial Separation and Concentration from Complex Sample Matrices: a Review. Grit. Rev. Microbial. 2004;30(1):7-24.
Takao, et al. A Pneumatically Actuated Full In-Channel Microvalve With MOSFET-Like Function in Fluid Channel Networks. Journal of Microelectromechanical Systems. 2002;11 (5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Thomas, et al. Application of Genomics to Toxicology Research. Environmental Health Perspectives. 2002;110(6):919-923.
Tice, et al. Formation of Droplets and Mixing in Multiphase Microfluidics at Low Values of the Reynolds and the Capillary Numbers. Langmuir. 2003;19:9127-9133.
Todd Thorsen, et al., "Microfluidic Large-Scale Integration", www.sciencemag.org, Science, vol. 298, Oct. 18, 2002, pp. 580-584.
Grover, et al. An integrated microfluidic processor for single nucleotide polymorphism-based DNA computing. Lab on a Chip. 2005;5(10):1033-1040.
Grover, et al. Development and multiplexed control of latching pneumatic valves using microfluidic logical structures. Lab on a chip. 2006;6:623-631.
Grover, et al. Monolithic membrane valves and diaphragm pumps for practical large-scale integration into glass microfluidic devices. Sensors and Actuators. 2003;889:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.
Harrison, et al. Micromachining a Miniaturized Capillary Electrophoresis-Based Chemical Analysis System on a Chip. Science. 1993;261(5123):895-897.
Hayes, et al. Edge: A Centralized Resource for the Comparison, Analysis, and Distribution of Toxicogenomic Information. Molecular Pharmacology. 2005;67(4):1360-1368.
Heath, et al. PCR primed with VNTR core sequences yields species specific patterns and hypervariable probes. Nucleic Acids Res. Dec. 11, 1993;21(24):5782-5.
Holland, et al. Point-of-care molecular diagnostic systems—past, present and future. Curr Opin Microbial. Oct. 2005;8(5):504-9.
Hultman, et al. Bidirectional Solid-Phase Sequencing of In Vitro-Amplified Plasmid DNA. BioTechniques. 1991;10(1):84-93.
International Preliminary Report for corresponding PCT Application No. PCT/CA2000/01421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/002721 dated Aug. 5, 2008.
International Preliminary Report for corresponding PCT Application No. PCT/US2007/007381 dated Sep. 23, 2008.
International Preliminary Report for corresponding PCT Application No. PCT/US2007/061573 dated Aug. 26, 2008.
International search report and written opinion dated Jan. 5, 2012 for PCT Application No. PCT/US2011/048527.
International search report and written opinion dated Jan. 29, 2016 for PCT Application No. PCT/US2015/56764.
International search report and written opinion dated Mar. 3, 2015 for PCT Application No. PCT/US2014/066008.
International search report and written opinion dated Mar. 24, 2011 for PCT Application No. PCT/US2010/058227.
International search report and written opinion dated Apr. 30, 2012 for PCT/US2012/021217.
International search report and written opinion dated Jun. 9, 2011 for PCT Application No. PCT/US2011/030973.
International search report and written opinion dated Jul. 22, 2013 for PCT Application No. US2013/028462.
International search report and written opinion dated Sep. 1, 2010 for PCT Application No. PCT/US2010/040490.
International search report and written opinion dated Oct. 26, 2011 for PCT Application No. PCT/US11/38180.
International search report and written opinion dated Oct. 26, 2015 for PCT/US2015/028510.
International search report and written opinion dated Mar. 8, 2013 for PCT/US2012/061223.
International search report dated Oct. 6, 2010 for PCT Application No. PCT/US10/37545.
International search report dated Apr. 5, 2001 for PCT Application No. PCT/CA2000/001421.
International search report dated May 14, 2010 for PCT Application No. PCT/US2009/006640.
International search report dated Jul. 11, 2008 for PCT Application No. PCT/US07/61573.
International search report dated Jul. 30, 2010 for PCT Application No. PCT/US2010/036464.
International search report dated Aug. 18, 2009 for PCT Application No. PCT/US09/00419.
International search report dated Aug. 23, 2006 for PCT Application No. PCT/US2005/033347.
International search report dated Aug. 26, 2004 PCT Application No. PCT/US2003/041466.
International search report dated Sep. 25, 2007 for PCT Application No. PCT/US2007/002721.
International written opinion dated Oct. 6, 2010 for PCT Application No. PCT/US10/37545.
International written opinion report dated Jul. 30, 2010 for PCT Application No. PCT/US2010/036464.
Jacobson, et al. Electrokinetic Focusing in Microfabricated Channel Structures. Anal. Chem., 1997, 69 (16), pp. 3212-3217.
Ju, et al. Fluorescence energy transfer dye-labeled primers for DNA sequencing and analysis. Proc. Natl. Acad. Sci. USA. 1995;92:4347-4351.
Kan, et al. A novel thermogelling matrix for microchannel DNA sequencing based on poly-N-alkoxyalkylaclylamide copolymers. Electrophoresis. 2003;24(24):4161-4169.
Koh, et al. Integrating Polymerase Chain Reaction, Valving, and Electrophoresis in a Plastic Device for Bacterial Detection. Analytical Chemistry. 2003;75(17):4591-4598.
Kopp, et al. Chemical Amplification Continuous-Flow PCR on a Chip. Science. 1998;280:1046-1048.
Krsek, et al. Comparison of different methods for the isolation and purification of total community DNA from soil. Journal of Microbiological Methods 39.1 (1999): 1-16.
Lagally, et al. Fully integrated PCR-capillary electrophoresis microsystem for DNA analysis. Lab on a Chip. 2001;1(2):102-107.
Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;863(3):138-146.

(56) References Cited

OTHER PUBLICATIONS

Lagally, et al. Single-Molecule DNA Amplification and Analysis in an Integrated Microfluidic Device. Analytical Chemistry. 2001;73(3):565-570.
Lazar, et al. Subattomole-Sensitivity Microchip Nanoelectrospray Source with Time-of-Flight Mass Spectrometry Detection. Analytical Chemistry. 1999;71(17):3627-3631.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Amendment and Request for Correction of Inventorship mailed Jan. 10, 2008 in U.S. Appl. No. 10/750,533.
Anderson, et al. A miniature integrated device for automated multistep genetic assays. Nucleic Acids Research. 2000;28:e60.
Armani, et al. Re-configurable fluid circuits by PDMS elastomer micromachining. Proceedings of IEEE Micro Electro Mechanical Systems: MEMS. 1999; 222-227.
Bennett, et al. Toward the 1,000 dollars human genome. Pharmacogenomics, 6 (4) 373-382. (Jun. 2005).
Blazej, et al. Microfabricated bioprocessor for integrated nanoliter-scale Sanger DNA sequencing. Proc. Natl. Acad. Sci. USA 2006;103:7240-7245.
Blazej, et al. Polymorphism Ratio Sequencing: A New Approach for Single Nucleotide Polymorphism Discovery and Genotyping. Genome Research. 2003;13:287-293.
Branton, et al. The potential and challenges of nanopore sequencing. Nat Biotechnol. Oct. 2008;26(10):1146-53. doi: 10.1038/nbt.1495.
Brenner, et al. Gene expression analysis by massively parallel signature sequencing (MPSS) on microbead arrays. Nature Biotechnology, 18: 630-634 (2000).
Buchholz, et al. The use of light scattering for precise characterization of polymers for DNA sequencing by capillary electrophoresis. Electrophoresis. 2001;22:4118-4128.
Caplus abstract of Krohkin et al. Modified silica as a stationary phase for ion chromatography. Journal of Chromatography A. 1995;706:93-8.
Chan, et al. Microfabricated Polymer Devices for Automated Sample Delivery of Peptides for Analysis by Electrospray Ionization Tandem Mass Spectrometry. Analytical Chemistry. 1999;71(20):4437-4444.
Charlieu, et al. 3' Alu PCR: a simple and rapid method to isolate human polymorphic markers. Nucleic Acids Res. Mar. 25, 1992;20(6):1333-7.
Chiem, et al. Microchip systems for immunoassay: an integrated immunoreactor with electrophoretic separation for serum theophylline determination. Clinical Chemistry. 1998;44(3):591-598.
Chiem, et al. Room temperature bonding of micromachined glass devices for capillary electrophoresis. Sensors and Actuators. 2000;863(3):147-152.
Coleman, et al. A sequential injection microfluidic mixing strategy. Microfluidics and Nanofluidics. 2005;319-327.
Collins PJ, Hennessy LK, Leibelt CS, Roby RK, Reeder DJ, Foxall PA. Developmental validation of a single-tube amplification of the 13 CODIS STR loci, D2S1338, D19S433, and amelogenin: the AmpFlSTR Identifiler PCR Amplification Kit. J Forensic Sci. Nov. 2004; 49(6):1265-77.
Curcio, et al. Continuous Segmented-Flow Polymerase Chain Reaction for High-Throughput Miniaturized DNA Amplification. Analytical Chemistry. 2003;75(1):1-7.
Datasheet Cycle Sequencing, Retrieved from the internet, URL:http//answers.com/topic/cycle sequencing. Printed Sep. 3, 2010, pp. 1-2.
Diehl et al. BEAMing: single-molecule PCR on microparticles in water-in-oil emulsions. Nature Methods 3(7):551-559 (2006).
Doherty, et al. Sparsely Cross-linked "Nanogel" Matrices as Fluid, Mechanically Stablized Polymer Networks for High-Throughput Microchannel DNA Sequencing. Analytical Chemistry. 2004 ;76:5249-5256.
Doherty, et al. Sparsely cross-linked "nanogels" for microchannel DNA sequencing. Electrophoresis. 2003;24(24):4170-4180.

Dorfman, et al. Contamination-Free Continuous Flow Microfluidic Polymerase Chain Reaction for Quantitative and Clinical Applications. Analytical Chemistry. 2005;77(11):3700-3704.
Doyle, et al. Self-Assembled Magnetic Matrices for DNA Separation Chips. Science. 2000;295:2237.
Dressman, et al. Transforming single DNA molecules into fluorescent magnetic particles for detection and enumeration of genetic variations. Proc Natl Acad Sci USA. 2003;100(15):8817-8822.
Eid, et al. Real-time DNA sequencing from single polymerase molecules. Science. Jan. 2, 2009;323(5910):133-8. doi: 10.1126/science.1162986. Epub Nov. 20, 2008.
Emrich, et al. Microfabricated 384-Lane Capillary Array Electrophoresis Bioanalyzer for Ultrahigh-Throughput Genetic Analysis. Analytical Chemistry. 2002;74(19):5076-5083.
Ericson, et al. Electroosmosis- and Pressure-Driven Chromatography in Chips Using Continuous Beds. Analytical Chemistry. 2000;72(1):81-87.
Erratum for Margulies, et al. Genome sequencing in microfabricated high-density picolitre reactors. Nature. 2005;437(7057):376-80.
European search report and search opinion dated Jun. 6, 2011 for Application No. 10011511.2.
European search report and search opinion dated Jun. 22, 2016 for EP Application No. 11818879.6.
European search report and search opinion dated Aug. 17, 2011 for Application No. 08799648.4.
European search report and search opinion dated Sep. 11, 2013 for EP Application No. 10784213.
European search report dated Jul. 13, 2016 for EP Application No. 09714332.5.
European search report dated Oct. 29, 2012 for EP Application No. 07853470.8.
European search report dated Dec. 18, 2009 for Application No. 03808583.3.
European search report dated Sep. 1, 2010 for Application No. 5804847.1.
European search report with written opinion dated Jul. 12, 2017 for EP14861199.
Ewing, et al. Base-Calling of Automated Sequencer Traces Using Phred. I. Accuracy Assessment. Genome Research. 1998;8:175-185.
Ewing, et al. Base-Calling of Automated Sequencer Traces Using Phred. II. Error probabilities. Genome Research. 1998;8:186-194.
Figeys, et al. A Microfabricated Device for Rapid Protein Identification by Microelectrospray Ion Trap Mass Spectrometry. Analytical Chemistry. 1997;69(16):3153-3160.
Figeys, et al. An Integrated Microfluidics-Tandem Mass Spectrometry System for Automated Protein Analysis. Analytical Chemistry. 1998;70(18):3728-3734.
Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications In Mass Spectrometry. 1998;12:1435-1444.
Figeys, et al. Nanoflow Solvent Gradient Delivery from a Microfabricated Device for Protein Identifications by Electrospray Ionization Mass Spectrometry. Analytical Chemistry. 1998;70(18):3721-3727.
Francis, et al. Flow analysis based on a pulsed flow of solution: theory, instrumentation and applications. Talanta. 2002;58(6):1029-1042.
Fuentes, et al. Detecting minimal traces of DNA using DNA covalently attached to superparamagnetic nanoparticles and direct PCR-ELISA. Biosens Bioelectron. Feb. 15, 2006;21(8):1574-80. Epub Aug. 29, 2005.
Fuller, et al. The challenges of sequencing by synthesis. Nat Biotechnol. Nov. 2009;27(11):1013-23. doi: 10.1038/nbt.1585. Epub Nov. 6, 2009.
Ghadessy, et al. Directed evolution of polymerase function by compartmentalized self-replication. Proc Natl Acad Sci USA. 2001;98:4552-4557.
Giddings, et al. A software system for data analysis in automated DNA sequencing. Genome Research. 1998;8:644-665.
Goll, et al. Microvalves with bistable buckled polymer diaphragms. Journal of Micromechanics and Microengineering. 1996;6:77-79.

(56) References Cited

OTHER PUBLICATIONS

Grodzinski, et al. Microfluidic System Integration in Sample Preparation Chip-Sets—a Summary. Cont. Proc. IEEE Eng. Med. Biol. Soc. 2004;4:2615-2618.

* cited by examiner

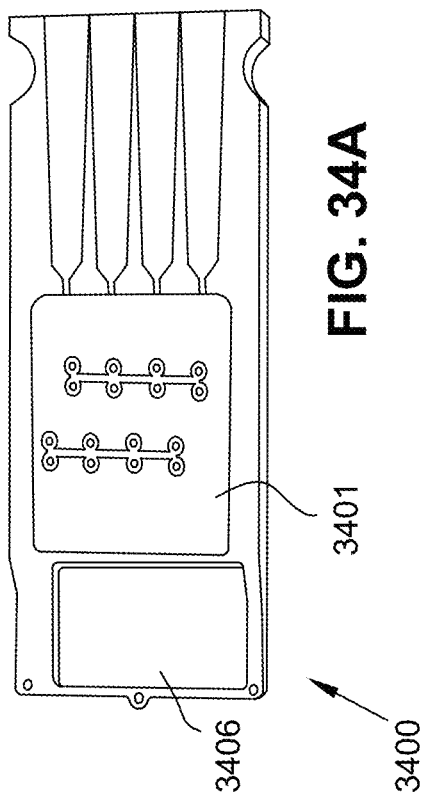
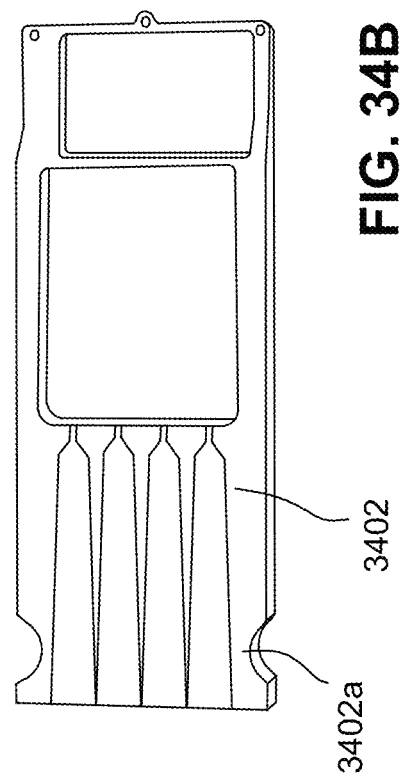
FIG. 34A
FIG. 34B

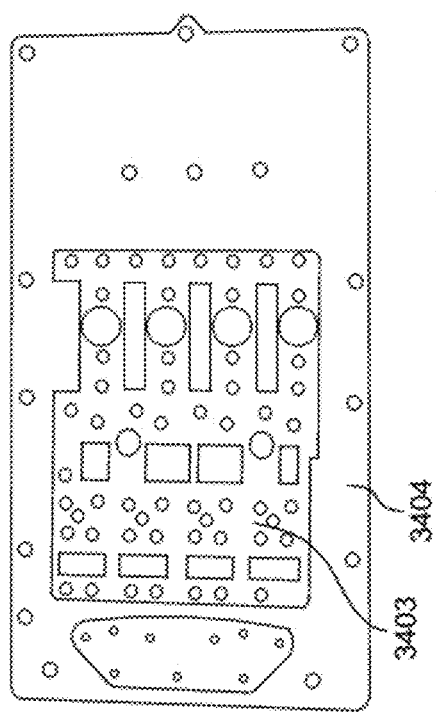
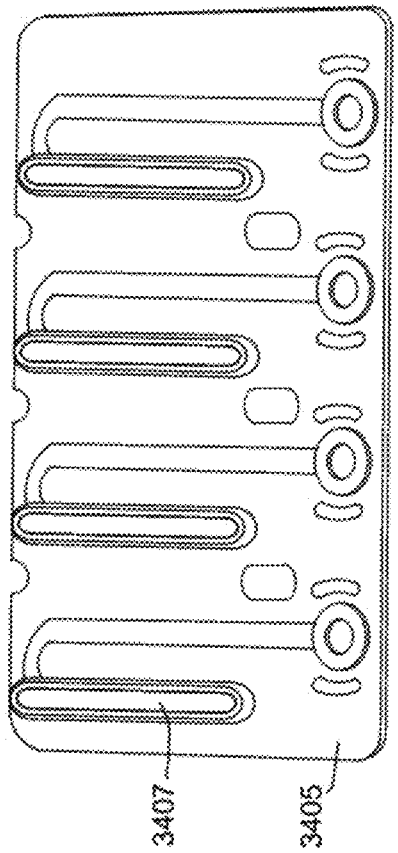

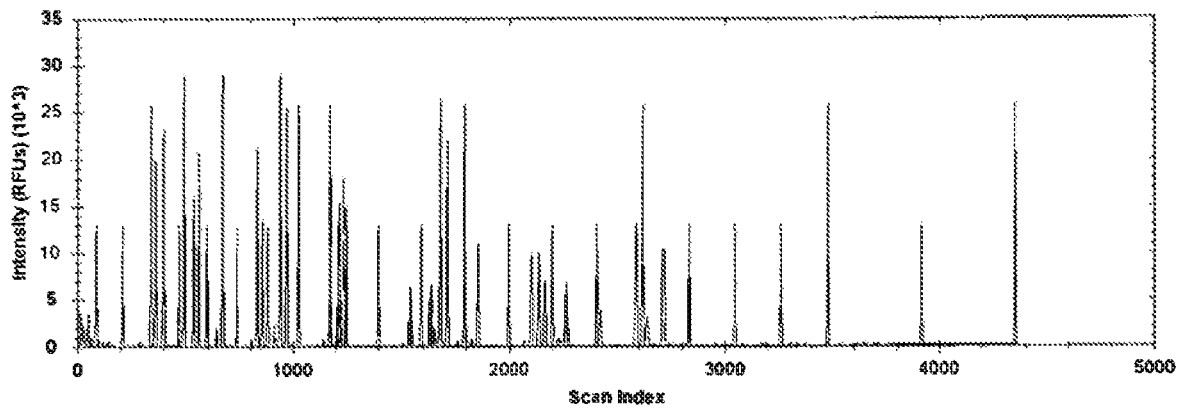
FIG. 51A. A typical electropherogram that can be generated from data collected
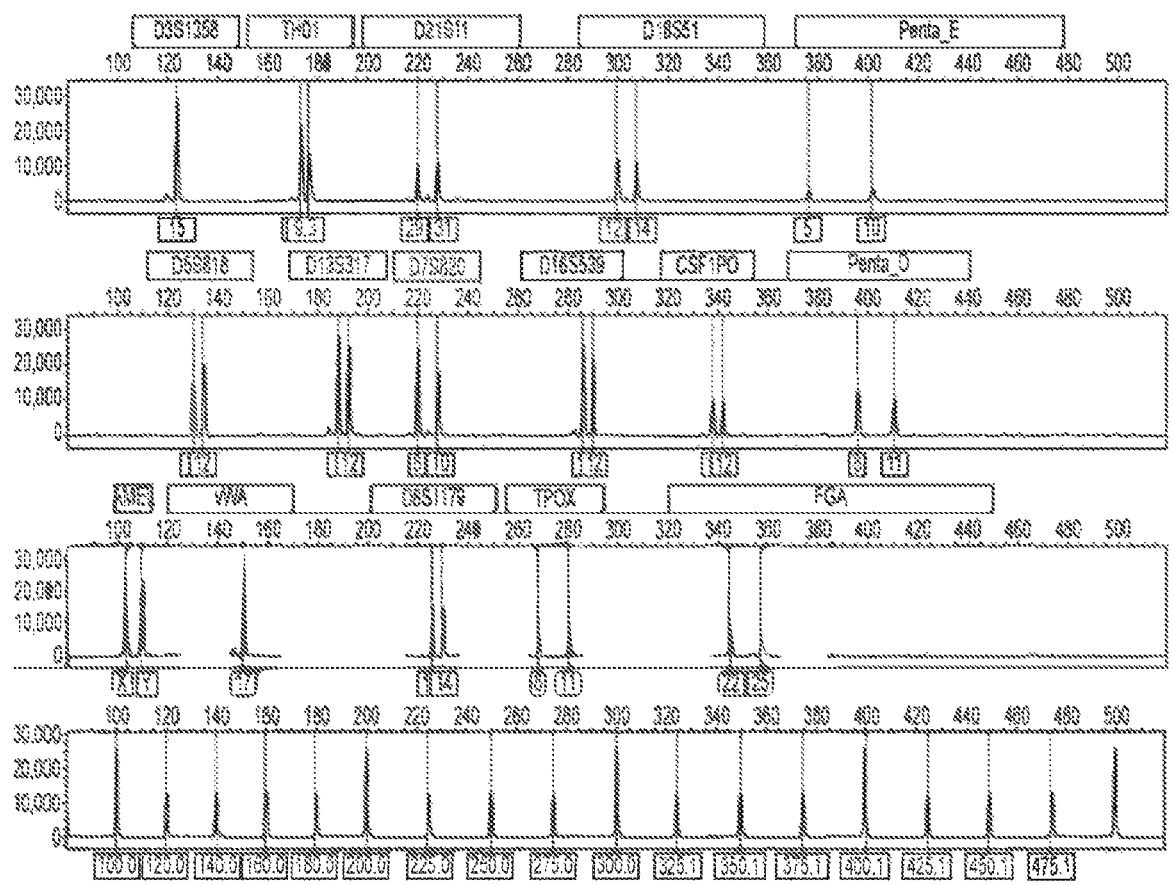
FIG. 51B. A typical plot of a nucleic acid profile that can be generated from data collected device for actuating premix delivery 7000A 7000B
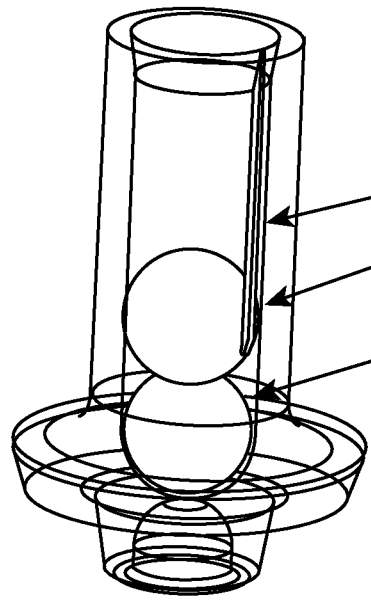
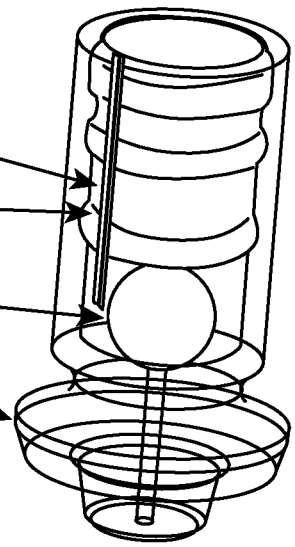
FIG. 70A  FIG. 70B
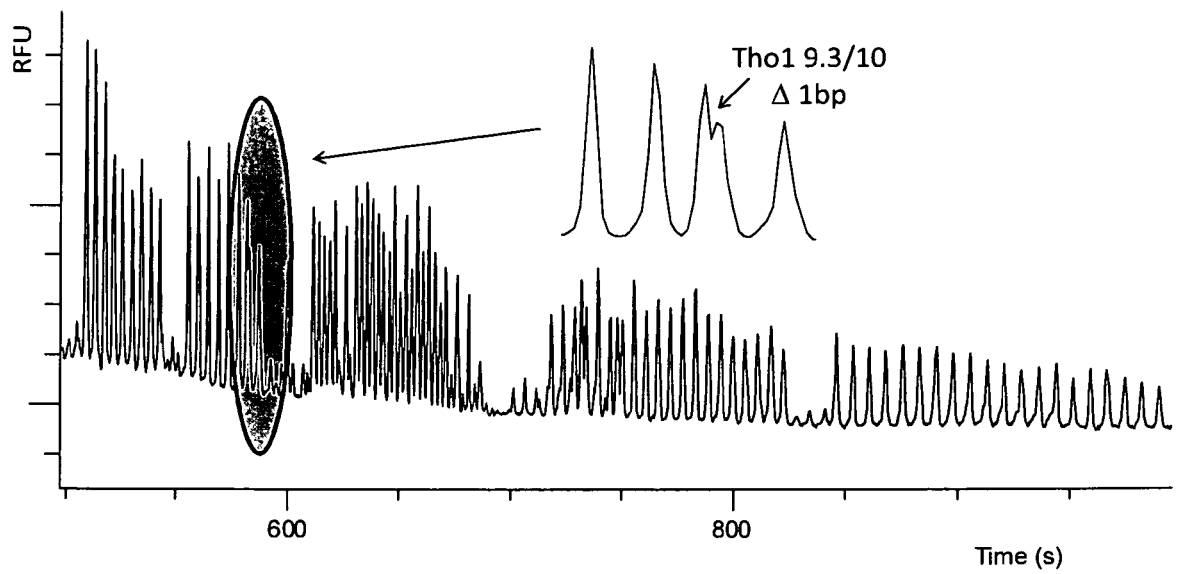
FIG. 71

SAMPLE PREPARATION, PROCESSING AND ANALYSIS SYSTEMS

CROSS-REFERENCE TO RELATED APPLICATIONS

This application is a divisional of U.S. application Ser. No. 14/381,179, filed Aug. 26, 2014, which is a nationalization of PCT Application No. PCT/US2013/028462, filed Feb. 28, 2013, which (1) claims the benefit of and priority to U.S. Provisional Patent Application No. 61/724,296, filed Nov. 8, 2012, U.S. Provisional Patent Application Ser. No. 61/703,194, filed Sep. 19, 2012, U.S. Provisional Patent Application No. 61/696,809, filed Sep. 5, 2012, U.S. Provisional Patent Application No. 61/691,242, filed Aug. 20, 2012, U.S. Provisional Patent Application No. 61/674,295, filed Jul. 20, 2012, U.S. Provisional Patent Application No. 61/671,592, filed Jul. 13, 2012, U.S. Provisional Patent Application No. 61/664,726, filed Jun. 26, 2012, U.S. Provisional Patent Application No. 61/654,749, filed Jun. 1, 2012, U.S. Provisional Patent Application No. 61/641,120, filed May 1, 2012, U.S. Provisional Patent Application No. 61/610,977, filed Mar. 14, 2012, and U.S. Provisional Patent Application No. 61/605,169, filed Feb. 29, 2012, and (2) is a continuation-in-part of U.S. application Ser. No. 13/656,503, filed Oct. 19, 2012, now U.S. Pat. No. 8,894,946, which claims the benefit of and priority to U.S. Provisional Patent Application Ser. No. 61/703,194, filed Sep. 19, 2012, U.S. Provisional Patent Application No. 61/696,809, filed Sep. 5, 2012, U.S. Provisional Patent Application No. 61/691,242, filed Aug. 20, 2012, U.S. Provisional Patent Application No. 61/674,295, filed Jul. 20, 2012, U.S. Provisional Patent Application No. 61/671,592, filed Jul. 13, 2012, U.S. Provisional Patent Application No. 61/664,726, filed Jun. 26, 2012, U.S. Provisional Patent Application No. 61/654,749, filed Jun. 1, 2012, U.S. Provisional Patent Application No. 61/641,120, filed May 1, 2012, U.S. Provisional Patent Application No. 61/610,977, filed Mar. 14, 2012, U.S. Provisional Patent Application No. 61/605,169, filed Feb. 29, 2012, and U.S. Provisional No. 61/550,364, filed Oct. 21, 2011, each of which is incorporated herein by reference in its entirety.

STATEMENT AS TO FEDERALLY SPONSORED RESEARCH

This invention was made with government support under Task Order #W91QUZ-09-D-0026-0004 awarded by Army Contracting Command (NCR). The government has certain rights in the invention.

BACKGROUND OF THE INVENTION

DNA profiling (also called DNA testing, DNA typing, or genetic fingerprinting) is a technique employed by forensic scientists to assist in the identification of individuals by their respective DNA profiles. DNA profiles may be encrypted sets of numbers that reflect a person's DNA makeup, which can also be used as the person's identifier.

DNA profiling, or genetic profiling, can be used to identify a suspect of a crime or verify the identity of a subject, such as to verify the identity of a victim of a crime. This can enable law enforcement personnel to accurately identify the perpetrator of a crime from a list of suspects, and minimize instances of misidentification. In a battlefield scenario, DNA profiling can, e.g., identify the opposition in asymmetric warfare, identify suspects in raids, identify suspected terrorists, link improvised explosive devices (IED's) to bomb makers, find captured soldiers (such as, e.g., by identifying their DNA from a tissue sample on a vehicle and tracking the vehicle), and unravel a combatant network.

DNA profiling typically involves sample preparation, processing and analysis. This is ordinarily done in a laboratory setting. Sample preparation is a ubiquitous problem in biological analytical systems. The issue of providing sufficiently purified targets from diverse raw sample types to reliably perform downstream analytical assays is pervasive and covers cell biology, genomics, proteomics, metabolomics, food biology, molecular diagnostics, and many other biological and medical assays.

Methods and systems currently available for DNA profiling have various limitations. For instance, sample preparation and analysis systems for DNA profiling are typically bulky and difficult to transport without substantial effort. This makes the use of such systems in the field, such as on a battlefield, difficult and impractical. In addition, current systems and methods are expensive to use and maintain, and genetic profiles take a substantially large amount of time to prepare. In some cases, a genetic profile of a subject is provided in one to two days. This is unappealing in cases in which time is of the essence, such as cases in which law enforcement officials are in pursuit of a suspect or can detain a suspect for only a limited period of time.

SUMMARY OF THE INVENTION

Recognized herein is the need for improved systems and methods for genetic profiling. In particular, recognized is the need for systems that have a smaller footprint in relation to other systems and in a faster time. In addition, there is a need for systems and methods that enable genetic profiling at lower cost with less skilled operators.

This disclosure provides an integrated and automated sample-to-answer system that, starting from a sample comprising biological material, generates a genetic profile in less than two hours. In certain embodiments, the biological material is DNA and the genetic profile involves determining one or a plurality of alleles at one or a plurality of loci (e.g., genetic loci) of a subject, for example, an STR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several integrated modules, including an analyte preparation module; a detection and analysis module and a control module. These modules are shown in FIG. 48 and FIG. 49. (One or more computer systems can communicate with and control the operation of various components (e.g., the fluidics manifold and the pneumatic manifold) of the analyte preparation module in FIG. 48; such computer system(s) are not shown in FIG. 48.)

Systems provided herein may be fully integrated. Sample processing can be accomplished in a single system without having to remove a sample and transferring the sample to another system. Systems provided herein can be fully automated, enabling a user to process a sample without substantial input from the user. Systems provided herein can be dimensioned to minimize footprint, thereby enabling portability. This can advantageously enable system use in on-the-go situations, such as remote locations, situations in which transportation is not readily available or user mobility is desired, such as battlefield scenarios.

An analyte preparation module includes a cartridge module assembly configured to engage and operate one or more than one sample cartridge. A sample cartridge is configured to receive one or more samples and to perform nucleic acid extraction and isolation, and DNA amplification when the cartridge is engaged with a cartridge module assembly in the system. It can also include controls and standards for assisting in analysis.

The sample cartridge includes a sample receptacle for receiving the sample; compartments for DNA extraction and isolation; on-board reagents in fluidically isolated compartments for nucleic acid extraction, purification and amplification (e.g., process beads to concentrate the samples); assemblies for thermal cycling; fluidic channels (e.g., microfluidic channels) for routing fluids to different functional compartments within the cartridge and ports to engage sub-assemblies in the cartridge module assembly that operate valves, pumps and routers on the cartridge; provide pressure for moving liquids; and provide consumables not stored on the cartridge. In some examples, diaphragm valves, pumps and routers, e.g., MOVe pumps, valves and routers transport, process and enable analysis of samples. When the cartridge is engaged with a cartridge receptacle in the cartridge module assembly, fluidically isolated chambers are brought into fluidic connection with fluidic channels in the cartridge, allowing movement and routing of fluids and reagents to functional compartments in the cartridge and, subsequently, to the detection and analysis module.

The analyte preparation module can include a receptacle for receiving one or more cartridges, an engagement assembly to engage the cartridge; a fluidic manifold configured to engage ports in a cartridge and to deliver pressure and/or fluids to the cartridge through the ports; a delivery assembly configured to deliver reagents, such as amplification pre-mix, from a compartment in the sample cartridge to an amplification compartment; a pneumatic manifold configured to engage ports in a cartridge and to deliver positive or negative pressure to the cartridge through the ports for moving fluids and operating valves, pumps and routers in the cartridge; a pump configured to deliver pressure to the fluidic and pneumatic manifold. Consumable reagents can be carried in a module, e.g., a buffer module, that is removably engagable with the cartridge module. Reagents can be provided (e.g., stored) in an aqueous solution, or can be provided (e.g., stored) in a solid or dry (e.g., lyophilized) form and then placed into solution by addition of a liquid (e.g., an aqueous solution) as appropriate. Alternatively, reagents can be provided (e.g., stored) in a substantially water-free non-ionic organic solvent (e.g., an alcohol solvent) or in a substantially water-free ionic organic solvent (e.g., a deep eutectic solvent) and can be re-hydrated by addition of an aqueous solution as appropriate, as described in U.S. Provisional Patent Application No. 61/709,417, which is incorporated herein by reference in its entirety.

An analysis and detection module is configured to receive analyte from the analyte preparation module; perform capillary electrophoresis on the analyte; to detect analytes separated by electrophoresis and to analyze the detected analytes. It can include a capillary electrophoresis assembly, a detection assembly and an analysis assembly.

The capillary electrophoresis assembly can include an injection assembly, that can include a denature heater assembly, a positioning assembly for positioning an analyte for capillary injection; a cathode assembly; a capillary assembly; an anode assembly; a capillary filling assembly for filling a capillary with separation medium and a power source for applying a voltage between the anode and the cathode. A denature assembly can include a heater configured to denature double stranded DNA molecules. A cathode assembly can include a cathode. The cathode can be a forked cathode for stacking analyte for capillary injection. The capillary assembly can include a capillary configured to receive a separation medium and a temperature control unit for regulating temperature in the capillary. For example, the temperature control unit can have a circuit board material including heating traces connected to current source and to temperature sensors to regulate temperature in the capillary. The anode assembly can comprise an anode. The anode can be comprised in an anode cartridge that is removably insertable into the analysis and detection module. An anode cartridge can include separation medium and optionally a buffer supply, and an electrode. A capillary filling assembly can include a source of separation medium, e.g., a separation polymer or gel comprised in an anode cartridge, and a pump for delivering separation medium into the capillary.

A detection assembly can comprise a laser configured to illuminate the capillaries and a detector. The laser can be configured to excite fluorescent dyes in the analyte. The detector can include a CCD array, for detecting light produced by excited dyes and for producing an output signal.

An analysis assembly can include a computer comprising memory and a processor for executing code (e.g., code on a tangible medium) for analyzing the output signal and producing a computer file containing an analysis of the signal. Such an analysis can include, for example, identification of alleles from various STR loci. The computer file can be in a format that is compatible with public databases. For example, the file can be in CODIS format which is compatible with the National DNA Index (NDIS) operated by the FBI. The analysis assembly can further comprise code that performs kinship analysis on a sample being tested and a reference sample. The analysis assembly can query databases that may be part of the system or remote databases to determine if a sample fully or partially matches a profile in the database. The results of the database query can be displayed to the user.

The system can be operated by a control module. The control module can include a user interface configured to receive instructions from and deliver information to a user. It can include software programmed to execute routines for performing the operations mentioned, above, and transmit and receive information, such as computer files, from remote locations, e.g., over the internet. The control module also can include sensors positioned in various parts of the instrument to detect and measure operation and to transmit such parameters to a computer for analysis by software configured to monitor operation of the instrument and alter operation of the instrument if measurements are not within selected parameters. Systems and methods of the invention are fully integrated and automated, which advantageously reduces processing times for sample processing while providing flexibility in processing and analyzing samples in various locations, including remote locations that may not be readily accessible.

For example, starting from the sample, the present invention can be applied to concentrate and separate components for further processing to detect and classify human and other organisms in matrices comprising aerosol samples, water, liquids, blood, stools, nasal, buccal and other swabs, bodily fluids, environmental samples with analysis by ELISA, PCR or other nucleic acid amplification techniques, single molecule detection, protein arrays, mass spectrometry, and other analytical methods well known to one skilled in the art.

The disclosure further provides devices and methods for storing reagents (e.g., PCR reagents) in stable form (whether stored in liquid or solid form) and for delivering such reagents, methods for performing nucleic acid amplification, and devices and methods for ruggedizing instruments and systems so that their components are protected from misalignment and damage that may result from motion (e.g., horizontal and vibrational motion) and shock.

INCORPORATION BY REFERENCE

All publications, patents, and patent applications mentioned in this specification are incorporated herein by reference in their entirety to the same extent as if each individual publication, patent, or patent application was specifically and individually indicated to be incorporated herein by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 34A-34D show embodiments of various components of a cartridge.

FIG. 51A shows a typical electropherogram that can be generated from the data collected.

FIG. 51B shows a typical plot of the nucleic acid profile generated from the data collected.

FIG. 54A shows three electrodes opposite a capillary inside the lumen of tubing; the third electrode is not electrically connected, but is independently electrified. FIG. 54B shows three electrodes opposite a capillary inside the lumen of tubing; all the electrodes are electrically connected.

FIGS. 70A and 70B illustrate embodiments of receptacles for storing, rehydrating and dispensing a solid or semi-solid (e.g., dehydrated or lyophilized) composition comprising reagents for performing a reaction (e.g., PCR).

FIG. 71 is an electropherogram of an electrophoretic separation of the PowerPlex® 16 allelic ladder at 80° C. using N-methyl-2-pyrrolidinone as a chemical denaturant.

DETAILED DESCRIPTION OF THE INVENTION

Figure 1:
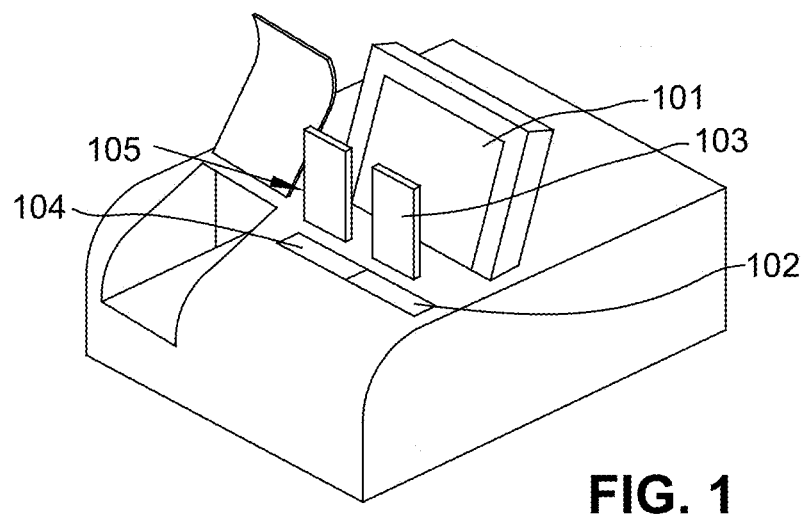
FIG. 1 shows an embodiment of a system for processing a sample.

It is understood that every embodiment of the disclosure may optionally be combined with any one or more of the other embodiments described herein which are consistent with that embodiment.

Whenever the term "about" or "approximately" precedes the first numerical value in a series of two or more numerical values or in a series of two or more ranges of numerical values, the term "about" or "approximately" applies to each numerical value in that series of numerical values or in that series of ranges of numerical values. In certain embodiments, the term "about" or "approximately" means within 10% or 5% of the specified value.

Whenever the term "at least" or "greater than" precedes the first numerical value in a series of two or more numerical values, the term "at least" or "greater than" applies to each numerical value in that series of numerical values.

Whenever the term "no more than" or "less than" precedes the first numerical value in a series of two or more numerical values, the term "no more than" or "less than" applies to each numerical value in that series of numerical values.

The term "sample", as used herein, refers to a sample containing biological material. A sample may be, e.g., a fluid sample (e.g., a blood sample) or a tissue sample (e.g., a cheek swab). A sample may be a portion of a larger sample. A sample can be a biological sample having a nucleic acid, such as deoxyribonucleic acid (DNA) or ribonucleic acid (RNA), or a protein. A sample can be a forensic sample or an environmental sample. A sample can be preprocessed before it is introduced to a system for analysis of the sample or an analyte isolated from the sample; the pre-processing can include, e.g., extraction of a material that would not fit into the system, quantification of the amount of cells, DNA or other biopolymers or molecules, concentration of a sample, separation of cell types such as sperm from epithelial cells, concentration of DNA using an Aurora system (Boreal Genomics) or bead processing or other concentration methods, or other manipulations of the sample. A sample can be carried in a carrier, such as a swab, a wipe, a sponge, a scraper, a piece punched out a material, a material on which a target analyte is splattered, a food sample, a liquid in which an analyte is dissolved, such as water, soda. A sample can be a direct biological sample such as a liquid such as blood, semen, saliva; or a solid such a solid tissue sample, flesh or bone.

The invention can also be applied to process and analyze a sample that has been previously preprocessed, for example, by extraction of DNA from large object such as a bed sheet or chair and other processing which may include quantification of DNA concentration, cell concentration, or other manipulations before input of the pre-processed sample into the sample cartridge.

The term "module" refers herein to a device or component as part of a larger device, instrument or system.

The terms "cassette" and "cartridge" are used interchangeably herein unless expressly indicated otherwise.

Whenever the term "sample cartridge" is used, the term refers to a sample cartridge or a control cartridge unless it is clear from the context that the term refers only to a sample cartridge. A "control cartridge" is a sample cartridge that comprises, or is pre-loaded with, an allelic ladder, a negative control or a positive control, or any combination thereof.

Reference will now be made to the figures, wherein like numerals refer to like parts throughout. It will be appreciated that the figures are not necessarily drawn to scale.

I. Introduction

FIG. 1 shows a system 100 for sample processing and analysis. The system comprises a display 101 having a graphical user interface (GUI) for enabling a user to, for example, initiate sample processing, and view the progress of sample processing and analysis or the results of an analysis. The system 100 includes a first port 102 for accepting and securing a sample cartridge 103 and a second port 104 for accepting and securing a second cartridge that can be a control cartridge 105. The first port 102 and second port 104 are configured to release the sample cartridges 103 and 104 following sample processing. The first port 102 and second port 104 are cartridge bays for mating with sample and/or control cartridges. As will be discussed in further detail below, various reagents for sample processing are included in the cartridges 103 and 105. The system 100 is used for sample preparation, processing and analysis.

Figure 2:
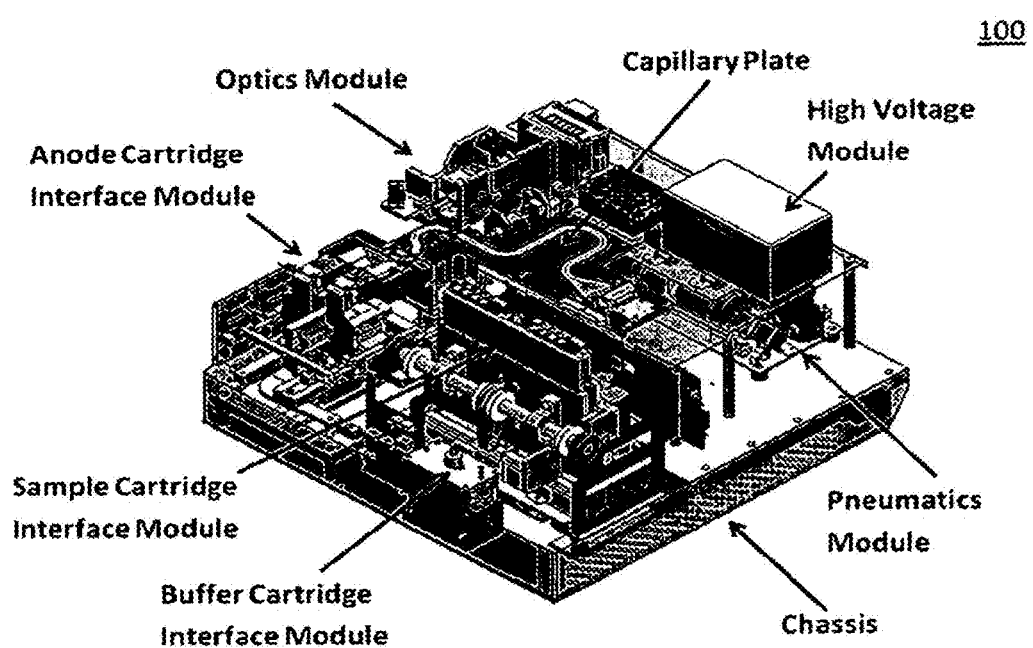
FIG. 2 shows an embodiment of the system of FIG. 1.

FIG. 2 shows the system 100 of FIG. 1 in further detail. The system 100 includes a sample cartridge interface module for holding the cartridges 103 and 105. A buffer cartridge interface module enables a user to provide a buffer for use by the system 100. The system 100 includes a chassis for structural support, which may be formed of a metallic material (such as aluminum or steel) or a polymeric material. The chassis may be structured so as to minimize the weight of the system 100. A pneumatics module provides air (or other gas) to operate the valves (e.g., MOVe) valves included in the cartridges 103 and 105. A power supply provides power to the system, including a controller of the system (e.g., central processing unit, CPU), system memory, cache, hard disks, and other electronic components of the system 100. A high voltage module can provide stepped up voltage to the electrophoresis system for separation of analytes. The system also includes a capillary plate, an optics module and anode cartridge interface module.

The system 100 can include a communications bus for enabling various modules of the system 100 to communicate with a controller of the system 100. The communications bus can be in electrical communication with the high voltage module, thereby enabling power to be provided to the various modules of the system.

The system of FIGS. 1 and 2 can be used in forensics analysis to determine a genetic profile of an organism. In some situations, the system 100 processes a biological sample from a subject in 20 steps or less, 15 steps or less, or 10 steps or less. In certain embodiments the steps are selected from cell lysis, DNA capture, DNA purification; DNA amplification; amplicon/analyte dilution; amplicon/analyte injection; amplicon/analyte separation; amplicon/analyte detection; and analysis of detected products. In some embodiments, the system 100 can determine the genetic profile of a subject in 3 hours, 2 hours, 1.5 hours, 1 hour, or less. Forensics analysis can include short tandem repeat (STR) analysis or restriction fragment length polymorphism (RFLP) analysis. In such a case, STR analysis may be performed within a time period of 3 hours, 2 hours, 1.5 hours, 1 hour, or less.

In some embodiments, the system 100 of FIGS. 1 and 2 is used for automated forensics. The system 100 can be used to determine a genetic profile of a subject in no more than any of 20 steps, 15 steps, 10 steps, using a fully integrated sample processing system having a volume of no more than any of 20 ft$^3$, 16 ft$^3$, 15 ft$^3$, 10 ft$^3$, 5 ft$^3$.

In some embodiments, the system is a complete sample-to-answer system, in some cases requiring coupling steps together to match volumes and concentrations. An integrated system can be configured to receive a sample comprising nucleic acid, e.g., a biological sample, and produce a genetic profile of the nucleic acid, e.g., an allelic analysis or an STR analysis, in the form of a computer file, e.g., a CODIS compatible file. It can also use the profile in the performance of kinship analysis. Kinship analysis involves comparing the genetic profiles (e.g., STR profiles) of two or more persons and estimating the likelihood of a familial relationship between the people, e.g., whether two people are parent and child, siblings, cousins, second cousins, grandparent and grandchild, uncle/aunt or niece/nephew.

The invention provides systems and methods for sample processing and/or analysis, including sample preparation. Such systems can process a sample for analysis by the system or another device. Some embodiments provide systems that facilitate sample processing with the aid of removable cassettes having reagents for sample processing and/or analysis, such as, for example, beads and nucleic acid amplification reagents. In some embodiments the system is a sample-to-answer system that receives a sample containing an analyte and reports a metric or characteristic of the analyte. The analyte can be, for example, a biological molecule such as a nucleic acid (e.g., DNA or RNA), a protein or a polysaccharide. The metric reported can be an amount of the analyte in the sample (including presence or absence or the analyte). The characteristic reported can be, for example, the identity of the analyte, the chemical composition of the analyte, the form or makeup of the analyte (e.g., the presence, form, size or identity of an allele at a locus (e.g., a genetic locus)).

An aspect of the invention provides a system for sample processing and/or analysis. The system can be configured for amplification, such as polymerase chain reaction (PCR) amplification or proteomics, which may be used for forensics analysis, animal (e.g., human) identification or kinship analysis. In some cases, the system is integrated and fully automated. In some cases, the system can process a sample for forensics analysis with little to no user involvement. In some embodiments, the system comprises subsystems configured to perform the following functions: nucleic acid (e.g., DNA) isolation from a sample (e.g., a sample containing a mixture of biological molecules); optional purification of the nucleic acid; amplification of selected nucleotide sequences within the isolated nucleic acid (e.g., sequences from one or more genetic loci, each locus containing one or more allelic forms in a species) to produce amplification products; optional purification of the selected amplified nucleotide sequences; optional reduction of the salt concentration of the amplicon solution (e.g., by dilution or removal of salts), and/or optional mixing of the amplification products with a fragment size standard; separation and detection of the amplification products (e.g., production of an electropherogram) and analysis of the detected amplification products electropherogram (e.g., identification of alleles at each locus (e.g., genetic locus)).

In some embodiments, a system for sample processing implements a macro-to-micro downscaling of sample volume during sample processing. In some cases, such a system implements a macro-to-micro and subsequently a micro-to-macro change in sample volume. Systems provided herein can decrease, e.g., minimize, if not eliminate, contamination during processing, providing improved reliability, performance, and coefficient of variation. This advantageously enables reliability in sample processing and analysis from one system to another. Furthermore, macro-to-micro downscaling of fluid volume by devices provided herein can reduce the amount of material (e.g., sample and reagents) needed for sample processing and/or analysis, and can reduce the size of the devices.

II. Analyte Preparation Module

Figure 48:
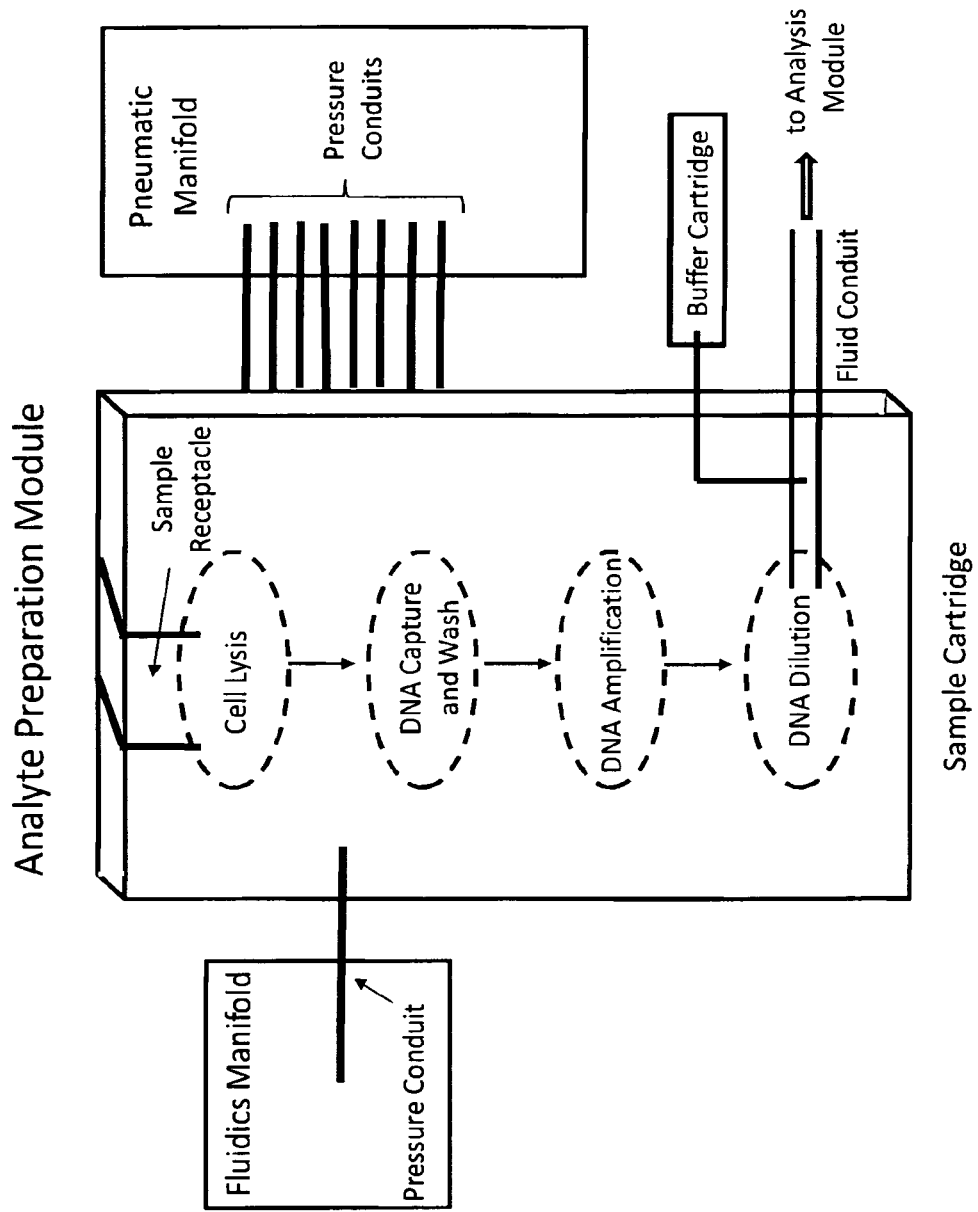
FIG. 48 shows a schematic of an analyte preparation module useful in the systems of this invention.

FIG. 48 shows an embodiment of an analyte preparation module of this invention. An analyte preparation module can comprise a sample cartridge module that receives a sample cartridge and is configured to move fluids within the cartridge. The sample cartridge comprises a sample receptacle to receive a sample and areas to perform functions such as cell lysis, DNA capture and wash, DNA amplification and DNA dilution. A fluidics manifold connected to a source of pressure can deliver pressure, e.g., air pressure, into the cartridge to move liquids within the sample cartridge. A reagent cartridge connected to a source of pressure can move reagents, such as buffer and/or water into the sample cartridge. Sample and buffer can be moved out of the cartridge through a fluid conduit to an analysis assembly. In one embodiment, the sample cartridge comprises a fluidic chip that comprises a fluidics layer comprising fluidic channels, an actuation layer comprising actuation channels and an elastomer layer sandwiched between them. The chip can include valves and pumps actuated by the actuation layer. In such an embodiment, the sample cartridge module can include a pneumatic manifold connected to a source of pressure that transmits pressure to the cartridge pneumatics when the manifold engages the cartridge. This pneumatic pressure can operate pumps and valves in the cartridge to move fluids around the cartridge and out of the cartridge.

A. Sample Cartridge

This invention provides a cassette that can be pre-loaded with reagents for performing one or a series of chemical or biochemical reactions. The cassette includes a container (see, e.g., FIG. 8) having closed compartments that can contain the reagents and that are, initially, fluidically separated from each other. Accordingly, the cassette is configured to prevent leakage of the reagents from the cassette, or of mixture of the reagents until desired. Such a configuration is useful for shipping or otherwise transporting reagents in isolation. The compartments in the container can have friable seals that can be punctured to provide access to the compartment and its contents. The cassette further includes a fluidic device having fluidic passages or channels. The fluidic device can be a microfluidic device containing microfluidic passages or channels. The fluidic device also can have puncturing elements adapted to puncture the friable seals of the container. The puncturing element itself can have an opening that is in fluidic communication with a fluidic channel in the fluidic device. The cassette is configured so that the fluidic device is engageable with the container. Engagement can be accomplished, for example, by pressing the container upon the fluidic device. Upon engagement, puncturing elements puncture the friable seals and put punctured compartments in fluidic communication with fluidic passages in the fluidic device.

In certain arrangements two previously isolated compartments are put in fluidic communication with each other through a common fluidic channel. In other arrangements, two fluidic channels are put in fluidic communication with a single compartment, for example, by puncturing the seal of a single compartment in two different places. For example, the device can be configured such that engagement, (1) creates a flow path between two compartments through a fluidic channel (e.g., a segment of a channel) on the fluidic device; and/or (2) creates a flow path between two fluidic channels (e.g., channel segments) on the fluidic device through a single compartment. In certain embodiments, the flow path between two compartments through a channel or between two channels through a compartment does not include a branch in the flow path. In other arrangements, a port leading out of the fluidic device that is in fluidic communication with a fluidic channel is put in fluidic communication with a compartment through the fluidic channel. The channels can include controllable valves. Such valves can be used to route the passage of fluids in the channels, e.g., between a first pathway and a second pathway. Fluid can be moved through the device by on-device pumps, such as diaphragm pumps. Alternatively, fluidic channels opening at ports can be connected to an outside source of pressure, e.g., pneumatic pressure, used to move fluids, especially bulk fluid volumes, through the device. The fluidic channels opening at ports can be connected to outside sources of reagents if desired. Accordingly, in certain arrangements, engagement of the fluidic device with the container creates fluidic paths that connect compartments in the container with each other and with ports leading off the cassette through fluidic paths in the fluidic device. The cassette also can comprise chambers which, when the cassette is engaged by a receiving element of a control instrument, becomes in thermal contact with a thermal control element. For example, the thermal control element can perform thermal cycling with heating and cooling. A pressure sensor can be used to indicate whether a port (e.g., a fluidic port or a pneumatic port) is blocked or has a leak and to identify the location of a blocked or leaking port.

In some cases, the plurality of closed and fluidically isolated chambers can be microfluidic chambers. Such chambers are configured to hold fluid volumes from microliters to nanoliters or lower. In other cases, the plurality of closed and fluidically isolated chambers are macrofluidic chambers, which are configured to hold fluid volumes on the order of at least one microliter or more.

An aspect of the invention provides cartridges (or cassettes) for sample processing, including sample preparation. Cartridges of the invention can be used with sample processing and/or analysis systems, such as the system 100 of FIG. 1. In some embodiments, a cartridge for processing a sample comprises a container (e.g., a reagent pack) comprising a plurality of closed and fluidically isolated chambers. The cartridge can be similar or identical to the cartridge of FIG. 4. Each of the plurality of chambers comprises a friable seal. In some cases, the cartridge further includes a microfluidic device comprising a plurality of puncturing elements and a microfluidic channel in fluid communication with one or more ports. Multiple puncturing elements are disposed opposite each of the plurality of chambers. Engaging the microfluidic device with the container punctures the friable seal of each of the plurality of chambers and creates a fluid flow path between each of the fluidically isolated chambers and the microfluidic channel. In some embodiments, engaging the microfluidic device with the container fluidically connects two isolated chambers. In some cases, this permits fluid flow from one chamber to another.

In some embodiments, 1, or 2, or 3, or 4, or 5, or 6, or 7, or 8, or 9, or 10, or more puncturing elements are disposed adjacent to each of the plurality of chambers of the container. At least some of the plurality of chambers can be prefilled with a reagent, such as a wash solution or buffer (see below). In an example, two puncturing elements are disposed adjacent to a chamber. In another example, three puncturing elements are disposed adjacent to a chamber. In another example, two puncturing elements are disposed adjacent to a first chamber and three puncturing elements are disposed adjacent to a second chamber.

The plurality of puncturing elements can include openings (or ports) that are in fluid communication with the microfluidic channel. Alternatively, the openings can be disposed adjacent to the puncturing elements. The openings may have various geometric shapes and sizes. In some cases, the openings are circular, triangular, square, rectangular, pentagonal, hexagonal, or have other polygonal cross-sections or partial cross-sections (e.g., semicircular).

During processing, the flow of a fluid having a sample from a sample chamber to the microfluidic channel can effect a macro-to-microscale downscaling of fluid volume, and the flow of the fluid from the microfluidic channel to a chamber of the container preloaded with a liquid can effect a micro-to-macroscale upscaling of fluid volume.

In some embodiments, a cassette for processing a biological sample comprises a microfluidic device comprising a microfluidic channel in fluid communication with one or more ports. The micro fluidic device includes a plurality of puncturing elements. The cassette further comprises a container disposed over adjacent to microfluidic device. The container has a plurality of sealed chambers. Each of the plurality of sealed chambers comprises a friable seal. The container can be attached to the microfluidic device with the aid of a layer of deformable material or an adhesive material (e.g., a material that is adhesive on both sides). Engaging the microfluidic device with the container punctures the friable seal of each of the plurality of sealed chambers and creates a fluid flow path between each of the sealed chambers and the microfluidic channel. In certain embodiments, puncture of the friable seal creates a flow path from a first channel segment in the microfluidic device, into the chamber, out of the chamber and into a second channel segment in the microfluidic device. In another embodiment, puncture of the friable seal creates a flow path from a port in the microfluidic device, through a first channel segment and into the chamber. In another embodiment, puncture of the friable seal creates a flow path from a first port in the microfluidic device, through a first channel segment, into the chamber, out of the chamber, into a second channel segment and out a second port in the microfluidic device.

In some embodiments, one or more, or all, of the chambers in the container of a sample cartridge comprise two or more openings (or apertures or ports) at the bottom of the chambers. In further embodiments, a compressible gasket made of a suitable material (e.g., a polymeric material, such as a natural or synthetic rubber or a hydrophobic polymeric material as described herein) is disposed underneath each of the openings at the bottom of chambers in the container, and/or a compressible gasket is disposed on the fluidic (e.g., microfluidic) device and is aligned with each opening at the bottom of chambers in the container or with each gasket underneath the openings of chambers. Engagement of the fluidic device with the container by pressing them together punctures the friable seal of each of the plurality of sealed chambers in the container and brings the chambers into fluidic communication with one another and with sample chambers and reaction chambers of the cartridge via fluidic (e.g., microfluidic) channels in the fluidic device. The compressible gasket underneath the openings of chambers in the container and/or the compressible gasket on the fluidic device are configured to prevent leakage of fluid from the chambers when the gaskets are compressed upon the engagement of the fluidic device with the container.

In some cases, the friable seal is formed of a metallic material, such as aluminum. In other cases, the friable seal is formed of a polymeric material.

Figure 4:
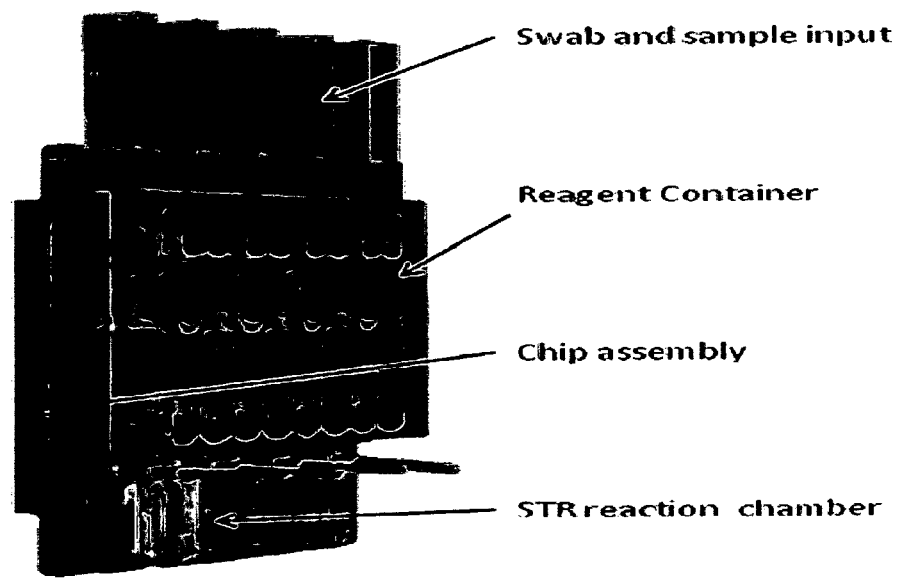
FIG. 4 shows a cartridge, in accordance with an embodiment of the invention.

FIG. 4 shows a cartridge for use with the system 100. In some embodiments, the cartridge is configured to perform all or substantially all sample processing, including fluidic sample preparation operations. The cartridge includes a swab and sample input port, a reagent container, a chip assembly with various microfluidic channels, valves and ports, and a reaction chamber. The cartridge is configured for insertion into the sample cartridge interface module either vertically or angled in relation to a horizontal plane having the system 100. For example, the system 100 can receive the cartridge at an angle of about 10°, 20°, 30°, 40°, 50°, 60°, 70°, 80°, or less than 90° in relation to the horizontal plane.

Figure 31:
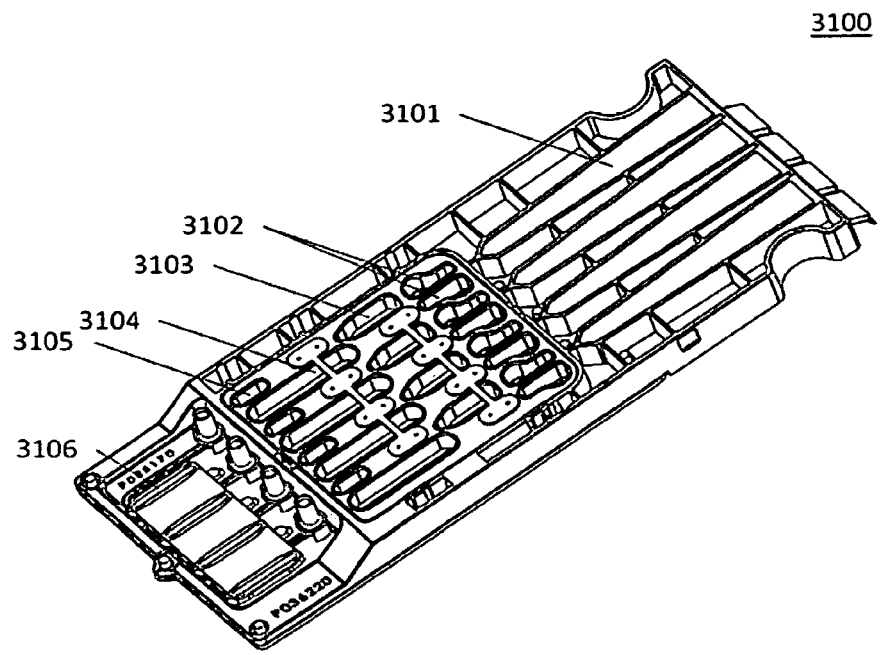
FIG. 31 shows an embodiment of an integrated cartridge.
Figure 32:
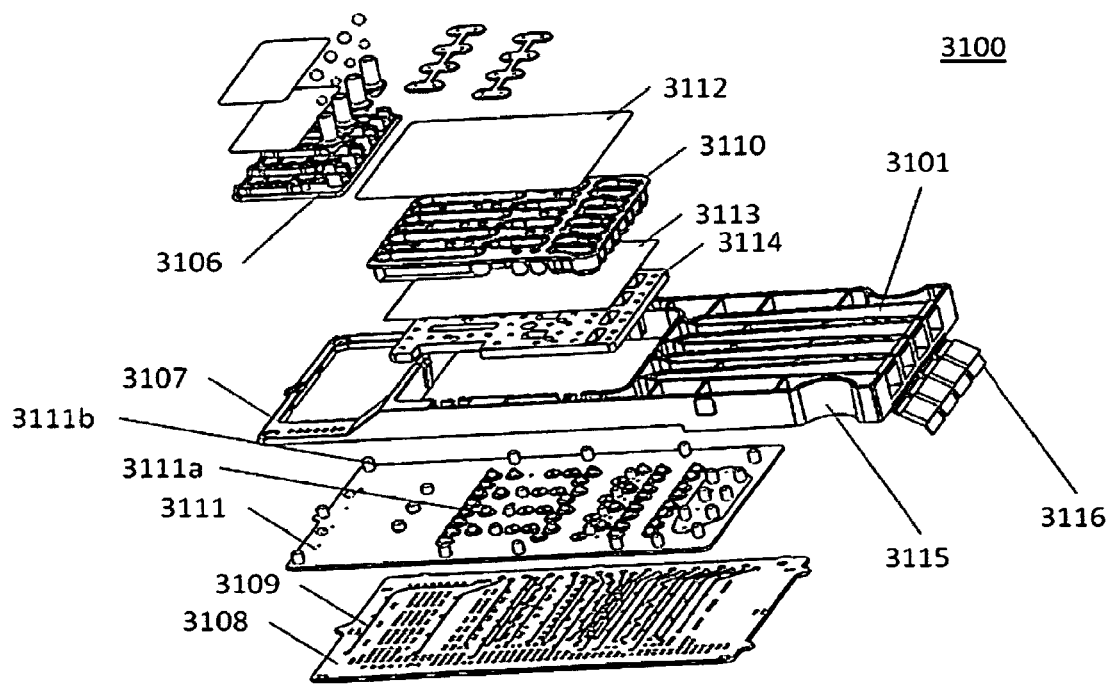
FIG. 32 is an exploded view of an embodiment of the cartridge of FIG. 31.

In an embodiment, shown, for example, in FIG. 31 and FIG. 32, a sample cartridge comprises a) a fluidic device comprising one or a plurality of fluidic channels (e.g., a microfluidic cannels) arranged substantially in a first plane; b) a sample container comprising one or plurality of sample receptacles, each receptacle having an elongate shape defined by an axis in a long dimension of the shape (e.g., an axis along which a swab can be inserted), wherein each elongate axis is arranged substantially in a second plane; and, optionally, c) a reagent container comprising one or a plurality of reagent chambers, each reagent chamber having an elongate shape defined by an axis in a long dimension of the shape (e.g., chamber 3104) wherein each elongate axis is arranged substantially in a third plane; and d) a reaction container comprising one or a plurality of reaction chambers, each reaction chamber having an elongate shape defined by an axis in a long dimension of the shape, wherein each elongate axis is arranged substantially in a fourth plane (e.g., 3106). The fluidic channels, the sample receptacles, the reagent chambers and the reaction chambers are fluidically connected to one another; and the first, second, third and fourth planes are substantially parallel to each other. In an embodiment, a sample cartridge comprises a) a fluidic device comprising one or a plurality of fluidic channels arranged substantially in a first plane; and b) a sample container comprising one or a plurality of sample receptacles, wherein the fluidic channels and the sample receptacles are fluidically connected to one another. The sample cartridge is configured to be loaded with a sample into sample receptacles and move analyte from the sample into the fluidic channels when the sample cartridge is engaged with a cartridge module configured to receive the sample cartridge, and the first plane is oriented at least 10°, at least 20°, at least 30°, at least 40°, at least 50°, at least 60°, at least 70°, at least 80°, or at least 90° off horizontal. (See, e.g., FIG. 1 or FIG. 39.)

Figure 8:
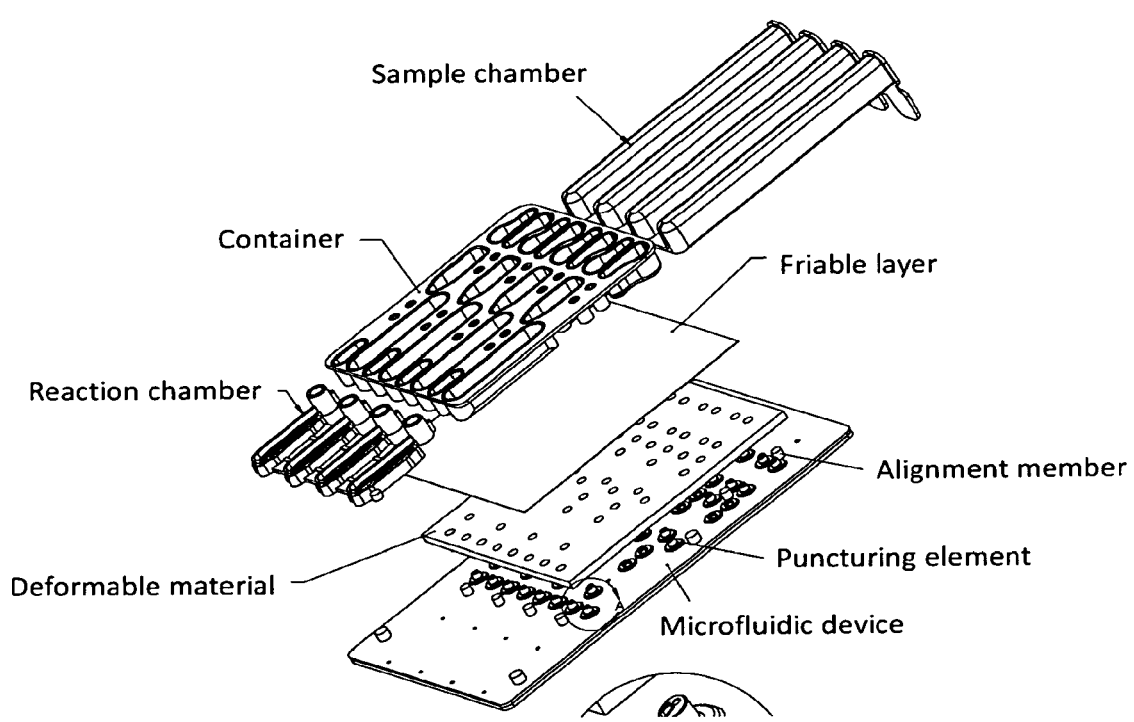
FIG. 8 shows an embodiment of a cassette for use with systems provided herein.

FIG. 8 is an exploded view of a cartridge for use with sample preparation and processing, in accordance with an embodiment of the invention. The cartridge includes a container having a plurality of chambers for holding one or more reagents, and a microfluidic device having microfluidic channels. The chambers are also for use during sample preparation and processing. Each of the chambers is sealed with the aid of a friable seal, which may be formed of a polymeric material or a metallic material. The cartridge includes a deformable layer (e.g., layer of deformable material) with holes (or openings) that are aligned with various puncturing elements (see FIG. 9) and alignment members of the microfluidic device configured to be disposed adjacent to the container. In some situations, two or more of the plurality of puncturing elements are disposed opposite each of the plurality of closed and fluidically isolated chambers. A sample chamber is configured to be mounted adjacent to the microfluidic device and the container, in the general orientation shown in the figure.

The cartridge can include a single friable seal adjacent to each chamber, or a plurality of friable seals. For instance, each individual chamber of the container can be sealed with a separate friable seal.

In some embodiments, to obviate potential contamination (e.g., run-to-run contamination or cross-lane contamination) by a contaminant (e.g., a DNA contaminant, such as a potentially amplifiable allelic ladder or size standard), a conformable or spongy material impregnated with a cleaning solution is placed under the container of FIG. 8. The conformable or spongy material can be the deformable material of FIG. 8, a material used in place of the deformable material, or a material adjacent to (e.g., above) the deformable material. Contact of a contaminant (e.g., a DNA contaminant) with the conformable or spongy material impregnated with the cleaning solution can degrade the contaminant. The cleaning solution can contain a decontaminating agent (e.g., bleach).

As described below, the sample cartridge interface module (cartridge module) includes a clamping system, such as, e.g., a cam driven clamping system for engaging the microfluidic device (or layer) of the cartridge with the container. In some situations, the cam applies a predetermined pressure against the cartridge, which presses the container of the cartridge against the microfluidic device of the cartridge. In some cases, the applied pressure can be constant or gradually increased.

The microfluidic channel can include one or more selectably closable channels. The selectably closable channels can be opened and closed with the aid of valves, such as diaphragm valves (or pumps). The microfluidic channel can be in fluid communication with one or more diaphragm valves, such as 1, 2, 3, 4, 5, 6, 7, 8, 9, 10 or more valves. A diaphragm valve can include a layer of a pressure-deformable material (e.g., elastomeric material) that is configured to rest against a valve seat, thereby regulating fluid flow. The one or more valves can be pneumatically-actuated valves, such as actuated with the aid of positive pressure or negative pressure (vacuum). In some cases, the one or more valves are piezoelectric valves, which are configured to open or close upon the application of an electrical potential to a piezoelectric material.

Figure 42:
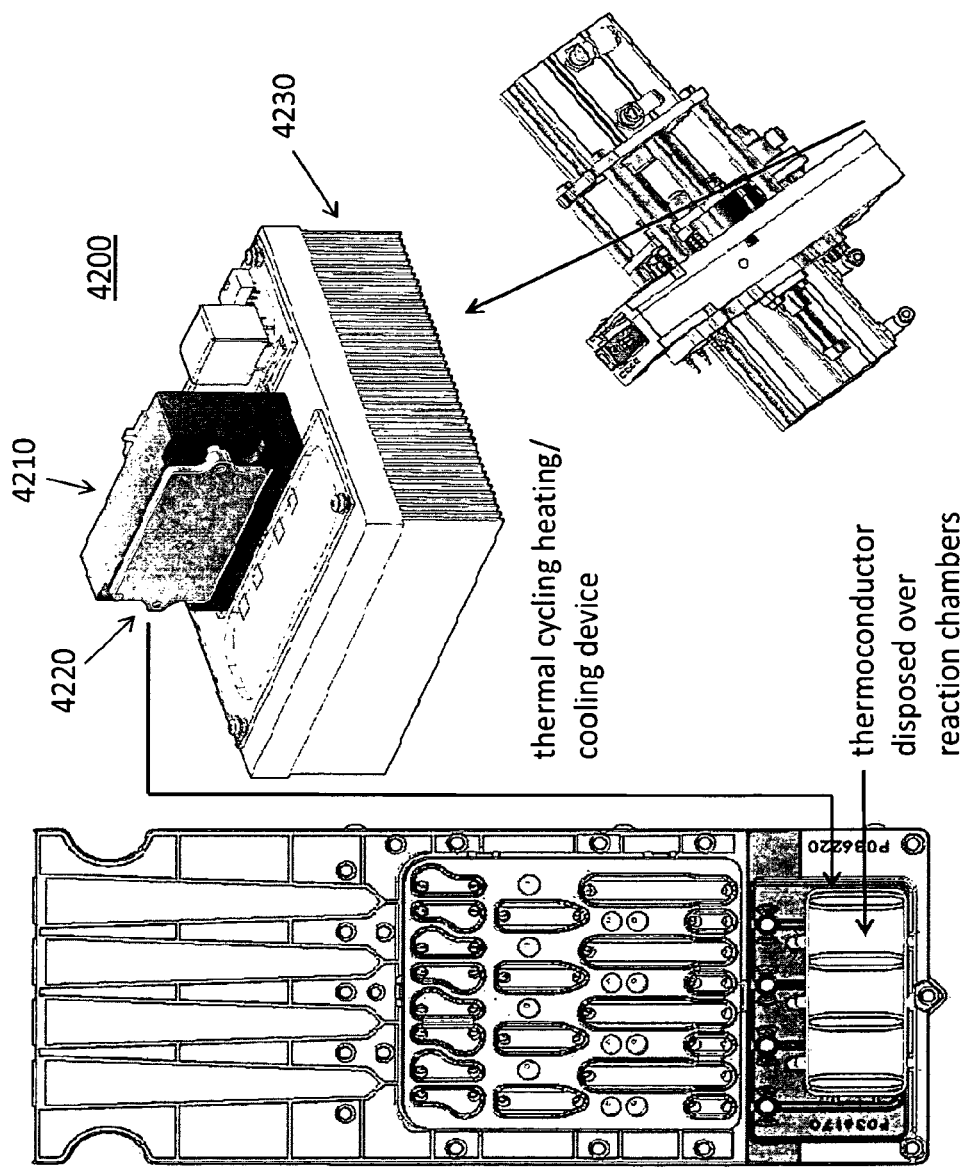
FIG. 42 shows an embodiment of a thermocycler assembly including four reaction chambers in a sample or control cartridge, a thermal conductor (or thermoconductor) disposed over the reaction chambers, and a thermal cycling heating and cooling device (including, e.g., a Peltier heating and cooling device).

In an embodiment, a cartridge comprises a frame that is attached on one side to a microfluidic chip that has a port leading to sample chambers (e.g., sample receptacles). The sample chambers are each adapted to accept a sample from a sample holder (e.g., cotton swab, punch or liquid). The cartridge also includes a hole (e.g., a slot, a receptacle, a receiving element, a compartment) adapted to accept a container having a plurality of chambers preloaded with reagents for sample processing. The cartridge includes a slot or receiving element that accepts part or all of a thermocycler assembly, e.g., a plurality of reaction chambers (thermocycling chambers) configured to perform amplification (e.g., by PCR) with thermal cycling and a plurality of reagent (premix) chambers for providing amplification reagents (e.g., an amplification premix) to the reaction chambers. Thermocycling chambers are in fluid communication with microfluidic channels in the microfluidic chip, which microfluidic channels are in communication with chambers of the container. In some cases, the thermocycling chambers are raised in relation to the microfluidic device and have openings that are in contact with or adjacent to a heat spreader (or thermoconductor that can spread/distribute heat and cooling), which in turn is in contact with or adjacent to a temperature control element (e.g., a heating element and/or a cooling element, such as a Peltier heating and cooling device) that is configured to perform thermal cycling. In certain embodiments, the temperature control element (e.g., a heating and cooling element, such as a Peltier heating and cooling device) is configured to move to come into contact with or become adjacent to the heat spreader or the reaction chambers. FIG. 42 illustrates an embodiment of a thermal cycling heating and cooling device that contacts the thermoconductor disposed over the reaction chambers when the cartridge is engaged with the cartridge module.

In some embodiments, the cartridge further comprises a sample receptacle that has a sample chamber adapted to receive a sample. The sample chamber has an opening that can be parallel to a surface of the microfluidic device disposed between the microfluidic device and the container. Such a configuration can advantageously permit a user to insert a tissue sample (e.g., cotton swab) using various tools and apparatuses for collecting the tissue sample, such as a Q-tip or a ball of cotton of various shapes and sizes, or to introduce a liquid sample (e.g., blood, semen, or a pre-processed or extracted sample such as a lysate or homogenate). The alignment of the opening permits the cartridge to be inserted into a system (e.g., the system 100 of FIG. 1) in a configuration that is vertical or angled with respect to a plane having the system.

A sample cartridge can comprise one or a plurality of lanes, each lane configured to process a sample or a control. Lanes can comprise a fluidic circuit that comprises channels, compartments and fluid control elements such as valves and pumps. Lanes in a sample cartridge can be fluidically isolated from one another, e.g., fluid from one lane cannot cross into another lane.

In some cases, the sample receptacle is unitary (or single-piece) with the microfluidic device. Such construction can help minimize processing cost, as the sample receptacle and microfluidic device may be formed during one or more overlapping processing steps.

The microfluidic channel can comprise a sample channel in fluid communication with the sample chamber. When the container has engaged the microfluidic device, the container covers all or a portion (e.g., a substantial portion) of the sample channel.

The microfluidic device can comprise a reagent channel in fluid communication with a reagent chamber of the plurality of closed and fluidically isolated chambers. When the container has engaged the microfluidic device, the container covers all or a portion (e.g., a substantial portion) of the reagent channel.

In some embodiments, the plurality of closed and fluidically isolated chambers comprise a first chamber holding a diluent, a second chamber holding one or more lysis reagents, a third chamber having capture particles, and a fourth and/or fifth chamber having a wash solution. The second chamber is in fluid communication with the sample chamber. In some cases, the second chamber is a waste chamber configured to hold a waste material.

In some embodiments, the cartridge comprises a layer of deformable material between the container and the microfluidic device. In some situations, the layer of deformable material is formed of closed foam, such as ethylene propylene diene monomer (EPDM), an open foam, such as ethylene vinyl acetate (EVA), or other polymeric material, such as silicone. The layer of deformable material may have a thickness between about 0.5 mm and 20 mm, or 1 mm and 5 mm. In an implementation, the layer of deformable material has a thickness of about 3 mm. The layer of deformable material can be compressed to a thickness between about 10 micrometers ("microns") and 1000 microns, or 100 microns and 800 microns, or 300 microns and 600 microns. The container can be attached to the microfluidic device with the aid of the layer of deformable material. In some situations, the layer of deformable material has a first sticky side and a second sticky side opposite from the first sticky side. The first sticky side is adjacent to the microfluidic device and the second sticky side is adjacent to the container. In some cases, the layer of deformable material is formed of a compressible material. In other cases, the layer of deformable material is formed of a heat pliable material. In an example, the layer of deformable material comprises springs or a polymeric material that is configured to compress upon the application of pressure to the layer of deformable material.

The microfluidic device includes pneumatically actuated valves. In some cases, a plurality of valves defines a pump. A pump can include at least 2, 3, 4, 5, 6, 7, 8, 9, 10, or more valves in a serial configuration.

Figure 55:
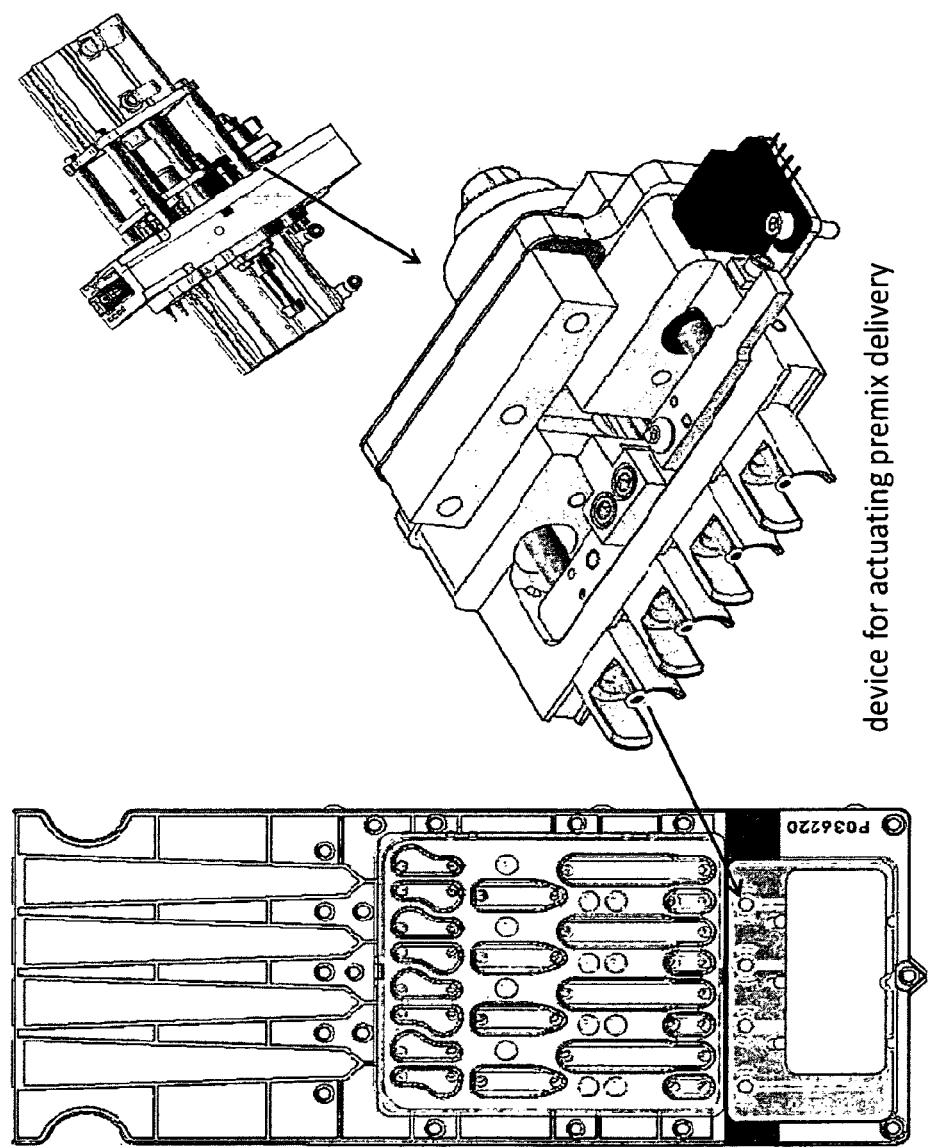
FIG. 55 illustrates an embodiment of a device configured to actuate delivery of amplification reagents from a premix vessel or chamber to a reaction chamber.

Referring to FIG. 8, the cartridge includes a thermocycler assembly for use in polymerase chain reaction (PCR). In the example, the thermocycler assembly of the cartridge includes four reaction chambers (thermocycling chambers) configured to perform nucleic acid amplification by PCR with thermal cycling, each thermocycling chamber in fluid communication with a channel of the microfluidic device. The thermocycler assembly further includes a plurality of reagent (premix) chambers for delivering a premix of amplification reagents to the thermocycling chambers. FIG. 55 illustrates an embodiment of a device configured to actuate delivery of amplification reagents from a premix chamber to a PCR reaction chamber. Such a device functions as a premix application member and can comprise, e.g., a plunger, a pin or a pneumatically actuated device for delivering positive pressure (e.g., pushing against a movable object (e.g., a plunger or ball) that forms the top seal of the premix chamber) to deliver the premix reagents for a reaction (e.g., PCR).

The device of FIG. 55 for actuating delivery of reagents for performing a reaction (e.g., PCR) can be configured to deliver reagents that are stored in a single chamber or container (e.g., vial) or in multiple (e.g., two) chambers or containers (e.g., vials). In some embodiments, for each reaction chamber the device comprises a single pin configured to apply pressure to (e.g., to push down on) a movable object (e.g., a ball or plunger) that seals the top of a single chamber or container (e.g., vial) that stores reagents for performing a reaction (e.g., PCR), such as the premix vial of FIG. 33. In other embodiments, for each reaction chamber the device comprises multiple (e.g., two) pins configured to apply pressure to (e.g., to push down on) a movable object (e.g., a ball or plunger) that seals the top of each of multiple (e.g., two) chambers or containers (e.g., vials) that store reagents for performing a reaction (e.g., PCR) in multiple (e.g., two) chambers or containers (e.g., vials), such as the two-chamber vials of FIGS. 57A and B and the two-vial embodiment of FIG. 59 which are configured to store, e.g., one or more primer oligonucleotides in one chamber or vial and a polymerase (e.g., a DNA polymerase), nucleotide triphosphates (e.g., deoxynucleotide triphosphates) and optionally other reagents (e.g., a buffer and magnesium chloride) in the other chamber or vial. The device for actuating delivery of reagents can provide a controlled rate of travel with sufficient force to operate one or more, or all, pins at a time, simultaneously or in any desired sequence (e.g., operate all pins simultaneously). In certain embodiments, the device comprises a linear stepper motor having a small pitch.

Figure 57A:
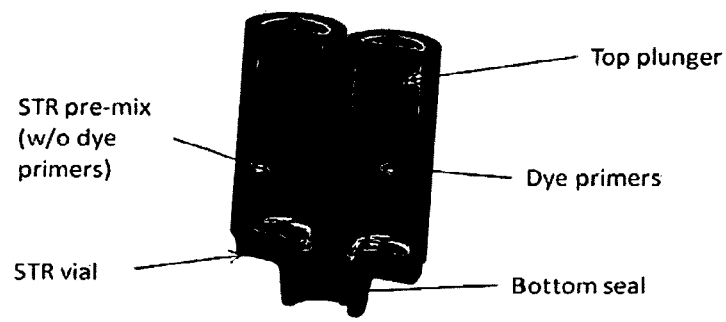
FIGS. 57A and 57B depict embodiments of a vial containing reagents for performing a reaction (e.g., PCR) in two separate chambers.

In some embodiments, the device for actuating delivery of reagents (e.g., PCR reagents) stored in multiple (e.g., two) chambers or containers (e.g., vials), such as the two-chamber vials of FIGS. 57A and B and the two-vial embodiment of FIG. 59, comprises a linear stepper motor, a small motor and a cam. Such a device can provide mixing of reagents delivered from multiple chambers or containers, e.g., by oscillating the flow of liquid content from one chamber or container relative to the flow of liquid content from the other chamber(s) or container(s), and/or by creating plugs in the flow to reduce the distance over which diffusion occurs. In certain embodiments, the actuating device comprises a rack substantially aligned with the axis of the stepper motor's motion, and a levered cam follower. As the stepper motor extends, the levered cam follower converts the perpendicular motion from following the rack to an additional motion in the direction of the motion of the stepper motor, thereby varying the flow of liquid contents released from multiple chambers or containers.

The thermocycling assembly can optionally include optical elements to allow interrogation of the thermocycling chambers to perform assays such as a real-time or quantitative PCR. The optical elements can include fiber optic delivery of a light source such as a laser or LED, and collection of fluorescent light for delivery to a detector such as a CCD, CMOS, photodetector, photo diode, or photomultiplier detector. The optical detection can be used to quantify the amount of DNA in the sample which can be further used to, for example, dilute the sample to known concentration of DNA, or to adjust the number of thermal cycles, or injection parameters.

In some embodiments, each chamber of the container is sealed from a top side by a sealing member, which may be transparent or opaque. A bottom side of the container, which is configured to rest adjacent to the microfluidic device, is sealed with the aid of the friable seal. The friable seal can form a hermetic (or airtight) seal between the container and the external environment.

Figure 9:
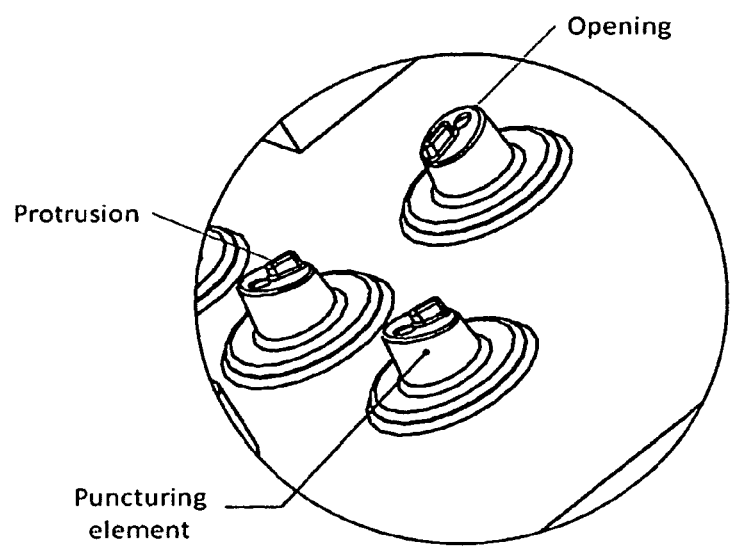
FIG. 9 shows an embodiment of puncturing elements.

FIG. 9 shows puncturing elements formed in the microfluidic device, in accordance with an embodiment of the invention. The puncturing elements are configured to form holes in the friable seal of the cartridge when the container is pressed against the microfluidic device. The puncturing elements include holes that are configured to bring the chambers of the container in fluidic communication with microfluidic channels in the microfluidic device, and various ports, including the sample chamber. This permits the flow of a fluid from the chambers of the container and the sample chamber through the microfluidic channels of the microfluidic device. The puncturing elements also include protrusions or raised ridges for facilitating the formation of holes in the friable seal.

Figure 10:
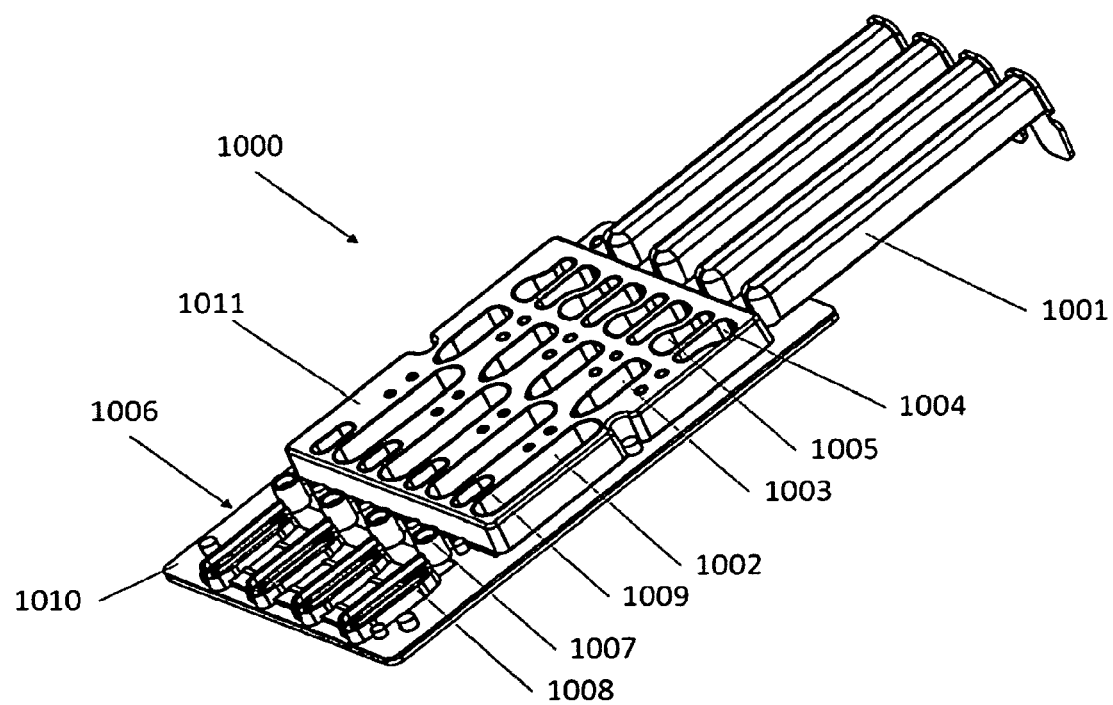
FIG. 10 shows an embodiment of an integrated cartridge.

FIG. 10 schematically illustrates the cartridge when the container and microfluidic device (including the intervening layers) have been engaged with one another, in accordance with an embodiment of the invention. The cartridge of FIG. 10 includes a plurality of separate or separable components, but in some embodiments one or more components of the cartridge can be single piece. For instance, the sample chamber can be formed in the microfluidic device.

Referring to FIG. 10, the cartridge 1000 includes a plurality of sample chambers 1001 and a container 1011 adjacent to a microfluidic device 1010 with microfluidic channels. The container 1011 includes four lysis reagent storage and waste chambers 1002, four bead suspension and capture chambers 1003, four pairs of first wash solution/buffer chamber 1004 and second wash solution/buffer chamber 1005, a thermocycler assembly 1006 having four pairs of premix chamber 1007 and reaction chamber 1008, and four diluent (or dilution) chambers 1009. The cartridge 1000 includes four pairs of premix chamber 1007 and reaction chamber 1008 in parallel (four pairs shown). Each of the chambers of the container 1011 is in fluid communication with a channel of the microfluidic device 1010 (see FIG. 15) of the cartridge 1000. In an embodiment, all of the sample chambers, wash chambers, bead suspension/capture chambers, lysis reagent/waste chambers, diluent chambers, and reaction chambers are substantially co-planar.

The container 1011 can be prefilled with the first wash solution or buffer, second wash solution or buffer, premix and beads. This advantageously provides for automated sample preparation, processing and analysis with minimal or no user intervention. The reagents can be those necessary to perform STR analysis. For example, the reagents can include Promega0 DNA IQ® and/or PowerPlex® reagents.

The cartridge 1000 includes four processing channels for parallel processing, such as processing samples in parallel (i.e., at the same time), or processing a sample and a control in parallel. A sample chamber 1001, microfluidic channel in the microfluidic device 1010 and a thermocycling chamber are comprised in a single processing channel or lane of the cartridge.

In some embodiments, the first and second wash solutions or buffers include water and a salt, such as sodium chloride. In other embodiments, the first wash solution and the second wash solution are aqueous solutions containing an alcohol, e.g., ethanol. The first wash solution and the second wash solution can contain any concentration of the alcohol in water (e.g., about 60% to about 95%, or about 70% to about 90%) suitable for purifying nucleic acid (e.g., DNA) captured to a substrate (e.g., magnetically responsive particles). In an embodiment, the first wash solution contains about 90% ethanol in water, and the second wash solution contains about 70% ethanol in water. In another embodiment, both the first wash solution and the second wash solution contain about 70% ethanol in water.

In some embodiments, the lysis reagent or buffer comprises a chemical or biochemical lysis reagent and a detergent/surfactant. Non-limiting examples of chemical lysis reagents that can be used for extraction of nucleic acid from cells include guanidinium salts (e.g., guanidinium thiocyanate and guanidinium hydrochloride) and urea. In certain embodiments, the detergent/surfactant comprises a zwitterionic detergent/surfactant and/or a non-ionic detergent/surfactant. Non-limiting examples of zwitterionic detergents/surfactants include 3-[(3-cholamidopropryl) dimethylammonio]-1-propanesulfonate (CHAPS), cocamidopropyl hydroxysultaine, and cocamidopropyl betaine. Non-limiting examples of non-ionic detergents/surfactants include polyoxyethylene glycol alkyl ethers (e.g., octaethylene glycol monododecyl ether and pentaethylene glycol monododecyl ether), polyoxypropylene glycol alkyl ethers, block copolymers of polyethylene glycol and polypropylene glycol (e.g., poloxamers (Pluronics®)), polyoxyethylene glycol octylphenol ethers (e.g., Tritons®, such as Triton® X-100 and Triton® X-114), polyoxyethylene glycol alkylphenol ethers (e.g., NP-40 and Nonoxynol-9), polyoxyethylene glycol sorbitan alkyl esters (e.g., Polysorbates/Tweens®, such as Polysorbate/Tween® 20), sorbitan alkyl esters (e.g., sorbitan monolaurate), glycerol alkyl esters (e.g., glyceryl laurate), and glucoside alkyl ethers (e.g., decyl glucoside, lauryl glucoside, and octyl glucoside). In certain embodiments, the lysis reagent or buffer comprises a guanidinium salt (e.g., guanidinium thiocyanate or guanidinium hydrochloride), a Triton® detergent/surfactant (e.g., Triton® X-100 or Triton® X-114), and CHAPS. In an embodiment, the lysis reagent or buffer includes about 50-70% guanidinium thiocyanate, less than about 2% polyethylene glycol tert-octylphenyl ether (Triton® X-114), less than about 2% 3-[(3-cholamidopropryl)dimethylammonio]-propanesulfonic acid (CHAPS), and about 44.2% water.

In further embodiments, the lysis reagent or buffer comprises a chemical or biochemical lysis reagent, a detergent/surfactant, and a buffering agent. In some embodiments, the buffering agent provides buffering in a basic pH range (e.g., about pH 8-11, about pH 8-10, about pH 10-11, about pH 9-10, or about pH 8-9). Non-limiting examples of buffering agents that provide buffering in a basic pH range include borate, N,N-bis(2-hydroxyethyl)glycine (bicine), N-tris(hydroxymethyl)methylglycine (tricine), tris(hydroxymethyl) methylamine (Tris), 3-amino-1-propanesulfonic acid, 4-(cyclohexylamino)-1-butanesulfonic acid (CABS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N-(2-hydroxyethyl)piperazine-N'-(3-propanesulfonic acid) (EPPS), and 3-{[tris(hydroxymethyOmethyl] amino}-propanesulfonic acid (TAPS).

In additional embodiments, the lysis reagent or buffer comprises: 1) a chemical or biochemical lysis reagent, a detergent/surfactant, and an anti-foaming agent (also called defoamer); or 2) a chemical or biochemical lysis reagent, a detergent/surfactant, a buffering agent, and an anti-foaming agent. Non-limiting examples of anti-foaming agents (defoamers) include water-based defoamers, silicone-based defoamers (e.g., defoamers containing a silicate or a siloxane (e.g., polydimethylsiloxane)), and EO/PO-based defoamers containing a copolymer of polyethylene glycol and polypropylene glycol.

If a sample is stored on a cellulosic substrate such as a piece of paper (e.g., FTA® paper), a lysis reagent or buffer suitable for extracting nucleic acid (e.g., DNA) from cells stored on the piece of paper can be utilized. A suitable lysis reagent or buffer includes without limitation GenSolve® (available from IntegenX Inc.), which can optionally contain one or more additional agents (e.g., an anti-foaming agent) for use in the system or instrument described herein.

Other reagents for use during processing may include an elution buffer having, for example, 10 mM Tris (pH 8.0), 0.1 mNI EDTA. DNA captured on beads may or may not be eluted off the beads as desired.

The diluent in the dilution chamber can be an aqueous solution. In some embodiments, the liquid of the diluent is water. The diluent can also comprise a control—e.g., 1) a size standard in a lane running a sample, 2) a size standard in a lane running a positive control, 3) a size standard in a lane running a negative control, and 4) both an allelic ladder and a size standard in a lane running neither a sample, a positive control nor a negative control.

Figure 11:
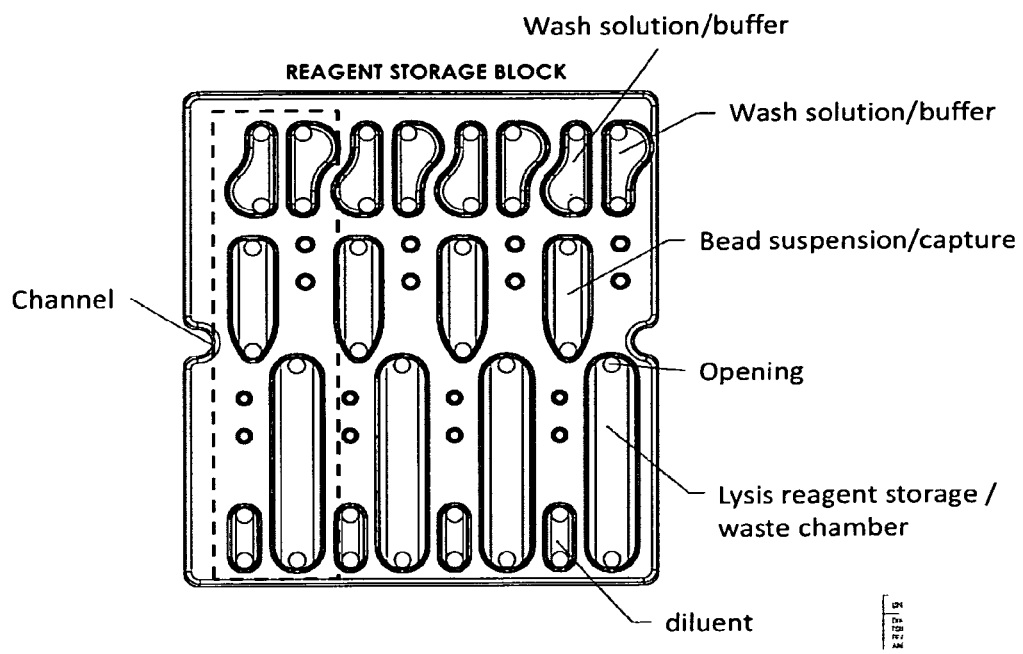
FIG. 11 shows an embodiment of a container having chambers for sample processing.

FIG. 11 is a schematic top view of the container showing various chambers, in accordance with an embodiment of the invention. The container includes wash solution/buffer chambers, a bead suspension and capture chamber, a lysis reagent storage chamber, and a diluent chamber. The lysis reagent storage chamber is used as a waste chamber during processing. The chambers define a single channel of the cartridge; the cartridge as illustrated has four channels for parallel processing of the sample or different samples. When the container is pressed against the microfluidic device, the puncturing elements form openings in the chambers. As illustrated, two openings are formed in each chamber. The openings permit fluid flow to and from the channels of the microfluidic device.

Figure 12:
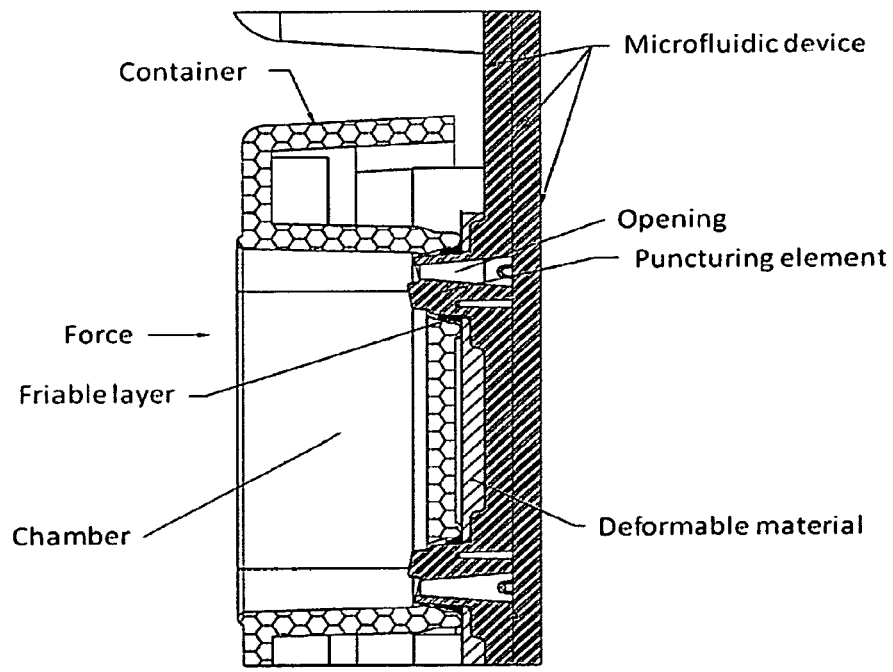
FIG. 12 is a schematic side view of an embodiment of a cartridge.

FIG. 12 is a schematic side view of an embodiment of the cartridge. The puncturing elements have pierced the friable layer (or seal) of the cartridge, bringing the openings of the puncturing elements and the micro fluidic channels of the microfluidic device in fluid communication with a chamber of the container.

Figure 13A:
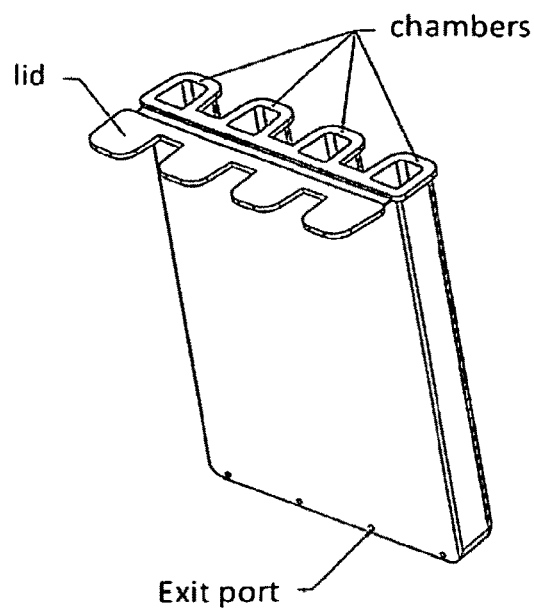
FIGS. 13A and 13B show an embodiment of a sample receptacle.
Figure 13B:
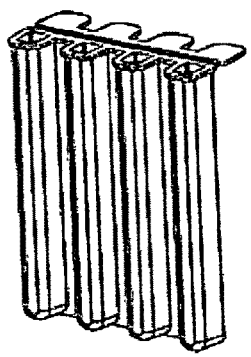

FIGS. 13A and 13A show the sample receptacle, in accordance with an embodiment of the invention. The sample receptacle includes a plurality of sample chambers, one chamber per channel of the cartridge. The sample chambers are configured to accept a sample, e.g., a cotton swab (such as with the aid of a Q-tip or ball of cotton) or analyte contained in another material (e.g., a punch or liquid). The sample receptacle can include a lid for sealing the sample chambers during processing.

Figure 14:
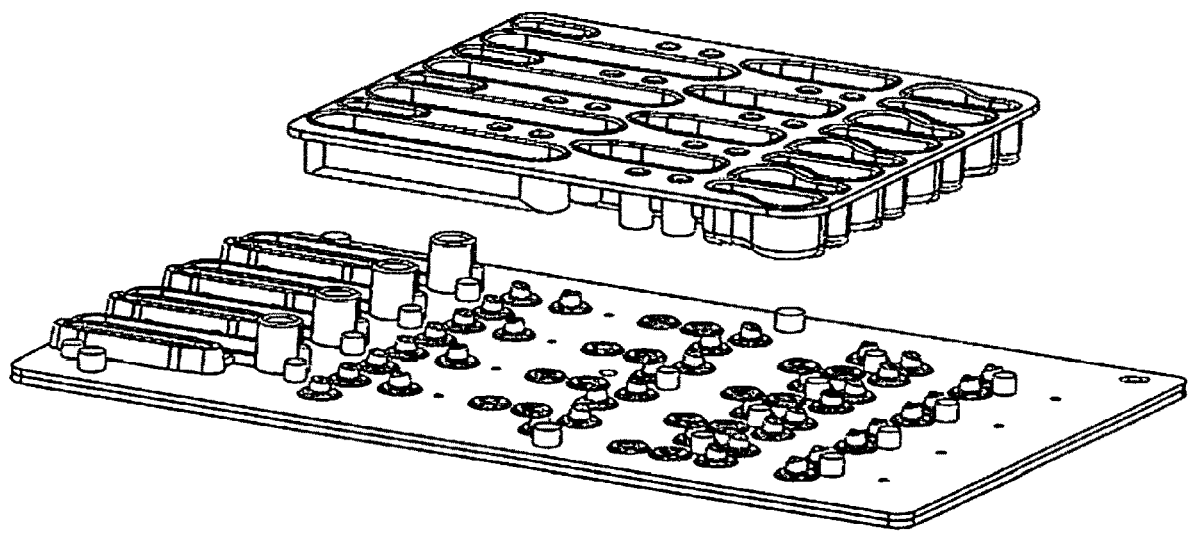
FIG. 14 shows an embodiment of a cartridge having a microfluidic device and a container.
Figure 15:
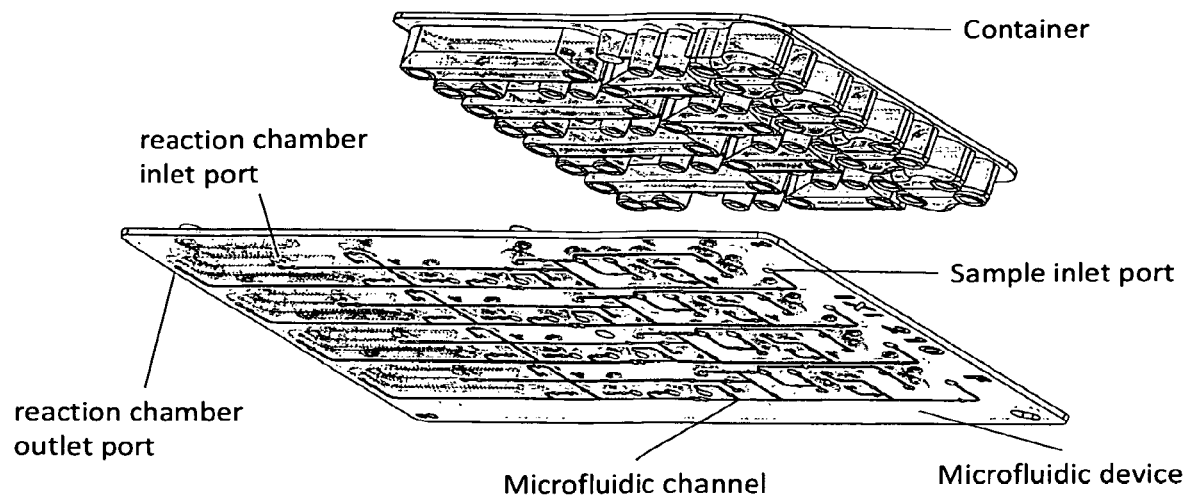
FIG. 15 is a bottom view of an embodiment of the microfluidic device and the container of FIG. 14.
Figure 16:
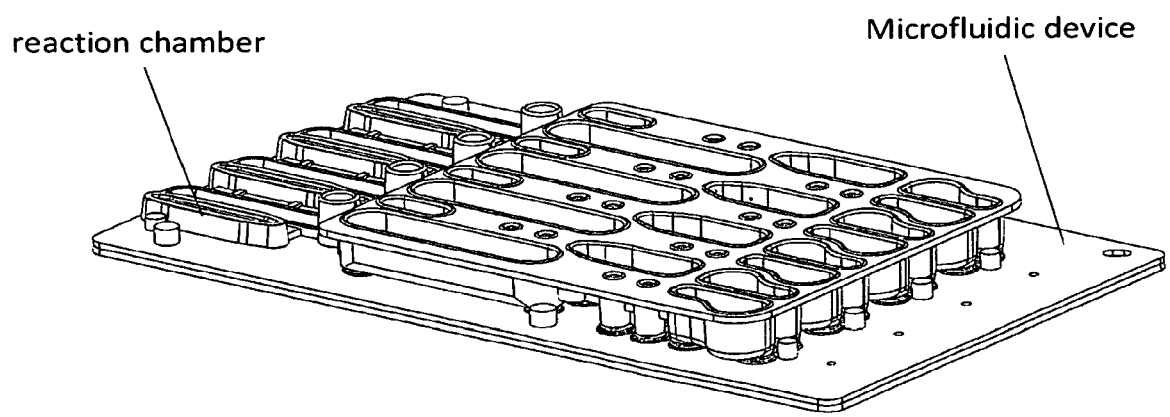
FIG. 16 is a schematic top view of the microfluidic device and the container of FIGS. 14 and 15, showing the container mounted on the microfluidic device, in accordance with an embodiment of the invention.

FIG. 14 shows the container and the microfluidic device, in accordance with an embodiment of the invention. A pair of puncturing elements are configured to bring channels in the microfluidic device in fluid communication with a chamber of the container. A bottom view of the cartridge is shown in FIG. 15. The microfluidic device has a microfluidic channel network per channel of the cartridge. The microfluidic device of FIG. 15 includes four reaction channels for parallel processing. A sample inlet port is configured to bring various chambers of the container in fluid communication with the sample chamber. A reaction chamber inlet port is configured to bring a microfluidic channel of the microfluidic device in fluid communication with a reaction chamber configured to perform nucleic acid amplification (e.g., by PCR) with thermal cycling (sometimes also referred to as a "thermocycling chamber" herein). A reaction chamber outlet port brings a reaction chamber in fluid communication directly or indirectly with a separation system, such as the electrophoresis capillaries. A reaction chamber can be in fluid communication with a diluent chamber, which can dilute amplification products with a diluent (e.g., water), can comprise a control (e.g., a size standard), and can in turn be in fluid communication with the separation system. FIG. 16 is a schematic side view of the cartridge, showing the container engaged with the microfluidic device, and the thermocycler assembly comprising four reaction chambers and attached to the microfluidic device, in accordance with an embodiment.

Figure 17:
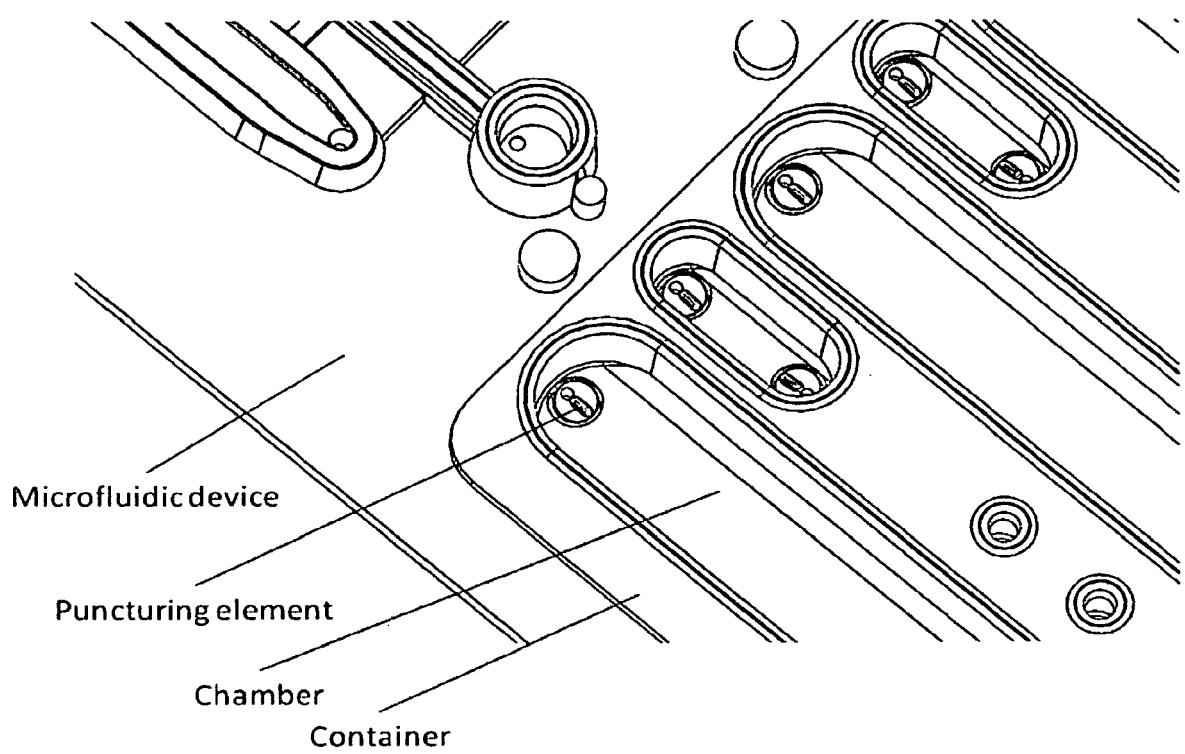
FIG. 17 shows various features of an embodiment of the microfluidic device and container of FIGS. 14-16.

With reference to FIG. 17, a puncturing element of the microfluidic device is in fluid communication with a chamber of the container. An opening of the puncturing element brings the chamber in fluid communication with a microfluidic channel of the microfluidic device.

The cartridge can be a disposable, single-use cartridge. In some embodiments, the cartridge has a size and shape that minimizes environmental waste after use and even environmental waste (e.g., CO2 and NOx emission) during construction. The cartridge can have a thickness that provides a smaller footprint in relation to other sample processing and/or analysis systems. In some cases, the size and thickness of the cartridge enables the minimization of the size of the system 100, which in turn enables ready transport of the system 100 and even a reduction of manufacturing costs and expenses during construction of the system 100.

Figure 35A:
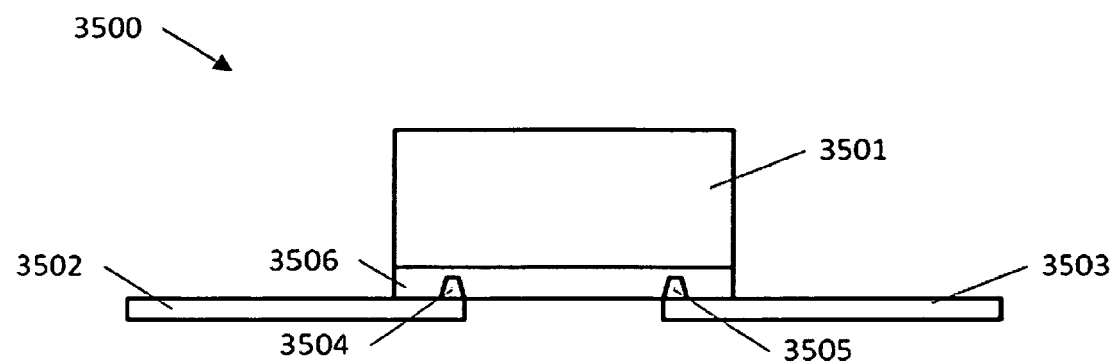
FIGS. 35A and 35B schematically illustrate an embodiment of a container engaging a microfluidic device.
Figure 35B:
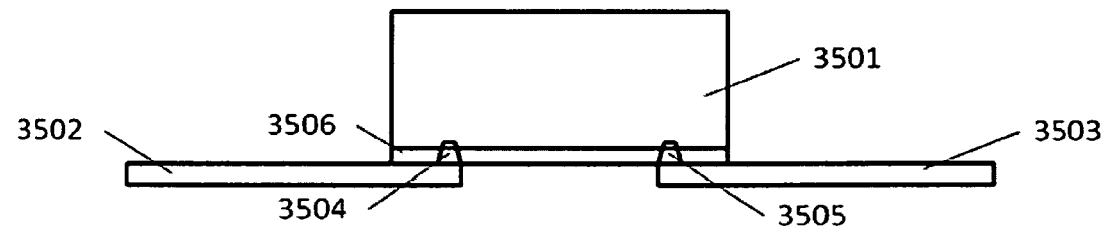

In some embodiments, engaging the container with the microfluidic device creates a fluid flow path from a first channel to a second channel through a chamber of the container. FIG. 35A shows a cartridge 3500 having a container with a chamber 3501, and a microfluidic device adjacent to the container. The microfluidic device comprises a first channel 3502 and a second channel 3503. The first channel is in fluid communication with a puncturing element 3504 and the second channel 3503 is in fluid communication with a second puncturing element 3505. The container 3501 is attached to the microfluidic device having the first channel 3502 and the second channel 3503 through a layer of deformable material 3506. The chamber 3501 is sealed at a side adjacent to the layer of deformable material 3506 with the aid of a friable (or puncturable) seal. The first channel 3502 can be in fluid communication with a first port to permit a fluid to enter or leave the first channel 3502, and the second channel 3503 can be in fluid communication with a second port for permitting a fluid to enter or leave the second channel 3503. The layer of deformable material 3506 supports the container but, absent sufficient force, keeps the puncturing elements 3504 and 3505 from piercing the friable seal. With reference to FIG. 35B, engaging the container against the microfluidic device deforms the layer of deformable material 3506 and brings the puncturing elements 3504 and 3505 in contact with a friable seal of the container. The puncturing elements pierce the layer of friable material and bring the chamber in fluid communication with the first channel 3502 and the second channel 3503.

Cassettes provided herein can be formed of multiple components and assembled to form an integrated unit. In some embodiments, assembling is performed prior to use by an end user.

FIG. 31 shows an integrated cassette 3100 for use with systems provided herein. An individual processing channel of the cassette 3100 has sample and lysis chambers 3101, wash solution/buffer chambers 3102, a bead suspension and capture chamber 3103, a lysis reagent storage and waste chamber 3104 and a diluent chamber 3105. The cassette 3100 has a thermocycler assembly comprising four reaction chambers 3106 configured to perform nucleic acid amplification (e.g., by PCR) with thermal cycling. The cassette 3100 has four processing channels or lanes.

With reference to FIG. 32, the cassette 3100 includes a holder 3107 that includes the lysis chamber 3101, a microfluidic device 3108 having a plurality of microfluidic channels 3109 and pneumatically actuated valves (e.g., MOVe valve), and a container 3110 having the chambers 3102-3105. A fluidic member 3111 brings the chambers 3102-3105 in fluid communication with the channels 3109. The fluidic member 3111 effects a macro-to-micro scale transition in fluid volume. The fluidic member 3111 includes puncturing elements 3111a and guides 3111b for coupling the fluidic member 3111 to the holder 3107.

The microfluidic device 3108 includes valves having a pneumatic layer, fluidic layer and an elastomeric layer disposed between the pneumatic layer and the fluidic layer. The valves are in fluid communication with a positive or negative pressure source for actuating the valves (see, e.g., FIGS. 36A and 36B). During use, the valves of the microfluidic device 3108 move fluid in and out of the chambers 3102-3105. The flow of fluid in and out of the chambers can be facilitated upon the application of positive or negative pressure to each of the chambers 3102-3105 through a space adjacent to each of the chambers 3102-3105, at a side opposite of the microfluidic device 3108.

The chambers 3102-3105 are sealed with the aid of layers 3112 and 3113. The layer 3113 is formed of a friable material, such as a polymeric material (e.g., elastomeric material) or other materials provided herein. The cassette 3100 includes a layer of deformable material 3114 that is configured to bring the puncturing elements in the fluidic member 3111 in contact with the layer 3113. Layers 3112 and 3113 form a hermetic seal in each of the chambers 3102-3105.

The cassette 3100 includes gripping members 3115 for enabling a user to grip the cassette 3100 with one or both of the user's hand. The gripping members 3115 are angular depressions in side walls of the cassette. In other instances, the gripping members may be ridges on a surface of the side walls.

The sample chamber 3101 is configured to hold a sample, such as with the aid of a swab (e.g., a cotton swab or a brush swab) or a cellulosic substrate (e.g., a paper, such as FTA® paper). The chamber 3101 is sealed with the aid of a door 3116 that is configured to be manually closed or, alternatively, closed with the aid of a motorized mechanism or actuation mechanism. The wash solution/buffer chambers 3102 can be preloaded with wash solutions or wash buffers. The bead suspension and capture chamber 3103 can be preloaded with beads for processing, e.g., magnetic (magnetically responsive) beads or particles such as paramagnetic beads or particles. In some embodiments, the bead suspension/capture chamber comprises (e.g., is preloaded with) silica-coated magnetic beads (e.g., Magnacel® beads from Promega). The lysis storage chamber 3104 can be preloaded with a lysis reagent. The diluent chamber 3105 can be preloaded with a diluent (e.g., water) that can comprise a control (e.g., a size standard).

FIGS. 8, 10, 11, 14, 16, 31 and 32 show two holes to the left of each reagent storage/waste chamber (viewing from the reaction chamber to the sample chamber), and two holes to the right of each bead suspension/capture chamber. In another embodiment, a cartridge comprises two holes to the left of each reagent storage/waste chamber, and one hole to the right of each bead suspension/capture chamber. In additional embodiments, viewing from the reaction chamber to the sample chamber, a cartridge comprises: (1) two or more holes to the left of each reagent storage/waste chamber and one or more holes to the right of each bead suspension/capture chamber; (2) two or more holes to the right of each reagent storage/waste chamber and one or more holes to the left of each bead suspension/capture chamber; (3) two or more holes to the left of each reagent storage/waste chamber and one or more holes to the left of each bead suspension/capture chamber; or (4) two or more holes to the right of each reagent storage/waste chamber and one or more holes to the right of each bead suspension/capture chamber.

B. Microfluidic Devices

The sample and control cartridges of this invention include fluidic devices. In certain embodiments, the fluidic devices are microfluidic devices.

In some embodiments, a passage is considered to be microfluidic if it has at least one cross-sectional dimension of no more than about 1 mm or 0.5 mm, e.g., if a sphere having a diameter of about 1 mm or 0.5 mm can pass through the passage without restriction. In other embodiments, a passage is considered to be microfluidic if it has no cross-sectional dimension greater than about 1 mm or 0.5 mm. In some embodiments, a microfluidic volume is a volume of no more than about 1 microliter. In further embodiments, a microfluidic volume is a volume of greater than about 1 microliter, e.g., at least about 2 microliters, at least about 10 microliters, at least about 50 microliters, at least about 100 microliters, at least about 500 microliters, or at least about 1 milliliter.

In some embodiments, the microfluidic device comprises selectably closable channels that are opened and closed with the aid of Micro-scale On-chip Valves (MOVe) device that miniaturize and automate complex workflows. Collectively, the MOVe devices, pumps, and routers and the instrumentation to operate them can be referred to as a microfluidic device (or microchip fluid processing platform). A MOVe device can include a series of three or more valves (e.g., diaphragm valves) in series. An individual valve of the MOVe device includes, in sequence, a pneumatic-actuation (also "pneumatic" herein) layer, elastomeric layer and fluidic layer. In certain embodiments, the actuation layer employs hydraulic actuation. The fluidic layer includes a valve seat, which may be a portion of a dome or cavity of the valve that is in fluid communication with the fluidic layer. The pneumatic layer is configured to provide positive or negative pressure to the elastomeric layer, thereby moving the elastomeric layer toward or away from the valve seat, which closes and opens the valve. In some cases, absent positive or negative pressure (i.e., actuation) from the pneumatic layer, the valve is in a normally open configuration in which elastomeric layer is disposed away from valve seat, thereby permitting fluid flow through the fluid layer. Upon actuation, the elastomeric layer comes in contact with a valve seat to close the valve and impede fluid flow through the valve. In other cases, absent positive or negative pressure from the pneumatic layer, the valve is in a normally closed configuration in which the elastomeric layer is in contact with the valve seat, thereby preventing fluid flow through the fluidic layer. Upon actuation, the elastomeric layer moves away from the valve seat to open the valve and permit fluid flow through the valve.

Accordingly, certain microfluidic devices used in this invention can have a pneumatic layer, fluidic layer and an elastomeric layer disposed between the pneumatic layer and the fluidic layer. In certain embodiments, the fluidic channels are comprised on the surface of the fluidics layer that faces the elastomeric layer. A valve can be formed where an interruption interrupts the channel. In this case, the port comprises that portion of the channel that meets the interruption and that will open into the valve chamber when the diaphragm is deflected. In another embodiment, a fluidic channel travels within a fluidics layer. In such an embodiment, the fluidics layer can comprise a plurality of layers. Certain layers can include vias, or bores, that put two sides of the layer in fluid communication with each other. Certain layers can comprise channels. Such channels can be closed when two layers are sandwiched together. In this case, ports are formed where two vias made in the fluidics layer communicate between two channels and the elastic layer across from an actuation valve body. (The two adjacent vias are separated by an interruption that can function as a valve seat.) For example, the structure can comprise four layers: two layers comprising a fluidics layer, an elastomeric layer and a pneumatics layer. In another embodiment, a fluidic channel is formed as a bore that traverses from one surface of the fluidic layer to the opposite surface which faces the elastic layer. A pair of such bores separated by an interruption can function as a valve. When the elastic layer is deformed away from the interruption (to which it is not bonded), a passage is created that allows the bores to communicate and fluid to travel in one bore, through the valve and out the other bore.

MOVe valves are described in further detail in U.S. Pat. Pub. Nos. 2004/0209354 to Mathies et al. ("FLUID CONTROL STRUCTURES IN MICROFLUIDIC DEVICES") and 2011/0005932 to Jovanovich et al. ("UNIVERSAL SAMPLE PREPARATION SYSTEM AND USE IN AN INTEGRATED ANALYSIS SYSTEM") ("Jovanovich"), U.S. Pat. Pub. 2010/0303687, U.S. Pat. Pub. 2011/0005932, U.S. Pat. Pub. 2011/0126911, which are entirely incorporated herein by reference.

MOVe valves, pumps and routers may have a normally open or normally closed configuration. In a normally closed configuration, absent actuation, a MOVe valve, pump or router is closed, thereby blocking fluid flow. A normally closed MOVe valve can be opened upon actuation, such as with the aid of positive pressure or a vacuum to move an elastomeric layer of the MOVe valve away from a valve seat of the valve. In a normally open configuration, absent actuation, a MOVe valve, pump or router is open, thereby permitting fluid flow. A normally open MOVe valve can be closed upon actuation, such as with the aid of positive pressure or vacuum to move an elastomeric layer of the MOVe valve to and in contact with a valve seat of the valve.

The MOVe valves and pumps can combine two glass and/or plastic microfluidic layers with an elastomeric layer, e.g., polydimethylsiloxane (PDMS), that opens and closes the valve, and a pneumatic layer to deform the membrane and actuate the valve. The microfluidic channel etched in the top glass fluidic wafer is discontinuous and leads to a valve seat which is normally closed. When a vacuum is applied to the pneumatic displacement chamber by conventional-scale vacuum and pressure sources, the normally closed PDMS membrane lifts from the valve seat to open the valve. PDMS can be bonded to plastic by coating the plastic with a layer of an oxide, e.g., a metal oxide, and then contacting the PDMS to the plastic, optionally with heat and pressure.

In some embodiments, the microfluidic device is provided in a cartridge. The cartridge can include sample capture and purification, micro-separations, micro-valves, -pumps, and -routers, nanofluidic control, and nano-scale biochemistry systems. MOVe pumps, valves, and routers transport, process, and enable analysis of samples. These externally actuated, pneumatically-driven, on-chip valves, pumps, and routers can control fluidic flow at manipulate volumes from 20 nL to 10 pL.

Figure 52B:
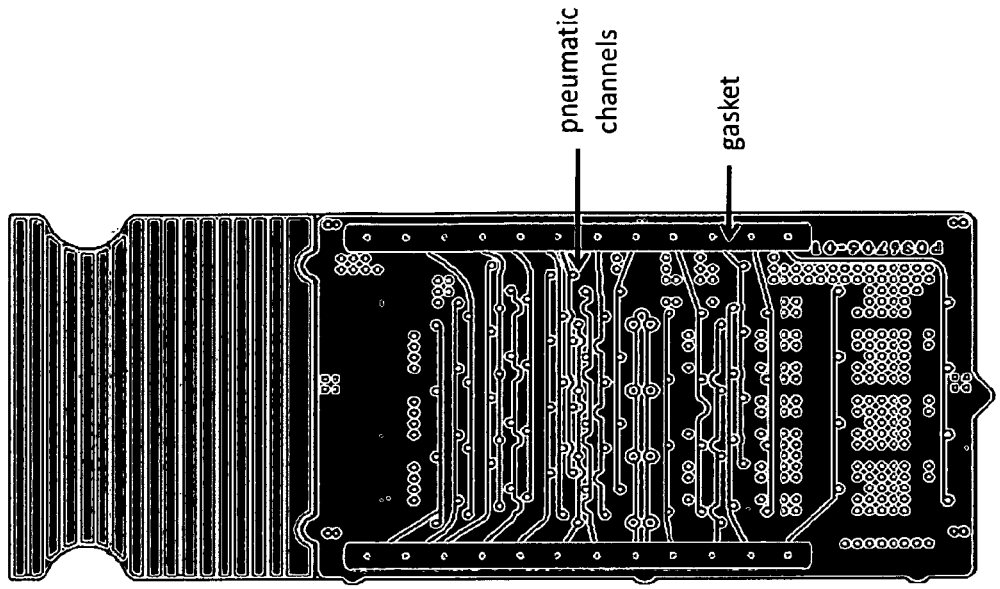
FIG. 52B shows a layout for a pneumatic side of a microfluidic chip usable in a cartridge of this invention.
Figure 52A:
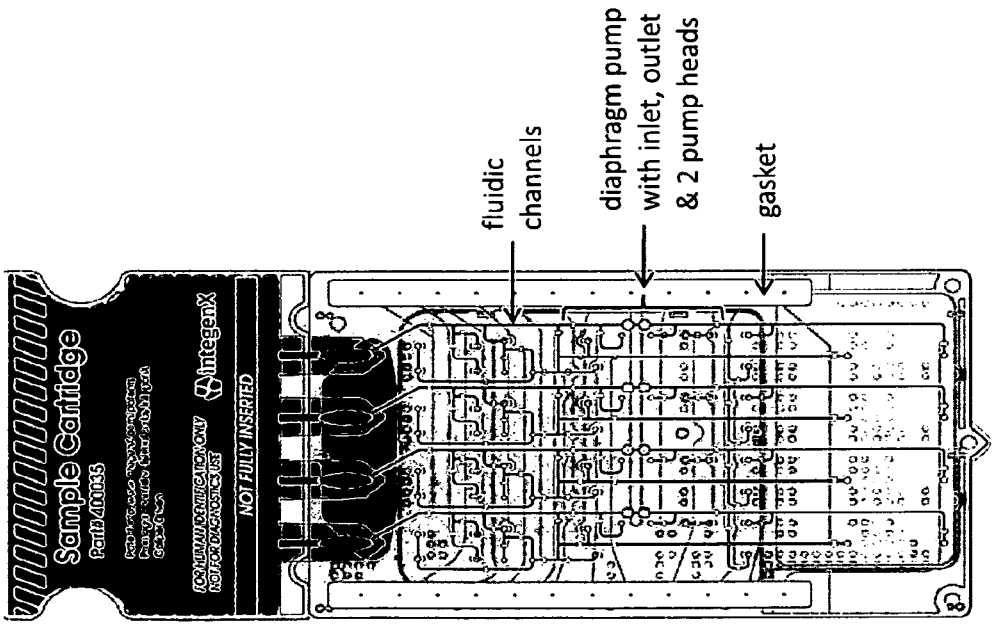
FIG. 52A shows a layout for a fluidics side of a microfluidic chip usable in a cartridge of this invention.

Three valves can be used to make a pump on a microchip to move fluids through a microfluidic channel. The valves can be microvalves or nanovalves, configured to move microliter or nanoliter fluid volumes, respectively. The fluids are moved by three or more valves. The valves can be created actuation of a deformable structure. In some embodiments a valve seat is created, and in other embodiments no valve seat may be needed. In one embodiment, a diaphragm pump can comprise an inlet (e.g., a valve such as a normally open valve), a pump head (e.g., one or two or more pumping chambers, optionally operated in tandem) and an outlet (e.g., a valve such as a normally open valve). (See, e.g., FIG. 52.)

Arrays of MOVe valves, pumps, and routers are readily fabricated on microchips. Significantly, all the MOVe valves, pumps, and routers on a microchip are created at the same time in a simple manufacturing process using a single sheet of PDMS membrane. In some cases, the manufacture of five MOVe micropumps on a microchip may be the same as the manufacture of five hundred micropumps.

Devices and methods useful in the present invention are described, for example, in U.S. Pat. No. 7,445,926, U.S. Pat. Pubs. 2004/0209354, 2005/0161669, 2006/0073484, 2007/0248958, 2008/0014576, 2009/0253181, 2010/0165784, 2010/0303687, 2011/0005932, 2011/0126911, 2011/0240127, 2012/0181460, 2012/0240127 and 2012/0290648; and PCT Pubs. WO 2008/115626, WO 2011/011172, and WO 2012/024657.

In some embodiments, a valve is in a normally open configuration. Alternatively, a valve can be in a normally closed configuration. In a normally open configuration, absent actuation the deformable membrane layer is not in contact with the seat, and the valve permits fluid flow through a dome (or chamber) of the valve. Actuating the deformable membrane layer causes the deformable membrane layer to contact the seat, thereby closing the valve. In a normally closed configuration, absent actuation the deformable membrane layer is in contact with the valve seat, which obstructs the flow of fluid through the dome of the valve. Actuating the deformable membrane layer causes the deformable membrane layer to move away from the valve seat, thereby opening the valve. Actuation of the deformable membrane layer is achieved with the application of positive or negative pressure through a pneumatic line to increase or decrease the pressure in a pneumatic chamber relative to the microfluidic channel, which can deform the deformable membrane layer.

Figure 43:
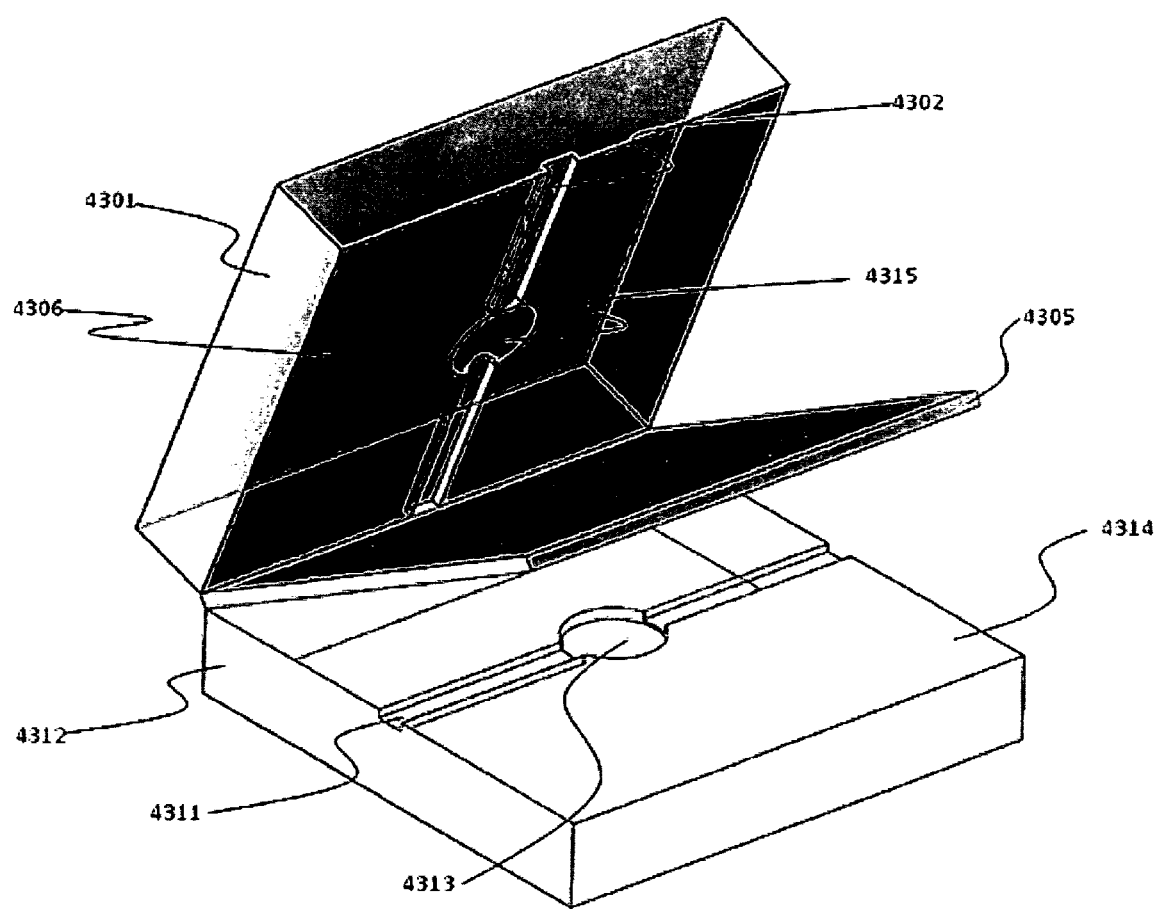
FIG. 43 is a schematic illustration of a diaphragm valve in a normally open configuration.

In an example, FIG. 43 shows a clamshell view of an embodiment of a normally open diaphragm valve of this invention, as can be used with microfluidic devices of the invention. A fluidics layer 4301 comprises a fluid conduit comprising a fluidic channel 4302, which opens into a recessed dome 4315 that functions as a valve seat. When no pressure or negative pressure is exerted on elastic layer 4305, the elastic layer 4305 sits away from the valve seat, allowing for an open valve in which a fluid path between the channels entering the valve are in fluidic contact, creating a fluid path. When positive pressure is exerted on elastic layer 4305, the elastic layer 4305 deforms toward the valve seat to close the valve.

In an embodiment of a normally open valve, the valve seat is not configured as an interruption in a fluidic conduit. Rather, it takes the form of a recess with respect to surface of the fluidics layer that normally contacts the elastic layer, so that the elastic layer does not sit against the recessed surface without application of pressure on the elastic layer, e.g., through the actuation chamber. In this case, the valve may not have a discrete valve chamber in the fluidics layer that is separate from the valve seat. The valve seat can take a curved shape that is concave with respect to the surface of the fluidic layer, against which the elastic layer can conform. For example, the valve shape can be an inverted dimple or a dome. Its shape can substantially conform to the shape of the elastic layer when deformed by pressure. It can take the shape substantially of a parabola or a portion of a sphere. Such a configuration decreases the dead volume of the valve, e.g., by not including a valve chamber that contains liquid while the valve is closed. This valve also comprises a surface against which the elastic layer can conform easily to close the valve. This configuration also eliminates the need to create a surface patterned so that valves do not comprise surface hydroxyl groups, e.g., for bonding with a polysiloxane elastomer such as PDMS, because the recessed surfaces do not bond with the elastic layer against which they are laid during construction. In another embodiment, the concave surface can comprise within it a sub-section having a convex surface, e.g., an inverted dimple comprising an extraverted dimple within it forming, e.g., a saddle shape. The convex area rises up to meet the elastic layer under pressure, creating a better seal for the valve.

In some embodiments of a normally open valve, the concavity is recessed less than the channels to which it is connected. For example, the deepest part of the concavity can be about one-third to one-half the depth of the channel (e.g., 30 microns to 50 microns for the concavity versus 100 microns for the channel). For example, the elastic layer may be about 250 microns, the channels about 100 microns deep and the valve seat about 30 microns deep. The thinner the elastic layer, the deeper that the concavity can be, because the elastic layer can conform to the concavity without excessive deformation. In certain embodiments the channels can enter partially into the concavity, for example forming a vault. In certain embodiments, the channels and concavity are formed by micromachining. In other embodiments they may be formed by hot embossing or injection molding or other methods. The actuation layer can comprise a valve relief into which the diaphragm deflects for opening the valve.

In some embodiments, a diaphragm valve is formed from a body comprising a chamber in the actuation layer (e.g., a valve relief) and in the fluidics layer (e.g., a pumping chamber), but without an interruption. In this embodiment, deforming the diaphragm into the actuation chamber creates a volume to accept fluid, and deforming the diaphragm into the fluidics chamber pumps liquid out of the chamber. In this configuration, the position of the diaphragm alters the effective cross-section of the fluidic conduit and, thus, can regulate the speed of flow through the valve. In such a configuration, the valve may not completely block the flow of fluid in the conduit.

Valves with concave valve seats displace defined volumes of liquid upon closing. Therefore, such valves are useful as pumps where pumping of uniform volumes is desired. Typically, pumping valves have greater volumes of than closing valves. For example, a pumping valve can have a displacement volume of between 50 AL to 150 µL, e.g., about 100 µL. Two pumping valves can be placed in series, e.g., without intervening features, to provide variable volume pumps. Such pumping valves typically are placed between two closing valves that function as pump inlets and pump outlets. The pump head can be configured such that an elastomer membrane, when actuated in the pump head, does not completely stop fluid from passing through the pump head. This contrasts with a closable valve.

In some embodiments, a microfluidic device is fabricated from an elastomeric polymer, such as GE RTV 615 (formulation), a vinyl-silane crosslinked (type) silicone elastomer (family). However, a microfluidic device is not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in Unger et al. (2000) Science 288:113-116, and PCT Publications WO 02/43615 (Unger et al.), and WO 01/01025 (Unger et al.), which are entirely incorporated herein by reference.

C. Thermocycler Assembly

The analyte preparation module can include a thermocycler assembly. The thermocycler assembly can be comprised in a combination of the sample cartridge and the cartridge module. The thermocycler assembly can be configured to deliver analyte (e.g., a polynucleotide, such as DNA) and reagents to a reaction chamber (or thermocycling chamber) and to cycle temperature (e.g., heating and cooling) of a liquid in the thermocycling chamber. In one embodiment, the thermal cycling chamber is attached to the sample cartridge and in fluidic communication with the fluidic device. An amplification reagent container can be fluidically isolated from the thermal cycling chamber and can be configured to deliver reagents to the chamber upon actuation. A device configured to actuate delivery of the reagents can be comprised by or integrated with the cartridge module (see, e.g., FIG. 55). A thermal controller, such as a Peltier device, can be configured to heat and cool for thermal cycling and can be comprised by or integrated with the cartridge module (see, e.g., FIG. 42), which can be configured to move the thermal controller into thermal contact with the thermal cycling chambers, e.g., through a heat spreader (or thermoconductor that can spread/distribute heat and cooling) disposed over each of the reaction chambers as shown in the embodiment of FIG. 42.

In some embodiments, the cartridge comprises a thermocycler assembly having one or more (e.g., 4, 8, 10, 16, 24, 32, 40, 48 or more) thermocycling chambers, each thermocycling chamber in fluid communication with a micro fluidic channel. The one or more thermocycling chambers can be configured for nucleic acid amplification, such as by polymerase chain reaction (PCR). In some situations, the cartridge includes a premix vessel or chamber in fluid communication with a thermocycling chamber. The premix vessel or chamber includes a premix, which can comprise one or more pairs of forward and reverse primers for amplifying one or more selected nucleotide sequences, a buffer, a metal salt (e.g., an $M^{+2}$ salt, such as magnesium chloride) and an enzyme (e.g., a DNA polymerase, such as a Taq polymerase) for nucleic acid amplification, such as by PCR, rolling circle amplification or other amplification methods.

Each of the one or more reaction chambers of the thermocycler assembly can be configured to perform standard PCR and variants thereof, such as allele-specific PCR, assembly PCR, asymmetric PCR, hot-start PCR, intersequence-specific PCR, inverse PCR, isothermal PCR (e.g., helicase-dependent amplification and PAN-AC), ligation-mediated PCR, mini-primer PCR, multiplex PCR, nested PCR, picotiter PCR, quantitative PCR, real-time PCR, restriction fragment length polymorphism PCR, reverse transcription PCR, single-cell PCR, solid-phase PCR (e.g., bridge PCR), thermal asymmetric interlaced PCR, touch-down (step-down) PCR, and universal fast walking PCR. Prior to PCR amplification, whole genome amplification can be performed to improve amplification of a low copy-number DNA or a degraded DNA. DNA can also be amplified using other methodologies that can be isothermal or can involve thermal cycling, such as ligase chain reaction, strand displacement amplification, self-sustained sequence replication, QS replicase amplification, repair chain reaction, cycling probe technology or reaction, and nucleic acid sequence-based amplification.

In some embodiments, nucleic acid amplification (e.g., by PCR) is performed at a substantially constant temperature (e.g., at a temperature in the range of about 50-75° C. or 50-65° C.) using, e.g., a chemical denaturant (e.g., formamide, urea or another chemical denaturant described herein).

In other embodiments, nucleic acid amplification (e.g., by PCR) is performed at two or more different temperatures or two or more different ranges of temperatures (e.g., denaturation at about 90-99° C. or 94-98° C., annealing at about 50-65° C. or 56-62° C., and optionally extension at about 65-80° C., 70-75° C. or 75-80° C.).

Formation of a primer dimer and amplification of the primer dimer can lead to primer artifact. To prevent primer dimerization, in some embodiments a mixture containing one or more pairs of forward and reverse primers for amplifying one or more selected nucleotide sequences, and optionally other reagents for performing nucleic acid amplification (such as a polymerase (e.g., a DNA polymerase), nucleotide triphosphates (e.g., deoxynucleotide triphosphates), and optionally a buffer and/or a metal salt (e.g., magnesium chloride)), is heated at a temperature substantially equal to (e.g., within about 10° C., 5° C., 3° C. or 1° C.) or above the annealing temperature (e.g., about 50-65° C. or 56-62° C.) of the amplification reaction, or at or above about 50° C., 55° C., 60° C. or 65° C., for a period of time (e.g., about 0.5-10 min, 1-5 min or 5-10 min) before the primers are mixed with the other amplification reagents (if not already contained in the primer mixture) and the sample nucleic acid (e.g., genomic, isolated or purified DNA) to faun a reaction mixture (the primers, and optionally other amplification reagents, are "pre-heated" in this context), and the reaction mixture is heated at one or more temperatures substantially equal to or above the annealing temperature of the reaction until the reaction is completed. In some embodiments, the primers, and optionally other amplification reagents, are pre-heated as described herein in a pre-heating chamber shortly (e.g, about 1 second to about 5 minutes, or about 1 sec, 15 sec, 30 sec, 1 min, 3 min or 5 min) before being delivered to a reaction chamber comprising the sample nucleic acid. The pre-heating chamber can be located close to the reaction chamber and/or close to a heating and cooling thermocycler to prevent primer dimerization by pre-heating the primers, and optionally other amplification reagents, in the pre-heating chamber shortly before the primers are combined with the sample nucleic acid. The pre-heating chamber can comprise a heating element that applies or distributes heat to the chamber (e.g., a thermoconductor disposed over the pre-heating chamber which contacts metal plate 4220 of thermocycler 4200 in FIG. 42). The pre-heating chamber can also be the reaction chamber, where the primers, and optionally other amplification reagents, are pre-heated before the sample nucleic acid is delivered to the reaction chamber. The primers and other amplification reagents can be initially stored in liquid form, or in a solid or semi-solid (e.g., dehydrated or lyophilized) form that is later rehydrated, in a single vessel (e.g., a chamber in the cartridge containing the reaction chamber, the receptacle of FIG. 33, the receptacle of FIG. 62 or the receptacles of FIG. 70), in separate chambers of a container (e.g., two chambers in the cartridge containing the reaction chamber, or the two-chamber vials of FIG. 57), or in separate containers (e.g., the two-vial embodiment of FIG. 59) before being delivered to the pre-heating chamber (or the reaction chamber) for pre-heating and optional mixing.

In further embodiments, to prevent primer dimerization a mixture containing the sample nucleic acid in a reaction chamber is heated at a temperature substantially equal to (e.g., within about 10° C., 5° C., 3° C. or 1° C.) or above the annealing temperature (e.g., about 50-65° C. or 56-62° C.) of the amplification reaction, or at or above about 50° C., 55° C., 60° C. or 65° C., for a period of time (e.g., about 10 sec to about 10 min, or about 0.5-5 min or 5-10 min) before one or more mixtures containing the primers and the other amplification reagents are delivered to the reaction chamber to form a reaction mixture, and the reaction mixture is heated at one or more temperatures substantially equal to or above the annealing temperature of the reaction until the reaction is completed. In additional embodiments, to prevent primer dimerization one or more mixtures containing the primers and the other amplification reagents at ambient temperature or lower are delivered to a mixture containing the sample nucleic acid at ambient temperature or lower in a reaction chamber to form a reaction mixture, and then the reaction mixture is quickly (e.g., within about 1 second to about 5 minutes, or within about 1 sec, 15 sec, 30 sec, 1 min, 3 min or 5 min, of the time when the primers and the other amplification reagents are delivered to the reaction chamber) heated to a temperature substantially equal to (e.g., within about 10° C., 5° C., 3° C. or 1° C.) or above the annealing temperature (e.g., about 50-65° C. or 56-62° C.) of the amplification reaction, or to a temperature of or above about 50° C., 55° C., 60° C. or 65° C., and the reaction mixture is heated at one or more temperatures substantially equal to or above the annealing temperature of the reaction until the reaction is completed.

Uracil-DNA-glycosylase (also known as uracil-N-glycosylase, UNG or UDG) in combination with deoxyuridine triphosphate (dUTP) can be used to prevent carry-over DNA contamination in PCR amplification of loci (e.g., STR loci). Amplification performed in the presence of dUTP in place of deoxythymidine triphosphate (dTTP) results in uracil-containing STR amplicons. Prior to amplification, a PCR reaction mixture can be pre-treated with UNG, which specifically degrades any uracil-containing PCR products carried over from previous PCR amplifications, thereby preventing their unwanted amplification. UNG is heat-inactivated during a subsequent PCR amplification, and only DNA from the specific sample of interest is amplified. It may be desirable to generate an allelic ladder with incorporated uracil bases in place of thymidine bases since the electrophoretic migration of uracil-containing STR fragments may differ from the electrophoretic migration of their thymidine-containing counterparts.

Carry-over contamination with products of previous PCR amplifications can also be minimized by UV irradiation at a suitable wavelength (e.g., 254 nm). For example, a solution potentially containing DNA contaminants can be UV-irradiated at a suitable wavelength (e.g., 254 nm) and at a suitable distance (e.g., 1 cm) from a UV bulb for a suitable period of time (e.g., 10 minutes) in a suitable instrument (e.g., a Stratalinker® UV Crosslinker 2400 device (Stratagene, Cedar Creek, USA) or a Spectrolinker XL 1500 UV crosslinker device (Spectronics, Westbury, N.Y.)).

In some embodiments, the cassette further comprises a magnetic field application member adjacent to the thermocycling chamber. The magnetic field application member may be configured to apply a magnetic field using a permanent magnet or an electromagnet, in which case the magnetic field application member includes a permanent magnet or an electromagnet. A permanent magnet can be comprised in the sample cartridge. Alternatively, the magnetic field application member can be a moveable magnet (e.g., permanent magnet or electromagnet) that can be moved to become adjacent to the thermocycling chamber.

In some embodiments, a thermocycler assembly includes one or more (e.g., 4, 8, 10, 16, 24, 32, 40, 48 or more) pairs of premix vessels/chambers and reaction chambers for nucleic acid amplification (e.g., by PCR). The thermocycler assembly in some cases comprises a polymeric material (e.g., plastic) that is attached to an external surface of a microfluidic device of the cartridge. In an example, at least a portion of the thermocycler assembly (e.g., one or more reaction chambers) is mechanically attached to the microfluidic device, e.g., bolted, snapped or press-fitted onto the microfluidic device. Alternatively, at least a portion of the thermocycler assembly is attached to the microfluidic device through adhesion, e.g., through a glue or an adhesive tape. Furthermore, at least a portion of the thermocycler assembly (e.g., one or more reaction chambers) can be made on the surface of the fluidics layer of the microfluidic device.

The thermocycler assembly can include a plurality of reaction chambers for nucleic acid amplification. Each reaction chamber can have an elongate shape. In some cases each chamber is an open container, such as a trough having a depth (as measured from an opening of the trough to a floor of the trough) of about 1 micron to 10,000 microns, or 10 microns to 800 microns, or 50 microns to 600 microns. A trough can have a volume between about 100 nanoliters and 1 microliter, or 1 microliter and 100 microliters, or 5 microliters and 50 microliters, or 10 microliters and 30 microliters. In an example, a trough has a depth of about 510 microns, and a volume of about 20 microliters. In some cases the chamber is a closed container that is cylindrical or rectangular in shape.

In some embodiments, the reaction chambers of the thermocycler assembly are in thermal contact with a thermal conductor (e.g., a heat spreader) for conducting heat and cooling to each reaction chamber and a sample in the reaction chamber during sample processing. The thermal conductor can rest over each reaction chamber of the thermocycler assembly, and away from the microfluidic device (see, e.g., layer 3406 of FIG. 34A, FIG. 42 and FIG. 44). The thermal conductor can be formed of graphite, graphene, aluminum, copper or a copper-containing alloy, though other metals or materials with suitable thermal conductivities can be used. In some cases, the thermal conductor is formed of a plurality of layers, such as a layer of a thermally conductive material (e.g, graphite) adapted to come in thermal communication with a temperature control element (e.g., heating element and/or cooling element), and a layer of a polymeric material (e.g., polypropylene) adjacent to the layer of the thermally conductive material that is adapted to come in contact with each reaction chamber or a sample in each reaction chamber of the thermocycler assembly. As an alternative, the thermal conductor can be adjacent to the microfluidic device of the cartridge, such as between the thermocycler assembly and the microfluidic device, or integrated into the thermocycler assembly and disposed adjacent to the cartridge.

During processing, a temperature control element (e.g., a heating element and/or a cooling element, which can be a heating and cooling element) is disposed adjacent to one or more reaction chambers of the thermocycler assembly, such as adjacent to the cartridge or over the reaction chambers and disposed away from the cartridge. The temperature control element of the thermocycler assembly can be integrated in the microfluidic device or the cartridge module, or brought in proximity to the thermocycler assembly chambers. The temperature control element can be a Peltier temperature control element (e.g., a Peltier heating and cooling element), which is configured to generate heat upon the application of an electrical potential across electrodes of the Peltier temperature control element. The temperature control element can be in thermal communication with the thermal conductor, which can aid in directing heat to the sample during sample processing. The Peltier can aid in maintaining a constant temperature in each chamber, or increase the temperature or decrease the temperature at a desired or otherwise predetermined heating or cooling rate, respectively. Alternative heating and cooling elements such as circulating air, water or other gases or liquids of different temperatures, IR heating, and other methods well known to one skilled in the art are also possible with air temperature control and IR heating providing advantages of non-contact.

FIG. 42 illustrates an embodiment of a thermal cycling device 4200 that can heat and cool. Thermal cycling device (or thermocycler) 4200 can be employed to perform thermal cycling for, e.g., nucleic acid amplification by PCR. Thermal cycling device 4200 comprises a heat sink 4230, a metal block 4210 composed of a suitable metal (e.g., copper), and a metal plate (also called a cold plate) 4220 composed of a suitable metal (e.g., aluminum). A Peltier heat and cooling element (not shown) is sandwiched between metal block 4210 and metal plate 4220. In the embodiment of FIG. 42, thermal cycling device 4200 is included in a cartridge module. Thermal cycling device 4200 floats in the cartridge module and is engaged with a sample/control cartridge by being pressed against the cartridge, which results in metal plate 4220 contacting the thermoconductor disposed over the reaction chambers of the cartridge. Once thermal cycling device 4200 is engaged with the cartridge, the device is held in place. The Peltier heat and cooling element both heats and cools (e.g., by thermoelectric heating and cooling), and the thermoconductor on the cartridge can spread/distribute thermal changes involving both heating and cooling. Because metal plate 4220 of thermal cycling device 4200 contacts the thermoconductor, heating and cooling of the Peltier element results in (e.g., conductive) heating and cooling of the thermoconductor, which in turn distributes heat and cooling to each of the four reaction chambers of the cartridge. To decrease the time of a reaction (e.g., PCR) involving thermal cycling, faster thermal cycling can be achieved, e.g., by employing a thinner metal plate 4220.

Figure 18A:
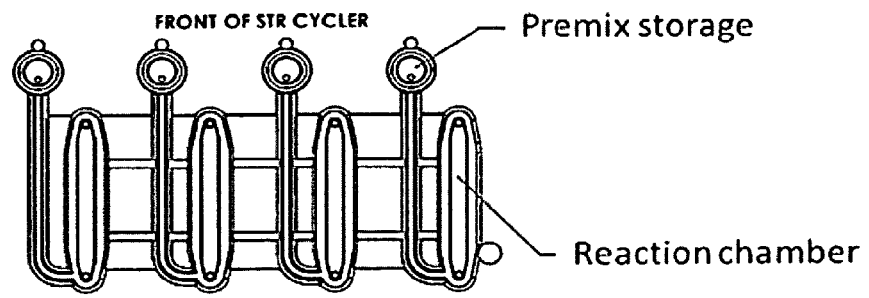
FIGS. 18A-18D show embodiments of a thermocycler assembly comprising four reagent (premix) chambers and four reaction chambers configured to perform amplification (e.g., by PCR) with thermal cycling.
Figure 18B:
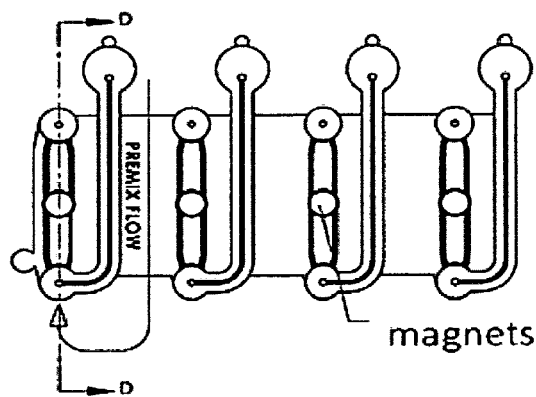
Figure 18C:
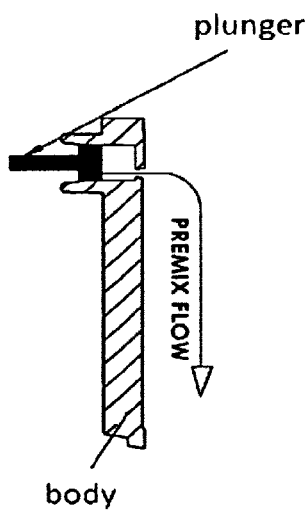
Figure 18D:
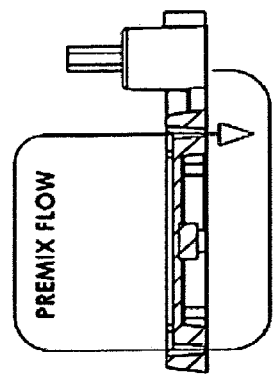
Figure 45:
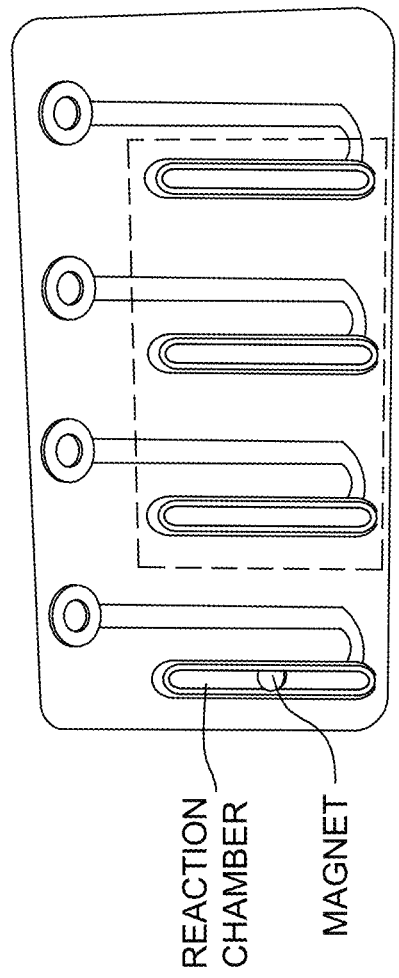
FIG. 45 shows a bottom view of an embodiment of a thermocycler assembly having four reaction chambers, with each reaction chamber having a magnet.

FIGS. 18A-18D schematically illustrate a thermocycler assembly, in accordance with an embodiment of the invention. Four thermocycling chambers are illustrated, one thermocycling chamber per channel or lane of the cartridge described above. The thermocycler assembly includes a premix storage chamber for storing and providing a premix to each thermocycling chamber, as shown in FIG. 18A. The premix can include primers, buffers and enzymes for reaction. The thermocycler assembly includes four reaction chambers for holding a sample and reagents during a reaction (e.g., PCR). In some embodiments, nucleic acid (e.g., DNA) obtained from a sample is captured on magnetic beads and the beads are held in place in a reaction chamber with the aid of a magnetic field, as can be supplied by a magnetic field source (e.g., magnet, induction coil), as shown in FIGS. 18B and 45. Premix is provided from a premix storage chamber to the reaction chamber with the aid of, e.g., a plunger, as shown in FIG. 18C. FIG. 18D shows an exemplary premix (or reagent) flow path.

The thermocycler assembly of FIGS. 18A-18D can be bolted or otherwise secured onto the body of a micro fluidic device. (See, e.g., 3106.) In an example, FIG. 16 shows four thermocycling chambers attached to a microfluidic device. The thermocycler assemblies include reaction chambers for sample processing (e.g., PCR). With reference to FIG. 34A, during sample processing, a temperature control element (e.g., heating element and/or cooling element such as a Peltier heating and cooling element) is configured to come in thermal communication with each chamber with the aid of a layer of a thermal conductor 3406 disposed over the chambers. The thermal conductor 3406 can include graphite, graphene, copper, tantalum, or aluminum, to name a few examples. In an example, the temperature control element (e.g., heating element and/or cooling element) rests against the thermal conductor 3406 during sample processing. Alternatively, the cartridge can include an integrated temperature control element which, for example, can be disposed between the microfluidic device and the thermocycler assembly. Accordingly, in certain embodiments, such as cassettes that include a microfluidic chip comprising channels and diaphragm valves involving polysiloxane membranes, such as polydimethylsiloxane (PDMS), the reaction chamber does not have to be included within the microfluidic chip. In other embodiments, the surfaces of the reaction chamber can be configured to not inhibit the activity of the enzymes either by selection of an appropriate material (e.g., polypropylene) for making the reaction chamber or by surface modification of the material by, for example, grafting polyethylene glycol (PEG) groups, silanization, plasma treatment, chemical vapor deposition or other methods.

In some cases, an amplification premix is provided to a sample prior to nucleic acid amplification (e.g., PCR), and the sample with the premix is subsequently thermally annealed to initiate nucleic acid amplification. The premix includes the reagents (e.g., primers, enzymes) for facilitating nucleic acid amplification. The premix can be a PCR premix, which can include short tandem repeat (STR) premix reagents.

There are various approaches for delivering a nucleic acid amplification premix to a processed or partially-processed sample prior to amplification. Following delivery of the premix, the temperature of the sample is raised, and in some cases cycled, in a thermocycling chamber in fluid communication with a channel that is coupled to the cartridge.

In some embodiments, the premix is delivered to the sample with the aid of a plunger. In other embodiments, the premix is delivered to the sample with the aid of a rehydration delivery device.

Figure 33A:
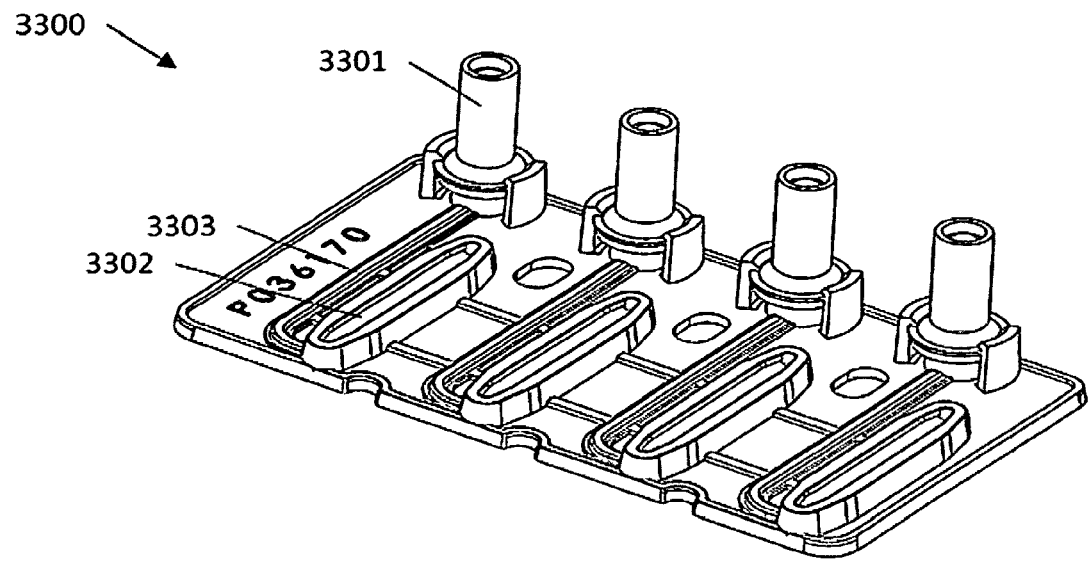
FIGS. 33A-33F show views and features of embodiments of a thermocycler assembly comprising four reagent (premix) chambers and four reaction chambers configured to perform amplification (e.g., by PCR) with thermal cycling.
Figure 33B:
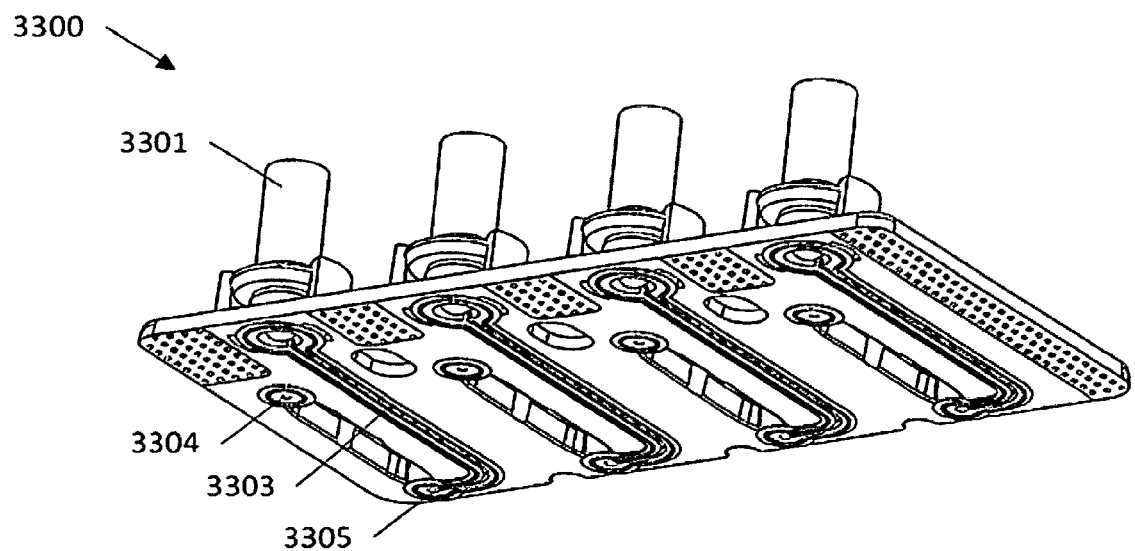

FIGS. 33A-33E illustrate a thermocycler assembly 3300 as can be used with systems and methods provided herein. The thermocycler assembly 3300 can be the thermocycler assembly 3106 of FIGS. 31 and 32. FIG. 33A is a schematic top view of the thermocycler assembly 3300. The thermocycler assembly 3300 includes four reagent delivery members 3301 (or reagent (or premix) vessels/chambers) for delivering a premix or other reagents to four thermocycling (or reaction) chambers 3302 of the thermocycler assembly 3300. In some cases, the thermocycling chamber 3302 is a trough that has an opening along the length of the thermocycling chamber 3302. The reagents or premix is delivered from a reagent delivery member 3301 to a thermocycling chamber 3302 through a channel 3303 in fluid communication with the reagent chamber and the thermocycling chamber 3302. In some embodiments, channel 3303 does not comprise a valve. The reagents or premix can be delivered to a thermocycling chamber with the aid of a plunger or an actuating device such as that shown in FIG. 55. FIG. 33B is a schematic bottom view of the thermocycler assembly 3300. An inlet port 3304 and outlet port 3305 are configured to come in fluid communication with an inlet port and outlet port, respectively, of a microfluidic device disposed adjacent to the thermocycler assembly 3300, such as the microfluidic device 3108 of FIG. 32.

For example, a sample to be processed is directed from the inlet port of the microfluidic deice to the inlet port 3304 and to the thermocycling chamber 3302. The reagent delivery member (or reagent vessel/chamber) 3301 delivers a reagent (e.g., premix) to the thermocycling chamber 3302. The sample is processed (e.g., STR processing). The processed sample is then directed to the outlet port 3305 and the outlet port of the microfluidic device for analysis, such as with the aid of capillary array electrophoresis. In some embodiments the electrophoresis system can include a memory device that records the number of times a capillary has been used.

Figure 33C:
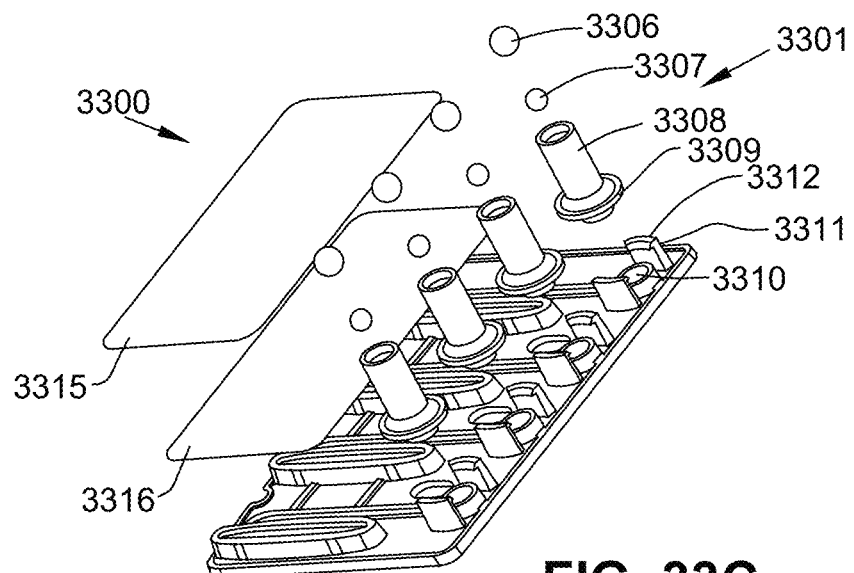

FIG. 33C is an exploded view of the thermocycler assembly 3300 showing the reagent delivery member (or reagent vessel/chamber) 3301. In some embodiments, the reagent delivery member is a dual plunger sealed chamber having a first stopper 3306 and a second stopper 3307, in this case configured as balls. The stoppers 3306 and 3307 seal a receptacle (e.g., a column or tube) 3308 having a reagent (e.g., premix, master mix), such as an STR master mix is. The application of force to the first stopper ball 3306 (such as, e.g., with the aid of a plunger or a syringe) actuates the movement of the second stopper ball 3307 ball into a larger chamber, cavity or channel that creates a flow path for the master mix to pass through the channel 3303 into the thermocycling chamber 3302. The thermocycler assembly 3300 includes a thermal conductor formed of a layer of a thermally conductive material 3315, such as graphite, laminated to a layer of a polymeric material 3316, such a polypropylene.

In some embodiments, the system 100 includes dual thermocycler (also called thermal cycler) units for use during sample processing (see below). The dual thermocycler units apply heat and cooling to each of the control and sample cartridges during processing. The thermocyclers can apply heat at a power output of at least about 10 watts (W), 20 W, 30 W, 40 W, 50 W, 100 W, 200 W, 300 W, 400 W, 500 W, or more. FIG. 42 illustrates an embodiment of a thermocycler that can be used as each of two thermocyclers included in a sample cartridge interface module. As described above, because metal plate 4220 contacts the thermoconductor disposed over the reaction chambers when the sample/control cartridge is engaged with the cartridge module, a Peltier heating and cooling element (not shown in FIG. 42) sandwiched between metal block 4210 and metal plate 4220 can conductively heat and cool the thermoconductor and hence the reaction chambers. In other embodiments, the thermocyclers may operate via resistive or radiative heating and cooling, though convective heating and cooling may be employed in some circumstances. An automated capture magnet of the system 100, which is disposed adjacent to the sample cartridge interface module, is used during processing in some cases to hold magnetically-attractable particles in place.

The flow of a reagent from the reagent delivery member (or reagent vessel/chamber) 3301 is activated by applying force to a stopper ball, such as with the aid of positive pressure to the first stopper ball 3306 or the application of negative pressure (or vacuum) to the second stopper ball 3307. Force may be applied with the aid of a mechanical device, pneumatics, or other force delivery mechanism or device, such as the device shown in FIG. 55. In some cases, force is delivered with the aid of a plunger in fluid communication with the stopper balls 3306 and 3307 and the receptacle (e.g., a column or tube) 3308. The plunger can be a metal plunger or a syringe-type device.

In some embodiments, the first stopper ball 3306 has a larger diameter than the second stopper ball 3307. In some situations, the first stopper ball 3306 has a shape that is different from the second stopper ball 3307.

The receptacle (e.g., a column or tube) 3308 can include one or more reagents. The stopper balls 3306 and 3307 can be used to compartmentalize the reagents in fluidically isolated containers. In some embodiments, upon the application of force to the first stopper ball 3306 (or alternatively, the application of vacuum to the second stopper ball 3307), the fluids may mix.

The stopper balls 3306 and 3307 can be spherical or other geometric shapes—i.e., the stopper balls 3306 and 3307 can have shapes that are not necessarily spherical. In some embodiments, the stopper balls 3306 and 3307 can have cross-sections that are circular, triangular, square, rectangular, pentagonal, hexagonal, heptagonal or octagonal, or partial shapes, such as semi-circular.

In other embodiments, the reagent application member comprises the second stopper ball 3307 and a plunger instead of the first stopper ball 3306. The force delivery mechanism or device for such a reagent application member can be the same as or substantially similar to that for a reagent application member comprising the first stopper ball 3306 and the second stopper ball 3307.

Figure 33D:
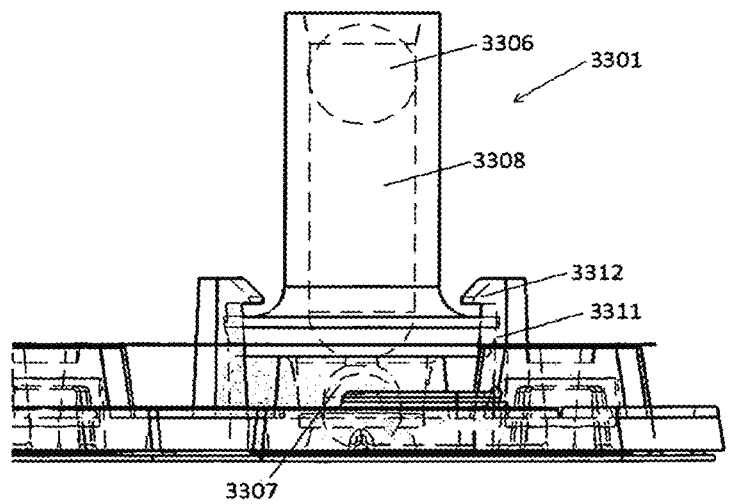

Referring to FIGS. 33C and 33D, the reagent delivery member (or reagent vessel/chamber) 3301 has a flange or collar 3309 that is configured to mate with a receptacle 3310 having two enclosing walls 3311 with protrusions 3312 for mating with the collar 3309. In an example, the reagent delivery member 3301 is configured to snap or press-fit in place.

Figure 33E:
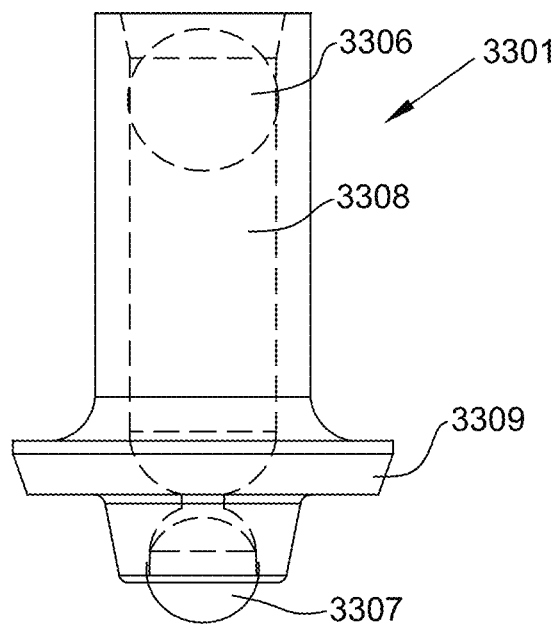

Referring to FIG. 33D, the first stopper ball 3306 is in fluid communication with the second stopper ball 3307 through the receptacle (e.g., a column or tube) 3308 (which includes a chamber for holding a reagent). In the example, the stopper balls 3306 and 3307 are in contact with walls of the reagent delivery member 3301, which configuration may not permit fluid flow. The configuration of the stopper balls 3306 and 3307 in such a case is shown in FIG. 33E.

Figure 33F:
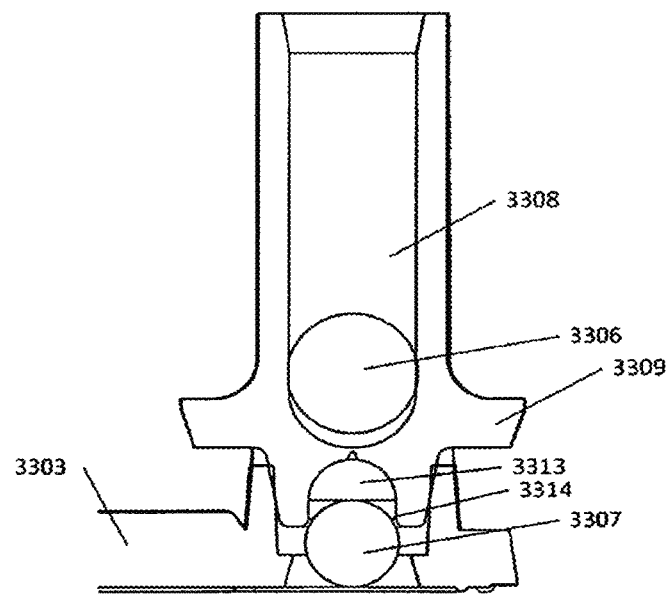

Upon the application of positive pressure to the first stopper ball 3306 or negative pressure to the second stopper ball 3307, fluid flow from the receptacle (e.g., a column or tube) 3308 into the channel 3303 and subsequently the thermocycling chamber 3302. In some embodiments, upon the application of positive pressure to the first stopper ball 3306, the first stopper ball moves along the receptacle (e.g., a column or tube) 3308 toward the second stopper ball 3307, as shown in FIG. 33F. Fluid pressure drives the second stopper ball 3307 out of a holding chamber 3313 having the second stopper ball 3307, thereby providing a fluid flow path 3314 around the second stopper ball 3307. Fluid will subsequently flow to the channel 3303.

In some embodiments, the reagent delivery member (or reagent vessel/chamber) 3301 can effect fluid mixing. For instance, the second stopper ball 3307 can be moved by a plunger (e.g., attached to a plunger) that enables the second stopper ball 3307 to retract into the holding chamber 3313. Alternatively, the second stopper ball can be replaced with a plunger. During use, the second ball 3307 can be expelled from the holding chamber 3313 upon the application of pressure to the second stopper ball 3307 and subsequently retracted into the holding chamber 3313. Accordingly, fluid can be expelled from the holding chamber 3313 and retracted into the holding chamber (e.g., from the channel 3303), which effects fluid mixing.

Nucleic acid amplification premixes can be delivered to a sample in liquid form. The reagent delivery (or application) member 3301 of FIGS. 33A-33F, for instance, is configured to deliver a liquid premix. In some embodiments, PCR reagents in liquid form are stored in a vial connected to the amplification reaction chamber via a delivery channel. The vial can be sealed at the bottom by a ball made of a suitable material (e.g., a rubber or plastic) and at the top by a second ball or a plunger made of a suitable material (e.g., a rubber or plastic). The liquid PCR reagents are delivered to the reaction chamber by pushing on the top ball or the plunger to break the seal formed by the lower ball, thereby delivering the liquid PCR reagents from the vial, through the delivery channel and to the reaction chamber.

The PCR vial, the top seal of the vial (e.g., a movable object such as a ball or plunger) and the bottom seal of the vial (e.g., a movable object such as a ball or plug, or a breakable seal) can independently be made of any suitable material (e.g., one or more polymers) using any suitable method (e.g., injection molding). For example, the PCR vial, the top seal of the vial (e.g., a ball or plunger) and the bottom seal of the vial (e.g., a ball or plug, or a breakable seal) can independently be composed of one or more polymers selected from cycloolefin polymers and copolymers, rubbers (e.g., natural and synthetic rubbers, such as liquid silicone rubber), plastics, ethylene propylene diene monomer (EPDM) copolymer, polypropylene, polyoxymethylene, and hydrophobic materials described herein. The selection of material can depend on factors such as ease of manufacturing (e.g., injection molding), PCR compatibility, etc. In some embodiments, the PCR vial is composed of a plastic (e.g., polypropylene or a cycloolefin polymer or copolymer). In certain embodiments, the top seal of the vial (e.g., a ball or plunger) and the bottom seal of the vial (e.g., a ball or plug, or a breakable seal) are composed of a plastic (e.g., EPDM copolymer or polypropylene). In further embodiments, the top seal of the vial (e.g., a ball or plunger) and the bottom seal of the vial (e.g., a ball or plug, or a breakable seal) are composed of a rubber or a hydrophobic material (e.g., a fluorinated or perfluorinated polymer, such as Teflon®). In additional embodiments, the surface of the top seal of the vial (e.g., a ball or plunger) and the surface of the bottom seal of the vial (e.g., a ball or plug, or a breakable seal) comprise a layer or coating of a hydrophobic material (e.g., a fluorinated or perfluorinated polymer, such as Teflon®).

Prolonged storage of PCR reagents in liquid form at ambient temperature may potentially result in degradation of PCR primers, which may lead to non-specific amplification and reduced amplification efficiency. To minimize degradation of a reagent, in some embodiments PCR reagents (or reagents for other chemical or biochemical reactions) in liquid form are stored at about 4° C. or cooler (lower), or stored in separate chambers or receptacles at ambient temperature or lower, or stored in a substantially anhydrous fluid medium at ambient temperature or lower. For example, reagents for performing a reaction (e.g., PCR) can be preserved at ambient temperature or lower in a substantially anhydrous non-ionic organic solvent (e.g., an alcohol solvent) or in a substantially anhydrous ionic organic solvent (e.g., a deep eutectic solvent) comprising an organic salt and an organic hydrogen bond donor, as described in U.S. Provisional Patent Application No. 61/709,417, which is incorporated herein by reference in its entirety. In other embodiments, PCR reagents or reagents for other chemical or biochemical reactions are stored in a solid or semi-solid form (e.g., dehydrated or lyophilized form), a dry form or other stabilized form at ambient temperature or lower, which can be hydrated for use in chemical or biochemical reactions as appropriate.

1. Storage of Reagents in Separate Chambers or Containers

To minimize degradation of any PCR reagent stored in liquid form, in some embodiments one or more pairs of forward and reverse primers (which can be labeled with the same dye or different dyes, such as fluorescent dyes) are stored separately from other PCR reagents (such as a polymerase (e.g., a DNA polymerase), nucleotides (e.g., deoxynucleotide triphosphates), and optionally other reagents (e.g., a buffer and a metal salt, such as magnesium chloride)) at ambient temperature or cooler (lower) and then mixed with the other PCR reagents shortly before PCR amplification is conducted. In some embodiments, one or more pairs of forward and reverse primers (which can be labeled with the same dye or different dyes, such as fluorescent dyes) and other PCR reagents (e.g., a polymerase, such as a DNA polymerase, and nucleotides, such as deoxynucleotide triphosphates) are stored in liquid form in separate chambers of a container (e.g., a cartridge having two or more chambers, or a vial partitioned into two chambers) or in separate containers (e.g., vials). In certain embodiments, the PCR reagents stored in liquid form in separate chambers or containers at ambient temperature or lower are stable for at least about 3 months, 6 months, 1 year, 1.5 years or 2 years.

Figure 57B:
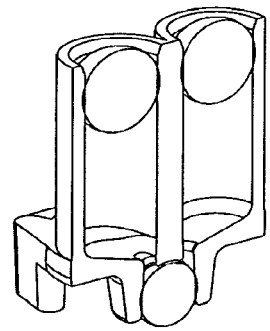
Figure 58:
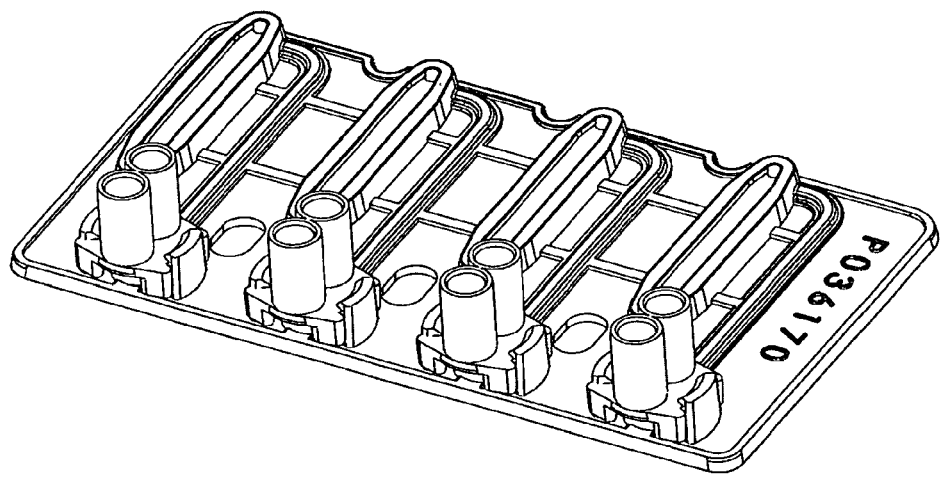
FIG. 58 shows an embodiment of four two-chamber reagent vials integrated with four reaction chambers.

FIGS. 57A and B illustrate embodiments of a PCR vial containing PCR reagents in two separate chambers, and FIG. 58 shows an embodiment of four two-chamber PCR vials integrated with four PCR reaction chambers. In some embodiments, a two-chamber vial contains one or more dye-labeled primers in one chamber and contains other PCR reagents (such as a polymerase (e.g., a DNA polymerase), nucleotides (e.g., deoxynucleotide triphosphates), and optionally other reagents (e.g., a buffer and a metal salt, such as magnesium chloride)) in the other chamber. FIG. 57A shows an embodiment of a two-chamber vial in which a plunger forms an upper seal of each chamber of the vial, but the upper seal of each chamber can have another configuration (e.g., a movable object in the form of a ball). There is no fluidic communication between the two chambers of the vial because the two chambers are partitioned from one another and the bottom seal of each chamber prevents liquid from leaking from the bottom of each chamber. In certain embodiments, a movable object (e.g., a ball or plug) or a breakable seal composed of a suitable material (e.g., a polymeric material, which can be the same polymeric material composing the vial) at the bottom of the two chambers of the vial seals the bottom of each chamber. FIG. 57B shows an embodiment of a two-chamber vial in which a ball forms an upper seal of each chamber of the vial and a ball at the bottom of the two chambers of the vial seals the bottom of each chamber. In certain embodiments, the volume of each chamber of the vial is about 50-150 µL or about 80-100 µL and about 10-50 µL or about 10-30 µL of liquid is stored in each chamber. In other embodiments, the volume of liquid in each of the chambers of the vial is less than about 10 !AL. The volume of liquid in each of the chambers of the vial can be the same or different. If each chamber of the vial contains a movable object (e.g., a plunger or ball) that acts to seal the top of each chamber, depressing the plunger or ball with sufficient force releases the liquid content out of each chamber by dislodging a movable object (e.g., a ball or plug) or breaking a seal at the bottom of the two chambers of the vial. The flow rate of the liquid contents from the two chambers can be the same if the force applied to the plungers or upper balls of the two chambers is the same. The flow rates of the liquid contents from the two chambers can also be different if the forces applied to the plungers or upper balls of the two chambers are different, or if the dimensions (such as the cross-sectional dimension (e.g., diameter) and/or the length) of the two chambers are different, which may be useful in effecting different mixing ratios between the two liquid contents. The liquid contents of the two chambers of the vial can also mix in the reaction chamber.

Figure 59A:
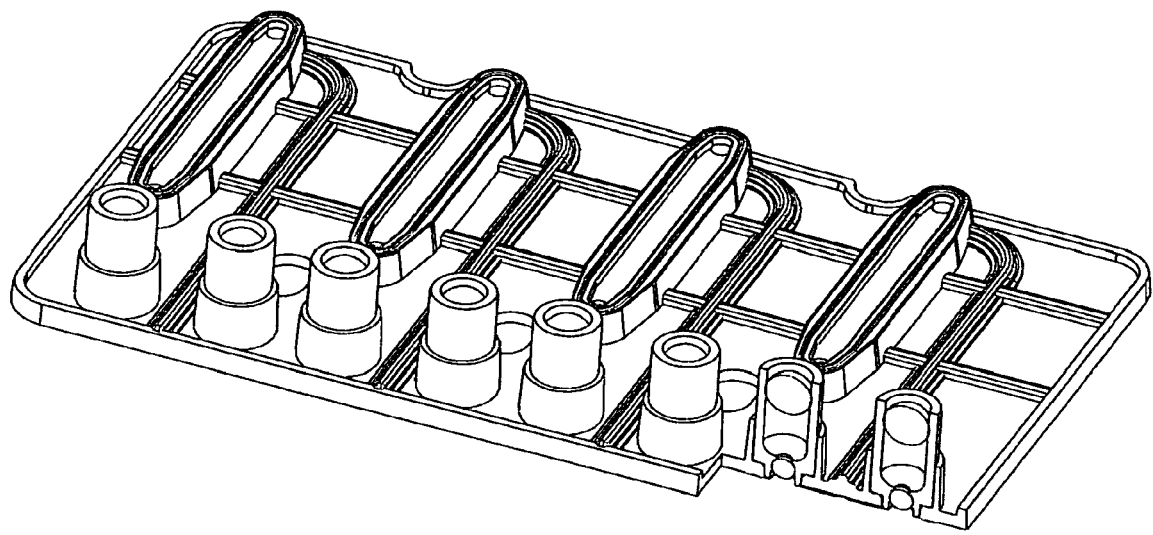
FIGS. 59A and B are top and bottom views of an embodiment of two vials containing reagents for performing a reaction (e.g., PCR) in two separate vials, a pair of reagent vials for each of four reaction chambers.
Figure 59B:
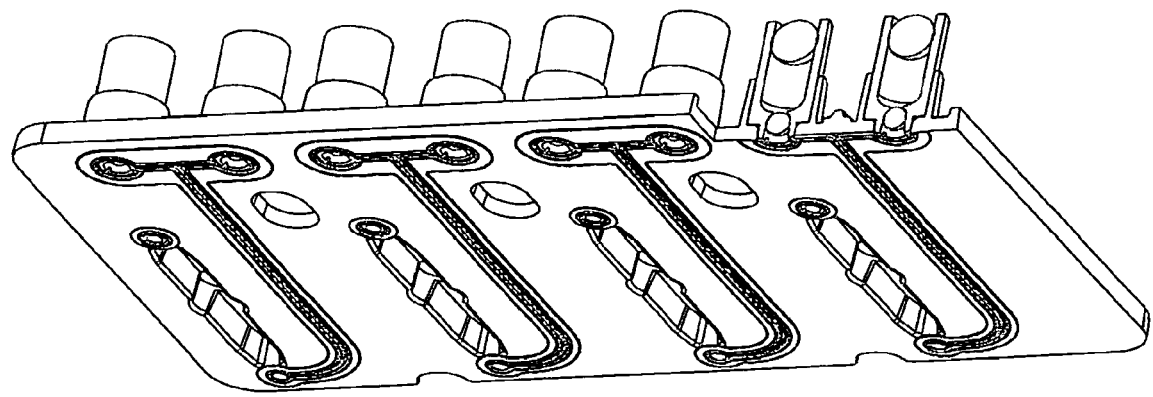

In additional embodiments, one or more pairs of forward and reverse primers (which can be labeled with the same dye or different dyes, such as fluorescent dyes) are stored separately from other PCR reagents (such as a polymerase (e.g., a DNA polymerase), nucleotides (e.g., deoxynucleotide triphosphates), and optionally other reagents (e.g., a buffer and a metal salt, such as magnesium chloride)) in separate containers (e.g., vials) at ambient temperature or lower. FIGS. 59A and B are top and bottom views of an embodiment in which PCR reagents are stored in two separate vials, where each vial has a bigger ball that seals the top of the vial and a smaller ball that seals the bottom of the vial, as shown in the cut-away view of the far-right pair of vials. The upper seal of each vial can also have another configuration (e.g., a movable object in the form of a plunger), and the bottom seal of each vial can also have another configuration (e.g., a movable object in the form of a plug, or a breakable seal composed of a suitable material (e.g., a polymeric material, which can be the same polymeric material composing the vial)). FIGS. 59A and B show a pair of PCR premix vials integrated with each of four reaction chambers. Each vial can be attached by being, e.g., snapped or press-fitted into place. The disclosure above relating to embodiments of the two-chamber vial also applies to two-vial embodiments. Depressing the upper movable object (e.g., a ball or plunger) with sufficient force forces the liquid content out of each vial by dislodging a movable object (e.g., a ball or plug) or breaking a seal at the bottom of the vial. The liquid contents of a pair of vials can converge in a channel that leads to a reaction chamber (as shown in FIG. 59B), and the liquid contents of the two vials can mix when they converge at the channel and/or mix in the reaction chamber. Alternatively, the liquid content of each vial in a pair can be delivered to a reaction chamber through a separate channel, and the liquid contents of the two vials in the pair can mix in the reaction chamber. The flow rate of the liquid contents from the two vials can be the same if the force applied to the upper movable object (e.g., a ball or plunger) of the two vials is the same. The flow rates of the liquid contents from the two vials can also be different if the forces applied to the upper movable object (e.g., a ball or plunger) of the two vials are different, or if the dimensions (such as the cross-sectional dimension (e.g., diameter) and/or the length) of the two vials are different, which may be useful in effecting different mixing ratios between the two liquid contents. The liquid contents of a pair of vials, or all pairs of vials, can be delivered from the vials simultaneously or in any desired sequence. Furthermore, the amount of liquid content released from any vial can be controlled.

Advantages of the two-vial embodiments or the two-chamber vial embodiments described herein include the ability to independently control the amount delivered, the rate of delivery and the timing of delivery of the liquid content from each of the two vials or from each of the two chambers of a vial (e.g., if a breakable seal seals the bottom of each chamber of the two-chamber vial). For example, the liquid content from each of the two vials among one or more pairs of vials, or the liquid content from each of the two chambers of a vial among one or more two-chamber vials, can be delivered in the same amount or different amounts, at the same rate or different rates, or at the same time or different times, or any combination thereof.

Reagents for performing any chemical or biochemical reaction can be stored in liquid form or other forms in multiple chambers or containers (e.g., vials) at ambient temperature or lower (e.g., about 4° C. or lower), if desired. For example, the two-chamber vials of FIGS. 57A and B and the two-vial embodiment of FIG. 59 can be used to store reagents for performing any chemical or biochemical reaction in liquid form or other forms at ambient temperature or lower (e.g., about 4° C. or lower).

2. Use of Dehydrated or Lyophilized Reagents

In additional embodiments, PCR reagents or reagents for other chemical or biochemical reactions are stored in a solid, semi-solid, dry, dehydrated or lyophilized (freeze-dried) form, which can be stored at ambient temperature or lower and can be hydrated for use in chemical or biochemical reactions as appropriate. In some embodiments, PCR reagents or reagents for other chemical or biochemical reactions are provided in the form of a lyosphere, which is configured to dissolve (e.g., at least about 70%, 80%, 90%, 95% or 99% by mass) in a liquid (e.g., water, a buffer or a sample-containing liquid). A lyosphere is a composition containing one or more lyophilized reagents, and can have any suitable shape and dimensions (e.g., a substantially spherical pellet having a diameter of about 1-5 mm, or about 1, 2, 3, 4 or 5 mm). Reagents in a lyosphere can be prepared for use in a reaction by hydrating the lyosphere.

Figure 60:
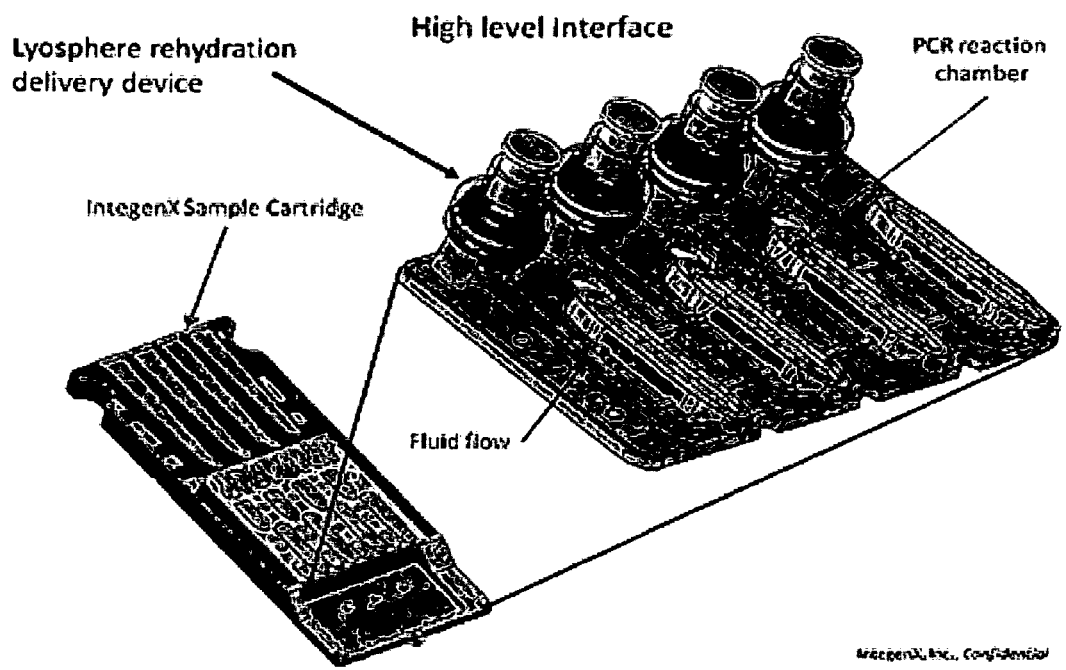
FIG. 60 illustrates an embodiment of a sample cartridge comprising four reaction (e.g., PCR) chambers that are integrated with four lyosphere rehydration delivery devices.

In some embodiments, a lyosphere is delivered for use in a chemical or biochemical reaction (e.g., PCR) with the aid of a rehydration delivery device. FIG. 60 shows an embodiment of a sample cartridge having four reaction chambers and four rehydration delivery devices, each rehydration delivery device comprising a blister pack containing a lyosphere. In the embodiment of FIG. 60, each rehydration delivery device is in fluidic communication with a reaction chamber and delivers reagents for performing a reaction (e.g., PCR) to the reaction chamber.

Figure 62:
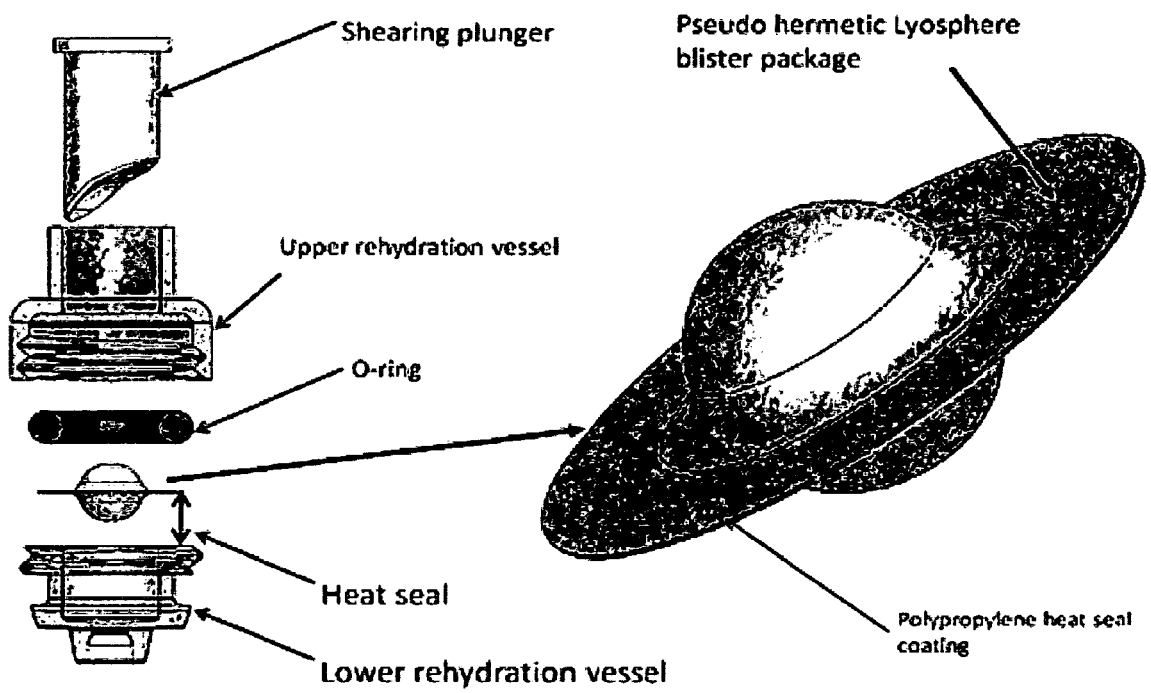
FIG. 62 shows an exploded view of an embodiment of a lyosphere rehydration delivery device and an enlarged view of a pseudo-hermetic blister pack.
Figure 63:
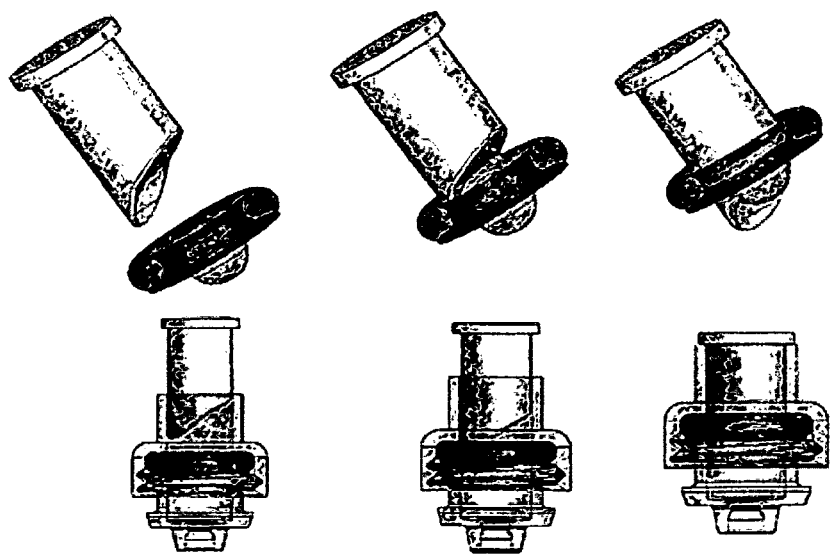
FIG. 63 shows various states of an embodiment of actuation of a lyosphere rehydration delivery device.

FIGS. 60, 62 and 63 illustrate embodiments of a lyosphere rehydration delivery device. The lyosphere rehydration delivery device comprises:
(a) a shearing plunger comprising:
   (1) a recess that engages a container having a lyosphere;
   (2) a shearing edge for shearing the container; and
   (3) a sealing surface for engaging an O-ring;
(b) a first (upper) vessel comprising:
   (1) a bore adapted to engage the shearing plunger; and
   (2) a seat to engage an O-ring;
(c) a second (lower) vessel adjacent to the first vessel, the second vessel having a chamber in fluidic communication with an exit port and configured to receive a container having a lyosphere;
(d) an O-ring engaged with or in the seat, the O-ring being capable of sealing against the sealing surface; and
(e) a container having a lyosphere, wherein the container is disposed between the O-ring and the second vessel. Actuation of the shearing plunger opens the container to deliver the lyosphere into the chamber of the second vessel, and forms a seal between the O-ring and the sealing surface, thereby sealing the chamber. The lyosphere is rehydrated by actuating the shearing plunger to deliver the lyosphere to the chamber of the second vessel, which can be pre-filled with a liquid (e.g., water or a buffer) or into which a liquid (e.g., water, a buffer or sample-containing liquid) can be pumped.

In the embodiment of FIG. 60, the lyosphere rehydration delivery devices can be snapped or press-fitted onto the sample cartridge, and can be removed from the cartridge after sample processing and analysis. This allows the rehydration delivery devices and the cartridge to be shipped in separate kits if desired and to be assembled prior to use.

Figure 61:
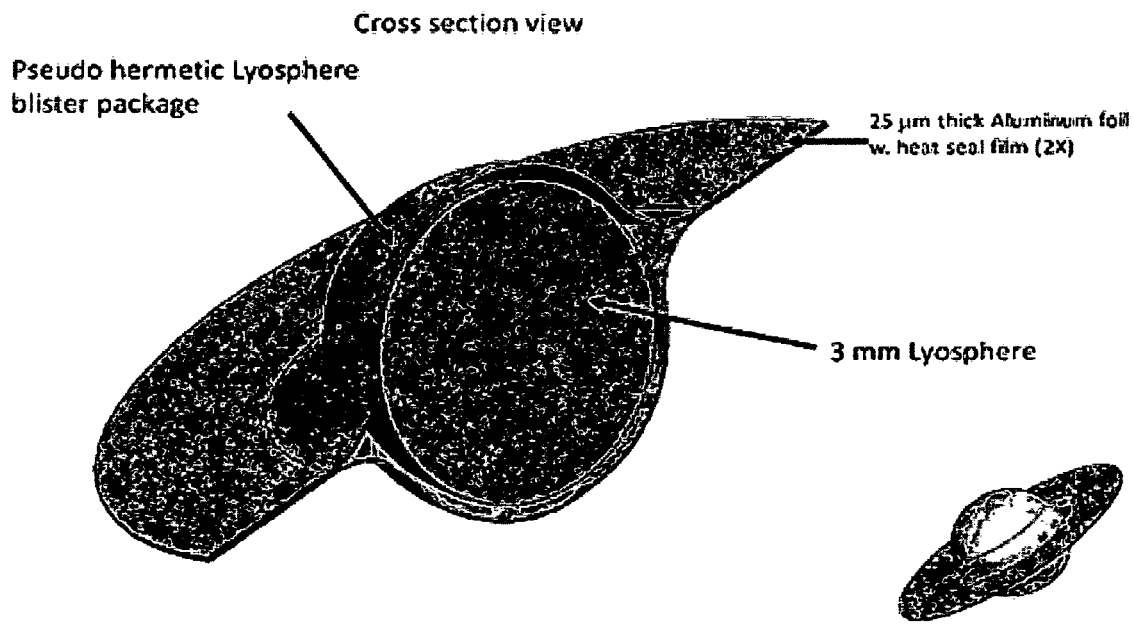
FIG. 61 shows a cross-section of an embodiment of a blister package (or pack) containing a lyosphere.

FIG. 61 depicts an embodiment of a blister pack containing a lyosphere, which can be provided in a rehydration delivery device. The blister pack includes a lyosphere that is enclosed in a container comprising one or more (e.g., two) layers of a polymeric or metallic material (e.g., aluminum in the embodiment of FIG. 61). The blister pack can enclose the lyosphere in a hermetic or pseudo-hermetic configuration. In certain embodiments, one or more layers of a metallic material (e.g., aluminum) forming the container of the blister pack are welded together, which can form a hermetic seal between the lyosphere and the external environment. In other embodiments, the one or more layers of a polymeric or metallic material forming the container of the blister pack are sealed (e.g., heat-sealed) together with the aid of a polymeric or metallic material (e.g., a polypropylene heat-seal coating in the embodiment of FIG. 62) or by joining the one or more layers of the polymeric or metallic Material together (e.g., by heating the one or more layers), which can form a hermetic or pseudo-hermetic seal. If a polymeric material (e.g., polypropylene) is used to seal the blister pack, the polymeric material can aid in securing the blister pack to the outer lip of the lower rehydration vessel during assembly of the rehydration delivery device (as shown in FIG. 62).

FIG. 62 shows an exploded view of an embodiment of a lyosphere rehydration delivery device. The delivery device comprises, from top to bottom, a shearing plunger, an upper rehydration vessel, an O-ring, a blister pack containing a lyosphere, and a lower rehydration vessel having a chamber. The O-ring can be composed of a polymeric material (e.g., a natural or synthetic rubber). The lower rehydration vessel comprises an outer lip and an inner lip. In an embodiment, the blister pack is heat-sealed to the outer lip, e.g., by heating the blister pack during assembly such that the polymeric material (e.g., polypropylene) used to seal the blister pack flows to the outer lip to form a seal upon drying. The inner lip of the lower rehydration vessel is configured to come into contact with the O-ring, thereby sealing the chamber of the lower rehydration vessel.

FIG. 63 shows various stages (or states) of actuation of a lyosphere rehydration delivery device. In an initial sealed state (left figure), the shearing plunger is disposed away from the blister pack, which is bounded by the O-ring. The blister pack initially seals on the O-ring and prevents flow of any fluid through a channel connected to the rehydration delivery device if the bottom of the device is not sealed by a movable object (e.g., a ball or plug) or a breakable seal. In a vented exposed state (middle figure), the plunger contacts the blister pack, thereby shearing (or cutting) the one or more polymeric or metallic layers forming the container of the blister pack which holds the lyosphere. The lyosphere moves to the chamber of the lower rehydration vessel and comes into contact with a liquid. In certain embodiments, the chamber of the lower rehydration vessel is pre-filled with a liquid (e.g., water or a buffer). In such embodiments, a movable object (e.g., a ball or plug), or a breakable seal, made of a suitable material (e.g., a polymeric material such as a rubber) can be used to seal the bottom of the lower rehydration vessel prior to delivery of the reagents in the lyosphere to the reaction chamber, and the blister pack can have one or more layers of a metallic material (e.g., aluminum) enclosing the lyosphere. In other embodiments, the bottom of the lower rehydration vessel is not sealed, and a liquid (e.g., water or a buffer) is pumped into the chamber of the lower vessel from a reservoir or container off or on the sample cartridge (e.g., from a wash chamber, the diluent chamber or the lysis reagent storage/waste chamber of the sample cartridge) once the lyosphere is in the chamber. In certain embodiments, one or more vent grooves on an inner surface of the lower rehydration vessel create a vent path to the external environment as the shearing plunger slides down and moves the lyosphere to the lower vessel. The vent path allows gas inside the rehydration delivery device to escape into the external environment as a liquid is pumped into the chamber of the lower rehydration vessel. Contact of the liquid with the lyophilized reagents results in dissolution of (e.g., at Least about 70%, 80%, 90%, 95% or 99% of) the reagents. In a sealed state (right figure), as the shearing plunger is substantially completely depressed to deliver the rehydrated reagents to the reaction chamber to perform a reaction (e.g., PCR), the plunger seals on the 0-ring (e.g., a lip portion of the plunger presses against the 0-ring, which action forms a seal between the 0-ring and the inner lip of the lower rehydration vessel). The seal prevents flow of fluid from the reaction chamber to the rehydration delivery device, prevents air from entering the reaction system through the delivery device, and prevents gas or vapor from leaving the chamber of the lower rehydration vessel, during the reaction (e.g., nucleic acid amplification) that may involve heating and cooling.

FIGS. 70A and 70B illustrate additional embodiments of receptacles for storing, rehydrating and delivering a solid or semi-solid (e.g., dehydrated or lyophilized) composition comprising one or more reagents for performing a reaction (e.g., PCR). In the embodiments of FIGS. 70A and 70B, receptacles 7000A and 7000B are configured as vials and comprise a lyosphere 7050 containing reagents. Receptacle 7000A comprises a movable object 7010 in the form of a ball that seals the top of the receptacle, and receptacle 7000B comprises a movable object 7010 in the form of a plunger that seals the top of the receptacle. In certain embodiments, receptacles 7000A and 7000B comprise a second movable object (e.g., a ball or plug), or a breakable seal made of a suitable material (e.g., a polymeric material), that seals the bottom of the receptacles (not shown). In other embodiments, receptacles 7000A and 7000B are not manufactured with a bottom seal, and after being manufactured, the receptacles containing a lyosphere can be protected from moisture by being stored in a sealed container (e.g., a pouch) that can include a desiccant, and can later be removably attached to a cartridge comprising a reaction chamber, which assembly can also be stored in a sealed container. Receptacles 7000A and 7000B further comprise a vent groove 7020 that creates a vent path as ball or plunger 7010 is depressed and dislodges or breaks the bottom seal of the receptacles. A receptacle can have one or more vent grooves, and a vent groove can be located in any position and can have any configuration and dimensions (e.g., an indentation on an inner surface of the receptacle in the form of a channel that can have any suitable width, depth and length) suitable for creating an initial sealed state, an intermediate vented state during rehydration, and a final sealed state for the receptacle. Furthermore, receptacles 7000A and 7000B can have a flange 7030 for snapping or press-fitting the receptacles onto a container (e.g., the sample cartridge described herein) comprising a chamber for performing a reaction. When removably attached to a sample cartridge, receptacles 7000A and 7000B are initially sealed, e.g., because the upper end of vent groove 7020 is below the area where ball 7010 initially contacts receptacle 7000A or because the upper end of vent groove 7020 is below the area where the upper end of plunger 7010 initially contacts receptacle 7000B (vent groove 7020 need not extend to the top of the receptacles). If receptacles 7000A and 7000B comprise a second movable object (e.g., a ball or plug) or a breakable seal that seals the bottom of the receptacles, depression of ball or plunger 7010 with sufficient force to dislodge the second movable object or to break the breakable seal creates a vent path between the lower portion of the receptacle containing the lyophilized reagents and the external environment. Alternatively, if the receptacles were not manufactured with a bottom seal, depression of ball or plunger 7010 by a sufficient distance down the receptacles creates such a vent path. The reagents are rehydrated by pumping a liquid (e.g., water or a buffer) into the lower portion of the receptacle from a reservoir or container off or on the sample cartridge (e.g., from a wash chamber, the diluent chamber or the lysis reagent storage/waste chamber of the sample cartridge). The position of ball or plunger 7010 in the rehydration/vent phase, along with the dimensions of the lower portion of the receptacle containing the reagents, establishes a liquid volume of the receptacle. As ball or plunger 7010 is substantially completely depressed to dispense the rehydrated reagents into a reaction chamber, ball or plunger 7010 seals the receptacle (e.g., because vent groove 7020 is above the area where ball 7010 contacts receptacle 7000A, or because vent groove 7020 is above the area where the lower end of plunger 7010 contacts receptacle 7000B). The seal prevents flow of fluid from the reaction chamber to the receptacle and prevents air from entering the reaction system through the receptacle during the reaction.

Liquid may potentially leak out of a rehydration receptacle (e.g., the rehydration delivery device of FIG. 62 or the receptacles of FIG. 70) during the rehydration step when the receptacle is in a vented state. To minimize or prevent leakage of liquid through the vent path during the rehydration step, in some embodiments a low-flow resistance path (e.g., in the microfluidic device of the sample cartridge) is opened or created once the receptacle is substantially or nearly filled with rehydration solution to slow down the filling rate of the receptacle.

Figure 64A:
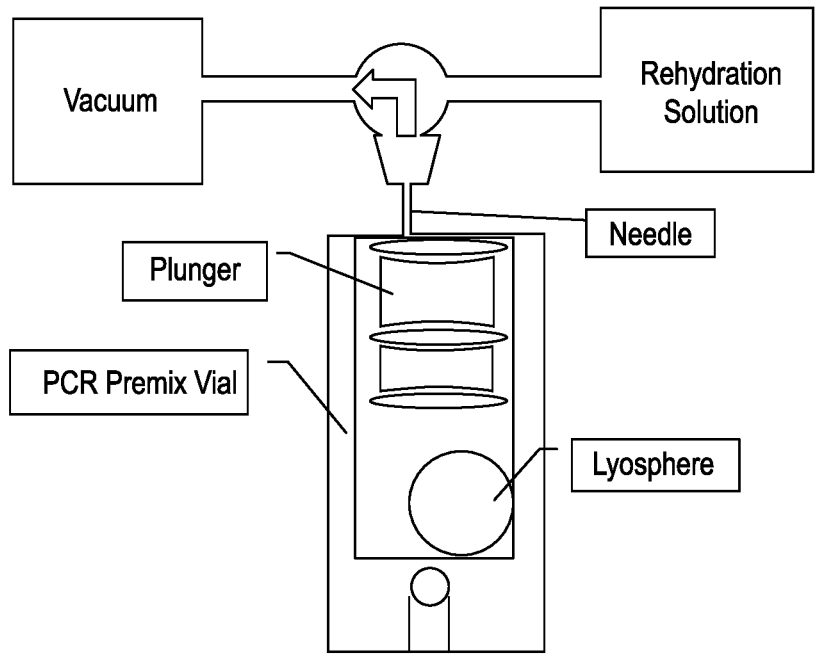
FIGS. 64A to 64C describe embodiments in which a lyosphere comprising PCR reagents and contained in a premix vial is rehydrated by a lyosphere rehydrating device that can be off or integrated with an instrument.
Figure 64B:
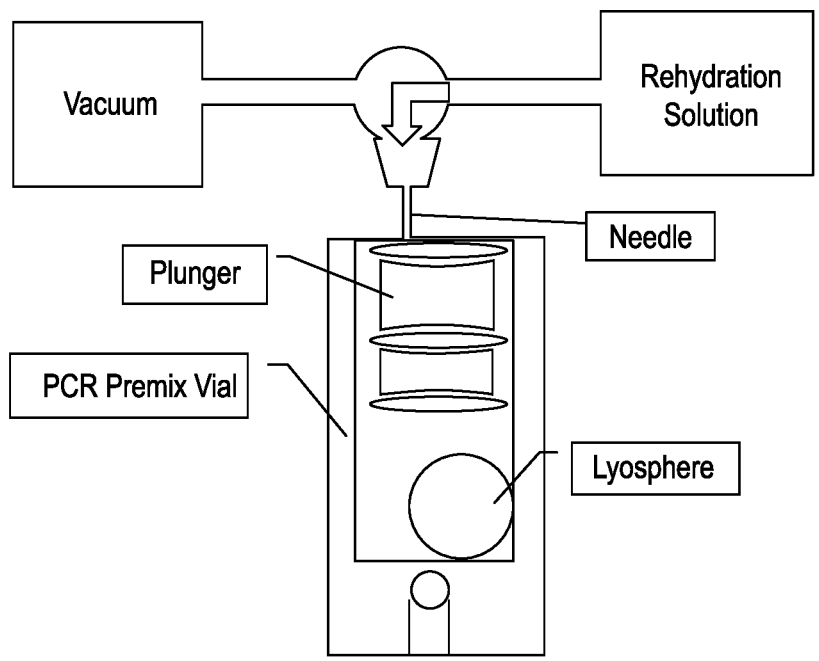
Figure 64C:
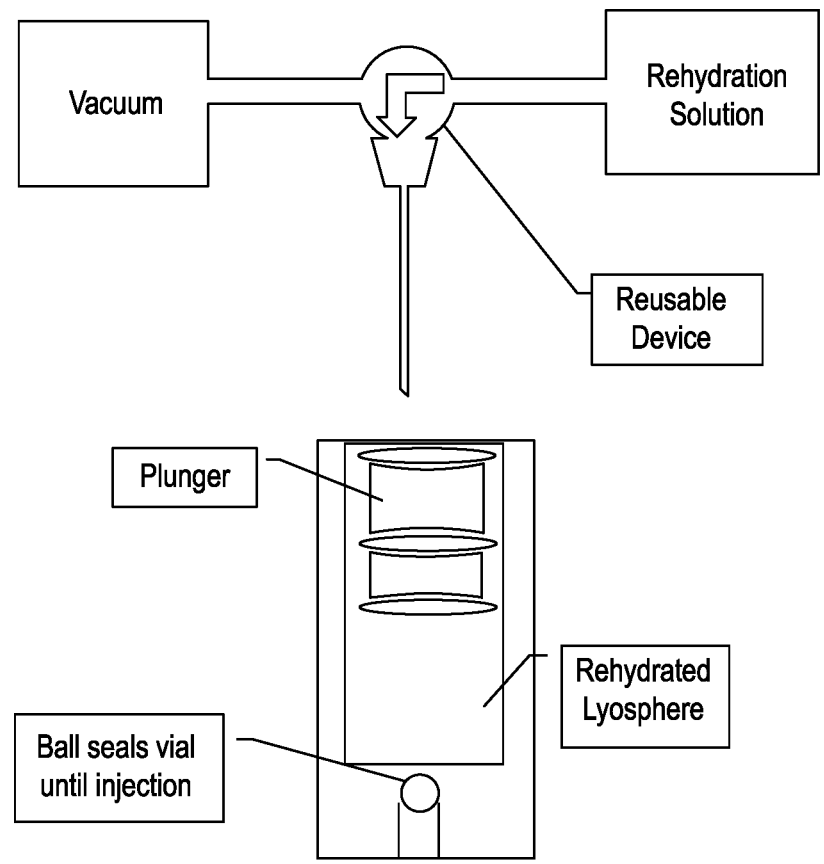

FIGS. 64A to 64C describe embodiments in which a lyosphere comprising reagents for performing a reaction (e.g., PCR) and stored in a container (e.g., a vial) is rehydrated by a lyosphere rehydration device that can be off or integrated with the instrument or system described herein. A lyosphere can be contained in a container attached to a sample cartridge that is stored in a desiccated package (e.g., a foil bag), or a lyosphere can be contained in a container that is stored in a desiccated package and is later attached to a sample cartridge. In FIG. 64A, the premix vial is sealed at the bottom by a movable object (e.g., a ball or plug), or a breakable seal, made of a suitable material (e.g., a polymeric material such as a rubber) and is sealed at the top by a movable object (e.g., a plunger) made of a suitable material (e.g., a polymeric material such as a rubber). If a plunger seals the top of the vial, the plunger is configured as a piercable septum so that a needle can pierce through the septum, and the septum can re-seal itself while the needle is inserted through the septum or after the needle is removed. Just before a premix vial or a sample cartridge is used, a needle made of a suitable material (e.g, stainless steel) is inserted through the plunger of the vial to subject the inside of the vial to vacuum. Alternatively, a needle can be inserted into a premix vial before use of the vial (e.g., at the time of manufacture), and the resulting assembly of needle and vial can be sealed off from the environment by being placed in a sealed container (e.g., a foil bag) during storage. The valve of the lyosphere rehydration device is then switched from vacuum, and the device delivers a rehydration solution (e.g., an aqueous solution that can contain only water, or optionally can also contain other solvent(s) and/or reagent(s) (e.g., a buffer and/or a metal salt such as magnesium chloride)) to the premix vial to rehydrate the lyosphere (FIG. 64B). Metering of the rehydration solution can be accomplished by the volume of the space that the lyosphere is in, which may involve pre-crushing the lyosphere. Alternatively, the rehydration solution can be metered using a syringe drive, in which case the plunger can be advanced to fill the remaining void after the rehydration solution is dispensed. Before the rehydration solution substantially completely fills (e.g., about 70%, 80% or 90% of the volume of) the chamber of the premix vial, vacuum is re-applied to the vial to remove any dissolved gas from the liquid and gas from the remaining headspace in the vial. Vacuum can be re-applied to the vial one or more times to remove any gas remaining in the liquid and the vial before the rehydration solution completely fills the vial. If the initial introduction of rehydration solution into the premix vial generates a pendant droplet that bridges from the needle to the lyosphere, rehydration of the lyosphere may commence immediately and re-application of vacuum to the vial may draw liquid contaminated with dissolved reagents into the needle. Formation of a bridging droplet can be avoided by introducing an initial amount (e.g., about 5, 10 or 15 µL) of rehydration solution into the premix vial followed by a burst of a gas (e.g., about 10, 15, 20 or 25 µL of air). The air can be introduced into the premix vial through the source of vacuum that can also provide positive pressure or through a vent that is connected to the rehydration device (e.g., the rehydration device can have a third line connected to a vent or source of positive pressure (not shown)). Once the rehydration solution completely fills (e.g., more than about 95% or 99%, or about 100%, of the volume of) the chamber of the premix vial, the needle is removed from the vial (FIG. 64C). The method for rehydrating a lyosphere described herein minimizes the amount of air bubbles (e.g., no more than about 2, 1, 0.5 or 0.1 µL of air bubbles) or eliminates air bubbles in the resulting liquid containing rehydrated reagents. The presence of air bubbles may deleteriously affect the performance of a reaction such as PCR. Lyospheres in additional premix vials attached to the same sample cartridge can be rehydrated if desired, or lyospheres in additional premix vials can be rehydrated and then the vials can be attached to the same sample cartridge if desired. The lyosphere rehydration device can be reused, and the needle thereof can be discarded after a single use or can be reused after being washed with a decontamination solution (e.g., an aqueous solution of bleach) if desired. Once the lyospheres in the desired number (one or more) of premix vials are rehydrated, the liquid containing rehydrated reagents can be delivered to reaction chamber(s) of the cartridge by pushing down the plunger to generate sufficient pressure for dislodging the ball at the bottom of the vials.

Figure 65:
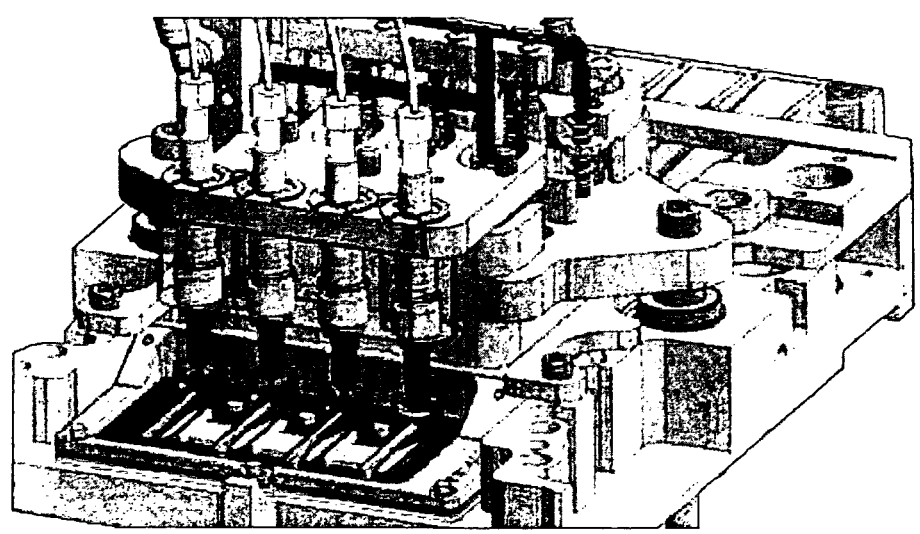
FIG. 65 depicts an embodiment of a needle press cartridge interface of a device or system that delivers reagents for performing a reaction (e.g., PCR).

In further embodiments, lyophilized reagents for performing a reaction (e.g., PCR) are stored within the instrument described herein and are rehydrated and delivered to cartridges by a reusable reagent (e.g., PCR reagent) delivery system that can be contained within the instrument or off the instrument and can be manually operated or controlled by the instrument's computer or a different device. The PCR reagent delivery system can rehydrate lyophilized PCR reagents and deliver them to multiple cartridges for multiple runs (e.g., 10, 50, or 100 or more runs). In some embodiments, a fluidics system incorporating a syringe pump for accurately metering volumes, a multiport valve providing one or more fluidic connectivities and a needle press cartridge interface rehydrates lyophilized PCR reagents stored within the instrument and delivers the rehydrated PCR reagents to the reaction chambers of a cartridge. FIG. 65 depicts an embodiment of the needle press cartridge interface that comprises a plurality of needles connected through tubing (e.g., Teflon® tubing) to a multiport valve. A needle pierces a septum of the cartridge and fluid is pumped, using a syringe pump, through the valve to the needle and ultimately to a reaction chamber. Volumes of rehydrated PCR reagents delivered to the reaction chambers can be about 10-100 µL and can be delivered serially, channel-by-channel, or in parallel. The septum which the needle pierces can be a molded feature of the cartridge and can be manufactured, e.g., using an injection co-molding technique, or can be a snap-in or press-fitted part. After the needle is withdrawn from the septum, the septum re-seals to prevent air leakage into or out of the cartridge. A spring mechanism controls the travel of the needle. The PCR reagent delivery system comprising the needle press cartridge interface can replace use of PCR vials or plungers. Alternatively or in addition to delivery of rehydrated lyophilized PCR reagents, the PCR reagent delivery system can deliver PCR reagents stored in liquid form (e.g., in water or a buffer, or in a substantially anhydrous fluid medium, as described in U.S. Provisional App. No. 61/709,417). In some embodiments, the PCR reagents are stored in the PCR reagent delivery system in liquid form (e.g., in water or a buffer) at 4° C. or lower, or in a substantially anhydrous fluid medium at ambient temperature or lower.

In other embodiments, a lyosphere filling device contains a sufficient amount of reagents for performing a reaction (e.g., PCR) in the form of lyospheres for multiple runs (e.g., 4, 10, 25, 50, or 100 or more runs). The device rehydrates the lyospheres with a rehydration solution (e.g., an aqueous solution that can contain only water, or optionally can also contain other solvent(s) and/or reagent(s) (e.g., a buffer and/or a metal salt such as magnesium chloride)) in the device, and then dispenses a solution of rehydrated reagents to multiple (e.g., 4, 10, 25, 50, or 100 or more) containers (e.g., vials) that are or can be attached to one or more sample cartridges. The lyosphere filling device can maintain the temperature of the rehydrated lyosphere solution below ambient temperature (e.g., at about 4° C.) to improve the stability of the reagents (e.g., PCR reagents). The lyosphere filling device can be off or integrated with the instrument or system described herein.

The devices and systems described herein for storing, rehydrating and delivering lyospheres or lyophilized reagents can also be used to store, rehydrate and deliver reagents in other solid, semi-solid, dry, dehydrated or stabilized forms, and can be used with any device or instrument configured to perform a function or reaction. The reagents can be used to perform any desired function (e.g., GenTegra™ reagents (from IntegenX Inc., Pleasanton, Calif.) for stabilizing DNA and RNA) or any desired chemical or biochemical reaction (e.g., PowerPlex® 16 reagents (from Promega Corporation, Madison, Wis.) for performing PCR, and Ready-to-Go® reagents (from GE Healthcare, Pittsburgh, Pa.) for performing DNA ligation, PCR, etc.). Furthermore, the reagents can be rehydrated and delivered to any desired destination (e.g., any desired chamber of the sample cartridge described herein).

D. Cartridge Module Assembly

Figure 3:
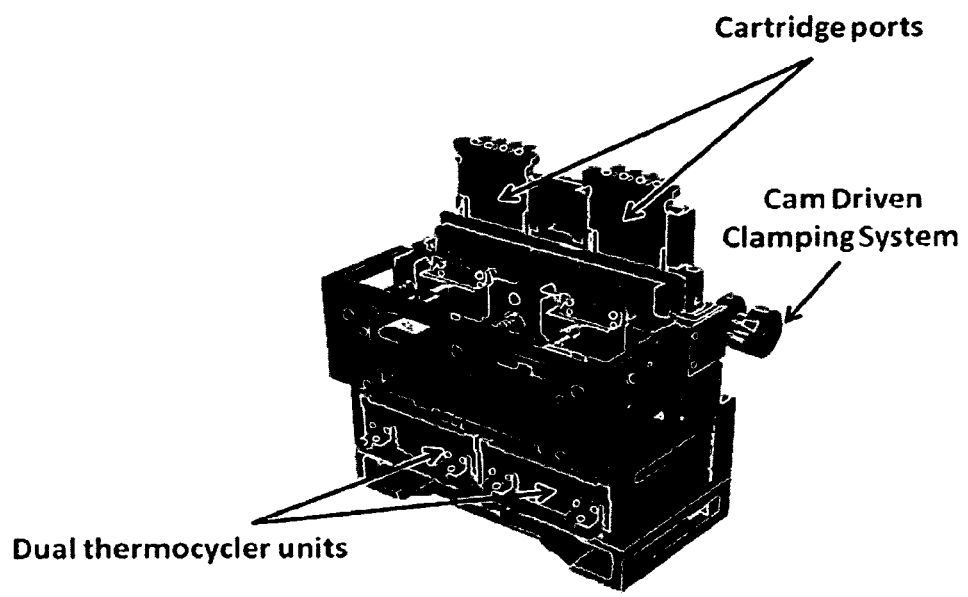
FIG. 3 shows an embodiment of a sample cartridge interface module.
Figure 39:
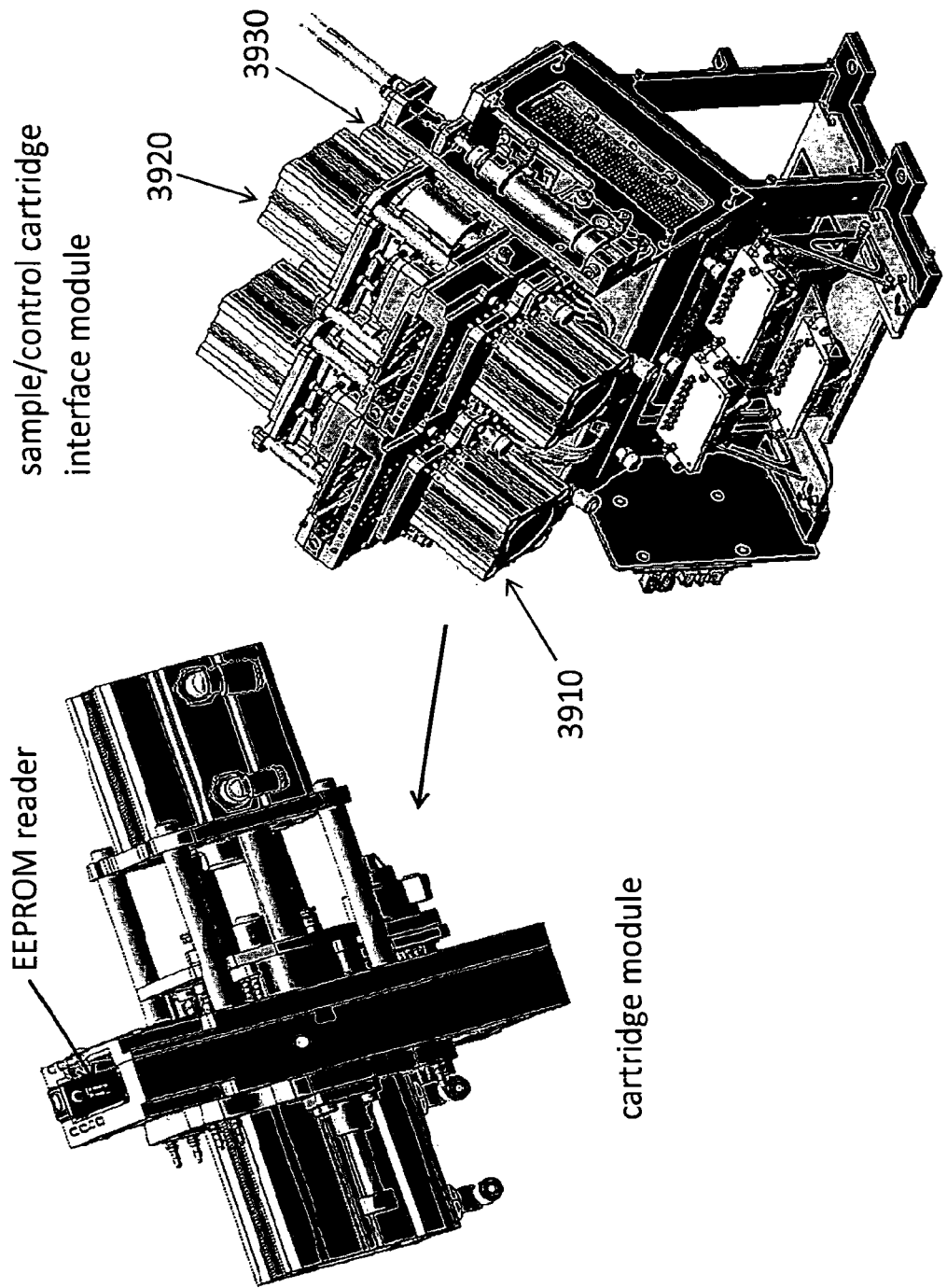
FIG. 39 depicts an embodiment of a cartridge module and a sample/control cartridge interface module having two cartridge modules for accepting two sample cartridges or a sample cartridge and a control cartridge.
Figure 40:
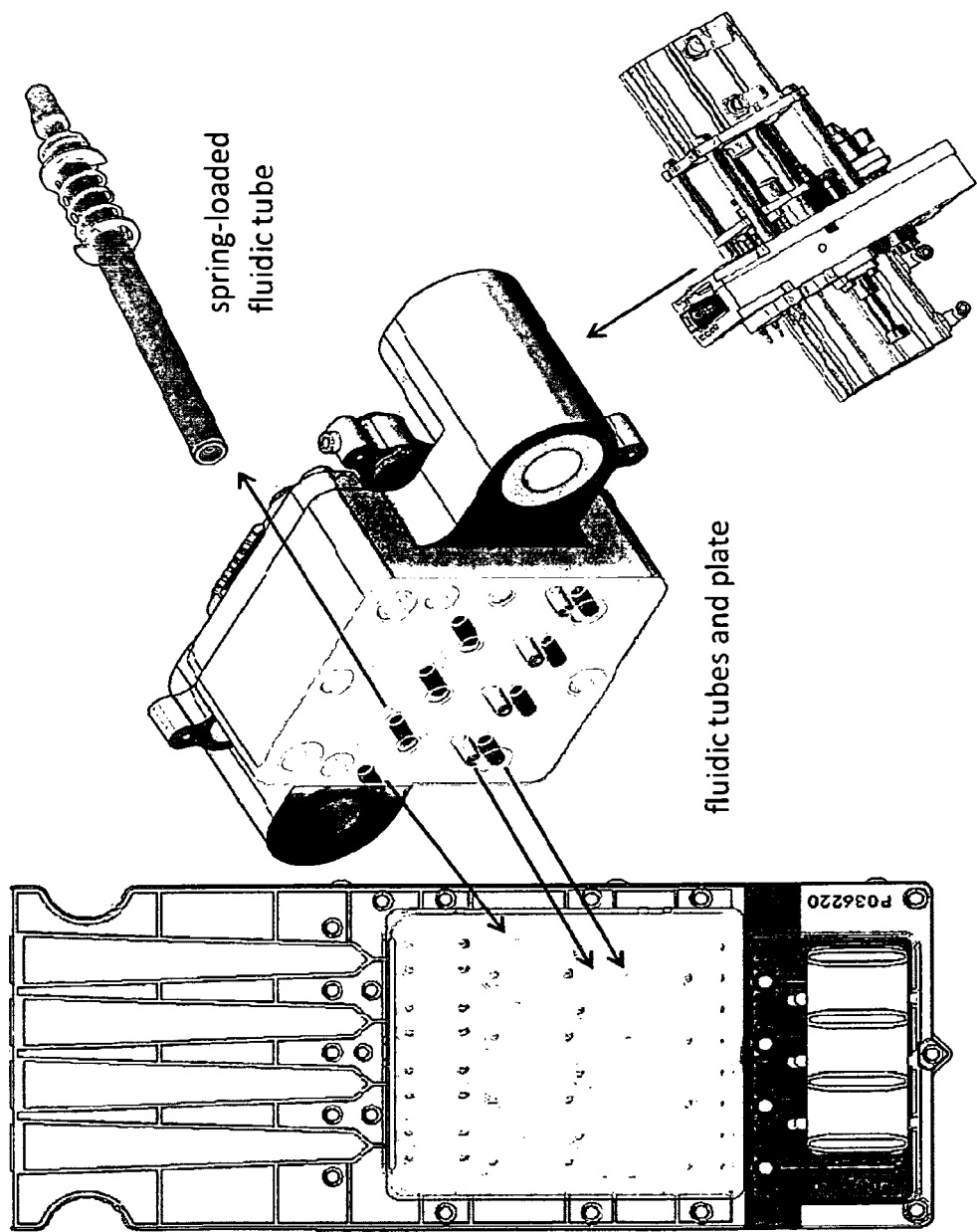
FIG. 40 shows an embodiment of a fluidic manifold of a cartridge module indicating mating of tubes with ports of a sample or control cartridge.
Figure 41:
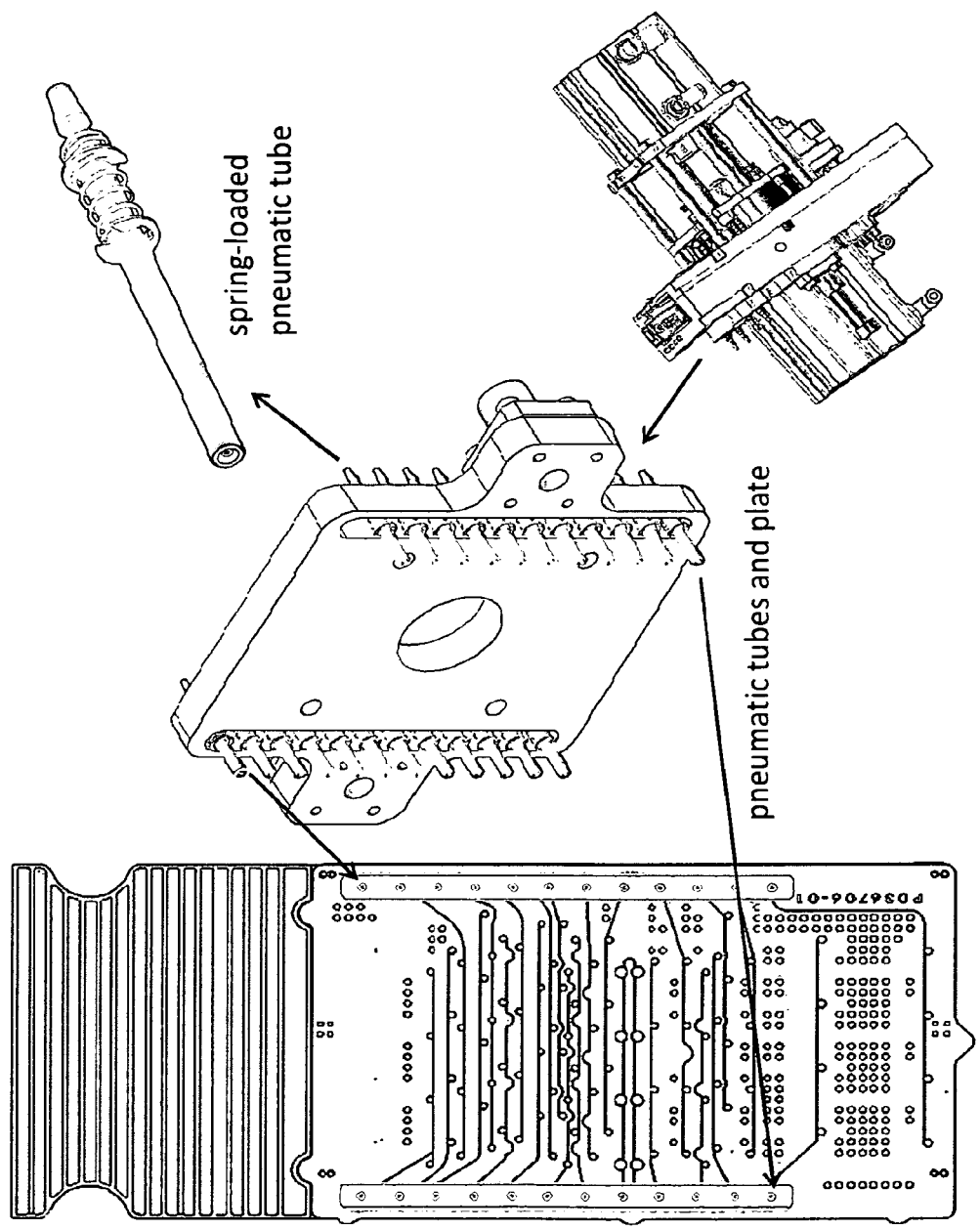
FIG. 41 shows an embodiment of a pneumatic manifold and a pneumatic side of a sample cartridge having ports for mating with pneumatic tubes.

With reference to FIG. 3 and FIG. 39, the sample cartridge interface module includes two cartridge modules for accepting sample cartridges, such as a control cartridge and a sample cartridge or two sample cartridges. The sample cartridge is for providing one or a plurality of samples (e.g., a fluid FTA card punch, solid material or tissue sample with genetic material) to be prepared, processed and analyzed. The control cartridge can be provided for a control sample having, for example, a known genetic profile and/or a negative control (e.g., containing no DNA sequences that can be amplified by the analyte preparation process). Controls can include an allelic ladder, a positive control having, for example, a known genetic profile and a negative control which does not have any DNA of interest, e.g., no human DNA. The control cartridge can also process one or more samples depending on the configuration.

In the embodiments shown in FIG. 3 and FIG. 39, the sample cartridge interface module comprises two cartridge modules. In other embodiments, the sample cartridge interface module comprises a single cartridge module for receiving a single sample cartridge. A sample cartridge interface module configured to receive a single sample cartridge would not need to provide pneumatic and fluidic connections to multiple (e.g., two) sample cartridges, which could reduce the weight and complexity of the system or instrument. Whether a sample cartridge interface module comprises a single cartridge module or multiple (e.g., two) cartridge modules, a sample cartridge can be configured to have 4, 8, 10, 16, 24, 32, 40, 48 or more sets of sample chamber, reagent chambers (e.g., one or more wash chambers, DNA capture chamber, lysis reagent/waste chamber, and diluent chamber), reaction chamber, and reaction reagent (e.g., premix) chamber, for receiving and processing 4, 8, 10, 16, 24, 32, 40, 48 or more samples, where one or more controls (e.g., an allelic ladder, a positive control and/or a negative control) can be run instead of one or more samples.

In some embodiments, the clamping system engages the cartridge and brings macroscale chambers of the cartridge in fluid communication with one another. In an example, the clamping system engages the cartridge and brings a lysis chamber in fluid communication with a buffer chamber through a micro fluidic channel of the cartridge. The system 100, with the aid of the cartridge, is thus configured to effect a macro-to-micro downscaling of fluid volume, and also a micro-to-macro upscaling of fluid volume.

In some embodiments, the system comprises a receptacle for receiving a cassette having a container comprising a plurality of closed and fluidically isolated chambers and a microfluidic device comprising a plurality of puncturing elements and a microfluidic channel in fluid communication with one or more ports. Each of the plurality of closed and fluidically isolated chambers comprises a friable seal. The system further includes a pressure application member for engaging the microfluidic device with the container. Engaging the microfluidic device with the container punctures the friable seal of each of the plurality of closed and fluidically isolated chambers and creates a fluid flow path between each of the plurality of closed and fluidically isolated chambers and the microfluidic channel.

In some embodiments, the system comprises a cartridge module having a receptacle for accepting a cartridge and a first assembly having a first pressure manifold that engages a first side of the cartridge and brings the one or more chambers in fluid communication with a pressure source. A second assembly has a second pressure manifold that engages a second side of the cartridge and brings the one or more valves in fluid communication with a pressure source for actuation, e.g., pneumatic or hydraulic actuation. An elongation or moving member moves one or both of the first assembly and the second assembly towards the cartridge module and adjacent to the cartridge.

The elongation or moving member can be coupled to one or both of the first assembly and the second assembly through a cable, such as a Bowden cable. The elongation or moving member can move one or both of the first pressure manifold and the second pressure manifold away from the cartridge module. In some embodiments, the elongation or moving member comprises an air-driven piston the movement of which moves one or both of the first assembly and the second assembly towards the cartridge module. A pneumatic piston can have one or more sensors to monitor motion of the piston—e.g., two sensors to indicate whether the piston is fully withdrawn or fully engaged.

1. Fluidic and Pneumatic Manifolds

Figure 36A:
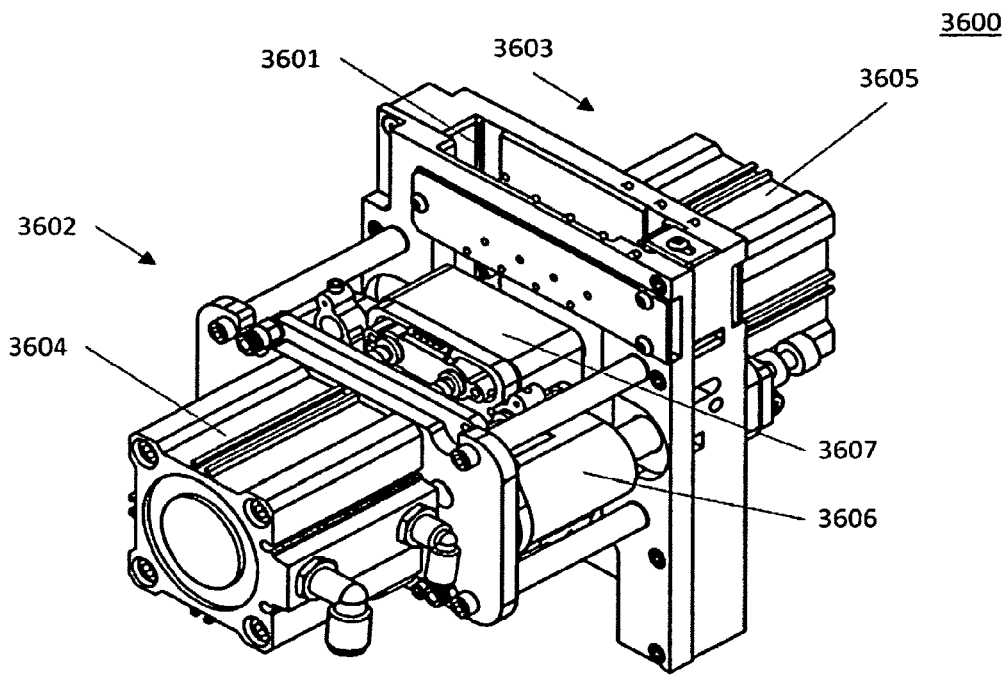
FIGS. 36A and 36B are views of an embodiment of a cartridge module for a sample cartridge.

FIG. 36A shows a cartridge module 3600 that is configured to accept a cartridge, in accordance with an embodiment of the invention. The cartridge module 3600 includes a cartridge receptacle 3601, a first assembly 3602 and a second assembly 3603. The first assembly 3602 includes a first air cylinder 3604 and the second assembly 3603 includes a second air cylinder 3605. The air cylinders are each in fluid communication with a positive or negative pressure source. In an example, the first air cylinder 3604 is in fluid communication with a positive pressure source, and the second air cylinder 3605 is in fluid communication with a positive pressure source.

The first air cylinder 3604 provides positive pressure or negative pressure (vacuum) to chambers of the cartridge (e.g., the waste chamber 3104 of FIG. 31) when the first assembly has engaged the cartridge. The second air cylinder 3605 actuates the valves in a microfluidic device of a cartridge, as described elsewhere herein.

With continued reference to FIG. 36A, the first assembly 3602 comprises a fluidic pusher assembly 3606. The fluid pusher assembly includes a manifold 3607 that is configured to rest adjacent to a cartridge that has been inserted into the cartridge receptacle 3601, and direct positive or negative pressure to one or more chambers of the cartridge. In some situations, the manifold 3607 directs positive pressure to the chambers of the cartridge to facilitate fluid flow. The first assembly can include an STR plunger assembly for actuating an STR plunger of the cartridge.

With a cartridge inserted in the cartridge receptacle 3601, the manifold 3607 is moved against the chambers of the cartridge with the aid of an elongation or moving member (not shown). The elongation or moving member can be coupled to the manifold 3607 through a cable, such as a Bowden cable.

Figure 36B:
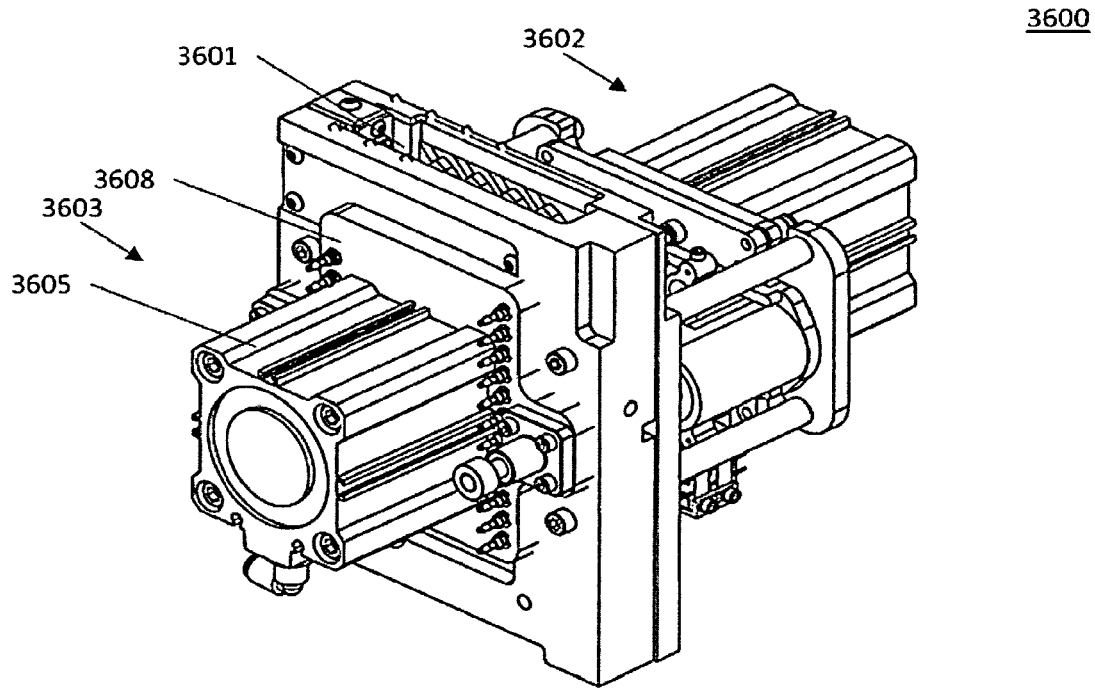
Figure 37:
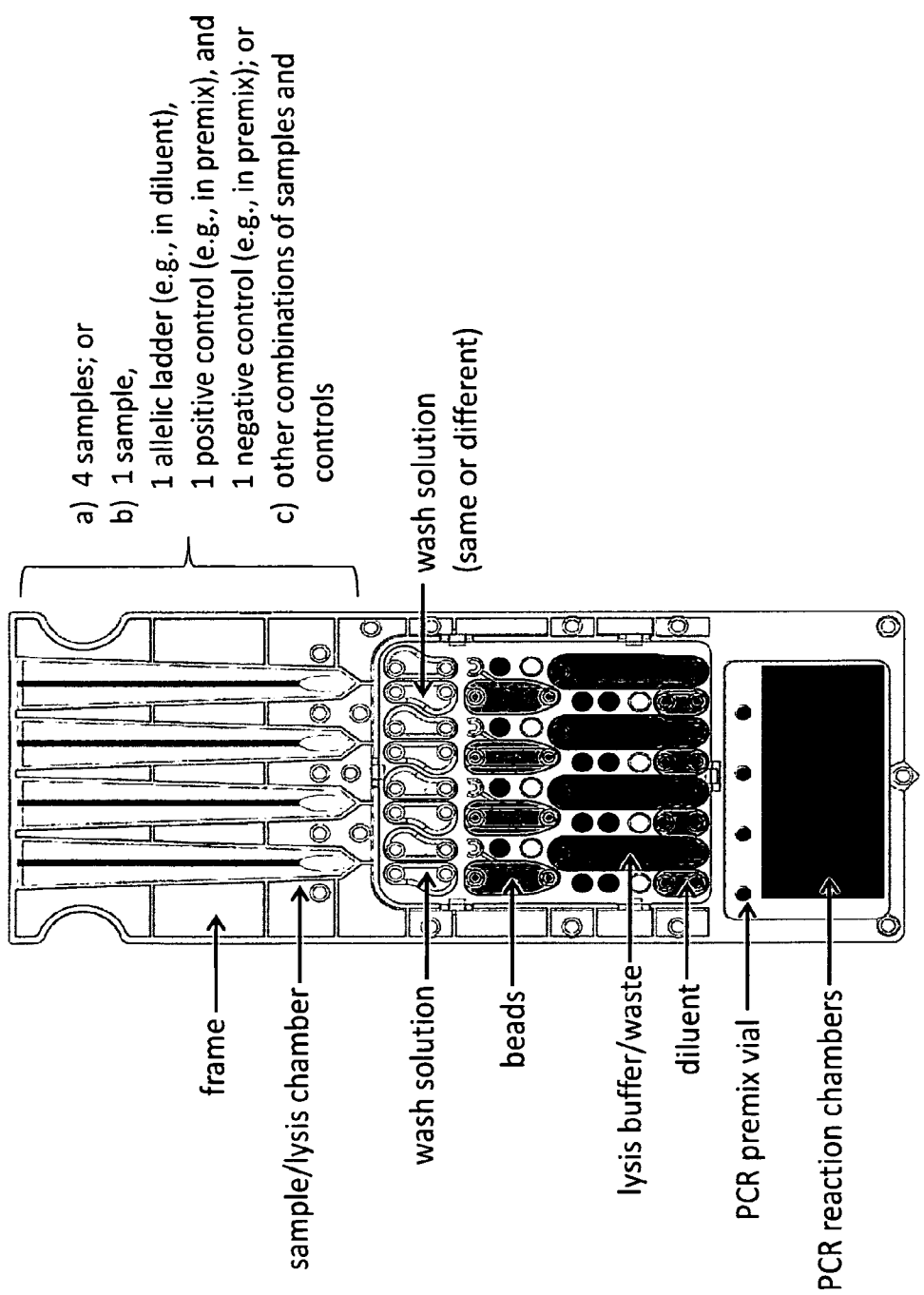
FIG. 37 shows embodiments of a sample cartridge of the invention.

FIG. 36B shows a perspective of cartridge module 3600 in which the cartridge module is rotated 180 degrees with respect to the cartridge module shown in FIG. 36A. With reference to FIG. 36B, the second air cylinder 3605 is disposed adjacent to a pneumatic pusher assembly (or pressure manifold) 3608. The second air cylinder 3605 provides air to the pneumatic pusher assembly 3608 that is in fluid communication with individual valves of the micro fluidic device of the cartridge. The second air cylinder 3605 and pneumatic pusher assembly 3608 are configured to actuate the valves of the microfluidic device.

In some embodiments, the instrument or system of the present disclosure comprises tubes made of a suitable material (e.g., a metal or metal alloy, such as stainless steel) which facilitate fluidic communication described herein by engaging ports. Such a tube can have the same or different dimensions with respect to other such tubes, and can have the same or different dimensions along the length of the tube. The tubes can comprise a rigid material. Each tube can independently biased against the port to which it is aligned. For example, each tube can be driven by a different pressure source, e.g., a different spring. Independent biasing can ensure proper sealing of each tube with each port, especially in situations in which the cartridge has limited compliance.

In some embodiments, the instrument or system comprises 10 or more tubes (e.g., tubes 3620 in FIG. 46) that reversibly contact gaskets on the pneumatic side of the microfluidic device, engage pneumatic ports, and facilitate fluidic communication via actuation of valves by application of pressure or vacuum. In some embodiments, the instrument or system comprises 15 or more, 20 or more, 25 or more, or 30 or more such tubes. In further embodiments, the instrument or system comprises from 20 to 30 such tubes. In certain embodiments, the instrument or system comprises 23, 24 or 25 such tubes. In some embodiments, the second pressure manifold of the second assembly of the system described herein comprises such tubes.

The system configured to engage the cassette can include a pneumatic manifold that mates with pneumatic ports on the pneumatic layer of the fluidic chip and a fluidic manifold that mates with ports on the fluidic layer. A pneumatic assembly comprising a pneumatic manifold can be controlled by solenoid valves to provide pressure and vacuum. A fluidic assembly can comprise a fluidic manifold that engages ports on the cassette and includes channels that connect passages in the cassette with an analytic assembly, e.g., capillary electrophoresis.

When fully engaged, the pneumatic manifold engages the pneumatic ports. In some cases, a pressure manifold is in fluid communication with one or more chambers of the cartridge. The pressure manifold provides positive or negative pressure to the one or more chambers. On the other side, the cassette has ports that communicate with ports on the chip that communicate with the microfluidic channels. In some cases, these first ports are engaged with a source of pressure to pump liquids not by the diaphragm pumps but by outside pressure.

The pneumatics module may include compressors and/or pumps for providing a pressurized gas (e.g., pressure greater than 1 atm) and/or vacuum to various pneumatically actuated valves, such as valves of the cartridges 103 and 105. The system 100 may include actuation conduits in fluid communication with the pneumatics module for providing communication of pressure (positive or negative) between the valves and the pneumatic module. Each actuation conduit is in fluid communication with a positive pressure source compared to ambient (e.g., air compressor) or a negative pressure source compared to ambient (e.g., vacuum pump), or both—that is, the system 100 may be configured to actuate valves with the aid of both positive and negative pressure, such as, for example, closing normally open valves using positive pressure, and opening the normally open valves using negative pressure. A pneumatics module also can provide pressure to a port in the fluidics of the sample cartridge and to a buffer module to move buffer from the buffer module to the fluidic system of the sample cartridge.

In further embodiments, the instrument or system comprises 4 or more tubes (e.g., tubes 3610 in FIG. 46) that traverse through one or more holes to the right (or to the left) of each bead suspension/capture chamber, reversibly contact gaskets on the fluidic side of the microfluidic device, engage ports of fluidic channels, and facilitate fluid movement between various places (e.g., between chambers) by application of pressure (e.g., air or liquid pressure). In an embodiment, the instrument or system comprises 4 such tubes that each separately traverse through one hole to the right (or to the left) of each of 4 bead suspension/capture chambers, one such tube for each such hole. In another embodiment, the instrument or system comprises 8 such tubes that each separately traverse through one of two holes to the right (or to the left) of each of 4 bead suspension/capture chambers, one such tube for each such hole. The number of such tubes can be based on the number of hole(s) to the right (or to the left) of each bead suspension/capture chamber and the number of bead suspension/capture chambers, or the number of fluidic ports to be engaged by such tubes. In an embodiment, the first pressure manifold of the first assembly of the system described herein comprises such tubes.

In additional embodiments, the instrument or system comprises 8 or more tubes (e.g., tubes 3614 and 3616 in FIG. 46) that traverse through two or more holes to the left (or to the right) of each reagent storage/waste chamber, reversibly contact gaskets on the fluidic side of the micro fluidic device, engage fluidic ports, and are conduits of fluid. In an embodiment, the instrument or system comprises 8 such tubes that each separately traverse through one of two holes to the left (or to the right) of each of 4 reagent storage/waste chambers, one such tube for each such hole. In certain embodiments, the tubes (e.g., tubes 3614 in FIG. 46) traversing through the upper hole to the left (or to the right) of each reagent storage/waste chamber connect the sample cartridge (the cartridge containing sample chambers) to a capillary electrophoresis system by application of pressure (e.g., air or liquid pressure), and the tubes (e.g., tubes 3616 in FIG. 46) traversing through the lower hole to the left (or to the right) of each reagent storage/waste chamber connect the sample cartridge to a buffer cartridge by application of pressure (e.g., air or liquid pressure). The tubes can be connected to a conduit, such as flexible tubing, that transports sample from the cartridge to an electrophoresis capillary. The number of such tubes can be based on the number of holes to the left (or to the right) of each reagent storage/waste chamber and the number of reagent storage/waste chambers, or the number of fluidic ports to be engaged by such tubes. In an embodiment, the first pressure manifold of the first assembly of the system described herein comprises such tubes.

In some embodiments, the manifold structure used to interface a sample cartridge (e.g., the first pressure manifold of the first assembly or the second pressure manifold of the second assembly of the system described herein) comprises a base pressure plate, a plurality of tube spring assemblies, and a pressure actuator. In certain embodiments, a tube spring assembly comprises a tube that has two snap ring grooves, two snap rings, a tip with an orifice that is surrounded by a raised sealing edge, a hose barb structure opposite the tip, and a coil spring. The coil spring is contained between the two snap rings and a thrust plate. The thrust plate comprises a plurality of tube spring assemblies in an arrangement configured to interface ports of the cartridge. The plurality of tubes are configured to fluidically interface the cartridge simultaneously, as groups or individually, e.g., if more than one thrust plate is used. The tubes are configured to individually impart a force sufficient to make a reliable Seal with the corresponding port (or an intervening gasket) for the tube on the cartridge. For all of the tubes to make a reliable seal, the array of tubes does not need to be a highly precise planar structure, and the cartridge does not need to be a highly precise structure. Each of the tubes can move and engage independently of the others to optimize each seal. By comparison, a monolithic solid sealing "block" may be less effective in sealing ports of the cartridge because the two planes of the sealing block and the cartridge may require a high degree of accuracy (e.g., within about 0.001 inch) and the force distribution on the seals may not be suitably uniform given the overall system accuracy.

Figure 46:
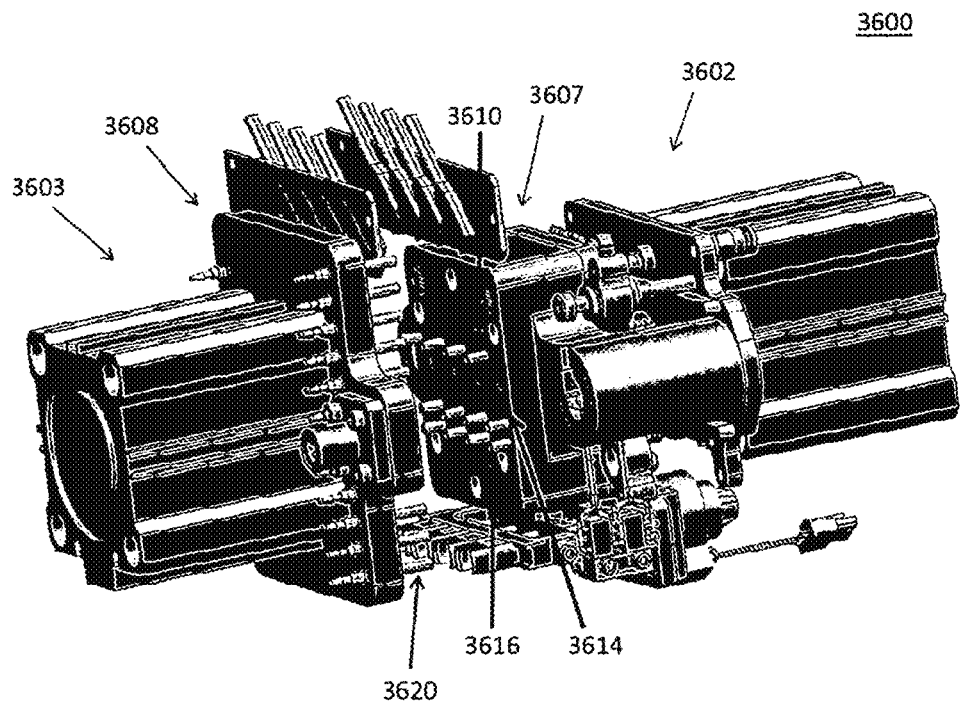
FIG. 46 shows an embodiment of cartridge module 3600 in which the first pressure manifold 3607 of the first assembly 3602 comprises tubes 3610, tubes 3614 and tubes 3616 that each engage ports on the fluidic side of the microfluidic device of a cartridge, and the second pressure manifold 3608 of the second assembly 3603 comprises tubes 3620 that each engage ports on the pneumatic side of the microfluidic device.
Figure 47:
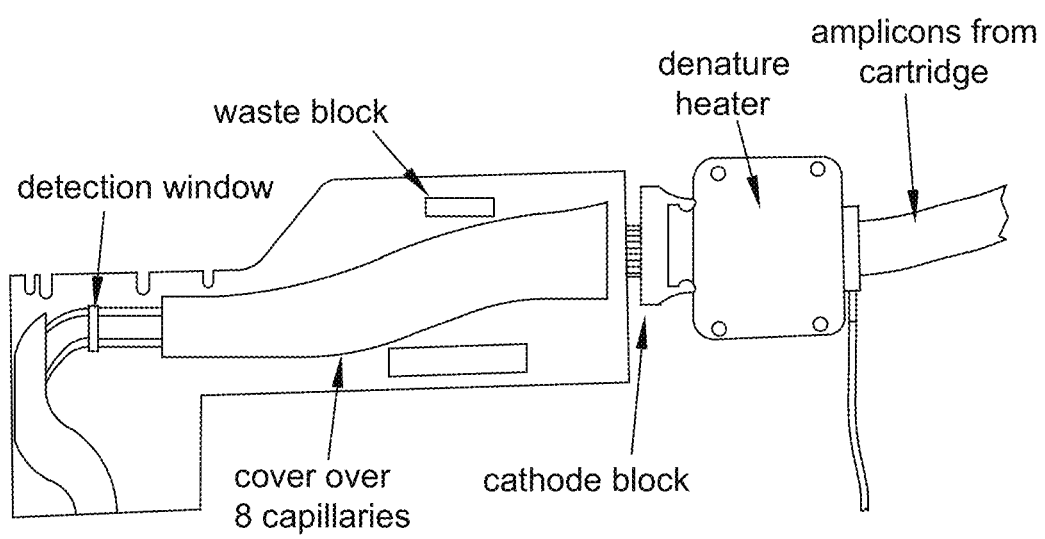
FIG. 47 shows an embodiment of a capillary electrophesis array having a capillary board and a denature heater.

FIG. 46 shows an embodiment of cartridge module 3600. In the embodiment of FIG. 46, the first pressure manifold 3607 of the first assembly 3602 comprises four tubes 3610 that each separately traverse through one hole to the right (or to the left) of each bead suspension/capture chamber, one such tube for each such hole, and engage ports on the fluidic side of the microfluidic device of a cartridge. The first pressure manifold of the first assembly also comprises four tubes 3614 and four tubes 3616 that each separately traverse through the upper hole and the lower hole, respectively, to the left (or to the right) of each reagent storage/waste chamber, one such tube for each such hole, and engage ports on the fluidic side of the microfluidic device. In FIG. 46, the second pressure manifold 3608 of the second assembly 3603 comprises 23 or 24 tubes 3620 that each engage ports on the pneumatic side of the microfluidic device.

Figure 56:
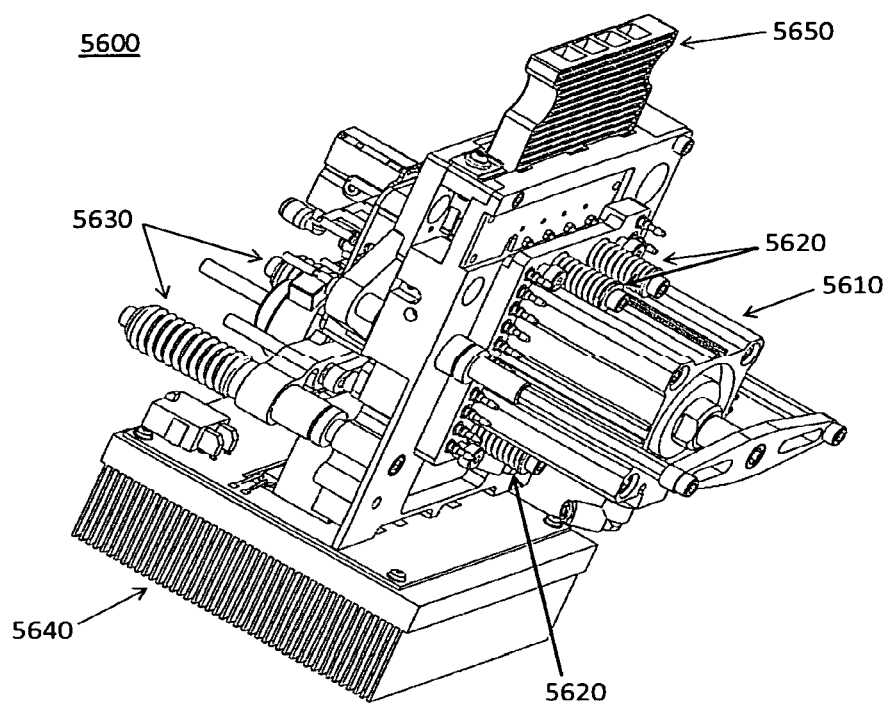
FIG. 56 shows an embodiment of a cartridge module for a sample cartridge in which springs are utilized in place of a pneumatic manifold cylinder and a thermocycler cylinder.

The cartridge module for receiving a sample cartridge and represented by the embodiments depicted in FIGS. 36, 39 and 46 can have other configurations. In some embodiments, the cartridge module for a sample cartridge has the embodiment illustrated in FIG. 56. FIG. 56 shows a sample cartridge 5650 inserted into cartridge module 5600. Cartridge module 5600 has a fluidics manifold cylinder 5610, which corresponds to fluidics manifold cylinder 3604 of cartridge module 3600 in FIG. 36A and fluidics manifold cylinder 3920 of each individual cartridge module in FIG. 39. However, cartridge module 5600 has four springs 5620 (the fourth spring is hidden in FIG. 56) which replace pneumatic manifold cylinder 3605 of cartridge module 3600 in FIG. 36A and pneumatic manifold cylinder 3910 of each individual cartridge module in FIG. 39. In addition, cartridge module 5600 in FIG. 56 has two springs 5630 in place of a pneumatically actuated thermocycler cylinder. Springs 5630 can be considered as part of cartridge module 5600 or integrated with the cartridge module. The cartridge interface module in FIG. 39 comprising two individual cartridge modules has a pneumatically actuated thermocycler cylinder 3930 for each individual cartridge module. Thermocycler cylinder 3930 can be considered as part of each individual cartridge module in FIG. 39 or integrated with each individual cartridge module. FIG. 56 shows thermocycler 5640, which corresponds to thermocycler 4200 in FIG. 42 and can be considered as part of cartridge module 5600 or integrated with the cartridge module. The thermocycler for each individual cartridge module in FIG. 39, which is hidden in FIG. 39, can also be considered as part of each individual cartridge module or integrated with each individual cartridge module. Actuation of thermocycler cylinder 3930 for each individual cartridge module in FIG. 39, and actuation of springs 5630 for cartridge module 5600 in FIG. 56, moves the thermocycler so that metal plate 4220 of thermocycler 4200 in FIG. 42 contacts the thermoconductor disposed over reaction chambers of a cartridge when a cartridge is engaged with the cartridge module or when a reaction (e.g., PCR) involving thermal cycling is performed.

Cartridge module 5600 in FIG. 56 simplifies the design and operation of each individual cartridge module in FIG. 39. For each individual cartridge module in FIG. 39, pneumatic manifold cylinder 3910, fluidics manifold cylinder 3920 and thermocycler cylinder 3930 are independently operated to control the movement of the pneumatic manifold and the fluidics manifold of the cartridge module and the thermocycler, respectively, e.g., when a sample cartridge is engaged with the cartridge module. In comparison, for cartridge module 5600 in FIG. 56, fluidics manifold cylinder 5610 actuates the fluidics manifold of the cartridge module as well as the pneumatic manifold of the cartridge module and thermocycler 5640 through the use of springs 5620 and springs 5630. In some embodiments, one side of fluidics manifold cylinder 5610 is pressurized to hold open the fluidics and pneumatic manifolds of the cartridge module and thermocycler 5640. When a sample cartridge is inserted into the cartridge module, both sides of the fluidics manifold cylinder are relaxed (or depressurized), which permits springs 5620 and springs 5630 to enable the pneumatic manifold (or tubes attached thereto) of the cartridge module and the thermocycler to engage with the pneumatic side of the cartridge and with the thermoconductor disposed over the reaction chambers, respectively. Pressure is then provided (e.g., by a pump) to the fluidics manifold cylinder (e.g., the opposite side of the fluidics manifold cylinder is pressurized) to engage the fluidics manifold (or tubes attached thereto) of the cartridge module with the fluidics side of the cartridge. Benefits of the design of cartridge module 5600 include reduction in the complexity, size, weight and cost of the cartridge module.

Other components that interface with a sample cartridge can also be designed for greater simplicity. For example, the presence of an actuator that applies and retracts a rare-earth magnet to control the movement of magnetically responsive (e.g., magnetic or paramagnetic) particles can be eliminated by using an electromagnet or a combination of an electromagnet and a rare-earth magnet.

In some embodiments, to obviate potential contamination (e.g., run-to-run contamination or cross-lane contamination) by a contaminant (e.g., a DNA contaminant, such as a potentially amplifiable allelic ladder or size standard), a membrane comprising a hydrophobic material is placed between fluidic ports and the terminus of tubes that traverse through one or more holes to the right (or to the left) of each bead suspension/capture chamber and engage such ports (e.g., tubes 3610 in FIG. 46). In an embodiment, a hydrophobic membrane is placed underneath the gasket that contacts such tubes. The hydrophobic membrane is designed to allow gas to pass through it but not a hydrophilic liquid (e.g., an aqueous solution). Non-limiting examples of material composing the hydrophobic membrane include fluorinated and perfluorinated polymers (e.g., perfluoroalkoxy (PFA) polymers, polytetrafluoroethylene (PTFE, Teflon®), fluorinated ethylene-propylene (FEP) polymers, polyethylenetetrafluoroethylene (PETFE), polyvinylfluoride (PVF), polyvinylidene fluoride (PVDF), polyethylene chlorotrifluoroethylene (PECTFE), and polychlorotrifluoroethylene (PCTFE)), hydrocarbon polymers (e.g., polyethylene and polypropylene), and silicon-containing materials (e.g., Silicon-containing polymers and silica).

In further embodiments, to preclude potential contamination (e.g., run-to-run contamination or cross-lane contamination) by a contaminant (e.g., a DNA contaminant, such as a potentially amplifiable allelic ladder or size standard), tubes (e.g., the inside thereof) that traverse through one or more holes to the right (or to the left) of each bead suspension/capture chamber and engage fluidic ports (e.g., tubes 3610 in FIG. 46) are washed with a decontaminating agent (e.g., bleach) upon completion of a sample-to-answer protocol. For example, a decontamination cartridge containing an aqueous solution of a decontaminating agent (e.g., bleach), and optionally other solution(s) (e.g., water and/or ethanol), can be used to wash the inside of such tubes with such solution(s) upon completion of a sample-to-answer protocol. Such a decontamination cartridge can be integrated with the instrument or system described herein or can be inserted into the instrument or system after completion of a sample-to-answer protocol.

2. Buffer Cartridge Module

Figure 7:
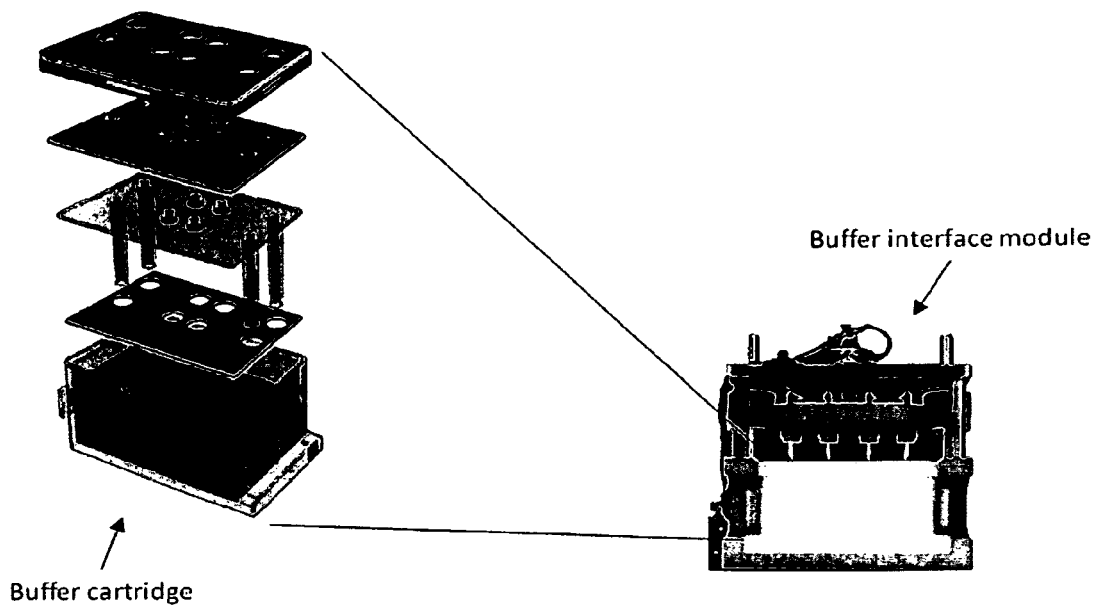
FIG. 7 shows embodiments of a buffer interface module and a buffer cartridge.

The buffer cartridge and interface module of the system 100 are shown in FIG. 7. The buffer cartridge and interface module includes a buffer interface module and a buffer cartridge. An exploded view of the buffer cartridge is shown on a left side of the figure. The buffer cartridge interface module includes an automated engagement mechanism for accepting the buffer cartridge, which may comprise (e.g., be prefilled with) one or more buffers and/or water. One or more buffers may be used for electrophoresis (e.g., capillary electrophoresis).

In some embodiments, the buffer cartridge comprises (e.g., is pre-loaded with) an aqueous buffer for electrophoresis which contains one or more buffering agents selected from N,N-bis(2-hydroxyethyl)glycine (bicine), N-tris(hydroxymethyl)methylglycine (tricine), tris(hydroxymethyl)methylamine (Tris), 3-amino-1-propanesulfonic acid, 4-(cyclohexylamino)-1-butanesulfonic acid (CABS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N-(2-hydroxyethyl)piperazine-N'-(3-propanesulfonic acid) (EPPS), and 3-{[tris(hydroxymethyl)methyl]amino}-propanesulfonic acid (TAPS). In an embodiment, the buffer cartridge comprises an aqueous buffer containing Tris and TAPS. In additional embodiments, the buffer cartridge further comprises (e.g., is further pre-loaded with) water, which can be used for, e.g., cathode preparation and clean up. In certain embodiments, the aqueous buffer and/or the water further contain a metal chelator. Non-limiting examples of metal chelators include aurintricarboxylic acid (ATA), boric acid, citric acid, salicylic acid, 1,2-bis(o-aminophenoxy)ethane-N,N,N',N'-tetraacetic acid (BAPTA), diethylene triamine pentaacetic acid (DTPA), ethylenediaminetetraacetic acid (EDTA), ethylene glycol tetraacetic acid (EGTA), glycoletherdiaminetetraacetic acid (GEDTA), N-(2-hydroxyethyl)ethylenediamine-N,N',N'-triacetic acid (HEDTA), nitrilotriacetic acid (NTA), 2,2'-bipyridine, o-phenanthroline, triethanolamine, and salts thereof. In an embodiment, the metal chelator comprises EDTA. In some embodiments, the buffer cartridge is further configured to collect waste.

A buffer and/or water is provided from the buffer cartridge with the aid of pressure (e.g., positive or negative pressure). A pressure/vent line can connect the buffer cartridge to a pressure solenoid valve. To capture any liquid that may come out of the buffer cartridge (e.g., due to overpressure in the cartridge) and enter the pressure/vent line, a liquid trap can be placed in the pressure/vent line between the buffer cartridge and the pressure solenoid valve. The liquid trap prevents liquid from migrating to the pressure solenoid valve. A check valve can also be placed in a line connecting a pressure source (e.g., a 10 psi pump) to the pressure solenoid valve. The check valve is designed to protect the pressure solenoid valve, e.g., by creating a static volume of air and no flow. A liquid trap and/or a check valve can also be used in other places of the instrument or system described herein where it is not desired for liquid to get into a line connecting a source of liquid to a valve or other structure. The buffer interface module includes an EEPROM reader for reading an on-board EEPROM of the buffer cartridge, which can be removably mounted on the buffer interface module. The buffer interface module may have a relatively small foot print. In some situations, the buffer interface module has a length of about 4.5 inches or less, a width of about 2.5 inches or less, and a height of about 5 inches or less. The buffer interface module of the system 100 advantageously permits a user to load the system 100 with different types of buffers. The buffer cartridge interface module also can include a chamber for receiving liquids (e.g., waste) from the fluidic conduit that moves liquids from the sample cartridge to the cathode assembly.

E. Methods for Processing Samples

In another aspect of the invention, methods for processing samples are provided. Methods provided herein can be used with systems provided herein, such as the system 100 of FIG. 1 and the cartridge of FIGS. 8-18.

In some embodiments, a method for processing a biological sample comprises (a) providing a cassette as described above, (b) providing a biological sample in the sample chamber, (c) engaging the microfluidic device with the container to form a fluid flow path between each of the plurality of closed and fluidically isolated chambers and the microfluidic channel, and (d) processing the biological sample. In some cases, the plurality of closed and fluidically isolated chambers comprise a first chamber holding a diluent, a second chamber holding one or more lysis reagents, a third chamber having capture particles, a fourth chamber having a wash solution, and optionally a fifth chamber having a wash solution or water or a buffer (the water or buffer can be used for, e.g, rehydrating reagents or washing). The second chamber is in fluid communication with the sample chamber. In some cases, engaging the microfluidic device with the container comprises applying pressure against the container in the direction of the microfluidic device.

In some embodiments, the sample is processed by directing the one or more lysis reagents from the second chamber to the sample chamber, contacting the one or more lysis reagents with the biological sample in the sample chamber to extract a nucleic acid sample from the biological sample, directing the nucleic acid sample from the sample chamber to the third chamber to bind at least a portion of the nucleic acid sample to capture particles, washing the nucleic acid-bound particles to remove impurities (e.g., salts, cellular debris and proteins), and directing the capture particles to a reaction chamber (or thermocycling chamber) in fluid communication with the third chamber through the microfluidic channel.

In some cases, the lysis reagents are directed from the second chamber to the sample chamber with the aid of negative or positive pressure (e.g., negative pressure provided by one or more pumps in the microfluidic device).

In some situations, the sample includes a nucleic acid. During processing, the nucleic acid is amplified in a reaction chamber (e.g., a reaction chamber configured to perform PCR with thermal cycling) of the cassette. The nucleic acid may be attached to capture particles (e.g., beads). In some cases, the nucleic acid sample is amplified by directing the capture particles to a reaction chamber of the thermal cycler assembly, providing a premix with primers, a buffer that can contain a metal salt (e.g., an $M^{+2}$ salt, such as magnesium chloride), and an enzyme (e.g., a DNA polymerase, such as a Taq polymerase) to the reaction chamber, heating the nucleic acid to amplify the nucleic acid, and subsequently directing the amplified nucleic acid to a separation system.

In an example, a cartridge, such as the cartridge 1000 of FIG. 10 having a microfluidic device 1010, is provided in a sample preparation, processing and analysis system, such as the system 100 of FIG. 1. A sample, such as a cotton swab containing nucleic acid or a cell-containing sample, is provided into the sample chamber 1001 either before or after the cartridge 1000 is provided in the system. The chambers of the cartridge 1000 (e.g., the chambers of container 1011) are then engaged with the microfluidic device 1010, thereby bringing the chambers in fluid communication with microfluidic channels of the microfluidic device 1010. Engaging the chambers with the microfluidic device 1010 also brings the chambers in fluid communication with one another through the microfluidic channels of the microfluidic device 1010. A manifold of a fluid pusher assembly (see, e.g., FIGS. 36A and 36B) is then brought in fluid communication with reagent and processing chambers of the cartridge 1000. Lysis buffer, contained in the lysis reagent storage chamber 1002, is pumped through the microfluidic device 1010 (having a microfluidic channel) into the sample chamber 1001, where the lysis buffer (e.g., NaOH and a detergent, such SDS; or a guanidinium salt (e.g., guanidinium thiocyanate), a zwitterionic detergent/surfactant (e.g., CHAPS) and/ or a non-ionic detergent/surfactant (e.g., Triton® X-114, and optionally an antifoaming agent) lyses cells in the sample, releasing nucleic acids of the sample. Bubbling of air or another gas can provide mild agitation to improve lysis. Heating (e.g., at a temperature of at least about 40° C., 50° C., 60° C. or 70° C.) can also facilitate lysis, as can application of an ultrasonic field. The resulting lysate is pumped into the bead suspension/capture chamber 1003. The bead capture chamber 1003 comprises magnetically responsive particles adapted to capture nucleic acids. In some embodiments, the bead capture chamber 1003 comprises silica-coated magnetic beads (e.g., Magnacel® beads from Promega). Upon nucleic acid capture, a magnetic field is used to immobilize the particles and captured nucleic acid in the bead capture chamber 1003, which is generally a multi-use chamber. The magnetic field may be applied inductively or using a rare earth magnet, such as neodymium, which is preferably moved closer to capture the beads and further away to release the beads. Any lysate material that is not captured by the magnetically responsive particles is transferred to the waste chamber 1002 while the particles and captured nucleic acid are immobilized in the bead capture chamber 1003. Next, a first wash solution or buffer (e.g., Tris EDTA and a salt; or an aqueous alcohol solution, e.g., 90% ethanol in water or 70% ethanol in water) from a first wash solution/buffer chamber 1004 is moved through the micro fluidic device into the bead capture chamber 1003. The first wash solution or buffer washes the particles, removing waste. The first wash solution or buffer and dissolved wastes are then moved into the waste chamber 1002 while the capture particles and captured nucleic acid are immobilized in the bead capture chamber 1003. Next, a second wash solution or buffer (e.g., Tris EDTA and a salt; or an aqueous alcohol solution, e.g., 70% ethanol in water) is moved from a second wash solution/buffer chamber 1005 into the bead capture chamber 1003. Next, the magnetic force is released, allowing the particles to mix with the second wash solution or buffer. The second wash solution or buffer, along with capture particles and captured target nucleic acid, are moved into the reaction chamber 1008 of the thermocycler assembly 1006 (see above). The device 1000 includes four reaction chambers in parallel which are configured to perform nucleic acid amplification (e.g., by PCR) with thermal cycling. A magnet adjacent to each reaction chamber 1008 immobilizes magnetically responsive particles having samples attached thereto in the reaction chamber 1008 of the thermocycler assembly 1006. The remaining solution is moved to the waste multi-use chamber 1002. A master mix (or premix) containing reagents sufficient to perform short tandem repeat (STR) amplification on selected loci is directed into the reaction chamber 1008. The master mix is moved from the premix chamber 1007 to the reaction chamber 1008 of the thermocycler assembly 1006 with the aid of, e.g., a plunger, a blister pack as described elsewhere herein, or an actuating device such as that shown in FIG. 55. The temperature of the reaction chamber 1008 and sample in the chamber 1008 can be cycled with the aid of a heating and cooling device (e.g., a Peltier temperature control element) in proximity to the reaction chamber 1008. The heating and cooling device (e.g., a Peltier device) can be contained, e.g., in the cartridge module (see, e.g., FIG. 42) and can be moved to come into proximity with each reaction chamber 1008. Cycling the temperature amplifies STRs defined by primers in the master mix, producing an amplified product. A solution containing amplified product is moved from the reaction chamber 1008 into a diluent (or dilution) chamber 1009, which contains an amount of diluent (e.g., water) and optionally a control (e.g., a size standard), selected to dilute the product for injection into the capillary array electrophoresis. The amplified product can be diluted by any suitable amount, e.g., diluted about 5-fold to about 20-fold, or about 10-fold. The diluted product is then moved from dilution chamber to the capillary array injector (see FIGS. 2 and 5) through the manifold adjacent to the cartridge 1000. For example, diluted product in each fluidic circuit in the cartridge can be transported from the chamber that holds it to the capillary for electrophoresis through a path that leads from the chamber, through a channel, out a port in the cartridge, through a tube that engages the port (e.g., tubes 3614 in FIG. 46), through a fluidic conduit (e.g., a sample line) to the capillary. In certain embodiments, the fluidic conduit can continue to a receptacle, e.g., a waste chamber (e.g., a waste chamber in the buffer cartridge).

F. Reagents and Controls

In some embodiments, one or more controls for determining the size, mass or length of nucleic acids (e.g., DNA and/or RNA) are employed. In an embodiment, a size standard (also called size marker, internal lane standard or molecular weight ladder) is used. In preferred embodiments, the size standard is provided in every lane that contains a sample. In another embodiment, an allelic ladder (a plurality of alleles at each of one or more loci) is used. In preferred embodiments, the allelic ladder is provided in a lane that contains no sample. In certain embodiments, the allelic ladder comprises a plurality of alleles at each of one or more STR loci, such as those STR loci used in a forensic database (e.g., CODIS). In some embodiments, the allelic ladder comprises a plurality of alleles at, and optionally adjacent to, one or more, or all, STR loci used in CODIS, and optionally a plurality of alleles of amelogenin (AMEL) and the STR loci designated Penta D and Penta E. CODIS presently uses STR loci designated CSF1PO, D3S1358, D5S818, D7S820, D8S1179, D13S317, D16S539, D18S51, D21S11, FGA, TH01, TPDX and vWA for human identification, and amelogenin for sex determination. In an embodiment, the allelic ladder comprises a plurality of alleles at, and optionally adjacent to, all the CODIS STR loci, plus amelogenin, Penta D and Penta E. In yet another embodiment, both a size standard and an allelic ladder are used. In preferred embodiments, the size standard is provided in every lane that contains a sample, the allelic ladder is provided in a lane that contains no sample, and the lane containing the allelic ladder also contains the size standard.

The size standard and/or the allelic ladder can be provided (e.g., pre-loaded) in any appropriate chamber. In an embodiment, the size standard and/or the allelic ladder are provided (e.g., pre-loaded) in the premix chamber. To obviate potential contamination (e.g., run-to-run contamination or cross-lane contamination) by a potentially amplifiable size standard and/or by a potentially amplifiable allelic ladder, the size standard and/or the allelic ladder can be provided (e.g., pre-loaded) in a post-amplification chamber or in the chamber immediately preceding introduction to a capillary electrophoresis system. In a preferred embodiment, the size standard and/or the allelic ladder are provided (e.g., pre-loaded) in the diluent (or dilution) chamber.

If both a size standard and an allelic ladder are employed, the size standard and the allelic ladder can be provided (e.g., pre-loaded) in any appropriate chamber(s). In an embodiment, the size standard and the allelic ladder are provided (e.g., pre-loaded) in the premix chamber of the same lane or separate lanes. In another embodiment, the size standard is provided (e.g., pre-loaded) in the premix chamber of a lane, and the allelic ladder is provided (e.g., pre-loaded) in the diluent chamber of the same lane or a separate lane. In a further embodiment, the size standard is provided (e.g., pre-loaded) in the diluent chamber of a lane, and the allelic ladder is provided (e.g., pre-loaded) in the premix chamber of the same lane or a separate lane. In an additional embodiment, the size standard and the allelic ladder are provided (e.g., pre-loaded) in the diluent chamber of the same lane or separate lanes. In preferred embodiments, the size standard is provided (e.g., pre-loaded) in the diluent chamber of every lane that contains a sample, the allelic ladder is provided (e.g., pre-loaded) in the diluent chamber of a lane that contains no sample, and the diluent chamber containing the allelic ladder also contains (e.g., is also pre-loaded with) the size standard.

In some embodiments, a size standard and/or an allelic ladder are provided in a solid, semi-solid, dry, dehydrated, lyophilized or other stabilized form. In certain embodiments, the composition comprising the size standard and/or the allelic ladder further comprises a stabilizing reagent (e.g., GenTegra™ reagents (IntegenX Inc.) for stabilizing DNA and RNA). In some embodiments, the composition comprising the size standard and/or the allelic ladder, and optionally a stabilizing reagent, is dehydrated. In certain embodiments, the size standard and/or the allelic ladder, and optionally a stabilizing reagent, are dried under reduced pressure but not at freezing (not freeze-dried) to produce a dehydrated composition. The stabilized (e.g., dehydrated) composition comprising the size standard and/or the allelic ladder, and optionally a stabilizing reagent, can be provided (e.g., pre-loaded) in any appropriate chamber (e.g., in the diluent chamber of a sample or control cartridge), and can be rehydrated with any suitable fluid (e.g., with the liquid containing amplification products or with an aqueous solution (e.g., water or a buffer) before or after being mixed with amplification products). In certain embodiments, the stabilized (e.g., dehydrated) composition comprising the size standard and/or the allelic ladder, and optionally a stabilizing reagent, is rehydrated in an appropriate chamber (e.g., the diluent chamber) with an aqueous solution (e.g., water or a buffer) supplied from a vessel off or in the sample cartridge (e.g., a wash chamber in the cartridge) before being mixed with amplification products.

In further embodiments, a positive control is used. In some embodiments, the positive control comprises purified genomic DNA of a known or unknown subject (e.g., a known or unknown human). In other embodiments, the positive control can be control nucleic acids provided by an article (e.g., a swab) or in a liquid. In certain embodiments, the DNA of the positive control undergoes PCR amplification at the same loci (e.g., all the CODIS STR loci, plus optionally Penta D, Penta E and amelogenin) as the DNA from a regular sample. In preferred embodiments, the lane containing the positive control also contains a size standard. The positive control and the size standard can be provided (e.g., pre-loaded) in any appropriate chamber(s). For example, the DNA of the positive control can be provided (e.g., pre-loaded) in the sample chamber or the premix chamber, and the size standard can be provided (e.g., pre-loaded) in the premix chamber or the diluent chamber. In preferred embodiments, the DNA of the positive control is provided (e.g., pre-loaded) in the premix chamber, and the size standard is provided (e.g., pre-loaded) in the diluent chamber.

In further embodiments, an internal positive control DNA can be provided by using a sequence not found in the STR panel of interest, or a non-human DNA, including an artificial DNA, can be used. The internal positive control DNA can be provided (e.g., pre-loaded) in any or every lane as desired. The primers and fluorescent dyes would be designed to have the amplification products generated from the internal positive control not overlap any of the alleles of the STR panel of interest, e.g., either in fluorescent color or fragment size. An advantage of this approach is that every sample could have an internal positive control without using a complete lane for the positive control, thus allowing one more sample to be analyzed per run, reducing cost and potentially improving the quality of the positive control.

In additional embodiments, a negative control is used. In some embodiments, the negative control contains no DNA to be amplified, but rather contains the same premix reagents, including the same dye-labeled primer oligonucleotides, used to amplify by PCR selected loci (e.g., selected STR loci, such as all the CODIS STR loci plus optionally Penta D, Penta E and amelogenin) of the DNA of a sample. In preferred embodiments, the lane containing the negative control also contains a size standard. The negative control and the size standard can be provided (e.g., pre-loaded) in any appropriate chamber(s). For example, the negative control can be provided (e.g., pre-loaded) in the premix chamber, and the size standard can be provided (e.g., pre-loaded) in the premix chamber or the diluent chamber. In preferred embodiments, the negative control is provided (e.g., pre-loaded) in the premix chamber, and the size standard is provided (e.g., pre-loaded) in the diluent chamber.

In certain embodiments, an allelic ladder, a positive control and a negative control are provided (e.g., pre-loaded) in a control cartridge, which optionally can also take a sample.

III. Detection and Analysis Module

An analysis and detection module can include a capillary electrophoresis assembly, a detection assembly and an analysis assembly.

Figure 49:
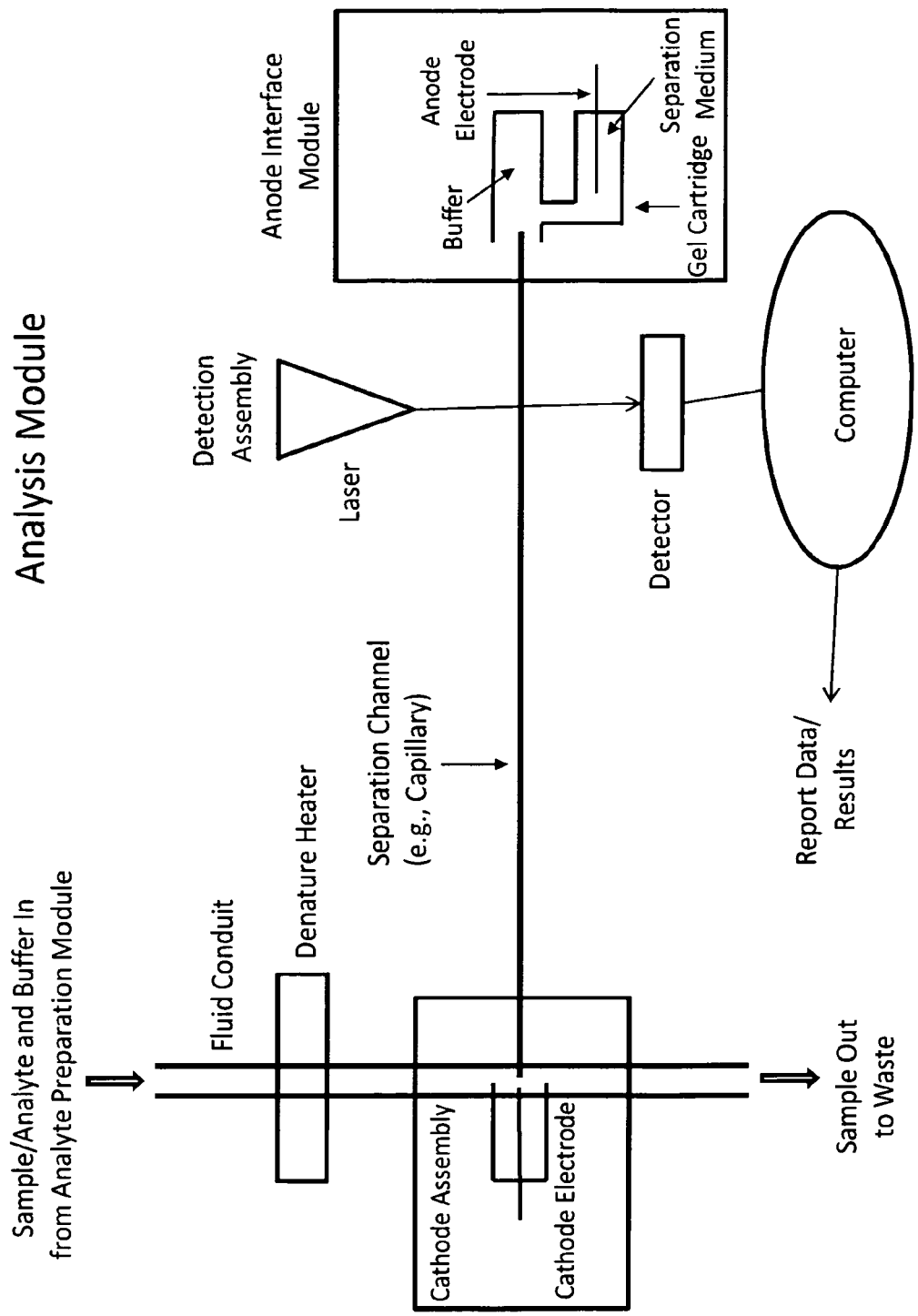
FIG. 49 shows a schematic of an analysis module useful in the systems of this invention.

FIG. 49 shows a schematic of an analysis module useful in the systems of this invention. Sample (e.g., amplified DNA or controls) and buffer (e.g., electrophoresis buffer) flow through a fluidic conduit, such as a tube, from a analyte preparation module in a path that can include a denature heater, a cathode assembly for injecting analyte into a capillary, and out to waste. A denature heater heats fluid containing DNA and denatures strands in double stranded DNA into single strands. The cathode assembly can include an electrode, such as a forked electrode, connected to a source of voltage. When a sample to be analyzed is positioned for injection, the electrode can provide voltage to inject the analyte into the capillary. The capillary is filled with a separation medium, such as linear polyacrylamide (e.g., LPA V2e, available from IntegenX Inc., Pleasanton, Calif.). The capillary ends are electrically connected to a voltage source, e.g., an anode and a cathode. Separated analyte is detected with a detection module. The detection module can employ, for example, a laser and a detector, such as a CCD camera, CMOS, photomultiplier, or photodiode. The anode assembly (e.g., anode cartridge interface) can include an anode in electrical connection with the capillary and a source of voltage. The anode assembly also can include a source of separation medium and a source of pressure for introducing separation medium into a capillary. The anode assembly can include electrophoresis buffer. The separation medium and/or the electrophoresis buffer can be included in an anode cartridge. The anode cartridge can be configured for removable insertion into the anode assembly. It can contain separation medium and/or electrophoresis buffer sufficient for one or more than one run.

A. Capillary Electrophoresis Assembly

The capillary electrophoresis assembly can include an injection assembly that can include a denture assembly, a cathode assembly; a capillary assembly; an anode assembly; a capillary filling assembly for filling a capillary with separation medium; a positioning assembly for positioning an analyte (or sample) for capillary injection; and a power source for applying a voltage between the anode and the cathode.

Figure 54A:
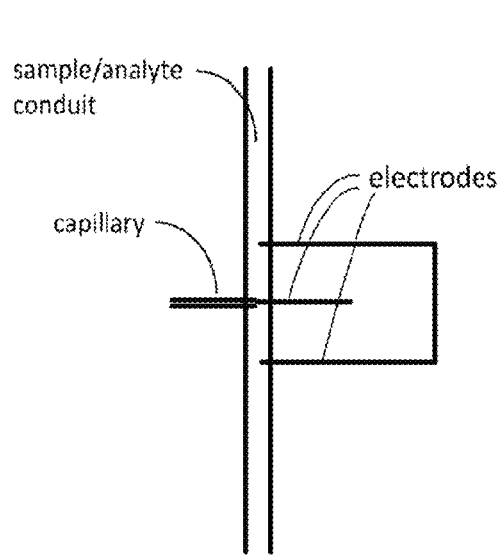
FIG. 54A and FIG. 54B shows an injection system for injecting a sample into an electrophoresis capillary.
Figure 54B:
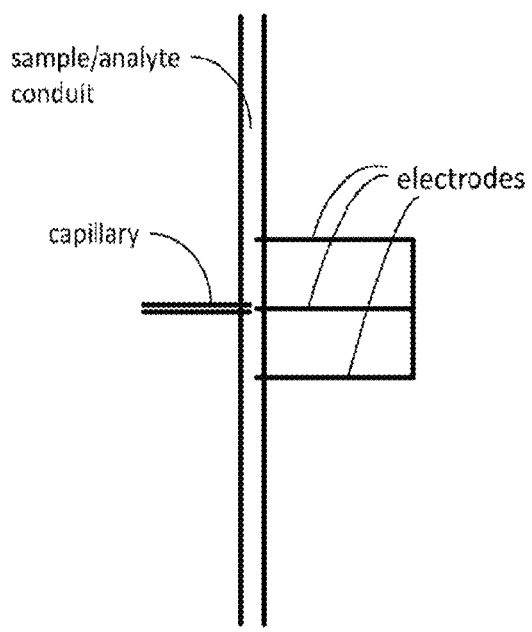

The capillary electrophoresis system can include one or more capillaries for facilitating sample or product separation, which can aid in analysis. In some embodiments, a fluid flow path directs a sample or product from the cartridge to an intersection between the fluid flow path and a separation channel. (See, e.g., FIGS. 49 and 54.) The sample is directed from the fluid flow path to the separation channel, and is directed through the separation channel with the aid of an electric field, as can be generated upon the application of an electrical potential across an anode and a cathode of the system (see below). U.S. Patent Publication No. 2011/0005932, which is entirely incorporated herein, provides examples of electrophoresis capillaries for use in analysis, as may be used with systems herein. The capillary can be inserted into the fluidic conduit for fluidic and electric communication.

1. Cathode Assembly

A cathode also can be in electric communication with the capillary through an electric communication with fluid in the fluidic conduit. The cathode can be disposed in the fluidic conduit near the connection with the capillary. For example the cathode can be positioned opposite the point at which the capillary connects with the fluidic conduit (e.g., neither upstream nor downstream of the connection). This can aid injection of the sample into the capillary and/or to provide voltage for the electrophoresis run. In certain embodiments, the cathode can comprise a forked electrode in which one fork is positioned upstream and one fork is positioned downstream of the point of connection of the capillary and the fluidic conduit. In other embodiments, the cathode comprises both a forked electrode and a third electrode positioned near the connection between the fluidic conduit and the capillary.

An electrophoresis sample (e.g., amplification products) can be prepared for injection into a separation channel (e.g., a capillary) by any suitable method. As an example, field-amplified stacking (FAS) can be performed by positioning in an electrophoresis sample channel a diluted mixture comprising the sample of lower salt concentration or lower ionic strength between areas comprising an electrophoresis buffer of higher salt concentration or higher ionic strength. As another example, a bolus of a material (e.g., air) can be positioned downstream of the sample in the sample channel, wherein the material has an electrical conductivity that differs from the electrical conductivity of the electrophoresis buffer or the sample, as described below. When the sample is positioned across the separation channel, the sample can be electrokinetically injected into the separation channel at an appropriate voltage (e.g., about 3 kV to about 5 kV, or about 4 kV) over an appropriate amount of time (e.g., about 10 sec to about 20 sec, or about 15 sec).

2. Capillary Assembly

Figure 5:
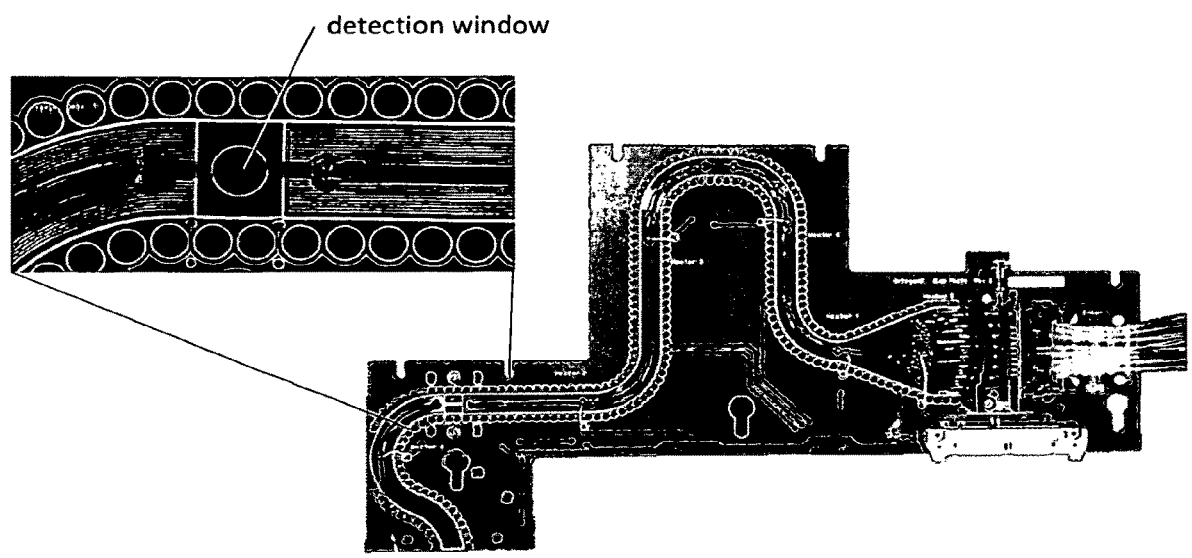
FIG. 5 shows an embodiment of capillaries for electrophoresis.

The system 100 is configured for sample (or sample product) analysis, such as with the aid of a capillary board. The capillary board (or plate) of the system 100 is shown in FIG. 5. The capillary board includes individual capillaries and integrated capillary and denature heaters. The capillary plate includes individual capillaries to be used in capillary electrophoresis on at least one sample. In some situations, the capillary board is for performing capillary electrophoresis on a plurality of samples, such as 1, 2, 3, 4, 5, 6, 7, 8, 9, 10, or more than 10 samples. To collect any liquid that may leak from, e.g., a capillary or the cathode of the electrophoresis system, a spill tray of sufficient collection capacity (e.g., up to about 50 mL, 75 mL, 100 mL, 125 mL or 150 mL) can be placed under the capillary board. The spill tray can optionally have a leak sensor for detection of any leak. A spill tray of sufficient collection capacity (e.g., up to about 50 mL, 75 mL, 100 mL, 125 mL or 150 mL) can also be placed under other components of the instrument or system described herein which may potentially leak liquid, e.g., under the buffer cartridge or the interface therefor, under the sample cartridge or the interface therefor, and/or under the anode cartridge or the interface therefor, where the spill tray can optionally have a leak sensor.

The system 100 includes a device for regulating the temperature of each of the electrophoresis capillaries. The capillaries may be held on an electrically insulating circuit board that has a generally curved path or a substantially straight path for placement of capillaries. In some embodiments, the capillaries are provided in one or more curvilinear paths, such as, e.g., a generally S-shaped path or a plurality of S-shaped paths. The capillary paths can be distributed into a plurality of sections. Each of the sections separately regulates the temperature in a portion of the capillaries in thermal communication with the section. Temperature is regulated with the aid of resistive heating, though other temperature control elements (e.g., heating element and/or cooling element) or devices may be used. Temperature can be measured with the aid of a temperature sensing device, such as a thermocouple, a thermistor or a resistive temperature device (RTD), in each section. Each of the different sections includes an electrical path that traverses the capillaries of each section. In some cases, the electrical path traverses back and forth (e.g., in a serpentine shape in that section). The electrical path includes one or more temperature control elements (e.g., heating elements and/or cooling elements) (e.g., resistive heaters) for providing heat to the capillaries. A portion of the electrical path is shown in the inset of FIG. 5.

On a circuit board, such as the circuit board shown in FIG. 5, electrophoresis capillaries are attached to a path (e.g., S-shaped path) with the aid of an adhesive, for example. In the illustrated embodiment, a bundle of eight capillaries are provided. In other embodiments, the path may include any number of capillaries, ranging from 1 to a higher number, depending on the requirements of a particular electrophoresis for parallel processing of analytes.

In some cases, an entrance of the capillaries has fanned out ends to facilitate injection of analytes into the different capillaries. One end of the capillaries may be bundled or the capillaries may be separate depending on whether all capillaries are filled together or if each capillary will be filled separately.

A thermal sensor is in contact with each of the separately thermally regulated areas or sections of the path. Examples of temperature sensors are thermistors or other temperature-varying resistance, or thermocouples or other temperature-varying voltage source. In some cases, the temperature data of the separately thermally regulated sections is not gathered by discrete temperature sensor, but by the electrical paths themselves such as by the resistances of the electrical paths. External temperature sensors may also be used.

Each section of the capillaries may be marked by a heater comprising one or more resistive heating elements. The heaters may be distributed across a path of the capillaries to provide temperature control.

With reference to FIG. 5, the electrophoresis separation channels (e.g., capillaries) can be electrically connected to a cathode and anode. The cathode and anode can be electrically connected to the high voltage module. The cathode is part of the capillary array and held in place by electrophoresis system hardware. The anode is part of the anode cartridge interface module and is connected to the electrophoresis system hardware (FIG. 5). In some embodiments, during electrophoresis high voltage is supplied to the anode electrode while cathode electrodes (e.g., sixteen cathode electrodes, two per channel) are held at ground. Current monitoring can be done between the cathodes and ground and can be monitored for individual channels on a high voltage board. The cathode electrodes are part of the capillary array and connections are made to the high voltage system during array installation.

Electrophoresis can be conducted at any voltage and over any period of time suitable for achieving good separation of the analyte (e.g., amplification products). In some embodiments, amplification products are separated at a voltage of about 6 kV to about 12 kV, or about 8 kV to about 10 kV, or about 9 kV, over a period of about 10 min to about 30 min, or about 15 min to about 25 min, or about 20 min. The length of the separation channels (e.g., capillaries) can also be selected to achieve good separation of the analyte. In certain embodiments, the length of a separation channel to the detection window is about 10 cm to about 40 cm, or about 15 cm to about 35 cm, or about 20 cm to about 30 cm, or about 25 cm.

The electrophoresis channels can be filled with a separation matrix (e.g., a separation polymer or gel) from the anode cartridge. Non-limiting examples of separation polymers and gels that can be used to separate nucleic acid fragments by electrophoresis include polyacrylamide (e.g., the LPA line (including LPA-1) of separation gels (Beckman Coulter), the POP™ line (including POP-4™, POP-6™ and POP-7™) of separation polymers (Life Technologies), and a modified LPA with a self-coating polymer (e.g., LPA V2E (IntegenX Inc.)), agarose, hydroxyethylcellulose, and other biopolymers. To separate single-stranded nucleic acid fragments, denaturing gel electrophoresis can be performed using a separation polymer or gel that comprises a chemical denaturant (e.g., urea, formamide or N-methyl-2-pyrrolidone) and/or at a temperature (e.g., about 60° C., 65° C., 75° C., 85° C. or 90° C. or higher) that denatures double-stranded nucleic acid fragments. Heat can be applied to nucleic acid fragments prior to their injection into a separation channel using a denature heater as described below, and/or during separation using a thermally controlled solid-state heating system (e.g., a heating system comprising one or more metal wires (e.g., copper wires) adjacent to the separation channels (e.g., under the board containing the capillary electrophoresis array)) as described herein.

In some embodiments, electrophoresis is performed using one or more chemical compounds that denature double-stranded nucleic acid (e.g., DNA) fragments to single-stranded fragments. In certain embodiments, the one or more chemical denaturants are hydrogen-bond acceptors or hydrogen-bond donors, or can function as both hydrogen-bond acceptors and hydrogen-bond donors. In some embodiments, the one or more chemical denaturants are selected from the group consisting of:

acyclic and cyclic amides, including formamides (e.g., formamide, N-methylformamide, and N,N-dimethylformamide); pyrrolidones (e.g., 2-pyrrolidone, N-methyl-2-pyrrolidone, N-ethyl-2-pyrrolidone, N-hydroxyethyl-2-pyrrolidone, 3-methyl-2-pyrrolidone, 4-methyl-2-pyrrolidone, 5-methyl-2-pyrrolidone, N-methyl-3-methyl-2-pyrrolidone, N-methyl-4-methyl-2-pyrrolidone, N-methyl-5-methyl-2-pyrrolidone, N-ethyl-3-methyl-2-pyrrolidone, N-ethyl-4-methyl-2-pyrrolidone, and N-ethyl-5-methyl-2-pyrrolidone); piperidones (e.g., 2-piperidone, N-methyl-2-piperidone, N-ethyl-2-piperidone, N-hydroxyethyl-2-piperidone, 3-methyl-2-piperidone, 4-methyl-2-piperidone, 5-methyl-2-piperidone, 6-methyl-2-piperidone, N-methyl-3-methyl-2-piperidone, N-methyl-4-methyl-2-piperidone, N-methyl-5-methyl-2-piperidone, N-methyl-6-methyl-2-piperidone, N-ethyl-3-methyl-2-piperidone, N-ethyl-4-methyl-2-piperidone, N-ethyl-5-methyl-2-piperidone, and N-ethyl-6-methyl-2-piperidone); and caprolactams (e.g., c-caprolactam, N-methyl-c-caprolactam, N-ethyl-c-caprolactam, and N-hydroxyethyl-E-caprolactam);

acyclic and cyclic ureas, including urea, N-methylurea, N,N-dimethylurea, N,N'-dimethylurea, tetramethylurea, hydroxyurea, N-methyl-N-hydroxyurea, N'-methyl-N-hydroxyurea, N',N'-dimethyl-N-hydroxyurea, N',N'-dimethyl-N-methyl-N-hydroxyurea, methoxyurea, N-methyl-N-methoxyurea, N'-methyl-N-methoxyurea, N',N'-dimethyl-N-methoxyurea, 2-imidazolidone (ethyleneurea), N-methyl-2-imidazolidone, N,N'-dimethyl-2-imidazolidone, trimethyleneurea, N-methyl-trimethyleneurea, and N,N'-dimethyl-trimethyleneurea;

acyclic and cyclic thioureas, including thiourea, N-methylthiourea, N,N-dimethylthiourea, N,N'-dimethylthiourea, tetramethylthiourea, 2-imidazolidinthione (ethylenethiourea), N-methyl-2-imidazolidinethione, N,N'-dimethyl-2-imidazolidinethione, trimethylenethiourea, N-methyl-trimethylenethiourea, and N,N'-dimethyl-trimethylenethiourea;

nitrogen-containing aromatic compounds, including pyridines (e.g, pyridine, 2-aminopyridine, 3-aminopyridine, and 4-aminopyridine), pyrimidines (e.g., pyrimidine, 2-aminopyrimidine, 4-aminopyrimidine, and 5-aminopyrimidine), and pyrazines (e.g., pyrazine and aminopyrazine);

acyclic and cyclic sulfides, sulfoxides and sulfones, including dimethylsulfoxide, sulfolane and sulfolene;

acyclic and cyclic ethers, including dioxanes (e.g., 1,4-dioxane); and acyclic and cyclic alcohols, including tetrahydro-3-furanol, tetrahydrofurfuryl alcohol (tetrahydrofuran-2-methanol), tetrahydrofuran-3-methanol, 2,5-dihydrofuran-2-methanol, tetrahydro-3-pyranol, tetrahydro-4-pyranol, and tetrahydropyran-2-methanol.

In certain embodiments, the one or more chemical denaturants comprise urea, 2-pyrrolidone, N-methyl-2-pyrrolidone, N-ethyl-2-pyrrolidone or tetrahydrofurfuryl alcohol, or any combination thereof.

In some embodiments, the concentration of each chemical denaturant, or the total concentration of the one or more chemical denaturants, in the separation polymer or gel is at least about 0.1 M, 0.5 M, 1 M, 2 M, 3 M, 4 M, 5 M, 6 M, 7 M, 8 M, 9 M or 10 M, or about 1-10 M, 2-8 M, 3-7 M or 4-6 M. In further embodiments, the concentration of each chemical denaturant, or the total concentration of the one or more chemical denaturants, in the separation polymer or gel is at least about 1%, 5%, 10%, 15%, 20%, 25%, 30%, 35% or 40% by mass or volume, or is about 10-40%, 15-35%, 15-30%, 20-30%, 15-20%, 20-25% or 25-30% by mass or volume. In yet further embodiments, the total concentration of the one or more chemical denaturants in the separation polymer or gel is about 10-40%, 15-35%, 15-30% or 20-30% by mass or volume.

In additional embodiments, electrophoresis is performed using one or more chemical denaturants and at a temperature of at least about 50° C., 60° C., 70° C., 80° C. or 90° C., or at about 50-90° C., 60-80° C., 70-90° C., 50-60° C., 60-70° C., 70-80° C. or 80-90° C. Heating can promote denaturation of double-stranded polynucleotides (e.g., DNA) to single-stranded fragments, and/or decrease the time (e.g., to no more than about 30, 25, 20, 15 or 10 minutes) of electrophoretic separation (e.g., from the point of injection of fragments into the separation channel until they pass through the detection region) through faster migration of fragments, with good resolution of fragments over a wide range of base lengths. In some embodiments, electrophoresis is performed using one or more chemical denaturants comprising urea, 2-pyrrolidone, N-methyl-2-pyrrolidone, N-ethyl-2-pyrrolidone or tetrahydrofurfuryl alcohol, or any combination thereof, and at a temperature of about 60-80° C., where the concentration of each chemical denaturant, or the total concentration of the one or more chemical denaturants, is about 3-7 M or about 15-30% by mass or volume. In certain embodiments, electrophoresis is performed using 2-pyrrolidone, N-methyl-2-pyrrolidone or N-ethyl-2-pyrrolidone at a concentration of about 15-30% (including about 15-20%, 20-25% or 25-30%) by mass or volume, and at a temperature of about 60-80° C. (including about 60-70° C. or 70-80° C.).

3. Anode Assembly

Figure 6:
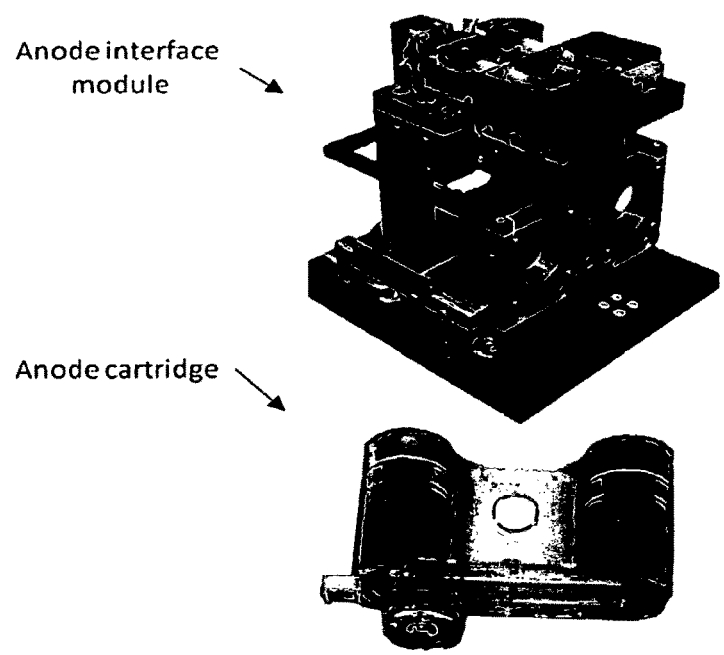
FIG. 6 shows embodiments of an anode interface module and an anode cartridge.

FIG. 6 shows an anode assembly (e.g., anode cartridge interface module) of the system 100. The anode cartridge interface module includes an anode interface module (top) and an anode cartridge (bottom). The anode cartridge in some cases is a disposable, limited use (e.g., single-use) cartridge. The anode cartridge may be formed by injection molding a polymeric material or by other methods. In one embodiment the anode cartridge can comprise two chambers. One chamber can contain separation matrix and the other chamber can contain electrophoresis buffer. In another embodiment, both chambers can contain separation matrix. In yet another embodiment, the anode cartridge can comprise a single chamber containing buffered separation matrix. The chamber comprising electrophoresis buffer can be in electrical communication with the anode. It also can be in electrical communication with the capillaries and with the chamber comprising the separation matrix, e.g., through one or more fluidic channels. Each chamber can comprise a plunger operatively linked with a pressure source and adapted to move separation matrix and/or buffer out of the chambers. Each plunger can be independently operable. The anode cartridge can be prefilled with a separation matrix and buffer. In some embodiments, the anode cartridge has an on-board memory, such as an electrically erasable programmable read-only memory (EEPROM), which may include calibration details and/or device configuration.

The anode cartridge is configured to be inserted into a port of the anode interface module. The anode interface module includes an automated engagement mechanism for engaging with the anode cartridge. In some cases, an integrated high voltage electrode in the anode interface module provides power to the anode cartridge. The anode interface module comprises a memory reader for being communicatively coupled to the on-board memory of the anode cartridge. In some situations, the memory reader is an EEPROM reader configured to communicate with (and read from) an EEPROM of the anode cartridge.

4. Filling Assembly

The anode cartridge includes (e.g., is pre-loaded with) a separation matrix (e.g., polymer or gel) that is used in electrophoresis. In some embodiments, the anode cartridge further comprises (e.g., is further pre-loaded with) an aqueous buffer for electrophoresis which contains one or more buffering agents selected from bicine, tricine, Tris, 3-amino-1-propanesulfonic acid, CABS, CAPS, CAPSO, CHES, EPPS, and TAPS. In an embodiment, the anode cartridge comprises an aqueous buffer containing Tris and TAPS. In certain embodiments, the aqueous buffer further contains a metal chelator, such as a metal chelator described herein. In an embodiment, the metal chelator comprises EDTA. The anode cartridge can further comprise a readable and/or writable memory device (e.g., an EEPROM chip) configured to store, receive and transmit information relating to the cartridge (e.g., the batch number of the cartridge, a recommended use-by date for the cartridge, the composition and the remaining amount of the aqueous buffer, the composition and the remaining amount of the separation matrix, and the condition of the anode electrode).

In one embodiment, during electrophoresis, high voltage is supplied to the anode electrode while cathode electrodes (e.g., two per channel) are held at ground. Current monitoring can be done between the cathodes and ground and can be monitored for individual channels on a system board. The separation matrix may be a separation polymer or gel. The separation polymer may be provided to the separation channels (e.g., capillaries) (see, e.g., FIG. 5) through an interface at the anode that connects to the electrophoresis system hardware for anode high voltage supply and control. The anode cartridge attaches to the anode interface module and supplies pressure and reagent for every run. The system is pressure driven and can be controlled by solenoids managed by the electronics. Pressure can be monitored by electronic transducers monitored by the electronic safety of the system 100. Safety can be provided by passive and active pressure relief paths and by current shut-off when any access doors are opened during a run.

After a separation run in a separation channel is completed, the same separation matrix (e.g., polymer or gel) can be re-used in one or more subsequent separation runs, or the separation matrix can be discarded and the separation channel can be re-filled with new separation matrix from the same anode cartridge. An anode cartridge can be filled with an amount of separation matrix and an amount of electrophoresis buffer sufficient for a desired number of separation runs.

5. Positioning Assembly

The disclosure provides a method for positioning a sample for injection into a capillary. According to one embodiment the method involves providing a fluidic conduit in fluid communication with a sample-containing container and capillary, wherein the capillary intersects a fluidic path of the fluidic conduit and wherein the capillary is in electric communication with an anode and a cathode and wherein the cathode is inserted into the fluidic conduit; positioning a bolus of a material having electrical conductivity that is distinctive from the electrical conductivity of either electrophoresis buffer or sample (e.g., the material comprises air) downstream of the sample in fluidic conduit; moving the bolus of material and the sample in the direction of the capillary while monitoring a current across the anode and the cathode; detecting a distinct current (e.g., a change in current) corresponding to movement of the bolus into an electrical path in the conduit between the cathode and the anode; based on detecting, moving the sample into the electrical path in the conduit between the cathode and the anode. Alternatively, an optical sensor can also be used to detect and control the position of a bolus. The method can further comprise applying an injection voltage and/or a run voltage to inject the sample into the capillary and to run the sample in the capillary. The bolus can be positioned by, for example, pumping a bolus of the material into the conduit using a pump such an on-chip pump in a cartridge containing the sample, e.g., a diaphragm pump; or a pumping mechanism that is not on the cartridge such as a peristaltic pump, syringe pump, etc. Accordingly, in another embodiment, the sample delivery subsystem is configured as (a) a sample channel having a channel inlet and a channel outlet; (b) an electrophoresis capillary having a capillary inlet and a capillary outlet, wherein the capillary comprises an electrically conductive medium and is in communication with the sample channel at a point of connection; (c) an anode and a cathode configured to apply a voltage across the capillary inlet and capillary outlet, wherein one of the anode or cathode comprises a forked electrode wherein the forks are in electrical communication with the sample channel on different sides of the point of connection; and (d) a second electrode in electrical communication with the sample channel substantially opposite the point of connection. In one embodiment of the device, the second electrode is comprised as a third fork in the forked electrode.

6. Denature Heater

Figure 53:
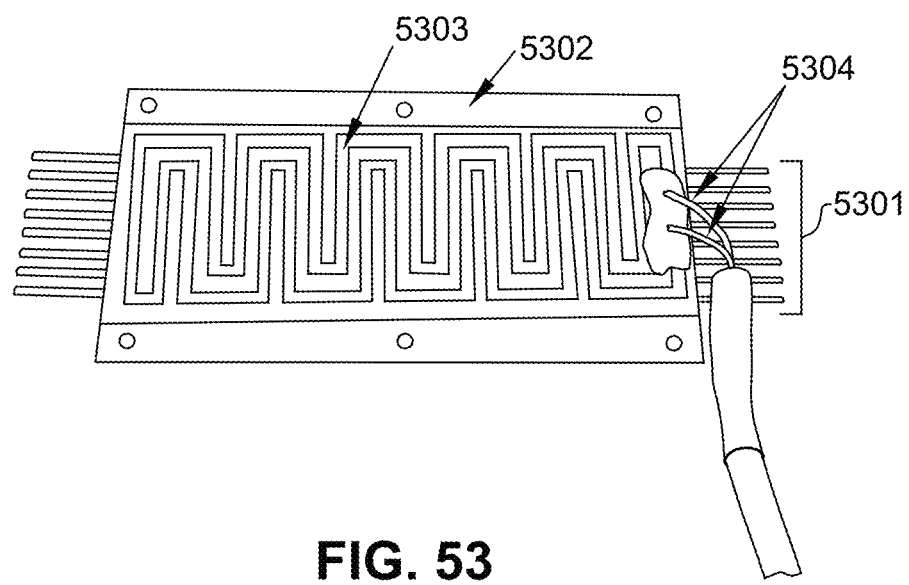
FIG. 53 shows a denature heater of this invention.

In certain embodiments, a denature heater is configured as a cannula (or a plurality of cannulae) in thermal contact with a heating element. The cannula can be fluidically connected on one end to the dilution chamber (see, e.g., chamber 1009 in FIG. 10) and on the other end to the capillary sample injector. The assembly comprising the cannula and the heating element can be configured to heat fluid inside the cannula to a temperature that denatures double-stranded nucleic acid such as DNA. In certain embodiments, the cannula can comprise a heat-conducting material, such as a metal tube. The heating element can comprise a resistive heater or other type of heating mechanism. For example, the heating element can comprise an electrically resistive material connected to a source of voltage. The cannula can be clamped between elements of a resistive heater, such as plates. The denature heater can be configured to electrically isolate each of a plurality of cannulae in the heater from each other and from the heating element. For example, the cannulae can be separated from each other and from the heating element by an electrically resistant material. For example, the cannulae can be embedded in an epoxy. The denature heater also can comprise an insulator configured to insulate elements in proximity to the denature heater from heat generated by it. FIG. 53 shows a denature heater of this invention. It includes cannulae 5301, heating element 5302 comprising resistive heater 5303 attached to wires 5304 leading to a source of voltage.

The denature heater can heat an electrophoresis sample to a temperature suitable for denaturing double-stranded nucleic acid (e.g., DNA) to single-stranded fragments prior to injection of the sample into a separation channel (e.g., a capillary). In certain embodiments, the denature heater heats an electrophoresis sample to a temperature of about 90-99° C. or 94-98° C., or about 90° C. or 95° C.

B. Detection Assembly

A detector can be used to observe or monitor materials in the electrophoresis capillaries (or channels). The detector can be, e.g., a charge-coupled device (CCD) camera-based system or a complementary metal oxide semiconductor (CMOS) camera-based system.

The system can include multiple (e.g., 4, 8, 10, 16, 24, 32, 40, 48 or more) electrophoresis separation channels (e.g., capillaries), a light source (e.g., a laser device or a light-emitting diode), an optical detector, and an optical selector. The laser device is positioned to deliver a beam from the laser device to at least one electrophoresis capillary. The optical detector is optically coupled to receive an optical signal from at least one electrophoresis capillary. The laser device, optical detector, and optical selector are in an arrangement that allows the optical detector to selectively detect an optical signal from any one or more of the multiple electrophoresis capillaries.

The laser device can be selected in part based on an output wavelength suitable for distinguishing the separated analyte (e.g., nucleic acid fragments). The nucleic acid fragments can be labeled with a certain number of (e.g., 2, 3, 4, 5 or more) spectrally resolvable fluorescent dyes (e.g., by using primers labeled with those dyes in amplification) so that fragments having different sequences but having the same size and the same electrophoretic mobility can still be distinguished from one another by virtue of being labeled with dyes having spectrally resolvable emission spectra. The laser device can be selected to have one or two output wavelengths that efficiently excite the fluorescent dyes used to label the nucleic acid fragments. The laser device can have a single output wavelength (e.g., about 488 nm) or dual wavelengths (e.g., about 488 nm and about 514 nm). The laser device can scan across the interior of each separation channel at an appropriate rate (e.g., about 1 Hz to about 5 Hz, or about 2 or 3 Hz). The fluorescence emission of each dye excited by the laser device can pass through a filter and a prism and can be imaged onto a suitable detector (e.g., a CCD camera or a CMOS camera).

In one embodiment, the capillaries are arranged as an array. In one embodiment, the optical selector is optically positioned between the laser device and the multiple electrophoresis capillaries. The beam from the laser device is delivered to a single electrophoresis capillary and not delivered to other electrophoresis capillaries. In one embodiment, the optical selector is a scanning objective directing the beam from the laser device to the single electrophoresis capillary and not to other electrophoresis capillaries. In one embodiment, the scanning objective is adapted to make a traversing motion relative to the beam from the laser device entering the scanning objective. In another embodiment, the optical selector is an aperture passing the beam from the laser device to the single electrophoresis capillary and not to other electrophoresis capillaries. One embodiment further includes a capillary alignment detector optically coupled to receive a reflection of the beam from the single electrophoresis capillary. The reflection indicates an alignment of the beam with the single electrophoresis capillary.

In one embodiment, the optical selector is optically positioned between the multiple electrophoresis capillaries and the optical detector. The optical signal from the multiple electrophoresis capillaries to the optical detector is limited to a single electrophoresis capillary.

Various embodiments further include a wavelength dependent beam combiner optically coupled between the laser device and the optical detector, or a spatial beam combiner optically coupled between the laser device and the optical detector.

C. Analysis Assembly

An analysis assembly can comprise a computer comprising memory and a processor for executing code in the computer for receiving the data output of the detection assembly, processing the data and producing a file that reports a metric or characteristic of the analyte(s) analyzed (e.g., an answer).

In a preferred embodiment, the analysis module can comprise memory and a processor that executes code that performs the analysis to classify STR fragments by length and by the spectral characteristics of an attached dye and then use this information along with ancillary information such as the separation of an allelic ladder to determine which STR alleles are present in the detected amplification products; this process is typically referred to as calling the STR alleles. In the case of STR analysis, the analysis assembly can receive raw electropherogram data, transform it into a format that is recognizable by, e.g., allele calling software, and, using the allele calling software, identify alleles and report them in a format understandable by a user or recognized by a database. For example, the analysis assembly can take an electropherogram and produce a CODIS file recognized by, e.g., the FBI's National DNA Index System (NDIS).

An electropherogram generated from separation of amplified STR fragments can be analyzed in the following way. The detection modality of the system (e.g., optical detection) will produce a data stream that is an amalgam of the signals coming from fluorescent dyes attached to the STR fragments as well as a host of optical and electronic background effects. This data stream can be processed into a form that is consumable by the STR calling software (e.g., an expert system).

The input data that is expected by most commercial STR-calling expert systems typically contains arrays of numbers of dimensionality N×M, where N is the number of dyes that are detected by the system, and M is a time sequence of points taken during the separation. Some expert systems have upper limits on N and M, and this can vary from product to product. There are a number of ancillary assumptions that commercial expert systems make about these data streams:

(1) Most electronic and optical noise from the detection mode has been removed.
(2) Each of the N channels nominally referenced to the same dark signal, defined to be "zero."
(3) Enough measurements have been taken of each fragment to insure sufficient base pair resolution for the minimum-size repeat pattern in the STR kit. Nominally, this means a sampling frequency sufficient to obtain 5-10 measurements over the time that it takes a fragment to migrate past the detector.
(4) Each individual channel in the N dimension represents the photonic signal coming from a single dye as much as is possible for the detection mode. To the degree that this condition isn't satisfied, it is called "bleed-through".

The functionality that STR calling software can provide includes:
(1) Sizing of fragments relative to an in-lane size standard.
(2) Calibration of allele bins using a (potentially optional) allelic ladder.
(3) Allele calling with morphological rejection filters (for common PCR effects such as stutter).
(4) Quality flag assignment based on mathematical measures such as signal-to-noise.
(5) Call summary output generation as text.

The practitioner can properly tune the performance of the STR calling software to minimize the false-positive measurement set. The procedures for this are known in the art and, for commercially available software, can be contained in the product documentation.

As described above, expert systems will provide services that identify the base pair size of fragments found in the data stream and attach a preliminary allele assignment to each fragment if such exists. In addition, a quality flag can be assigned to the allele call which is reported to the analyst. The practitioner then decides what the STR profile actually is based on information from the flags. The process can be further automated by putting into place a rules engine to process the calls and quality flags into a final profile. This rules engine can be trained on the system's data to know when to keep and when to reject an allele based on The specific content of the quality flags coming from the system.

Figure 50:
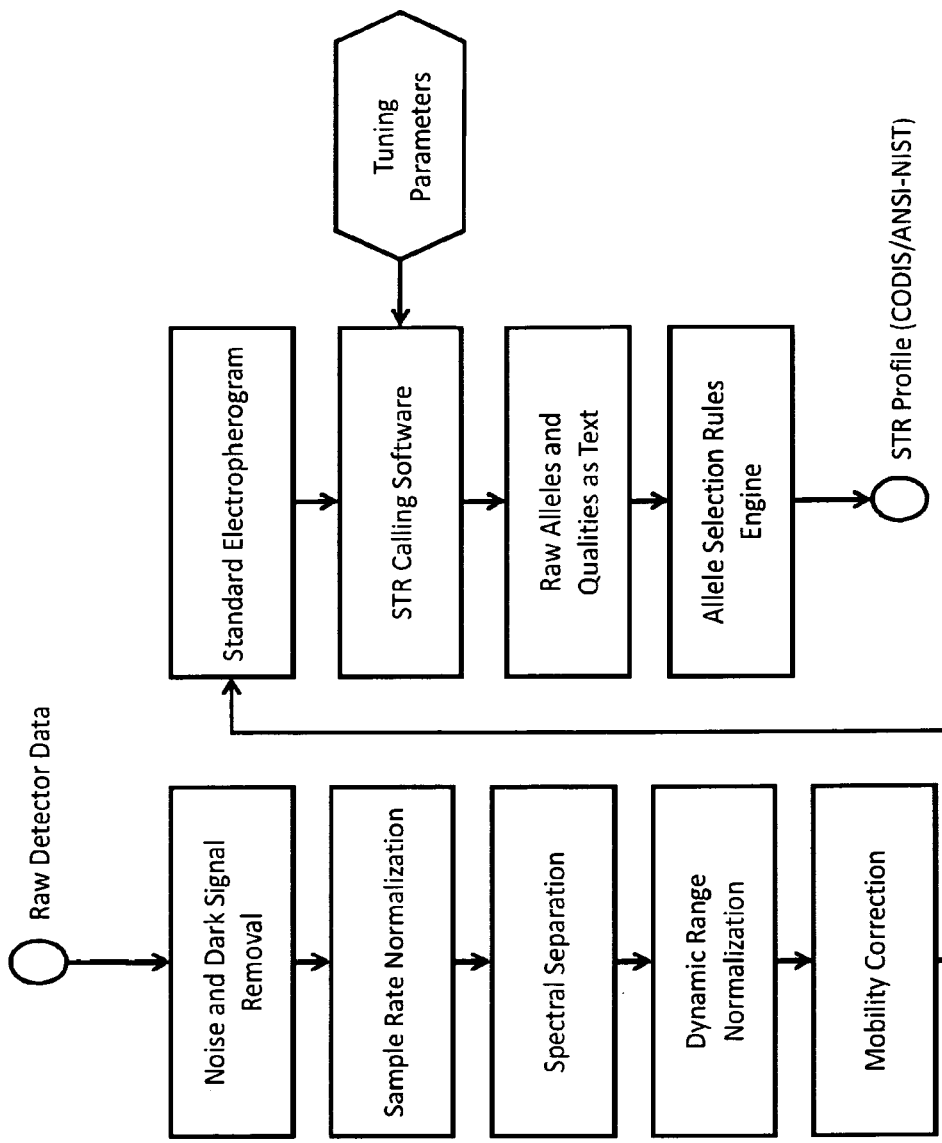
FIG. 50 shows a process for transforming data from an electropherogram into a format usable by STR allele-calling software.

An entire process is shown in FIG. 50: The first five boxes on the left of the diagram show how to generically process data in a way that reflects the input assumptions 1-4 mentioned above. Some of these steps may be optional depending on the quality of the separation and type of detector used. These steps culminate in the generation of an electropherogram in a standard format, typically *.fsa. These are fed to the STR calling package that processes the electropherograms using an implementer-supplied parameter tuning. Finally, these calls are filtered by a rules engine to create the final, reliable STR profile.

Software to perform STR and kinship analysis are commercially available from, for example, GeneMarker®HID STR Human Identity software and GeneMarker® kinship analysis software (SoftGenetics, State College, Pa., USA)); DNA-VIEW™ v29.11 (Charles Brenner); LISA (Future Technologies Inc., Fairfax, Va., USA); KInCALcv3.1 (California Department of Justice); and GeneMapper (Life Technologies, Carlsbad, Calif.).)

Additional methods for transforming electropherograms are described below.

1. Segmentation Base-Lining

In some specific embodiments, a system as described herein may include or work with a separable logic module or method for improved base-lining in electrophoresis data. A "base line" or "zero level" in signal processing generally refers to the level below which signal and signal variations is considered due to noise or otherwise not of interest. Baselining in signal processing generally describes methods for determining, for an entire signal or for specific samples or locations of a signal, which level of the signal is due to noise and removing or subtracting that level from the signal. Correctly determining a baseline level for capillary electrophoresis signals and similar signals is challenging when the signals are rapidly changing and/or are collected over a time period during which the baseline noise may change. In rapidly changing signals with a variable signal noise, it can be difficult to accurately determine a base-line correction.

In one embodiment, a novel segmentation base-lining logic module or method first determines segments or periods of the collected data where no signal of interest is determined to be present (referred to at times as "flat" segments) and areas of high variation that contain signal of interest (referred to at times as "signal segments" or "variable segments"). Generally, the flat regions and signal regions alternate, such that each signal region is bounded by two flat regions. A base line correction curve can be determined for each of the flat regions. In a preferred embodiment, this determination is done separately for each region and is generally a polynomial fit curve, which can be linear or some higher order. The endpoints for the base-line correction for the two different flat regions are then used to determine a base-line correction for the signal region. The base line correction for the signal region is also a polynomial and can be a line or a spline and is generally fit so as to be continuous to the flat regions on either side at least to the 1st derivative or forward difference and optionally also to the 2nd derivative or forward difference.

With the flat and varying regions identified, various curve fitting techniques are applied to different segments to construct a piece-wise continuous overall curve representing the baseline correction. This curve effectively is then subtracted from the data stream (for example, data derived from a detector such as a chromatogram trace or binned chromatogram trace as described herein) to provide a "baselined" or "zeroed" data set. It has been found that in some embodiments or situations and in some systems such as described herein, a segmented baselining approach provides more accurate results.

2. Dynamic Spectral Correction

In some specific embodiments, a system as described herein may include or work with a separable logic module or method for dynamic spectral correction. Capillary electrophoresis systems typically use fluorescently labeled primers to help distinguish to which locus a particular DNA fragment is related. Because some alleles from different loci might overlap in terms of their bp length, the different spectral profile or color of each dye is used to distinguish to which locus a particular detected allele is related. However, labeling dyes have somewhat broad and overlapping spectral response. As a result, a single dye in a multi-spectral-channel detector causes a signal in multiple spectral channels. The characteristic frequency response of a dye is a times referred to as the dye's spectral profile. Thus, a detection in multiple channels at a particular time period may involve a complex mixture of signal from different dyes. Many electrophoresis systems employ some type of spectral calibration in which a matrix is created. This matrix is used to determine the detection of specific dyes from the multi-channel data. Thus, in many systems, overlap of spectral profiles is automatically calculated and subtracted using fluorescence "matrix" standards.

However, the spectral profiles of different dyes as detected can vary in different electrophoresis runs. In a preferred embodiment, a dynamic spectral correction module examines the collected data and determines time periods when the spectral energy detected is from one dye only. Machine learning and/or clustering algorithms (for example, Principal Component Analysis) are used to identify the pure multi-spectral peaks. The three highest intensity values from those peaks can then be used to determine a corrective phase shift whereby the spectral profile for one or more dyes can be resampled in software and the spectral correction matrix recalculated on a per-chromatogram or per-trace basis.

3. Differential Mobility Correction

As referenced above, capillary electrophoresis data is typically gathered over a relatively long period (e.g., 10-45 minutes). This creates numerous problems in determining various calibrations for the capillary electrophoresis data to particular systems and run conditions. One such calibration is typically made to the reference allele (or allelic) ladder that is used to call particular detected alleles in a sample. In one form, the allelic ladder is a reference set of sequence lengths that generate reference signal peaks at particular base-pair (bp) lengths that are compared to the sample peaks in order to identify (or call) the allele of the particular peaks in the sample.

When an allele ladder mixture is placed into an electrophoresis capillary for reading (generally alongside a sample capillary) both the ladder and the sample can also include a set of known length DNA fragments, referred to as a "size standard," and "internal size standard" or a "size ladder". After the electrophoresis of the allele ladder is run, it is often the case that the peaks produced as indexed by the Size Standard peaks are not at the locations (or within the bins) indicated by the expected allele values. This can lead to both false positives and false negatives in allele calling. Many systems use automated methods to provide some adjustments to the allele ladder to correspond to the expected allele values. These methods can work when migration characteristics are varying slowly. However, there are cases where strong non-linearities in the migration (which generally takes place over a period of time of about 10-45 minutes) cause marked shifts in ladder peak locations relative to the sizing peaks.

A Differential Mobility Correction module as described above uses a three phase adjustment where a metric is calculated representing the quality of the allelic ladder panel fit to the expected bins. This metric is calculated (1) first for the allelic ladder panel as a whole, (2) then for each locus in the allelic ladder panel in turn, and (3) then for each allele bin of the allelic ladder individually. During locus calibration, a special optimal metric search is used that contains monotonic telescoping of spacing to prevent phase shifting in locus alignment to peaks.

IV. Control Module

A. Computer

Systems provided herein include various hardware and software. In some embodiments, a system for sample preparation, processing and analysis, such as the system 100 of FIG. 1 (or any other system provided herein), includes a controller with a central processing unit, memory (random-access memory and/or read-only memory), a communications interface, a data storage unit and a display. The communications interface includes a network interface for enabling a system to interact with an intranet, including other systems and subsystems, and the Internet, including the World Wide Web. The data storage unit includes one or more hard disks and/or cache for data transfer and storage. The data storage unit may include one or more databases, such as a relational database. In some cases, the system further includes a data warehouse for storing information, such as user information (e.g., profiles) and results. In some cases, the data warehouse resides on a computer system remote from the system. In some embodiments, the system may include a relational database and one or more servers, such as, for example, data servers. The system 100 may include one or more communication ports (COM PORTS), one or more input/output (I/O) modules, such as an I/O interface. The processor may be a central processing unit (CPU) or a plurality of CPU's for parallel processing.

The system 100 may be configured for data mining and extract, transform and load (ETL) operations, which may permit the system to load information from a raw data source (or mined data) into a data warehouse. The data warehouse may be configured for use with a business intelligence system (e.g., Microstrategy®, Business Objects®). It also can be configured for use with a forensic database such as the National DNA Index System (NDIS)) in the USA or NDAD in the United Kingdom, State DNA Index Systems (SDIS), or Local DNA Index Systems (LDIS) or other databases that contain profiles from known and unknown subjects, forensics samples, or other sample types such as organism identifications.

Aspects of the systems and methods provided herein may be embodied in programming. Various aspects of the technology may be thought of as "products" or "articles of manufacture" typically in the form of executable code and/or associated data that is carried on or embodied in a type of machine readable medium. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Thus, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media thus include, e.g., a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Figure 19:
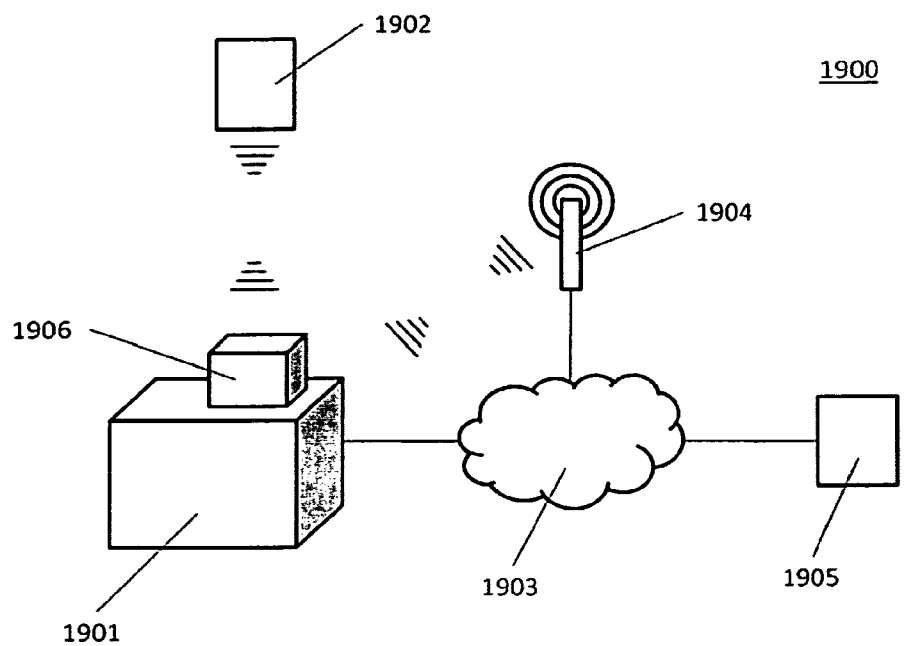
FIG. 19 shows an embodiment of a system for sample processing.

In some embodiments, the system 100 is configured to communicate with one or more remote devices, such as a remote electronic device (see FIG. 19). Such remote connection is facilitated using the communications interface. In some situations, the system 100 presents information to (or requests information of actions from) the user by way of a user interface on an electronic device of the user (see below). The user interface can be a graphical user interface (GUI). In some cases, the GUI operates on an electronic device of the user, such as a portable electronic device (e.g., mobile phone, Smart phone). The electronic device can include an operating system for executing software and the graphical user interface of the electronic device.

Figure 38B:
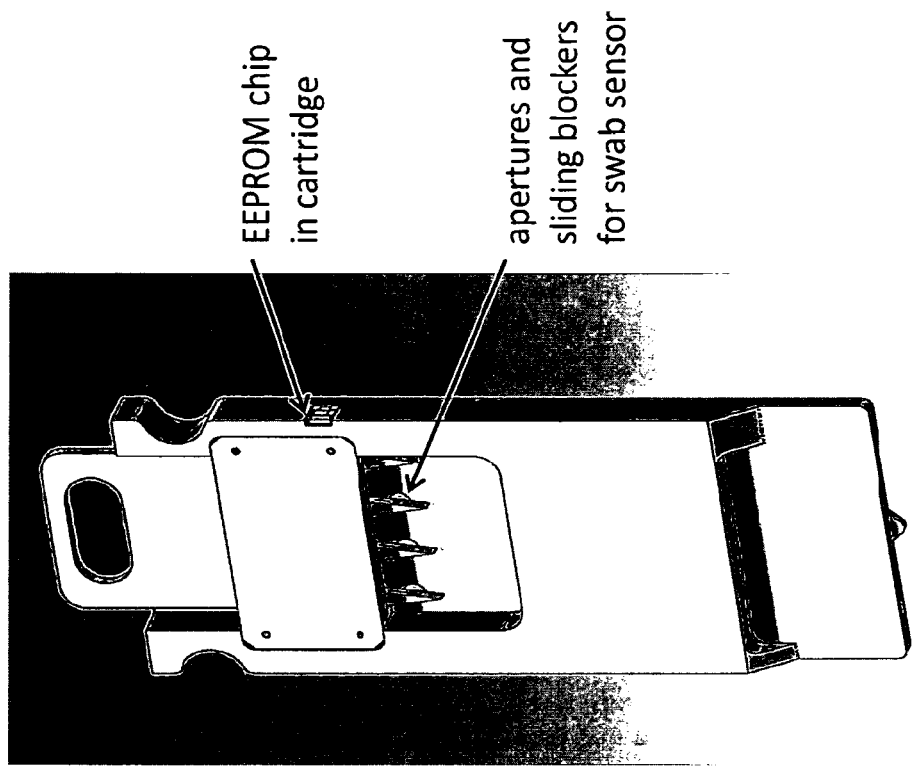
FIG. 38B shows an embodiment of a cartridge comprising an embedded EEPROM chip and apertures and sliding blockers for swab sensing.
Figure 38A:
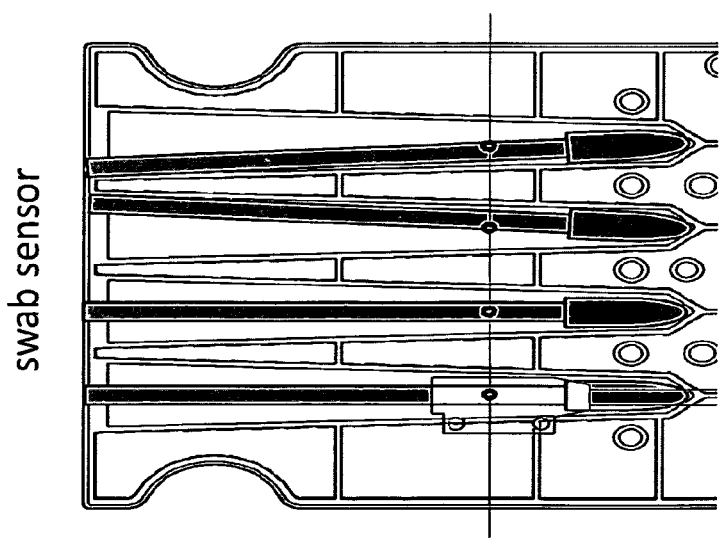
FIG. 38A shows an embodiment of a swab sensor.

In some embodiments, the system 100 provides alerts, updates, notifications, warnings, and/or other communications to the user by way of a graphical user interface (GUI) operating on the system or an electronic device of the user. The GUI may permit the user to access the system to, for example, create or update a profile, view status updates, setup the system 100 for sample preparation and processing, or view the results of sample preparation, processing and/or analysis. The system can be configured to operate only when a user provides indicia of permission, such as a key card and/or a password. The system can record and provide information on sample chain of custody, contamination or tampering. Systems to record and provide such information can include controls on access to operate the system (e.g., operator permission requirements); sample control (e.g., sensors to indicate introduction or removal of a sample from a cartridge) (see, e.g., FIGS. 38A and 38B); enclosure control (e.g., sensors indicating door opening and closing) and cartridge control (e.g., sensors for indicating insertion, proper seating and removal of cartridge).

In some embodiments, the system includes one or more modules for sample processing and/or analysis, and a controller for facilitating sample processing and/or analysis. The controller can include one or more processors, such as a central processing unit (CPU), multiple CPU's, or a multi-core CPU for executing machine-readable code for implementing sample processing and/or analysis. The system in some cases directs a sample sequentially from one module to another, such as from a sample preparation module to an electrophoresis module.

B. User Interface

In another aspect of the invention, a user interface is provided for enabling a user to interact with systems provided herein. In some embodiments, the user interface is a graphical user interface (GUI) that includes various graphical objects (e.g., icons, etc.) and, in some cases, auditory elements for permitting a user to interact with a sample preparation, processing and analysis system ("the system"), such as the system 100 of FIG. 1. The GUI can be configured to recognize gestures or other visual or auditory user commands for implementing a predetermined task or by touching or swiping a touch screen or by use of a 'mouse' or other standard input devices. In some cases, a particular gesture is linked to a particular task. The GUI is configured to be displayed on a display of the system or a remote electronic device (see FIG. 19 and the related text). In an example, the GUI is configured to be displayed on the display 101 of the system 100 of FIG. 1.

Figure 20:
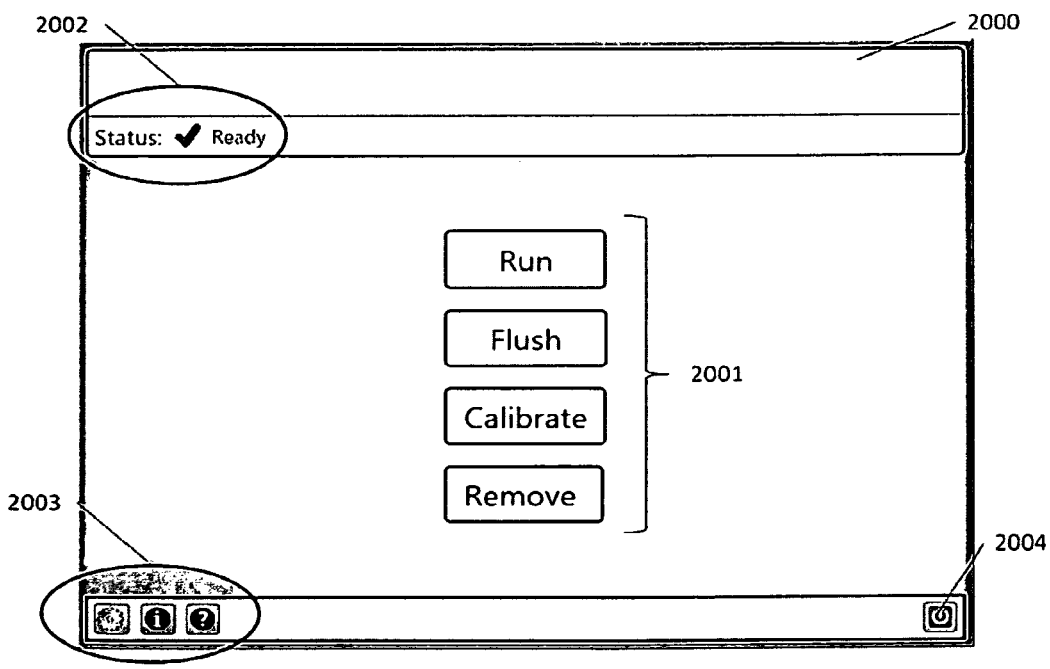
FIGS. 20-30 show embodiments of a graphical user interface for use with a system for processing a sample.

In some embodiments, a graphical user interface is provided that includes various visual elements for enabling a user to execute various commands of a system having the GUI. FIG. 20 shows a GUI 2000 having "Run", "Flush", "Calibrate" and "Remove" buttons 2001 for implementing various commands, in accordance with an embodiment of the invention. The "Run" button starts sample preparation and processing. The "Flush" button flushes the capillary with buffer or other solution. The "Calibrate" button is used to calibrate the system and verify data generated by the system. The "Remove" button initiates the process for removing the capillary.

The ten-n "button" in this context refers to two or pseudo-three dimensional graphical elements that may resemble buttons, but that may be activated (or depressed) with the aid of user touch or an electronic pointing device, such as a mouse. The GUI 2000 includes a status indicator for providing the status of the system. In the illustrated example, the system (e.g., the system 100 of FIG. 1) is ready for sample preparation, processing and analysis ("Ready"). The GUI 2000 also includes buttons 2003 for providing help and information about the system (right button), providing menu and run status information (middle button), and enabling a user to access system settings (left button). A power button 2004 enables a user to turn the system on and off In some cases, the system is configured to enter an "off" state after a predetermined period of inactivity. A user can then turn the system "on" by pressing button 2004. In some cases, GUI 2000 may require a user to input a password or provide other identifying information as part of a security measure to help prevent unauthorized use of the system.

Figure 21:
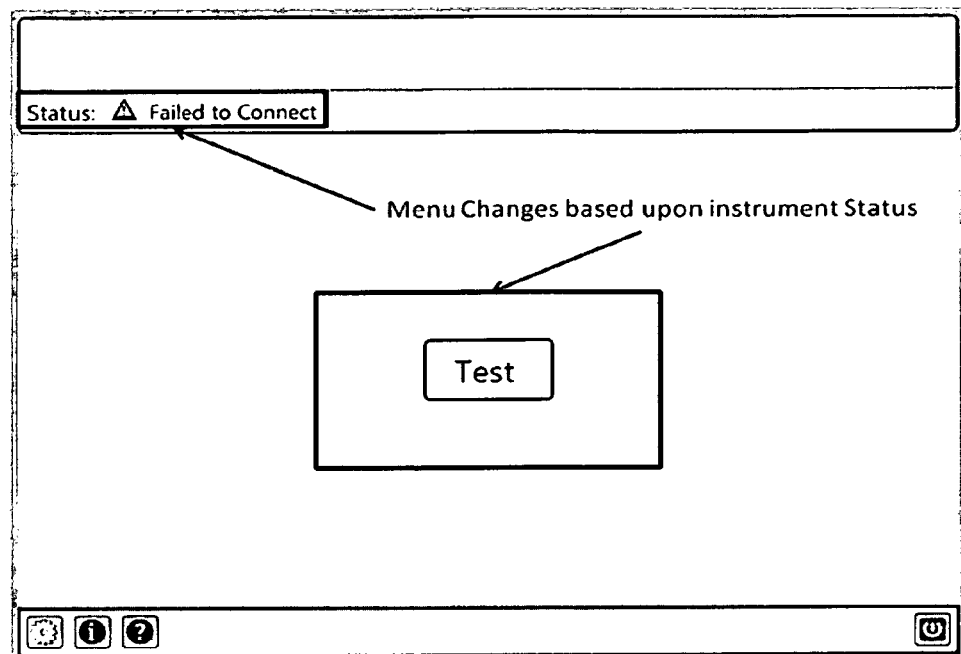

The GUI 2000 is configured to present system updates and other status information at predetermined intervals or in real time. With reference to FIG. 21, the status menu has changed from "Ready" to "Failed to Connect" in response to a change in the status of the system. The GUI 2000 presents the user with a "Test" button to run various diagnostic tests to determine whether there are any issues with the system.

The GUI 2000 is configured to guide a user through various stages of sample preparation, processing and analysis, and to request user input when required. The GUI communicates to the user various instructions or system requests, such as inputting a cartridge. GUI 2000 presents the user with a progress indicator (i.e., the present progress in relation to the steps required to reach completion) which can be at a bottom panel of the GUI or in other locations.

Figure 22:
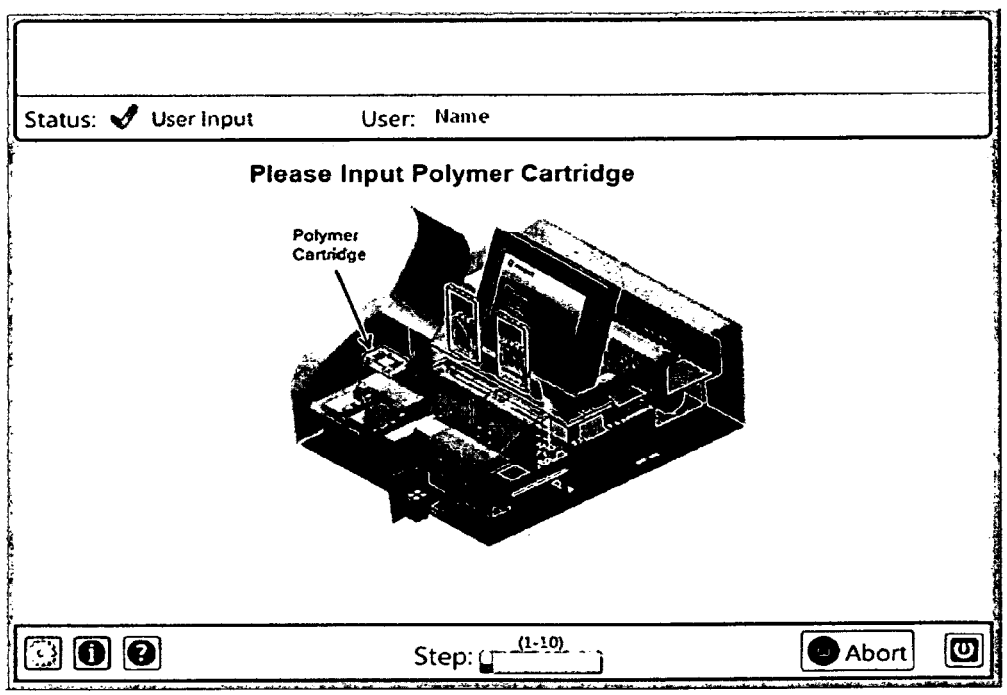
Figure 23:
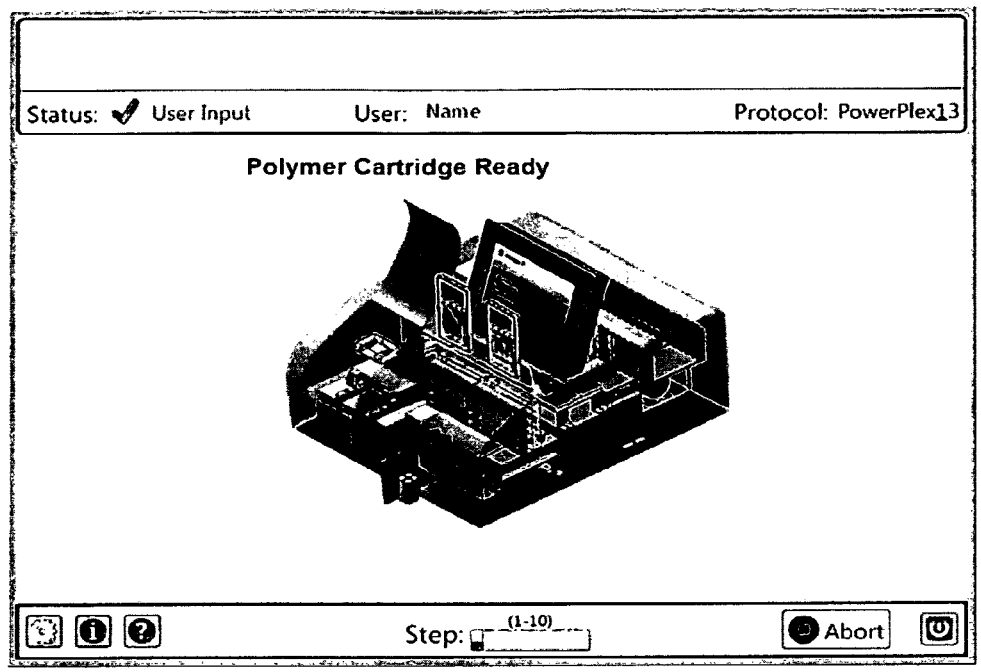
Figure 24:
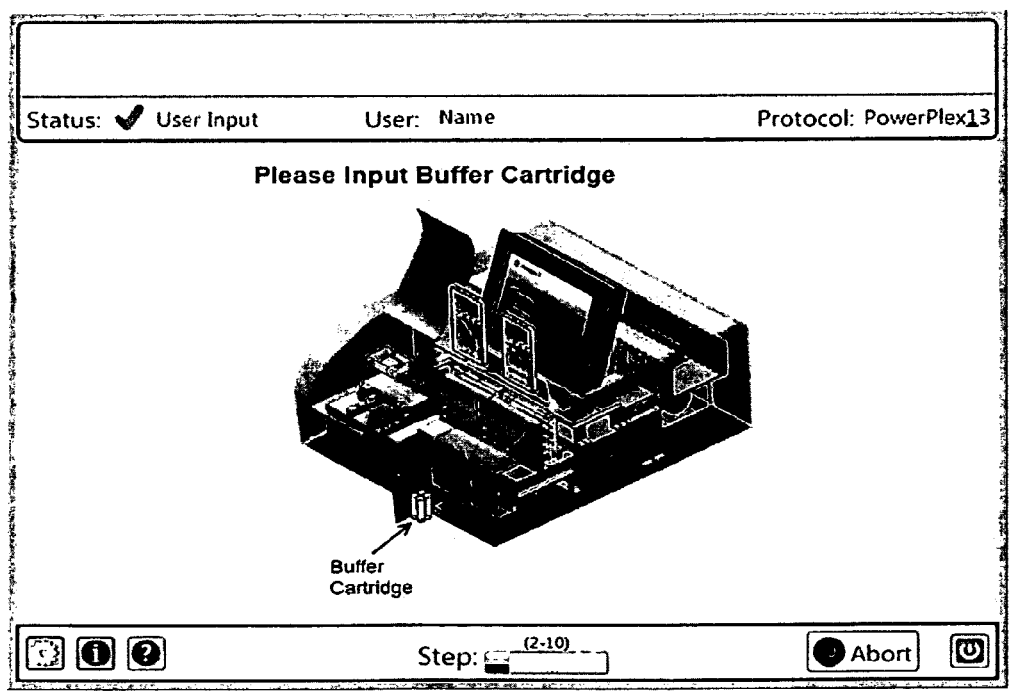
Figure 25:
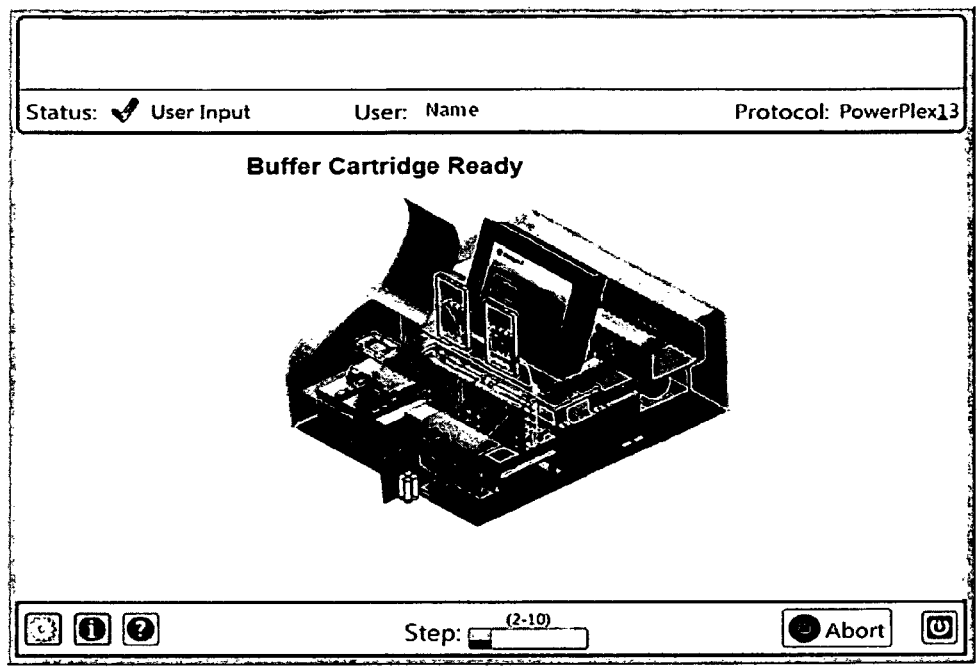
Figure 26:
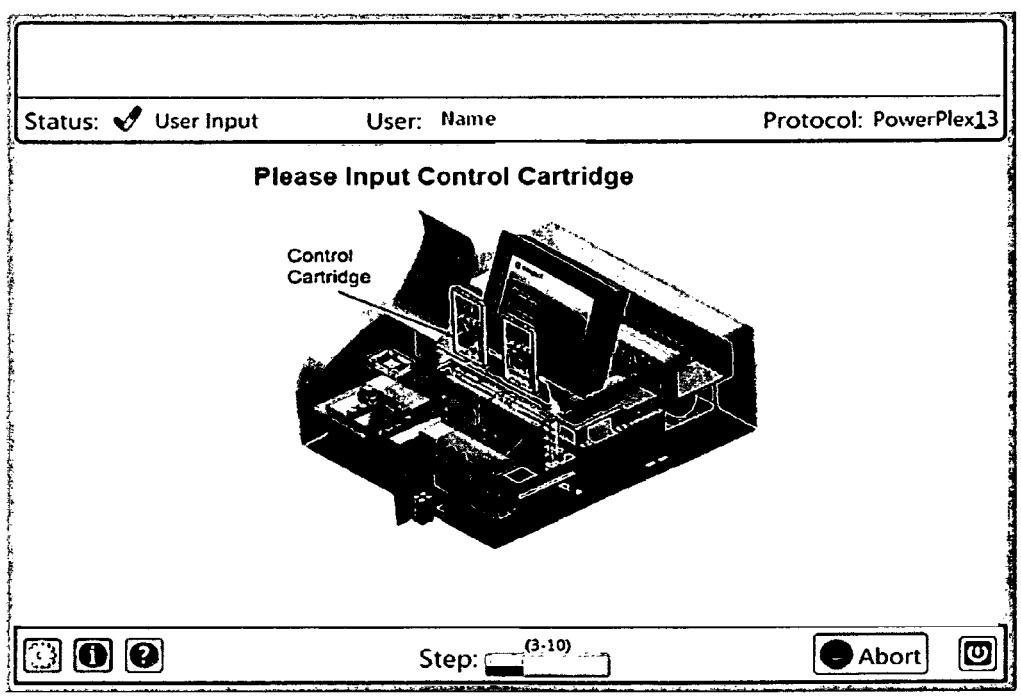
Figure 27:
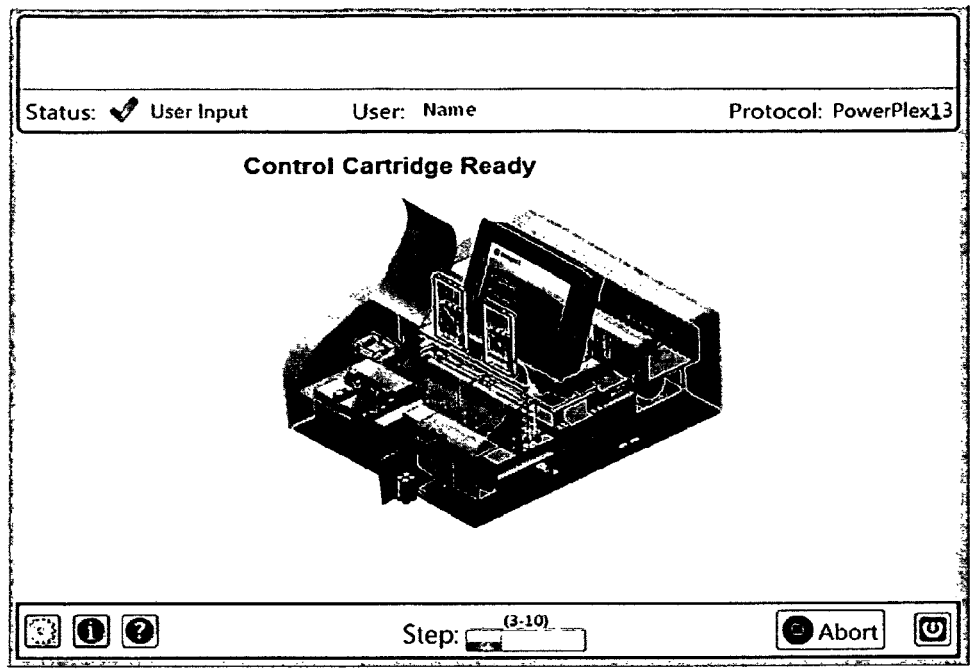
Figure 28:
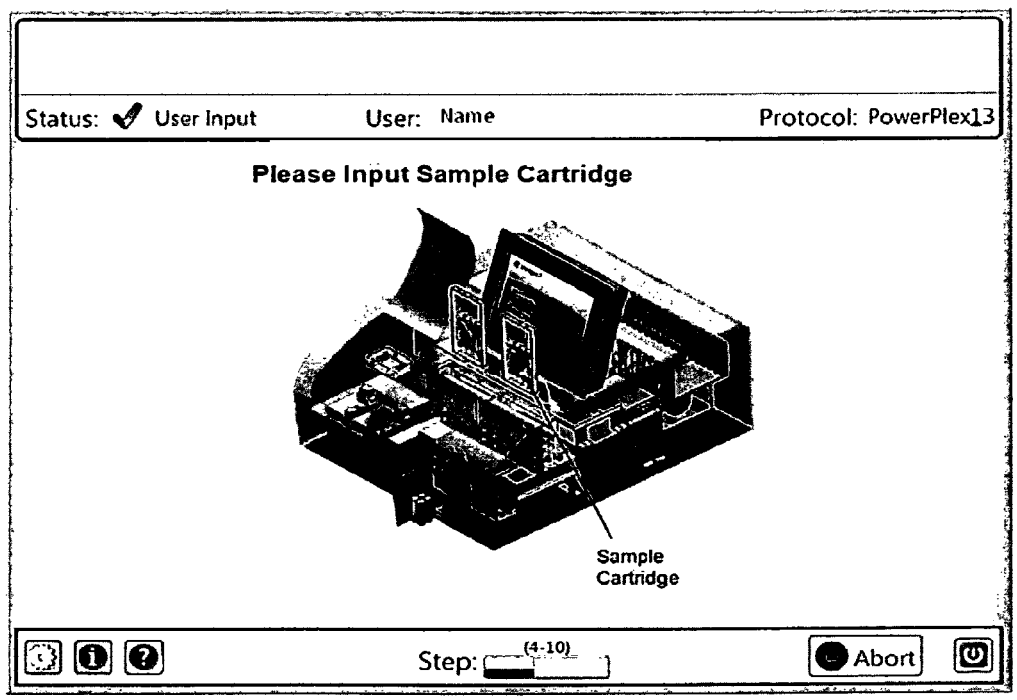
Figure 29:
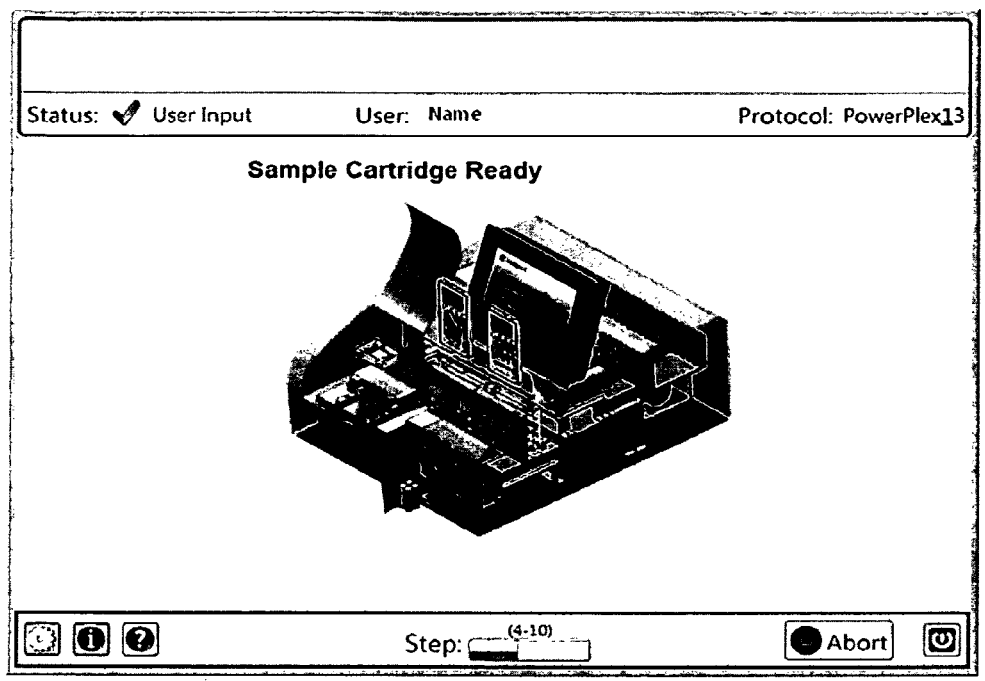

With reference to FIG. 22, the GUI 2000 requests that the user input a polymer cartridge into the anode interface module of the system (see FIG. 6). The progress indicator shows that the user is at a first step ("Step: (1-10)"). The system waits for user input or enables the user to abort by pressing the "Abort" button. The GUI then indicates that the polymer cartridge is ready for use, as shown in FIG. 23. With reference to FIG. 24, the GUI indicates that the system has requested that the user input a buffer cartridge (see FIG. 7). Upon the user inserting the buffer cartridge, the system indicates that the buffer cartridge is ready, as shown in FIG. 25. In FIG. 26 the GUI instructs the user to input a control cartridge. Upon successfully insertion of the control cartridge (FIG. 27), the GUI instructs the user to input a sample cartridge, as shown in FIG. 28. The GUI then indicates that the sample cartridge is ready for use, as shown in FIG. 29.

Figure 30:
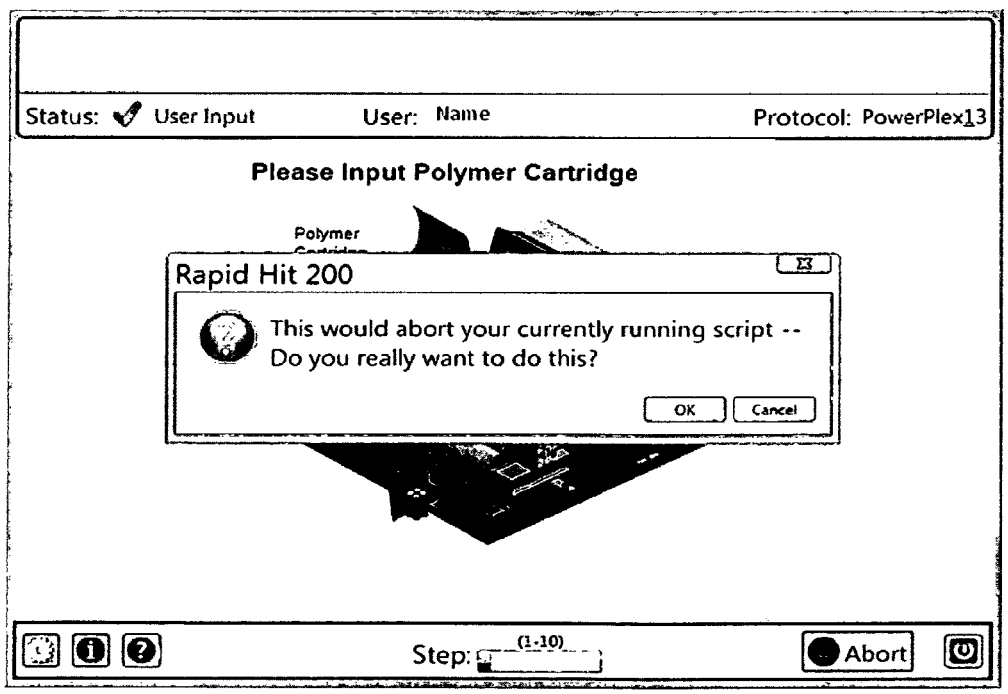

Referring to FIG. 30, at any point during system setup, the user can abort the setup process by pressing the "Abort" button. The user or another user may then start a new process prior to sample preparation, processing and analysis. In some cases, the system starts the setup process where a previous user aborted the setup process. For example, if a previous user aborted the setup process after inputting a buffer cartridge and a new user desires to use the system, the system may not require the new user to input a buffer cartridge. In cases where a particular type of buffer is required for certain processing, the system may recognize (e.g., with the aid of on-board EEPROM) that the buffer cartridge presently in the system is not adequate for use and request that the user input the required buffer cartridge.

The GUI 2000 can be implemented on a display of the system (e.g., the display 101 of the system 100 of FIG. 1) or a display of a remote system (e.g., the portable electronic device 1902 or electronic device 1905 of FIG. 19). In some situations, remote access may enable a user to interact with the system and to setup and run sample processing remotely. The results of sample processing and/or analysis, such as the genetic information of or related to a sample, may be obtained remotely.

C. Timing Control in an Integrated and Automated System

In some embodiments, the instrument or system described herein performs sample-to answer processing and analysis (e.g., "commence process" to answer display) in no more than 2 hours, e.g., in no more than about 90 minutes. The functions performed include: DNA isolation; DNA amplification; amplicon separation and data collection; and system wrap up (e.g., disengagement of instrument from consumable cartridges, line clearing) and data analysis. In a system that performs sample-to-answer processing in no more than about 2 hours, DNA isolation can be performed in about 20% of the time; DNA amplification can be performed in about 33% of the time; amplicon separation and data collection can be performed in about 33% of the time and system wrap up and data analysis can be performed in about 10% of the time. For example, times for each of these functions in a 90 minute run can be as follows: DNA isolation: ~20 minutes; DNA amplification: ~30 minutes; amplicon separation and data collection: ~30 minutes; system wrap up and data analysis: ~10 minutes. In further embodiments, the instrument or system described herein performs sample-to answer processing and analysis within about 60 minutes, during which DNA isolation can be performed within about 10 minutes, DNA amplification within about 20 minutes, amplicon separation and data collection within about 25 minutes, and system wrap up and data analysis within about 5 minutes.

In some embodiments, the instrument or system described herein performs sample-to-answer processing and analysis in no more than about 4 hours (hr), 3.5 hr, 3 hr, 2.5 hr, 2 hr, 1.5 hr, 1 hr or 0.5 hr. In further embodiments, the instrument or system performs sample-to-answer processing and analysis in about 0.5 hr to about 3 hr, or about 0.5 hr to about 2 hr, or about 0.5 hr to about 1.5 hr, or about 0.5 hr to about 1 hr, or about 1 hr to about 2 hr, or about 1 hr to about 1.5 hr, or about 1.5 hr to about 2 hr. In some embodiments, sample-to-answer processing and analysis time comprises the time from starting sample processing (e.g., pressing a start or run button of the instrument or system, or initiating the sample-to-answer protocol) to generation of a nucleic acid profile (e.g., a DNA profile, such as a profile of one or more, or all, STR loci used in a forensic database (e.g., CODIS), and optionally of other loci useful in human identification or sex determination (e.g., Penta D, Penta E and amelogenin)) in a computer system or computer-readable medium of the instrument or system or on a screen thereof. In further embodiments, sample-to-answer processing and analysis time comprises the time from pressing the start or run button of the instrument or system, or initiating the sample-to-answer protocol, to posting of the nucleic acid profile onto an internal or external database.

In some embodiments, sample-to-answer processing and analysis comprise nucleic acid (e.g., DNA and/or RNA) extraction and isolation, nucleic acid amplification (e.g., by PCR), nucleic acid separation (e.g., by capillary electrophoresis) and collection of data on separated analytes, and analysis of collected data. In some embodiments, nucleic acid extraction and isolation comprises lysis of nucleic acid-containing cells, binding of nucleic acids to capture particles (e.g., magnetic or paramagnetic particles (e.g., beads)), and washing of nucleic acid-bound particles. In certain embodiments, the instrument or system described herein performs nucleic acid extraction and isolation in no more than about 2 hr, 1.5 hr, 1 hr, 45 minutes (min), 30 min, 20 min, 15 min, 10 min or 5 min. In further embodiments, the instrument or system performs nucleic acid extraction and isolation in about 0.5 hr to about 2 hr, or about 0.5 hr to about 1.5 hr, or about 0.5 hr to about 1 hr, or about 1 hr to about 2 hr, or about 1 hr to about 1.5 hr, or about 5 min to about 30 min, or about 10 to about 20 min, or about 10 min to about 15 min. In certain embodiments, nucleic acid extraction and isolation begins when the start or run button of the instrument or system is pressed, or when the sample-to-answer protocol is initiated. The duration of nucleic acid extraction and isolation may depend on, e.g., the nature and concentration of the lysis reagents, the pH of the lysis mixture, the temperature at which lysis is performed, or the nature of the nucleic acid-containing medium, or any combination thereof. For example, a more basic pH can promote lysis of cells. As another example, a higher temperature can facilitate lysis of cells. In certain embodiments, lysis is performed at a temperature of at least about 40° C., 50° C., 60° C. or 70° C. As a further example, extraction of nucleic acids from cells contained in a cellulosic medium (e.g., FTA® paper) may take longer time than extraction of nucleic acids from cells contained in swabs.

In certain embodiments, the instrument or system performs amplification (e.g., by PCR) of nucleic acids (e.g., at, and optionally adjacent to, one or more, or all, STR loci used in a forensic database (e.g., CODIS), and optionally other loci useful in human identification or sex determination (e.g., Penta D, Penta E and amelogenin)) in no more than about 2 hr, 1.5 hr, 1 hr, 45 min, 40 min, 30 min, 20 min, 15 min, 10 min, or 5 min. In further embodiments, the instrument or system performs amplification (e.g., by PCR) of nucleic acids (e.g., at, and optionally adjacent to, one or more, or all, STR loci used in a forensic database (e.g., CODIS), and optionally other loci useful in human identification or sex determination (e.g., Penta D, Penta E and amelogenin)) in about 5 or 10 min to about 2 hr, or about 20 min to about 1 hr, or about 20 min to about 40 min, or about 20 min to about 30 min, or about 30 min to about 40 min. The duration of nucleic acid amplification may depend on, e.g., the number of loci amplified, the temperature ramp rates or heating and cooling rates, the hold time at a particular temperature, or the number of amplification cycles, or any combination thereof. For example, nucleic acid amplification (e.g., by PCR) can be accomplished in a shorter period of time (e.g., within about 20 minutes) using faster thermal cycling (e.g., at least about 5° C./sec, 10° C./sec or 15° C./sec heating and cooling rates), which can be achieved, e.g., by appropriately modifying the thermocycler (e.g., by employing a thinner metal plate 4220 for the thermocyler of FIG. 42). Faster nucleic acid amplification (e.g., by PCR) can also be accomplished, e.g., by utilizing a faster thermal cycling methodology (e.g., continuous flow PCR), by performing shuttle cycling, or by performing the amplification reaction in a valve (which can be isothermal or vary in temperature) or in multiple valves having different temperatures.

In some embodiments, nucleic acid separation comprises separation (e.g., by capillary electrophoresis) of nucleic acid fragments (e.g., those resulting from PCR amplification at one or more, or all, CODIS STR loci, and optionally other loci) and collection of data (e.g., collection of laser-induced fluorescence by a CCD camera). In certain embodiments, the instrument or system performs nucleic acid separation in no more than about 1 hr, 45 min, 40 min, 30 min, 20 min, 15 min, 10 min, or 5 min. In further embodiments, the instrument or system performs nucleic acid separation in about 5 or 10 min to about 1 hr, or about 15 min to about 45 min, or about 20 min to about 40 min, or about 20 min to about 30 min, or about 30 min to about 40 min. The duration of nucleic acid separation may depend on, e.g., the gel used, the length of the electrophoretic capillary, the voltage ramp rate, or the size of the nucleic acid fragments.

In some embodiments, the system processes a biological sample within a time period of 4 hours or less, or 3.5 hours or less, or 2.5 hours or less, or 2 hours or less, or 1.5 hours or less, or 1 hour or less, or 45 minutes or less, or 30 minutes or less, or 15 minutes or less, or 10 minutes or less, or 5 minutes or less. In other embodiments, the system processes and analyzes a biological sample within a time period of 4 hours or less, or 3.5 hours or less, or 2.5 hours or less, or 2 hours or less, or 1.5 hours or less, or 1 hour or less, or 45 minutes or less, or 30 minutes or less, or 15 minutes or less, or 10 minutes or less, or 5 minutes or less.

In some embodiments, analysis comprises analysis of collected data and generation of a nucleic acid profile (e.g., a DNA profile, such as a profile of one or more, or all, STR loci used in a forensic database (e.g., CODIS), and optionally of other loci useful in human identification or sex determination (e.g., Penta D, Penta E and amelogenin)) in a computer system or computer-readable medium of the instrument or system or on a screen thereof. In other embodiments, analysis further comprises posting of the nucleic acid profile onto an internal or external database. In certain embodiments, the instrument or system performs analysis in no more than about 15 min, 10 min, 5 min, 3 min, 2 min, 1 min, 30 sec, or 10 sec. In further embodiments, the instrument or system performs analysis in about 2 min to about 10 min, or about 2 min to about 5 min, or about 2 min to about 4 min, or about 3 min to about 4 min, or about 10 sec to about 2 min, or about 30 sec to about 2 min, or about 30 sec to about 1 min.

In additional embodiments, sample-to-answer processing and analysis further comprise transfer of nucleic acid-bound beads from the bead suspension/capture chamber to the reaction chamber, delivery of a premix reagent to the reaction chamber, transfer of the amplification reaction product to the diluent chamber, and delivery of the diluted amplification product to a separation (e.g., capillary electrophoresis) system. The premix reagent can be in liquid or lyophilized form and can contain, e.g., primers, polymerase, buffer and any other reagent suitable for amplification (e.g., a metal salt, such as magnesium chloride). In certain embodiments, the instrument or system transfers nucleic acid-bound beads from the bead suspension/capture chamber to the reaction chamber in no more than about 10 min, 5 min, 4 min, 3 min, 2 min, 1 min or 30 sec, or in about 30 sec or 1 min to about 5 min, or about 2 min to about 4 min, or about 2 min to about 3 min, or about 1 min to about 2 min. In further embodiments, the instrument or system delivers the premix reagent to the reaction chamber in no more than about 10 min, 8 min, 6 min, 5 min, 4 min, 3 min, 2 min or 1 min, or in about 5 min to about 10 min, or about 5 min to about 8 min, or about 6 min to about 8 min, or about 0.5 min to about 5 min, or about 1 min to about 5 min, or about 2 min to about 5 min, or about 0.5 min to about 3 min, or about 1 min to about 3 min, or about 1 min to about 2 min. Delivery of a lyophilized premix reagent to the reaction chamber may take longer time than delivery of a premix reagent in liquid form due to, e.g., the need to rehydrate the lyophilized reagent.

In certain embodiments, the instrument or system transfers the amplification reaction product to the diluent chamber in no more than about 3 min, 2 min, 1 min, 30 sec or 10 sec, or in about 10 or 30 sec to about 3 min, or about 1 min to about 3 min, or about 1 min to about 2 min. In some embodiments, delivery of the diluted amplification product to the separation (e.g., capillary electrophoresis) system comprises transfer of the diluted amplification product to an injector and injection of the diluted amplification product into the capillary. In certain embodiments, the instrument or system delivers the diluted amplification product to the separation system in no more than about 8 min, 6 min, 5 min, 4 min, 3 min, 2 min, 1 min or 30 sec, or in about 30 sec or 1 min to about 6 min, or about 2 min to about 5 min, or about 2 min to about 4 min, or about 1 min to about 3 min.

In some embodiments of processing of a sample (e.g., a swab having nucleic acid containing cells), the instrument or system described herein delivers lysis reagents to the sample chamber and performs lysis of nucleic acid-containing cells in no more than about 15 min, 10 min, 8 min, 6 min, 5 min, 4 min or 3 min, or in about 2 min to about 10 min, or about 5 min to about 10 min, or about 4 min to about 8 min, or about 2 min to about 5 min. In certain embodiments, the instrument or system transfers the resulting lysate from the sample chamber to the bead suspension/capture chamber in no more than about 5 min, 4 min, 3 min, 2 min or 1 min, or in about 0.5 min to about 5 min, or about 0.5 min to about 3 min, or about 1 min to about 3 min, or about 1 min to about 2 min. In further embodiments, the instrument or system performs binding (or capture) of nucleic acids (e.g., DNA and/or RNA) to magnetic or paramagnetic particles (e.g., beads) in the bead suspension/capture chamber in no more than about 10 min, 8 min, 6 min, 5 min, 4 min, 3 min or 2 min, or in about 1 min to about 10 min, or about 2 min to about 8 min, or about 4 min to about 8 min, or about 4 min to about 6 min. In some embodiments, the first wash chamber delivers to the bead suspension/capture chamber a reagent or solution (e.g., 95%-100% ethanol, 90% ethanol in water or 70% ethanol in water) that promotes binding of nucleic acids to the beads, and the second wash chamber delivers to the bead chamber a reagent or solution (e.g., 70% ethanol in water) that removes impurities (e.g., salts, cellular debris and proteins) while promoting retention of nucleic acids to the beads. In other embodiments, one of the two wash chambers comprises a reagent or solution (e.g., 70% ethanol in water) that removes impurities (e.g., salts, cellular debris and proteins) from nucleic acid-bound beads while promoting retention of nucleic acids to the beads, and the other wash chamber comprises a rehydration solution (e.g., water or a buffer) that can be used to rehydrate reagents in solid, semi-solid, dehydrated or other stabilized forms (e.g., dehydrated or lyophilized PCR reagents in a premix vial, or dehydrated or lyophilized allelic ladder and/or size standard in the diluent chamber). In certain embodiments, the instrument or system performs washing of the nucleic acid-bound beads with the reagent or solution from the second wash chamber in no more than about 3 min, 2 min, 1 min or 0.5 min, or in about 0.5 min to about 2 min, or about 1 min to about 2 min, or about 0.5 min to about 1.5 min, or about 0.5 min to about 1 min. In further embodiments, while the beads are retained in the bead suspension/capture chamber by magnetization, the instrument or system transfers the liquid from the bead chamber to the waste chamber after completion of bead capture and before addition of the reagent or solution from the second wash chamber, and/or after addition of the reagent or solution from the second wash chamber, in no more than about 2 min, 1 min or 0.5 min, or in about 15 seconds (sec) to about 2 min, or about 0.5 min to about 1.5 min, or about 0.5 min to about 1 min.

In additional embodiments, the instrument or system transfers the nucleic acid-bound beads from the bead suspension/capture chamber to the reaction chamber in no more than about 5 min, 4 min, 3 min, 2 min or 1 min, or in about 0.5 min to about 5 min, or about 1 min to about 4 min, or about 2 min to about 3 min. In certain embodiments, the instrument or system delivers the premix reagent (e.g., in liquid form) to the reaction chamber in no more than about 5 min, 4 min, 3 min, 2 min or 1 min, or in about 0.5 min to about 5 min, or about 0.5 min to about 3 min, or about 0.5 min to about 2 min, or about 0.5 min to about 1 min. In further embodiments, the instrument or system performs PCR amplification of nucleic acids (e.g., at, and optionally adjacent to, one or more, or all, STR loci used in a forensic database (e.g., CODIS), and optionally other loci useful in human identification or sex determination (e.g., Penta D, Penta E and amelogenin)) in no more than about 1 hr, 50 min, 40 min, 30 min, 20 min, or 10 min, or in about 10 min to about 1 hr, or about 20 min to about 40 min, or about 30 min to about 40 min, or about 20 min to about 30 min. In certain embodiments, the instrument or system transfers the amplification reaction product from the reaction chamber to the diluent chamber in no more than about 3 min, 2 min or 1 min, or in about 0.5 min to about 3 min, or about 1 min to about 2 min, or about 0.5 min to about 1 min. In some embodiments, the diluent chamber contains a size standard and a suitable solvent (e.g., water). In further embodiments, the instrument or system transfers the diluted amplification product from the diluent chamber to an injector in no more than about 5 min, 4 min, 3 min, 2 min or 1 min, or in about 0.5 min to about 5 min, or about 1 min to about 4 min, or about 0.5 min to about 3 min, or about 1 min to about 2 min. In certain embodiments, the injector injects the amplification product into a separation channel (e.g., a capillary) of an electrophoresis system in no more than about 2 min, 1 min, 30 sec or 15 sec, or in about 10 sec to about 2 min, or about 10 sec to about 1.5 min, or about 0.5 min to about 1 min.

In some embodiments, the instrument or system performs nucleic acid separation by electrophoresis (e.g., capillary electrophoresis), optionally at elevated temperature (e.g., at about 60° C.), and collection of data in no more than about 1 hr, 40 min, 30 min, 20 min or 10 min, or in 15 min to about 45 min, or about 10 min to about 40 min, or about 20 min to about 40 min, or about 15 min to about 30 min, or about 20 min to about 30 min. In further embodiments, the instrument or system analyzes collected data and generates a nucleic acid profile (e.g., a DNA profile, such as a profile of one or more, or all, STR loci used in a forensic database (e.g., CODIS), and optionally of other loci useful in human identification or sex determination (e.g., Penta D, Penta E and amelogenin)) in a computer system or computer-readable medium of the instrument or system or on a screen thereof, and optionally posts the nucleic acid profile onto an internal or external database, in no more than about 10 min, 6 min, 5 min, 4 min, 3 min, 2 min, 1 min or 30 sec, or in about 30 sec or 1 min to about 10 min, or about 2 min to about 6 min, or about 2 min to about 4 min. FIG. 51A shows a typical electropherogram that can be generated from the data collected. FIG. 51B shows a typical plot of the nucleic acid profile generated from the data collected.

In certain embodiments, the time from start (e.g., initiation of the sample-to-answer protocol) to production of purified DNA (e.g., completion of capture of DNA to beads and bead wash after lysis) takes no more than about 65 minutes (e.g., if a sample is stored on a paper (such as FTA® paper), as extraction of DNA from cells stored on a paper can take longer than extraction of DNA from cells stored on a swab), the time from production of purified DNA to beginning of electrophoresis (e.g., capillary injection) takes no more than about 80 minutes, the time from beginning of electrophoresis to completion of data collection takes no more than about 80 minutes, and the time from completion of data collection to generation of a data file (e.g., a file containing a DNA profile) takes no more than about 15 minutes, for a total of no more than about 240 minutes.

In further embodiments, the time from start (e.g., initiation of the sample-to-answer protocol) to production of purified DNA (e.g., completion of capture of DNA to beads and bead wash after lysis) takes no more than about 30 minutes, the time from production of purified DNA to beginning of electrophoresis (e.g., capillary injection) takes no more than about 45 minutes, the time from beginning of electrophoresis to completion of data collection takes no more than about 40 minutes, and the time from completion of data collection to generation of a data file (e.g., a file containing a DNA profile) takes no more than about 5 minutes, for a total of no more than about 120 minutes.

In additional embodiments, the time from start (e.g., initiation of the sample-to answer protocol) to production of purified DNA (e.g., completion of capture of DNA to beads and bead wash after lysis) takes no more than about 20 minutes, the time from production of purified DNA to beginning of electrophoresis (e.g., capillary injection) takes no more than about 35 minutes, the time from beginning of electrophoresis to completion of data collection takes no more than about 30 minutes, and the time from completion of data collection to generation of a data file (e.g., a file containing a DNA profile) takes no more than about 5 minutes, for a total of no more than about 90 minutes.

In some embodiments, the system processes a biological sample at a coefficient of variation that is less than about 20%, 15%, 10%, 5%, 1%, 0.5%, 0.1% or less. In some cases, the system processes a biological sample at an accuracy of at least about 80%, 90%, 95%, 99%, 99.9%, or more.

D. Monitoring Systems

A system facilitates sample processing and/or analysis with the aid of a cartridge (or cassette) that is configured to accept a sample and perform various processing routines. The system includes a receptacle for accepting the cartridge. The cartridge can be removable from the system. The cartridge can include identifying information, such as a bar code, serial number or electrically erasable programmable read-only memory (EEPROM) or an electrically programmable read-only memory (EPROM) or a radio frequency ID (RFID) tag. In some examples, such identifying information enables a controller of the system to identify the cartridge and configure the system for an appropriate processing and/or analysis routine. Accordingly, each fluidic circuit in the cassette can be labeled with information about the sample being loaded. For example, information taken, e.g., at a collection site can be associated with the cassette in a fluidic circuit corresponding to the sample. Such information can include, for example, time of collection, place of collection, and information about a subject from whom a sample is taken.

For example, the cartridge can include a readable and/or writable memory device (e.g., an EEPROM chip) configured to store information and to communicate with the system to transmit or receive various kinds of information. Such information can include, for example, information about the configuration and/or the history of the cartridge, such as the batch number of the cartridge, place/time source information, expiration date of the cartridge, pumping parameters/sequences of the cartridge, identification of chemistries performed by each lane of the cartridge (e.g., reagents on board, chemical reactions performed), and locations of samples and/or controls. The memory device can be utilized, e.g., to identify and track the cartridge and to customize sample processing. The memory device also can be configured to transmit a signal to the system when the cartridge is properly engaged, e.g., seated, in the cartridge receptacle. The signal can be transmitted if, for example, an electrical connection is made between the memory device and the cartridge receptacle. The system can be configured to run only if the a signal from the memory device indicates that the cartridge is properly seated. The memory device can be configured to receive information about nature of the samples being run in particular lanes, for example date, time and location sample collected, method of collection, type of sample (e.g., blood, saliva), identity of person from whom taken. The memory device can be configured to record a signal from the system indicating that the cartridge has been run or if the cartridge lot number has expired, and the system can be configured not to run a cartridge carrying a record that the cartridge has previously been run. The memory device also can be configured to receive information about results of the run. For example, the memory device can be configured to record information about the time and date of run, results from the run (e.g., record an STR profile or the presence or absence of an analyte).

A cartridge can also comprise a device that enables tracking of the cartridge by the Global Positioning System (GPS) satellite system or any other satellite system. In addition, the sample-to-answer instrument or system itself can have a satellite-traceable (e.g., GPS) device to enable tracking of the instrument or system.

Sensors that detect the presence of a cartridge in its appropriate slot/receptacle and the condition of the cartridge in the system at any time assist in determining the chain of custody of the cartridge. The cartridge sensors can be EEPROM memory chips that recognize, read and store the state of each cartridge inserted in the system. The software recognizes the presence of a cartridge in a slot/receptacle, and denotes an empty slot/receptacle as EMPTY. The software also recognizes the state of a cartridge in a slot/receptacle as, e.g., NEW, USED or EXPIRED. Sample and control cartridges, or the system, can also have sensors that indicate the insertion of, e.g., a swab into a sample chamber or the removal of a swab from a sample chamber, as described herein, which also assists in determining the chain of custody of a cartridge or a sample.

In some embodiments, the cartridge is physically altered to prevent reuse, such as puncturing a friable seal or PDMS layer of the cartridge, or physically breaking, chemically degrading or otherwise altering the cartridge to prevent reuse of the cartridge. In some cases, an on-board EEPROM of the cartridge can be reset, and/or a reagent chamber of the cartridge can be refilled.

In some embodiments the system is configured to detect the presence or absence of an article in the sample receptacle. The article can be, for example, an article configured to hold a biological sample for analysis, such as a swab (e.g., a cotton swab or a brush swab) or a piece of paper (e.g., FTA® paper). The cartridge module, when engaged with the cartridge, can comprise a sensor configured to detect the presence or absence of an article in the receptacle. The sensor can be configured to detect, for example, changes in transmission of light or in an electrical field. Changes in an electrical field can be detected using capacitive or inductive sensors. Changes in transmission of light can be detected using a light source and a detector. For example, the system can comprise a light source that produces light that travels along an optical path that traverses the sample receptacle. The path can include, for example, windows in the module that are transparent to light. The system can comprise a light source, such as an LED or laser, and a detector, positioned to transmit light along the optical path. When the sample receptacle contains no article, or is empty or transparent, the light can traverse the optical path to the detector. When an article is introduced into the sample receptacle, it blocks or attenuates the optical path, decreasing or preventing light from the light source from reaching the detector. The presence or absence of an article in the sample receptacle, as determined by lack of detection or detection, respectively, of a signal from the light source, is reported to software that can run a number of sub-routines based on the result. For example, the software can report the status of each sample receptacle to a user, e.g., whether or not each receptacle contains or does not contain an article, or whether or not an article has been introduced and then removed from a receptacle. The software can run a sub-routine based on these results, for example, if an article has been introduced and then removed from a receptacle, the sub-routine can prompt the user to run or nullify the results from the article in the receptacle. The system also can include a door which closes to enclose the cartridge within the system. The system can further comprise a sensor that indicates whether the door is open or closed and whether and when, after having been closed, the door has been opened during a run. This information can be written to a database or displayed on a user display.

To enhance maintenance of the chain of custody of a sample-containing article (e.g., a swab), a radio frequency identification (RFID) tag or a 2-D bar code can be affixed (e.g., permanently affixed) to a portion of the article, e.g., to a portion of the article (e.g., an end of a swab) that would not contact a reagent or a liquid in a sample receptacle/chamber of a cartridge. The RFID tag or 2-D bar code can be used to keep track of the sample-containing article throughout the whole process including collection of the sample, testing of the sample, storage of the sample, and transfer of the sample to any other possessor.

E. Remote Communication and Data Storage

In some embodiments, a sample preparation, processing and analysis system is communicatively coupled to one or more remote systems. This permits the system, such as the system 100 described above, to transmit information to and from a remote system. This can be used for remote data storage or for interrogation of a remote database or to provide the information to a remote analysis system. Remote communication can be used for cloud computing.

FIG. 19 shows a system 1900 having a sample preparation, processing and analysis device 1901 (which may be the system 100 of FIG. 1) that is operatively coupled to various components. The sample preparation, processing and analysis system is configured to communicate with a remote portable electronic device 1902, such as a portable personal computer (PC), a smart phone (e.g., Apple iPhone®, Android enabled phone, Black Berry), a tablet or slate PC (e.g., Apple iPad®, Galaxy Tab), or other portable device. The portable electronic device 1902 may include a graphical user interface for permitting a user to interact with the device 1901. This can enable a user to review results and setup processing tasks remotely. The device 1901 may communicate with the portable electronic device 1902 wirelessly, such as with the aid of a wireless network interface (e.g., WiFi interface) or Bluetooth.

With continued reference to FIG. 19, the device 1901 is configured to communicate with a network 1903 (e.g., an intranet or the Internet) via wired or wireless network connectivity, or a satellite. The system may wirelessly communicate with the network 1903 with the aid of a wireless communications device 1904, which may be a wireless router or a cell tower for various over-the-air communications protocols (e.g., 2G, 3G, 4G or LTE connectivity). An electronic device 1905 is in communication with the device 1901 with the aid of the network 1903. In some situations, the electronic device 1905 is a remote computer to permit a user to interact with the device 1901 remotely. In other situations, the electronic device 1905 is a data storage system, such as a computer system having one or more databases for storing preparation, processing and/or analysis data remotely. This can advantageously permit the device 1901 to store information remotely and retrieve information when required. In some instance, the remote data storage system can permit the device 1901 to backup information and/or retrieve information from storage.

In some situations, the device 1901 is device 100 described above in the context of FIG. 1. The device 1901 may include a display 1906 that has a user interface, such as a graphical user interface (GUI), to permit a user to interact with the device 1901. In some embodiments, the device 1901 includes a controller with one or more processors, such as, e.g., one or more central processing units (CPU's). The device 1901 in some cases also includes one or more of memory (e.g., read-only memory, random access memory), cache, and hard disks.

The display of the device 1901, the portable electronic device 1902 and the electronic device 1905 may be a touch screen, such as a capacitive touch or resistive touch screen, which may permit a user to interact with a graphical user interface (GUI) of the electronic devices using the user's fingers. Device 1901 can also be controlled by voice commands or other input modalities.

The system 1900 may permit sample preparation, processing and analysis to be performed on the device 1901 in a first location, and information retrieved for use from a second location that is different from the first location. In an example, the device 1901 is used to process a tissue sample in the first location, and data is transmitted wirelessly to the second location, which is remote from the first location, for analysis. Such analysis may include data comparison for a match. The system 1900 can be advantageous in cases in which data comparison is required to be done in a remote location different from the location at which a sample is processed.

The data collected can be transferred to a database located either within the system or outside the system using either a copy function, a USB drive or over an ethernet connection. The collected data can be transferred in its raw format or the data may be broken into components amenable for searches. For example, electropherogram data may be broken into numbers that represent the peak height, arrival times, or STR count for a particular locus. The database stores the parsed data from runs to create a population of individuals considered possible matches with the donor of a biological sample. Search function allows a quick search of the data in the database against an STR profile derived from the donor sample (minimum search speed: 100 trial matches per second) or against any other numbers parsed into the database. Matches can be performed at various defined levels of stringency. Matching data record can be displayed, including identifying information and ancillary biometrics data, if available.

V. Ruggedization of Instrument or System

If an instrument (e.g., an analytical instrument) experiences excessive motion (e.g., translational, rotational and/or vibrational motion) or excessive shock, the performance of the instrument can be deleteriously affected, or the instrument can be damaged. For example, components of the instrument (e.g., optical components, such as a light source, a detector, mirrors and lenses) can become misaligned or damaged, thereby deleteriously affecting the performance of the instrument. The sample-processing and analytical instrument or system described herein can be ruggedized for protection against damage from a drop or for implementation in a non-stationary environment, such as in a moving vehicle or on the field by law enforcement or military personnel. Vibration-sensitive components of the system and the system as a whole can be ruggedized to attenuate any vibration and shock experienced by the components and the system.

A. Ruggedization of Vibration-Sensitive Components

Figure 66:
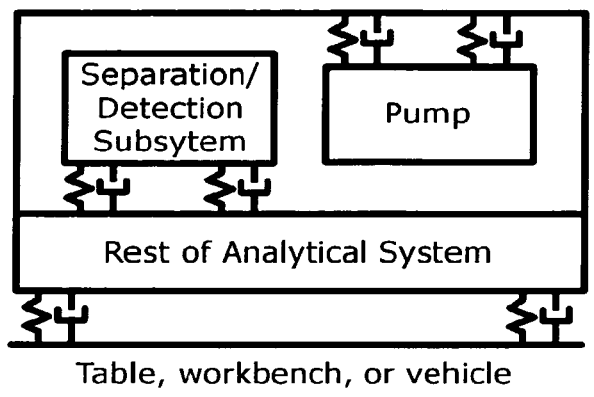
FIG. 66 shows a schematic for ruggedizing an analytical system.

FIG. 66 is a schematic of embodiments for ruggedizing an analytical instrument (e.g., the sample-to-answer instrument described herein). Vibration-sensitive components (e.g., elements, devices and assemblies) of the instrument can have dampening devices such as springs or coils (e.g., metal springs or coils, air springs, or elastomeric columns or springs, or any combination thereof, such as those described herein) at appropriate positions (e.g., at the base of the components or their subframe) to dampen vibration and shock. Furthermore, vibration-sensitive components (or assemblies comprising such components) in close proximity to one another can be connected (e.g., rigidly mounted) to one another so that they move together as a unit rather than move relative to one another in response to vibration, shock or translational motion, as damage to the components may result from their relative motion. The components can better withstand relatively small movement due to vibration and moderate movement due to shock if they move as a unit.

Vibration-sensitive components may include the separation and detection system of an analytical instrument. The separation and detection system can comprise an electrophoresis system (e.g., a capillary array and associated components, such as a cathode and an anode) and a detection system (e.g., a light source (such as a laser or a light-emitting diode), a detector (e.g., a CCD or CMOS camera), and associated components, such as one or more lenses, mirrors and filters). Components of a separation and detection system may be sensitive to vibration and shock. Misalignment of and damage to the components of a separation and detection system can be prevented by employing dampening devices and appropriately connecting the components (or the assemblies comprising them) to one another so that they move as a unit rather than move relative to one another in response to vibration, shock or translational motion.

Figure 67:
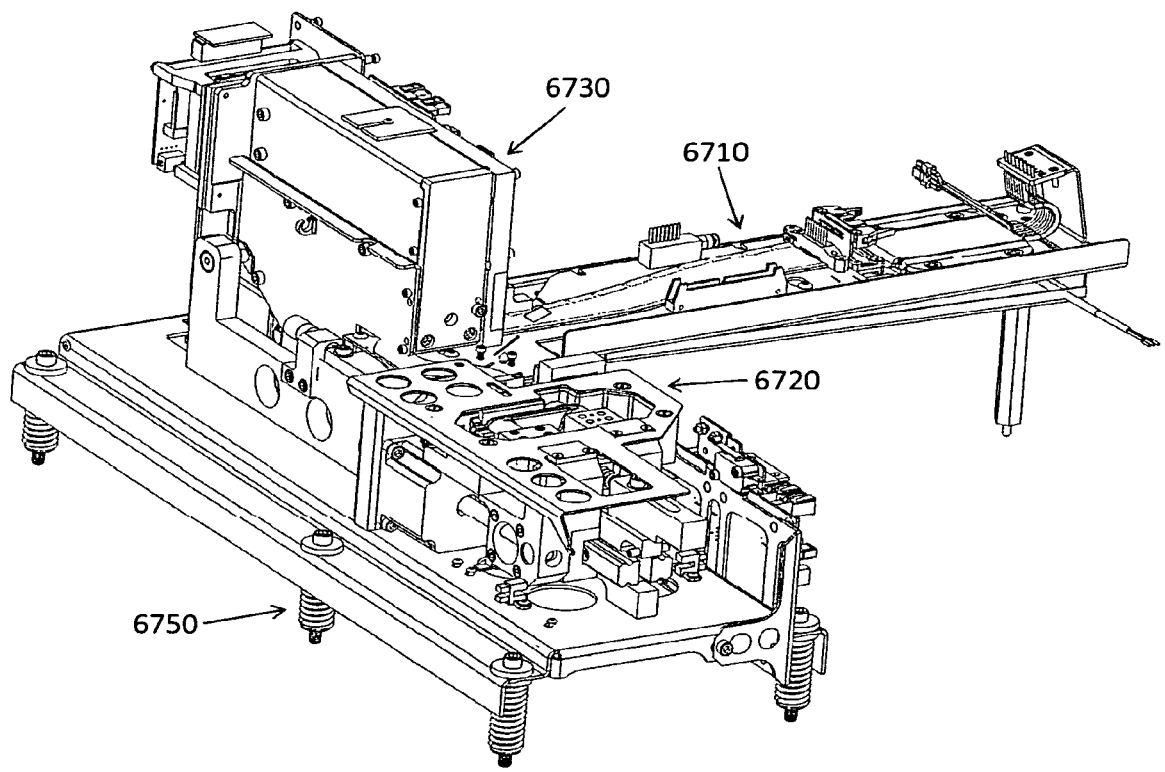
FIG. 67 illustrates an embodiment for ruggedizing the separation and detection system of the sample-to-answer instrument described herein.

FIG. 67 illustrates an embodiment for ruggedizing the separation and detection system of the sample-to-answer instrument described herein. The separation and detection system comprises an electrophoresis module 6710 comprising a capillary array and a cathode block, an anode module 6720 comprising an anode cartridge, and an optics module 6730 comprising a laser and a detector. Electrophoresis module 6710, anode module 6720 and optics module 6730 are rigidly mounted to one another so that they move together as a unit rather than move relative to one another in response to vibration, shock or translational motion. To further ruggedize the separation and detection system, one or more elements (e.g., hard stops such as screws, bosses and brackets) can be employed to prevent the optics module from bouncing up and from contacting the capillary board. In the embodiment of FIG. 67, multiple springs 6750 are implemented at the base of the platform or subframe supporting the modules to attenuate any vibration or shock experienced by the components of the separation and detection system.

The schematic in FIG. 66 also shows that sources of vibration (e.g., separate pumps generating positive pressure and vacuum, or a single pump generating positive pressure and vacuum) can be mechanically isolated from vibration-sensitive components and other parts of an analytical instrument. For example, a vibrating component (e.g., a pump) can be isolated from other components of the instrument by suspending or mounting the vibrating component flexibly and using travel stops to limit the travel of the vibrating component in all directions. Flexible suspension or mounting of the vibrating component can reduce transmission of vibration to other components of the instrument when the instrument is operating. Furthermore, the travel stops can prevent damage to the vibrating component and to other components of the instrument which may result from internal and external vibration and shock.

In addition, FIG. 66 shows that other parts (e.g., non-vibrating components and less vibration-sensitive components) of an analytical instrument can be mechanically isolated from the vibrating components and the vibration-sensitive components of the instrument and from the environment. The instrument as a whole can be ruggedized for general use, or ruggedization of the instrument can be customized to the environment of its intended use. For example, the instrument can rest on rubber bumpers (for use, e.g., on a table or a laboratory workbench), can rest on or be mounted onto a high-travel, vibration-isolation base (such as the base of FIGS. 68B and C for use, e.g., in a moving vehicle), or can be rigidly mounted. Ruggedization of the instrument as a whole can protect the vibration-sensitive components, the vibrating components and the remaining parts of the instrument by attenuating external vibration and shock.

B. Ruggedization of Instrument or System as a Whole

The disclosure provides devices for reducing motion (e.g., translational, rotational and/or vibrational motion) and shock that an instrument (e.g., an analytical instrument, such as the sample-to-answer instrument described herein) or components thereof (e.g., optical components) may experience. In some embodiments, metal springs or coils are used to reduce motion and shock. In certain embodiments, the disclosure provides a plurality of taller, more flexible metal springs or coils configured to dampen, e.g., steady-state vibration, and a plurality of shorter, stiffer metal springs or coils configured to absorb, e.g., excessive shock. The metal springs or coils can comprise (e.g., be wrapped with) an elastomeric material to enhance their ability, e.g., to dampen vibration and shock. Other kinds of springs or coils, such as gas springs (e.g., air springs) and elastomeric columns or springs composed of one or more elastomeric materials, can also be employed to reduce motion and shock. Constraining elements (e.g., those having a doughnut-like or toroidal shape) can be used to limit the range of horizontal translational motion that the instrument may experience. Furthermore, other elements (e.g., bumpers) can be employed to limit the range of vertical translational motion that the instrument may experience. The motion- and shock-reducing devices can prevent misalignment of or damage to components of the instrument that can otherwise be caused by excessive motion or shock, e.g., when the instrument is dropped onto a surface (e.g., a table or the ground), or when a vehicle carrying the instrument goes over a bump (e.g., a speed bump or a pot-hole in the road), swerves or accelerates quickly. Accordingly, the motion- and shock-reducing devices allow the instrument to be used (e.g., to perform processing and/or analysis) while in motion (e.g., in a moving vehicle).

1. Motion- and Shock-Reducing Devices Having Metal Springs or Coils

In some embodiments, a motion- and shock-reducing device comprises a base comprising a top plate, a bottom plate, and metal springs or coils. In certain embodiments, the device comprises a plurality of taller, more flexible metal springs or coils, and a plurality of shorter, stiffer metal springs or coils, wherein the taller metal springs or coils are attached (e.g., screwed) to the bottom plate and to the top plate of the base, and the shorter metal springs or coils are attached (e.g., screwed) to the bottom plate but not to the top plate. In some embodiments, the shorter, stiffer metal springs or coils have a greater vibration spring constant (Ky) and a greater shock spring constant (Ks) than the taller, more flexible metal springs or coils, e.g., in compression testing, 45° compression/roll testing, and shear/roll testing.

The taller, more flexible metal springs or coils and the shorter, stiffer metal springs or coils can be configured to apply or absorb force over a reasonably large displacement in a controlled manner. The taller, more flexible metal springs or coils are configured to dampen, e.g., steady-state vibration (e.g., vibration resulting from normal use of an instrument removably attached to the base that is on a stable table), a lower amount of vibration, or vibration resulting from horizontal motion of the instrument (e.g., when the instrument is inside a moving vehicle). The shorter, stiffer metal springs or coils are configured to absorb, e.g., excessive shock or force when the top plate of the base drops down and contacts the shorter, stiffer metal springs or coils (e.g., when the instrument is dropped onto a surface (e.g., a table or the ground) or when a vehicle carrying the instrument goes over a bump (e.g., a speed bump or a pot-hole in the road)).

In certain embodiments, an instrument removably attached to the base and dropped no more than about 12, 10, 8, 6 or 4 inches onto a surface (e.g., a table or the ground) experiences no more than about 14, 12, 10, 8 or 6 g's of force. In an embodiment, an instrument removably attached to the base and dropped about 6 inches or less onto a surface (e.g., a table or the ground) experiences no more than about 10 g's of force.

In some embodiments, the taller, more flexible metal springs or coils, and the shorter, stiffer metal springs or coils, independently can be compressed by at least about 10%, 20%, 30%, 40%, 50%, 60%, 70%, or 80% and can return (or rebound) to substantially their original height when the compressing force is removed.

The taller, more flexible metal springs or coils, and the shorter, stiffer metal springs or coils, can have any height suitable for reducing motion and shock, bearing the weight of an instrument removably attached to the base, and balancing the instrument. In certain embodiments, the taller metal springs or coils have a height of about 2-4 inches, or about 2, 2.5, 3, 3.5 or 4 inches, and the shorter metal springs or coils have a height of about 1-3 inches, or about 1, 1.5, 2, 2.5 or 3 inches.

The base can comprise any number of the taller, more flexible metal springs or coils and any number of the shorter, stiffer metal springs or coils, and the taller and shorter metal springs or coils can be arranged in any manner, suitable for reducing motion and shock, bearing the weight of an instrument removably attached to the base, and balancing the instrument. In certain embodiments, the base comprises 4-20 (e.g., 4, 8, 9, 12, 16 or 20) taller, more flexible metal springs or coils and 4-20 (e.g., 4, 7, 8, 12, 16 or 20) shorter, stiffer metal springs or coils near or along the edges of the base, and 1-12 (e.g., 2, 3, 4, 6, 9 or 12) taller, more flexible metal springs or coils and 1-12 (e.g., 1, 2, 3, 4, 6, 9 or 12) shorter, stiffer metal springs or coils away from the edges of the base. The number of the taller, more flexible metal springs or coils and the number of the shorter, stiffer metal springs or coils can depend on, e.g., the weight of the instrument. For example, about a two-fold greater number of metal springs or coils can be used to bear the weight of an instrument that is about two-fold heavier. The taller, more flexible metal springs or coils and the shorter, stiffer metal springs or coils can be arranged to provide a center of support under (e.g., substantially directly under) the center of mass of the instrument so that the instrument does not, e.g., tilt in any direction.

The load-bearing portion (e.g., wire, rope or cable) of the taller, more flexible metal springs or coils, and the load-bearing portion of the shorter, stiffer metal springs or coils, independently can be composed of any metal or any metal alloy that provides the metal springs or coils with the desired compressibility, reboundability, strength, resistance to fatigue, and any other desired properties. In certain embodiments, the load-bearing portion of the more flexible metal springs or coils, and the load-bearing portion of the stiffer metal springs or coils, independently are composed of stainless steel, an aluminum alloy, a cobalt alloy, an iron alloy, a lead alloy, a manganese alloy, a molybdenum alloy, a nickel alloy, a silver alloy or a titanium alloy, or any combination thereof. The metal alloy composing the load-bearing portion of the metal springs or coils can comprise any two or more suitable metal atoms in any suitable concentrations, and optionally any one or more suitable non-metal atoms in any suitable concentrations, including without limitation aluminum, cobalt, iron, lead, manganese, molybdenum, nickel, silver, titanium, silicon or carbon, or any combination thereof.

In some embodiments, the taller, more flexible metal springs or coils and the shorter, stiffer metal springs or coils are selected from the CR1 series (including CR1-100 to CR1-400), the CR2 series (including CR2-100 to CR2-400), the CR3 series (including CR3-100 to CR3-400), the CR4 series (including CR4-100 to CR4-400), the CR5 series (including CR5-100 to CR5-400), and the CR6 series (including CR6-100 to CR6-400) of wire rope vibration isolators (ITT Enidine Inc., Orchard Park, N.Y.). Each of the CR1, CR2, CR3, CR4, CR5 and CR6 wire rope vibration isolators has a cable (or wire rope) composed of 302/304 stainless steel, and top and bottom mounting bars composed of 6061-T6 aluminum alloy. In certain embodiments, the taller, more flexible metal springs or coils and the shorter, stiffer metal springs or coils are selected from the CR6 series of wire rope vibration isolators, including CR6-100, CR6-200, CR6-300 and CR6-400 wire rope isolators, which have an uncompressed height of about 1.83 inches (about 47 mm), about 2.15 inches (about 55 mm), about 2.51 inches (about 64 mm) and about 3.09 inches (about 79 mm), respectively, as supplied by the manufacturer. In an embodiment, the taller, more flexible metal springs or coils are CR6-300 wire rope isolators, and the shorter, stiffer metal springs or coils are CR6-100 wire rope isolators.

The metal springs or coils can have a configuration different from that of the CR1 to CR6 series of wire rope vibration isolators. As a non-limiting example, the taller, more flexible metal springs or coils and/or the shorter, stiffer metal springs or coils can be coiled springs.

The taller, more flexible metal springs or coils, and/or the shorter, stiffer metal springs or coils, can comprise (e.g., be wrapped with) an elastomeric material to enhance their ability, e.g., to dampen vibration and absorb shock. The elastomeric material can be, e.g., any elastomeric material described herein.

In further embodiments, the motion- and shock-reducing device further comprises pairs of lower constraining elements and upper constraining elements, wherein the lower constraining elements are attached (e.g., screwed) to the bottom plate of the base and the upper constraining elements are attached (e.g., screwed) to the top plate of the base. The pairs of lower constraining elements and upper constraining elements are configured to limit the range of horizontal translational motion that an instrument removably attached to the base may experience. In certain embodiments, the lower constraining elements have a substantially circular, doughnut-like (or toroidal) shape with a hole in the middle, and the upper constraining elements are substantially cylindrical. In an embodiment, the upper constraining elements are screws attached to the top plate of the base. For each pair of upper and lower constraining elements, the upper constraining element is aligned above the hole of the doughnut-like lower constraining element. When the top plate is pressed down by a sufficient amount, the bottom end of the upper constraining elements enters the hole of the doughnut-like lower constraining elements, and the range of horizontal motion of the instrument is limited by the diameter (or the radius) of the hole of the doughnut-like lower constraining elements, which limits the range of horizontal motion of the upper constraining elements. In certain embodiments, the inner diameter of the substantially circular, doughnut-like lower constraining elements is (no more than) about 3, 2.5, 2, 1.5 or 1 inch or less. The lower constraining elements have a shorter height than the shorter, more rigid metal springs or coils so that the top plate, when pressed down, would contact the shorter springs or coils before it makes any contact with the lower constraining elements.

The pairs of lower and upper constraining elements can be of any number, and can be arranged in any manner, suitable for limiting the horizontal motion of the instrument. In certain embodiments, the number of pairs of lower constraining elements and upper constraining elements is 1 to 10 (e.g., 1, 2, 3, 4, 5, 6, 8 or 10).

The lower constraining elements and the upper constraining elements independently can be composed of any sufficiently strong and durable material. In certain embodiments, the lower constraining elements and the upper constraining elements independently are composed of a sufficiently strong and durable polymeric material or resin (e.g., a natural or synthetic rubber, or an acetal resin, such as Delrin®). In embodiments where the upper constraining elements are screws, the upper constraining elements can alternatively be composed of any suitable metal or metal alloy, e.g., a metal alloy described herein (e.g., stainless steel).

In additional embodiments, the motion- and shock-reducing device further comprises a plurality of bumpers that are attached (e.g., screwed) to the bottom plate of the base. The bumpers have a lower height than the shorter, more rigid metal springs or coils, so that the top plate, when pressed down, would contact the shorter springs or coils before it makes any contact with the bumpers. In some embodiments, the bumpers have a higher height than the lower constraining elements, so that the top plate would contact the bumpers and not the lower constraining elements, thereby limiting the range of vertical translational motion of an instrument removably attached to the base. The bumpers can have a height selected to limit the vertical motion of the instrument. In certain embodiments, the bumpers have a height of (no more than) about 2, 1.75, 1.5, 1.25 or 1 inch or less.

The bumpers can be composed of any sufficiently strong and durable material that is able to absorb shock. A bumper can be composed of the same material along the whole length of the bumper, or can be composed of different materials along the length of the bumper. For example, the lower portion of a bumper can be composed of a harder polymeric material or resin (e.g., an acetal resin, such as Delrin®), and the upper portion of the bumper can be composed of a softer polymeric material that is able to absorb shock (e.g., a natural or synthetic rubber). The material along the whole length of a bumper, or the material of the upper portion of a bumper, is selected to be not too hard so that the bumper is able to absorb shock in the event the top plate contacts the bumper.

The bumpers can be of any number, and can be arranged in any manner, suitable for absorbing excessive shock or force and preventing the top plate from contacting the bottom plate of the base. In certain embodiments, 4 to 12 (e.g., 4, 6, 8, 10 or 12) bumpers are attached (e.g., screwed) along the edges and/or at the corners of the bottom plate.

The bumpers can have any suitable shape. In certain embodiments, the bumpers are substantially cylindrical. In an embodiment, the bumpers have substantially the same diameter along the whole length of the bumpers. In another embodiment, the bumpers have substantially the same diameter along most of the length of the bumpers and are tapered (e.g., slightly tapered) at the top of the bumpers.

Figure 68A:
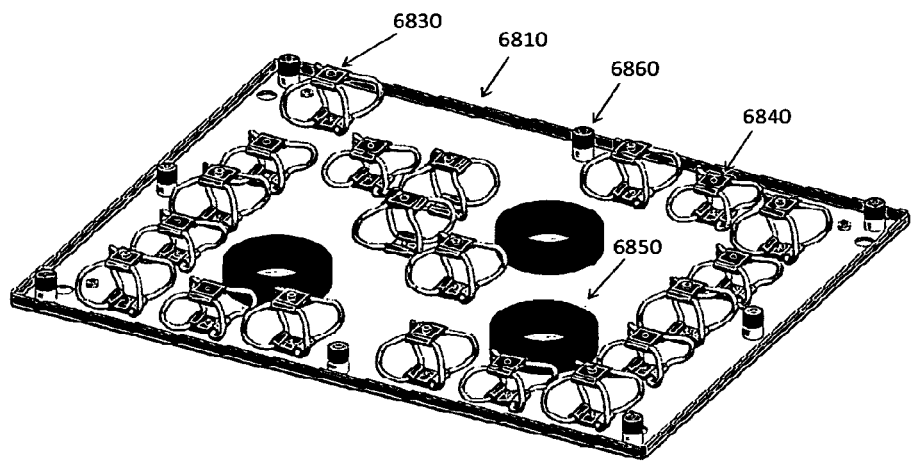
FIGS. 68A-C show different views of embodiments of a motion- and shock-reducing device that comprises a top plate and a bottom plate of a base; taller, more flexible metal springs; shorter, more rigid metal springs; upper and lower constraining elements; and bumpers.

FIG. 68A is a top view of an embodiment of a motion- and shock-reducing device. The device comprises a bottom plate 6810 (a top plate is not shown); twelve taller, more flexible metal springs 6830 that are, e.g., CR6-300 wire rope vibration isolators; eight shorter, more rigid metal springs 6840 that are, e.g., CR6-100 wire rope vibration isolators; three lower constraining elements 6850 that have a doughnut-like or toroidal shape; and eight bumpers 6860; wherein all the aforementioned components are attached (e.g., screwed) to the bottom plate.

Figure 68B:
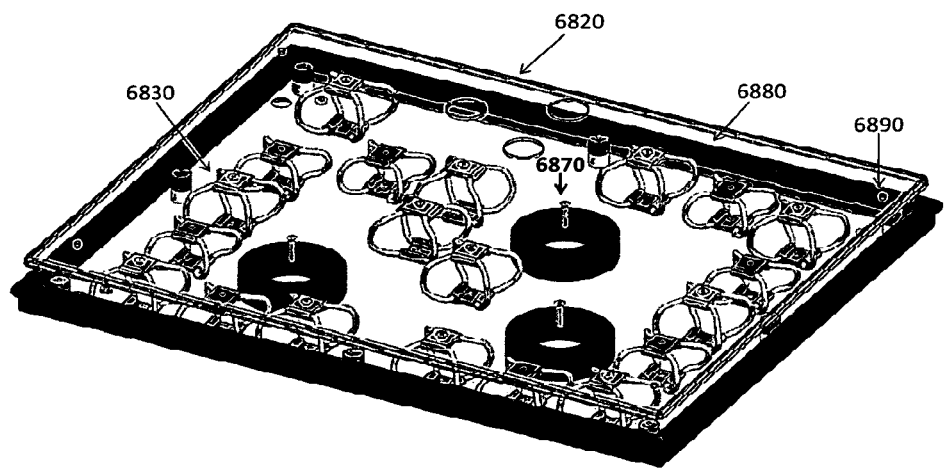
Figure 68C:
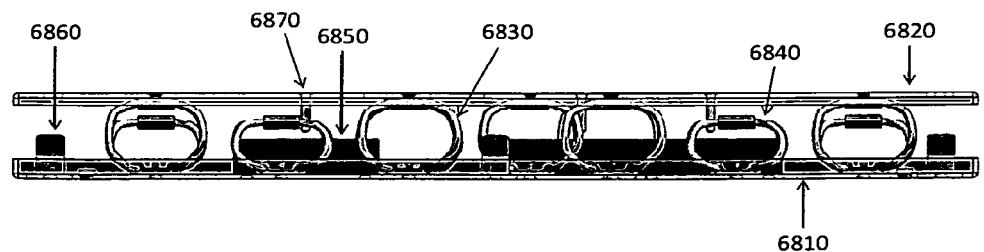

FIG. 68B is an embodiment of the motion- and shock-reducing device of FIG. 68A and shows top plate 6820 of the device (or base). The twelve taller, more flexible metal springs 6830 are attached (e.g., screwed) to top plate 6820 of the base, and three upper constraining elements 6870 are also attached (e.g., screwed) to the top plate. The top plate is transparent in FIG. 68B to show the components of the device. In the embodiment of FIG. 68B, the upper constraining elements 6870 are screws, and lining 6880 lines the side walls of bottom plate 6810. Lining 6880 provides cushioning in case the top plate contacts the bottom plate, and can be any sufficiently protective and durable material (e.g., a polymeric material, such as a natural or synthetic rubber). A lining can also be disposed along the edges of the top plate. Top plate 6820 has four holes 6890 at the corners of the top plate (fewer or more holes can be used) for removably attaching (e.g., screwing) an instrument to the top plate. For example, bumpers on which an instrument normally rests can be removed and the instrument can be removably attached to the top plate of the base using the same threaded holes for attaching the bumpers. The device of FIG. 68B is configured to reduce the motion (e.g., horizontal, vertical, rotational and vibrational motion) and shock that an approximately 150-200 pound instrument (e.g., one weighing about 175 lb) may experience. The instrument can be, e.g., an analytical instrument, such as the sample-processing and analytical instrument described herein. The top plate and the bottom plate of the base independently can be composed of any sufficiently strong and durable material, such as a metal or a metal alloy. In an embodiment, the top plate and the bottom plate are composed of an aluminum alloy (e.g., 3003 aluminum alloy). FIG. 68C is a side view of an embodiment of the motion- and shock-reducing device of FIGS. 68A and B. FIG. 68C shows the relative heights of the components of the device. Lining 6880 is not shown in FIG. 68C so that other components of the device can be more easily seen.

In other embodiments, the base of the motion- and shock-reducing device does not comprise a top plate, but rather the taller, more flexible metal springs or coils of the base are attached (e.g., screwed) to the case or chassis of an instrument. In further embodiments, the base does not comprise bumpers, or comprises fewer bumpers than otherwise, and the top plate has holes (e.g., four holes) through which bumpers made of a suitable material (e.g., a rubber) and attached to an instrument can traverse, so that the bumpers attached to the instrument function like bumpers in the base.

2. Motion- and Shock-Reducing Devices Having Elastomeric Columns or Springs

In further embodiments, devices for reducing motion (e.g., translational, rotational and/or vibrational motion) and shock that an instrument or components thereof may experience comprise elastomeric columns or springs composed of one or more elastomeric materials. Such devices can comprise elastomeric columns or elastomeric springs, or both. Moreover, such devices can optionally further comprise metal springs or coils, or gas springs (e.g., air springs), or both. In some embodiments, a motion- and shock-reducing device comprises a base comprising a top plate, a bottom plate, and elastomeric columns or springs. The device can further comprise constraining elements (e.g., substantially cylindrical upper constraining elements and toroidal lower constraining elements) configured to limit the range of horizontal motion, and other elements (e.g., bumpers) configured to limit the range of vertical motion, that an instrument may experience, as described herein.

In some embodiments, the motion- and shock-reducing device comprises elastomeric columns that do not have a hollow interior, or elastomeric springs that have a hollow interior, or both. The elastomeric columns and/or elastomeric springs can have any suitable shape. In some embodiments, the elastomeric columns and/or elastomeric springs have a substantially cylindrical, squarish or rectangular shape. In certain embodiments, the elastomeric columns are substantially L-shaped, and/or the elastomeric springs are substantially cylindrical.

An elastomeric column or an elastomeric spring can be composed of any one or more elastomeric materials that provide the column or spring with the desired compressibility, reboundability, strength and any other desired properties. For example, an elastomeric column or spring can be composed of one elastomeric material or a combination of a softer elastomeric material and a harder (or firmer) elastomeric material. In some embodiments, the one or more elastomeric materials composing an elastomeric column or spring are open-cell or closed-cell foam(s), or open-cell or closed-cell sponge(s), or any combination thereof. In certain embodiments, an elastomeric column or spring comprises a closed-cell foam or sponge.

In some embodiments, an elastomeric column or spring is composed of one or more elastomeric materials selected from rubbers (including natural rubbers and synthetic rubbers), thermoset elastomers, thermoplastic elastomers, and elastomeric biopolymers. Rubbers include unsaturated rubbers that can be cured by sulfur or non-sulfur vulcanization ("unsaturated rubbers"), saturated rubbers that cannot be cured by sulfur vulcanization ("saturated rubbers"), and other kinds of rubber (e.g., polysulfide rubber). Non-limiting examples of unsaturated rubbers include natural polyisoprene (e.g., cis-1,4-polyisoprene natural rubber and trans-1,4-polyisoprene gutta-percha rubber), synthetic polyisoprene (isoprene rubber, such as Cariflex™), polybutadiene (butadiene rubber), polychloroprene (chloroprene rubber, such as Neoprene and Baypren®), copolymers of isobutylene and isoprene (butyl rubber), halogenated butyl rubbers (e.g., chloro butyl rubber and bromo butyl rubber), copolymers of styrene and butadiene (styrene-butadiene rubber), copolymers of butadiene and acrylonitrile (nitrile rubber), and hydrogenated nitrile rubbers (e.g., Therban® and Zetpol®). Non-limiting examples of saturated rubbers include polyethylene, copolymers of ethylene and an alpha-olefin [e.g., copolymers of ethylene and vinyl acetate (EVA), copolymers of ethylene and an acrylic or acrylate compound, copolymers of ethylene and propylene (ethylene propylene (EPM) rubber), and copolymers of ethylene, propylene and a diene (ethylene propylene diene (EPDM) rubber)], chlorosulfonated polyethylene (e.g., Hypalon®), polyacrylic rubber, epichlorohydrin rubber, silicone rubber, fluorosilicone rubber, fluoroelastomers (e.g., Viton®, Tecnoflon®, Fluorel™, Aflas® and Dai-E1™), perfluoroelastomers (e.g., Tecnoflon® PFR, Kalrez®, Chemraz® and Perlast®), and polyether block amides. Non-limiting examples of thermoplastic elastomers include blends of a plastic and a rubber, blends of polyolefins, copolymers of olefins (e.g., ethylene-octene copolymers such as Engage®), styrenic block copolymers (e.g., Mediprene®), thermoplastic copolyesters (e.g., Arnitel® and Hytrel®), thermoplastic polyamides, and thermoplastic polyurethanes (e.g., Avalon, Desmopan®, Elastollan®, Epaline, Estane®, Irogran®, Isothane®, Laripur®, Pearlthane®, Pellethane®, and Poron®). Examples of elastomeric biopolymers include without limitation resilin and elastin.

Whether an elastomeric column or spring is composed of one elastomeric material or a plurality of elastomeric materials, the column or spring can be monolithic or comprise a plurality of layers of the one or more elastomeric materials. As an example, if an elastomeric column or spring is composed of one elastomeric material, the column or spring can be monolithic or comprise multiple layers of the same elastomeric material (e.g., to achieve a desired height of the column or spring). As another example, if an elastomeric column or spring is composed of a plurality of elastomeric materials, the column or spring can be a monolithic structure comprising a mixture of the elastomeric materials, or can comprise a plurality of layers, where a layer comprises an elastomeric material and the layers can be arranged in any desired order. For example, an elastomeric column or spring composed of a harder (or firmer) elastomeric material and a softer elastomeric material can have a lower layer of the harder material and an upper layer of the softer material. Multiple layers of the same elastomeric material or different elastomeric materials can be bonded together by any suitable method (e.g., by lamination or using an adhesive).

The elastomeric columns and/or elastomeric springs can have any height suitable for reducing motion and shock, bearing the weight of an instrument removably attached to the base, and balancing the instrument. Furthermore, the base can comprise elastomeric columns having substantially the same height or different heights, and/or elastomeric springs having substantially the same height or different heights. In certain embodiments, the base comprises elastomeric columns and/or springs having substantially the same height (e.g., about 2-4 inches, or about 2, 2.5, 3, 3.5 or 4 inches). In other embodiments, the base comprises taller elastomeric columns and/or springs composed of a softer elastomeric material and configured to dampen vibration, and shorter elastomeric columns and/or springs composed of a harder (or firmer) elastomeric material and configured to absorb shock. The taller elastomeric columns and/or springs can have any suitable height (e.g., about 2-4 inches, or about 2, 2.5, 3, 3.5 or 4 inches), and the shorter elastomeric columns and/or springs can have any suitable height (e.g., about 1-3 inches, or about 1, 1.5, 2, 2.5 or 3 inches). The taller elastomeric columns and/or springs are attached (e.g., adhered) to the bottom plate and the top plate of the base, while the shorter elastomeric columns and/or springs are attached (e.g., adhered) to the bottom plate but not to the top plate. The taller elastomeric columns and/or springs can have a greater thickness or width than the shorter elastomeric columns and/or springs.

The base can comprise any number of elastomeric columns and/or elastomeric springs, and the elastomeric columns and/or springs can be arranged in any manner, suitable for reducing motion and shock, bearing the weight of an instrument removably attached to the base, and balancing the instrument, where the elastomeric columns and/or springs can have substantially the same height or different heights. In certain embodiments, the base comprises from 4 to 24 (e.g., 6, 8, 12, 16 or 20) elastomeric columns and/or springs near or along the edges of the bottom plate, and 2 to 12 (e.g., 3, 4, 5, 6, 8 or 10) elastomeric columns and/or springs away from the edges of the bottom plate.

In some embodiments, the base comprises substantially L-shaped elastomeric columns near or along the edges of the bottom plate and substantially L-shaped elastomeric columns away from the edges of the bottom plate. The substantially L-shaped elastomeric columns can have substantially the same height or different heights. In certain embodiments, the elastomeric columns have substantially the same height (e.g., about 2-4 inches, or about 2, 2.5, 3, 3.5 or 4 inches). Furthermore, the substantially L-shaped elastomeric columns can be composed of the same elastomeric material or different elastomeric materials. In certain embodiments, the elastomeric columns comprise a lower layer of a harder (or firmer) elastomeric material and an upper layer of a softer elastomeric material.

In other embodiments, the base of the motion- and shock-reducing device does not comprise a top plate, but rather the elastomeric columns and/or springs having substantially the same height, or the taller elastomeric columns and/or springs, of the base are attached (e.g., adhered) to the case or chassis of an instrument.

VI. Kits

The disclosure also provides kits comprising consumable reagents. The kits can comprise a first container configured to receive a sample for analysis and a second container comprising at least one consumable reagent for use in analysis of the sample. Consumable reagents for use in sample analysis can include, for example, solutions (e.g., wash solutions, reaction buffers or electrophoresis buffers), enzymes for performing chemical or biochemical reactions (e.g., polymerases), chemical reagents (e.g., amplification primers, labeling reagents). One or more of the containers can be cartridges that are configured to engage an assembly of an analytical instrument that performs part or all of the sample analysis. For example, the container adapted to receive a sample can be a sample cartridge of this invention. A container comprising at least one consumable reagent can be a buffer cartridge or an anode cartridge of this invention. In some embodiments the first container or cartridge also can comprise consumable reagents for use in sample analysis. For example, the sample cartridge can contain one or more than one reagent necessary for performing a chemical reaction on an analyte. In some embodiments, the containers in the kits provided can be configured for a single analysis run in an instrument. The containers can be disposable. Accordingly, the kit can include a disposable single-use container (e.g., cartridge) for receiving a sample (and, optionally, for performing a chemical or biochemical reaction on an analyte in the sample). In further embodiments, second containers, e.g., cartridges, containing at least one consumable reagent can be figured for one or more than one analysis run. Containers configured for more than one analysis run can contain consumable reagents sufficient for more than one analytical run. In some embodiments, the kit comprises a plurality of first containers, each first container configured to receive a sample and configured for use in a single analysis run; and one or more second containers, each of the second containers containing one or more consumable reagent for use in the sample analysis in quantities sufficient for a number of analytical runs equal to the plurality of first containers. For example, the kit could contain ten sample cartridges and a consumable reagent cartridge with a reagent in an amount sufficient for ten analytical runs. In some embodiments, the kit can include all consumable reagents necessary for every step in an analysis run performed by an analytical instrument for which the kit is configured. For example, a kit for STR analysis can include reagents for DNA extraction from a sample (e.g., lysis buffer, capture particles, wash solutions), reagents for performing STR amplification (e.g., primers, polymerase) and reagents for electrophoresis (e.g., electrophoresis buffer, separation medium). Such a kit also can include controls and standards (e.g., allelic ladders, size standards).

VII. Portable Instrument or System

Some embodiments of the disclosure relate to portable versions of the sample-to-answer instrument or system described herein which can be made sufficiently rugged for intended uses, e.g., by military or law enforcement personnel operating in the field. Nonlimiting examples of applications of such a portable instrument or system include sensitive site exploitation, intelligence operations, confirmation or denial of hostages, expeditionary forensic capabilities, criminal identification and crime scene evaluation. Features of the portable instrument or system can include, e.g., reagents storable at ambient temperature, shorter sample-to-answer time (e.g., no more than about 45 min, 60 min, 75 min or 90 min), reduced weight, and enhanced ruggedization to withstand vibration and shock that may be encountered during transport across rough terrain and operation across a broad range of environmental conditions, including high altitude, extreme temperatures, and extreme humidity.

In some embodiments, the portable instrument or system is configured to be transportable in a container that can be carried by hand, by the shoulder or on the back (e.g., a backpack), where the instrument or system can comprise one or more modules, and where each of the one or more modules can be transported in a container (e.g., a backpack). In certain embodiments, each of the one or more modules weighs no more than about 30 pounds (lb), 35 lb, 40 lb, 45 lb, 50 lb, 55 lb, 60 lb, 65 lb or 70 lb. The weight of the portable instrument or system can be reduced, e.g., by reducing the weight of various components of the instrument or system, and/or by eliminating or redesigning certain components. For example, the instrument or system can be designed to use a single sample cartridge, which would not require a sample cartridge interface module that provides pneumatic and fluidic connections to two sample cartridges. The sample cartridge can be configured to receive and process a plurality of different samples, such as 8, 10, 16, 24, 32, 48 or more different samples. As another example, mounts having reduced weight can be used for various components, such as the anode cartridge interface module, the optics module and/or any other modules, or all modules, of the portable instrument or system. As a further example, each of the one or more modules can have a chassis and a case of reduced weight. For instance, each of the one or more modules can have a chassis and/or a case made of a lighter metal, such as aluminum or sheet metal.

Figure 69A:
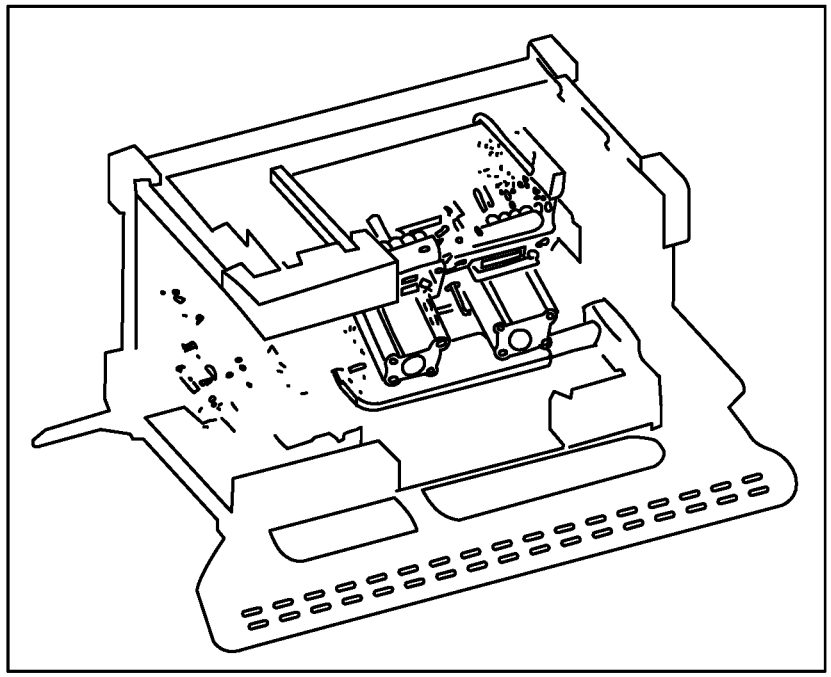
FIGS. 69A and 69B show embodiments of a portable instrument or system comprising two modules.
Figure 69B:
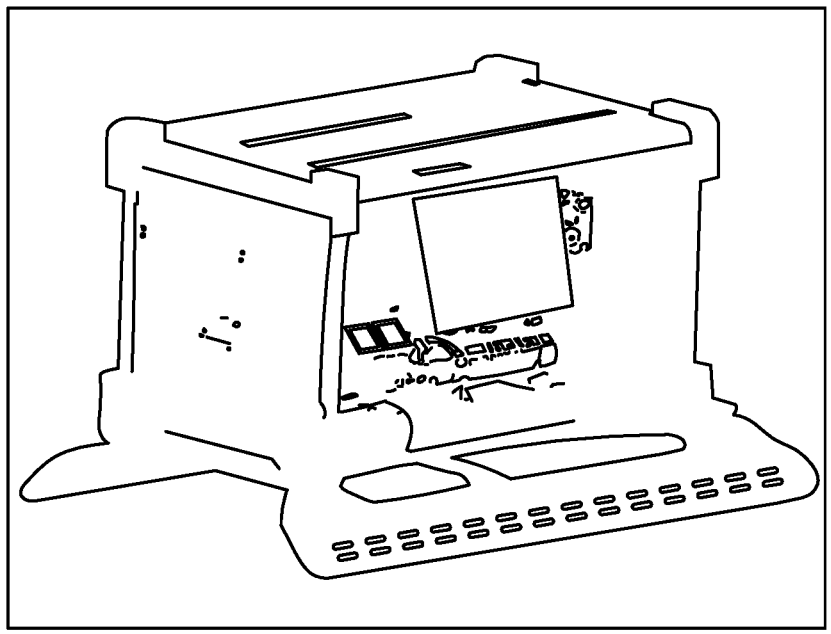

In certain embodiments, the portable instrument or system comprises two modules which each can be transported in a separate container that can be carried by hand, by the shoulder or on the back (e.g., a backpack), and which can be connected to each other at a destination point to create a functional nucleic acid (e.g., DNA) analysis instrument or system. FIGS. 69A and 69B show embodiments of a portable instrument or system comprising two modules that are transportable in a backpack format. In some embodiments, one of the two modules of the portable instrument or system is a sample analysis module (FIG. 69A) that comprises, among other components, an interface for one or more sample cartridges, a separation and detection system (including a capillary electrophoresis array, a pump for filling the capillaries with gel, and a detector), a means for rehydrating dried reagents, and a high voltage power supply. In certain embodiments, the sample analysis module is configured to take a single sample cartridge. In other embodiments, the sample analysis module is configured to take multiple sample cartridges (e.g., two sample cartridges). All sample processing, including DNA extraction and separation and detection of amplified DNA (e.g., STR) fragments, can be performed in the sample analysis module. In certain embodiments, the sample analysis module has dimensions of about 14.5 inches×about 14.5 inches×about 23 inches, or within about 10% or 20% less than or greater than those dimensions. In certain embodiments, the sample analysis module weighs about 50, 53 or 55 lb, or about 10% or 20% less than or greater than about 50, 53 or 55 lb. In further embodiments, the other module of the portable instrument or system is a support module (FIG. 69B) that comprises, among other components, a pump to supply vacuum and pressure to the one or more sample cartridges and the interface therefor, a computer system, and a touch screen display. In some embodiments, the support module has dimensions substantially similar to those of the sample analysis module. In certain embodiments, the support module weighs about 40, 42 or 45 lb, or about 10% or 20% less than or greater than about 40, 42 or 45 lb. FIGS. 69A and 69B show the sample analysis module and the support module each mounted on a backpack frame. In certain embodiments, the backpack frame for the sample analysis module and the support module weighs about 1 lb, 2 lb, 3 lb, 4 lb or 5 lb.

The sample analysis module and the support module can be ruggedized to withstand vibration and shock, e.g., by having a sprung subframe. In some embodiments, the sample analysis module and the support module each have at least two layers of ruggedization. All eight corners of the case enclosing each of the sample analysis module and the support module are covered with a tough, energy-absorbing material (e.g., a plastic or a rubber). Such covered corners of the case can attenuate stresses due to a drop of the case onto a surface (e.g. the ground), particularly a drop onto any of the protected corners. Toughened corner caps, corrugated aluminum walls and end plates of the case form a durable, protective and lightweight case for the sample analysis module and the support module. Furthermore, inside the case, metal springs or coils, gas springs (e.g., air springs), or elastomeric columns or springs, or any combination thereof, at the base of the subframe supporting the sample analysis module or the support module, and/or at all eight corners of the case, can protect the components of the modules from misalignment or damage by attenuating vibration and shock.

In some embodiments, one of the two modules comprises systems for performing nucleic acid extraction and purification and PCR amplification, and the other module comprises systems for performing separation, detection and data analysis. In other embodiments, one of the two modules comprises systems for performing nucleic acid isolation, nucleic acid amplification (e.g., by PCR), separation (e.g., by electrophoresis) and detection, and the other module comprises systems for performing data analysis (e.g., a computer) and providing positive pressure and negative pressure (e.g., a pump).

In certain embodiments, the portable instrument or system performs sample-to-answer processing and analysis in no more than about 45 min, 60 min, 75 min or 90 min. In some embodiments, the instrument or system achieves a shorter sample-to-answer time by employing a faster thermal cycler and/or a faster thermal cycling methodology. In certain embodiments, the instrument or system has a Peltier-based thermal cycling system that has a heating rate of about 10-15° C./sec or greater, and a cooling rate of about 5-10° C./sec or greater. A faster thermal cycler can allow PCR amplification (e.g., of STR loci) to be performed in about 30 min, 25 min, 20 min, 15 min or less. Faster PCR amplification can also be accomplished by utilizing a faster thermal cycling methodology, e.g., continuous flow PCR amplification. Continuous flow PCR amplification can achieve fast PCR amplification by having the PCR fluid undergo rapid temperature transitions as it moves between fixed temperature zones. Faster PCR amplification can also be achieved by performing shuttle cycling or by performing PCR in a valve (which can be isothermal or vary in temperature) or in multiple valves having different temperatures. In further embodiments, the portable instrument or system achieves a faster sample-to-answer time by separating DNA fragments (e.g., amplicons of STR loci) in a shorter time. Faster electrophoretic separation of DNA fragments can be accomplished in various ways, e.g., by decreasing the injected sample plug length and increasing the quantity of DNA injected into a capillary. As another example, a narrower sample injection plug can allow separation in a shorter capillary with sufficient resolution of DNA fragments. As a further example, use of an electrokinetic sample stacking injection process (e.g., transient isotachophoresis) can substantially increase the efficiency of sample injection in electrophoresis, which can result in improved sensitivity of sample detection and can decrease the number of PCR cycles required for amplification. Fewer PCR cycles can shorten the amplification time.

VIII. Representative Embodiments

The following embodiments of the disclosure are provided by way of example only:
1. A cartridge comprising one or more sets of chambers and fluidic channels, wherein:
    the cartridge is configured to be removably engagable with a cartridge module;
    for a cartridge comprising a plurality of sets of chambers and fluidic channels, each set of chambers and fluidic channels is fluidically isolated from every other set of chambers and fluidic channels prior to and subsequent to engagement of the cartridge with the cartridge module;
    each set of chambers and fluidic channels comprises a plurality of chambers that are closed and fluidically isolated from one another and from the fluidic channels prior to engagement of the cartridge with the cartridge module;
    the chambers in each set of chambers and fluidic channels come into fluidic communication with one another via the fluidic channels when the cartridge is engaged with the cartridge module; and
    for each of the plurality of closed and fluidically isolated chambers in each set of chambers and fluidic channels, engagement of the cartridge with the cartridge module creates a fluid flow path comprising a fluidic channel in fluidic communication with a first port of the chamber, the chamber, and a fluidic channel in fluidic communication with a second port of the chamber.
2. The cartridge of embodiment 1, wherein the first port and the second port of each of the plurality of closed and fluidically isolated chambers in each set of chambers and fluidic channels are on substantially the same plane, on the same surface, or at the base or the bottom of the chamber, or any combination thereof.
3. The cartridge of embodiment 1 or 2, wherein each of the plurality of closed and fluidically isolated chambers is closed and fluidically isolated, prior to engagement of the cartridge with the cartridge module, with the aid of a friable or puncturable seal.
4. The cartridge of embodiment 3, wherein when the cartridge is engaged with the cartridge module, two puncturing elements in the cartridge puncture the friable or puncturable seal of each of the closed and fluidically isolated chambers, thereby creating a fluid flow path comprising a fluidic channel in fluidic communication with a first port of the chamber, the chamber, and a fluidic channel in fluidic communication with a second port of the chamber.
5. The cartridge of embodiment 4, wherein the fluid flow path at each port of the chamber is sealed with the aid of one or more (e.g., two) gaskets.
6. The cartridge of embodiment 4 or 5, wherein each puncturing element has an opening that is in fluidic communication with a fluidic channel.
7. The cartridge of any one of embodiments 4 to 6, wherein each fluidic channel in fluidic communication with a port of a chamber can provide a fluid (e.g., a liquid or a gas) to the chamber.
8. The cartridge of any one of embodiments 3 to 7, wherein the friable or puncturable seal is composed of a metallic material (e.g., an aluminum foil).
9. The cartridge of any one of embodiments 3 to 8, wherein the friable or puncturable seal is composed of a polymeric material.
10. The cartridge of any one of embodiments 1 to 9, which further comprises one or more ports for each set of chambers and fluidic channels which bring the chambers in each set in fluidic communication with a source of positive pressure or negative pressure via the fluidic channels.
11. The cartridge of any one of embodiments 1 to 10, wherein for a cartridge comprising a plurality of sets of chambers and fluidic channels, the path of the fluidic channels in each set of chambers and fluidic channels is substantially parallel to and/or does not intersect the path of the fluidic channels in every other set of chambers and fluidic channels.
12. The cartridge of any one of embodiments 1 to 11, which is configured to:
    extract nucleic acid (e.g., DNA) from a sample;
    isolate the extracted nucleic acid (e.g., by capturing the extracted nucleic acid to a substrate (e.g., magnetically responsive particles));
    optionally purify the isolated nucleic acid;
    amplify one or more selected nucleotide (e.g., short tandem repeat (STR)) sequences of the isolated nucleic acid (e.g., by polymerase chain reaction (PCR)) to produce amplification products; and
13. The cartridge of embodiment 12, wherein each set of chambers comprises:
    (a) a chamber comprising a reagent (e.g., a lysis reagent) in a solution or buffer for extracting nucleic acid from a sample, and optionally an anti-foaming reagent;
    (b) a chamber comprising a substrate (e.g., magnetically responsive particles), optionally in a solution or buffer, for isolating extracted nucleic acid;
    (c) one or more (e.g., two) chambers comprising a solution (e.g., a wash solution or buffer) for purifying isolated nucleic acid; and
    (d) a chamber comprising a solution (e.g., water) for diluting amplification products prior to separation of the amplification products.
14. The cartridge of embodiment 13, wherein for each set of chambers:
    chamber (a) is configured to receive and/or store waste material; and
    chamber (d) optionally further comprises a control (e.g., a size standard in a set of chambers comprising a sample, or an allelic ladder (and optionally a size standard) in a set of chambers not comprising a sample).
15. The cartridge of embodiment 13 or 14, wherein for each set of chambers:
   chamber (a) is pre-loaded with a reagent (e.g., a lysis reagent) in a solution or buffer for extracting nucleic acid from a sample, and optionally an anti-foaming reagent;
   chamber (b) is pre-loaded with a substrate (e.g., magnetically responsive particles), optionally in a solution or buffer, for isolating extracted nucleic acid;
   one or more (e.g., two) chambers (c) are pre-loaded with a solution (e.g., a wash solution or buffer) for purifying isolated nucleic acid; and
   chamber (d) is pre-loaded with a solution (e.g., water) for diluting amplification products, and optionally a control (e.g., a size standard in a set of chambers that will comprise a sample, or an allelic ladder (and optionally a size standard) in a set of chambers that will not comprise a sample).
16. The cartridge of any one of embodiments 13 to 15, wherein for each set of chambers, chamber (b) comprises, or is preloaded with, an amount of magnetically responsive particles selected to control the amount of nucleic acid isolated.
17. The cartridge of any one of embodiments 13 to 16, wherein for each set of chambers:
   each of chambers (a), (b), (c) and (d) is closed and fluidically isolated prior to engagement of the cartridge with the cartridge module; and
   for each of chambers (a), (b), (c) and (d), engagement of the cartridge with the cartridge module creates a fluid flow path comprising a fluidic channel in fluidic communication with a first port of the chamber, the chamber, and a fluidic channel in fluidic communication with a second port of the chamber.
18. The cartridge of any one of embodiments 12 to 17, wherein each set of chambers comprises:
   a chamber configured to receive a sample; and
   a chamber configured to amplify one or more selected nucleotide sequences of isolated nucleic acid (e.g., by PCR).
19. The cartridge of embodiment 18, wherein the sample chamber is configured to receive a cellulosic substrate (e.g., FTA paper) or a swab (e.g., a cotton swab or a brush swab).
20. The cartridge of embodiment 18 or 19, wherein the sample chamber is further configured to extract nucleic acid from the sample.
21. The cartridge of any one of embodiments 18 to 20, wherein the amplification reaction chamber is further configured to perform nucleic acid amplification with thermal cycling with the aid of a heating and cooling device (e.g., a Peltier heating and cooling element).
22. The cartridge of embodiment 21, further comprising a thermoconducting element configured to apply or distribute heat and cooling to the amplification reaction chamber in each set of chambers.
23. The cartridge of embodiment 22, wherein the thermoconducting element is disposed over the amplification reaction chamber in each set of chambers.
24. The cartridge of any one of embodiments 13 to 23, which further comprises a source of magnetic field (e.g., a magnet) adjacent to chamber (b) and/or the amplification reaction chamber in each set of chambers.
25. The cartridge of any one of embodiments 18 to 24, wherein each set of chambers further comprises one or more (e.g., two) chambers comprising (e.g., pre-loaded with) reagents for amplifying one or more selected nucleotide sequences.
26. The cartridge of embodiment 25, wherein the reagents for amplifying one or more selected nucleotide sequences comprise a polymerase (e.g., a DNA polymerase, such as a Taq polymerase), one or more pairs of forward and reverse primers for amplifying the one or more selected nucleotide sequences, nucleotide triphosphates (e.g., deoxyribonucleotide triphosphates), and optionally a buffer and a metal salt (e.g., magnesium chloride), and wherein the one or more pairs of forward and reverse primers optionally are labeled with a dye (e.g., a fluorescent dye).
27. The cartridge of embodiment 25 or 26, wherein:
   each set of chambers comprises two chambers comprising (e.g., pre-loaded with) amplification reagents;
   one of the two amplification reagent chambers comprises one or more pairs of forward and reverse primers, and the other chamber comprises a polymerase (e.g., a DNA polymerase), nucleotide triphosphates (e.g., deoxyribonucleotide triphosphates), and optionally a buffer and/or a metal salt (e.g., magnesium chloride); and
   the two amplification reagent chambers can be part of a vessel (e.g., two chambers in the cartridge or two chambers of a vial connected to the cartridge) or can be two separate vessels (e.g., two vials connected to the cartridge).
28. The cartridge of any one of embodiments 25 to 27, wherein for each set of chambers, the one or more amplification reagent chambers come into fluidic communication with the amplification reaction chamber upon actuation of a delivery mechanism (e.g., a plunger pushing down to break a seal at the bottom of the one or more amplification reagent chambers).
29. The cartridge of any one of embodiments 25 to 28, wherein the reagents for amplifying one or more selected nucleotide sequences are delivered to the amplification reaction chamber via a channel that does not comprise a valve.
30. The cartridge of any one of embodiments 25 to 29, wherein for a set of chambers that does not, or will not, comprise a sample, the one or more amplification reagent chambers further comprise, or are further pre-loaded with, a positive control (e.g., a purified genomic DNA).
31. The cartridge of any one of embodiments 13 to 30, wherein for all of the one or more sets of chambers, all of chambers (a), (b), (c) and (d), the one or more sample chambers and the one or more amplification reaction chambers, and optionally the one or more amplification reagent chambers, are all substantially co-planar.
32. The cartridge of any one of embodiments 12 to 31, which comprises a separation channel for each set of chambers and fluidic channels.
33. The cartridge of embodiment 32, which further comprises:
   one or more heating elements configured to apply heat to denature amplification products during separation, or prior to and during separation; and
   a thermal-control device configured to control heating of the amplification products.

34. The cartridge of any one of embodiments 1 to 33, wherein for each set of chambers, each of the chambers can be macrofluidic or microfluidic.

35. The cartridge of any one of embodiments 1 to 34, wherein one or more, or all, of the fluidic channels in each set of chambers and fluidic channels comprise one or more valves.

36. The cartridge of embodiment 35, wherein one or more, or all, of the one or more valves are diaphragm valves.

37. The cartridge of embodiment 36, wherein the diaphragm valves comprise normally open valves or normally closed valves, or both.

38. The cartridge of embodiment 37, wherein a normally open diaphragm valve is comprised in a combination that comprises a fluidic layer, a pneumatic layer and an elastic layer sandwiched between the fluidic layer and the pneumatic layer, and wherein the normally open diaphragm valve comprises:
  (a) a diaphragm in the elastic layer and composed of an elastomeric material (e.g., polydimethylsiloxane);
  (b) a valve seat in the fluidic layer and recessed from a surface of the fluidic layer (e.g., the valve seat has a concave shape with respect to the surface of the fluidic layer) so that the diaphragm does not close the diaphragm valve unless positive pressure is exerted on the diaphragm; and
  (c) a valve inlet and a valve outlet in the fluidic layer and in fluidic communication with a fluidic channel;
  wherein the diaphragm is actuated by positive pressure or negative pressure transmitted to the diaphragm via a pneumatic conduit in the pneumatic layer.

39. The cartridge of any one of embodiments 35 to 38, wherein one or more, or all, of the one or more valves are pneumatically actuated valves.

40. The cartridge of any one of embodiments 35 to 39, wherein one or more, or all, of the one or more valves are electrically actuated valves.

41. The cartridge of any one of embodiments 1 to 40, wherein one or more, or all, of the fluidic channels in each set of chambers and fluidic channels comprise one or more pumps.

42. The cartridge of embodiment 41, wherein one or more, or all, of the one or more pumps comprise a plurality of (e.g., three or four) valves (e.g., diaphragm valves).

43. The cartridge of any one of embodiments 1 to 42, which comprises 4, 8, 10, 16, 24, 32, 40, 48 or more sets of chambers and fluidic channels, wherein each set of chambers and fluidic channels can be used to run a different sample, or one or more sets of chambers and fluidic channels can be used to run a different control (e.g., an allelic ladder, a positive control and/or a negative control) and every other set of chambers and fluidic channels can be used to run a different sample.

44. The cartridge of embodiment 43, wherein:
  a first set of chambers comprises an allelic ladder and a size standard;
  a second set of chambers comprises a positive control and a size standard;
  a third set of chambers comprises a negative control and a size standard; and
  every other set of chambers comprises a different sample and a size standard.

45. The cartridge of any one of embodiments 1 to 44, wherein one or more, or all, of the fluidic channels in each set of chambers and fluidic channels are microfluidic channels.

46. The cartridge of any one of embodiments 1 to 45, which can be configured for a single use or multiple uses.

47. The cartridge of any one of embodiments 1 to 46, which further comprises a readable and/or writable memory device (e.g., an EEPROM memory chip) configured to store, receive and/or transmit information relating to the cartridge (e.g., information relating to the history, a recommended use-by date, the current use (e.g., whether the cartridge is operably engaged with a cartridge module, information input from a user, and/or information generated by the system/instrument employing the cartridge in operation), the configurations, the conditions, the physical features and/or the chemical features of the cartridge).

48. The cartridge of any one of embodiments 1 to 47, wherein when the cartridge is engaged with the cartridge module, the longitudinal axis of the cartridge is at an angle of about 15-45 degrees, 20-40 degrees or 25-35 degrees, or about 30 degrees, relative to a vertical plane perpendicular to the plane of the surface on which a system comprising the cartridge module rests.

49. The cartridge of any one of embodiments 1 to 48, which is a sample cartridge or a control cartridge.

50. The cartridge of any one of embodiments 1 to 49, wherein at least about 50%, 60%, 70%, 80%, 90%, 95% or 99% of the cartridge by mass, without addition of any sample or reagents, is composed of one or more polymeric materials (e.g., one or more plastics, such as a polyalkylene (e.g., polypropylene) and/or a cycloolefin homopolymer or copolymer (e.g., Zeonor® 1060R)).

51. The cartridge of embodiment 50, wherein the frame (including the outer portions), the chambers, the fluidic channels, and the fluidic layer and the pneumatic layer of valves (e.g., normally open valves and/or normally closed valves) of the cartridge are formed of one or more polymeric materials (e.g., one or more plastics, such as a polyalkylene (e.g., polypropylene) and/or a cycloolefin homopolymer or copolymer (e.g., Zeonor® 1060R)).

52. The cartridge of embodiment 50 or 51, wherein at least about 50%, 75%, 90% or 95% of the cartridge by mass is made by injection molding.

53. A cartridge module comprising:
  a cartridge receptacle configured to receive and hold a cartridge that comprises a plurality of chambers and fluidic channels and a plurality of valves for regulating fluid flow to and from the chambers via the fluidic channels;
  a first manifold configured to engage a first side of the cartridge and thereby bring the valves in fluidic communication with a source of positive pressure or negative pressure for pneumatic actuation of the valves;
  a second manifold configured to engage a second side of the cartridge and thereby bring the chambers in fluidic communication with a source of positive pressure or negative pressure;
  a first plurality of springs configured to actuate the first manifold;

a second plurality of springs configured to actuate a thermocycling device; and a pressure cylinder configured to actuate the second manifold and to control the first plurality of springs and the second plurality of springs.

54. The cartridge module of embodiment 53, wherein pressurization of (e.g., one side of) the pressure cylinder holds open the first manifold, the second manifold and the thermocycling device.

55. The cartridge module of embodiment 54, wherein relaxation of (e.g., both sides of) the pressure cylinder actuates the first plurality of springs and the second plurality of springs so that the first manifold engages with the first side of the cartridge and the thermocycling device engages with the cartridge (e.g., a metal plate of the thermocycling device contacts a thermoconducting element disposed over reaction chambers of the cartridge).

56. The cartridge module of embodiment 55, wherein pressurization of (e.g., the opposite side of) the pressure cylinder actuates the second manifold so that the second manifold engages with the second side of the cartridge.

57. The cartridge module of any one of embodiments 53 to 56, wherein the first plurality of springs is 4 springs.

58. The cartridge module of any one of embodiments 53 to 57, wherein the second plurality of springs is 2 springs.

59. The cartridge module of any one of embodiments 53 to 58, wherein:
the first manifold and the second manifold each comprise a plurality of tubes;
each of the tubes is independently pressure-driven (and optionally spring-loaded) and is configured to sealingly engage with one of a plurality of ports on the first side and the second side of the cartridge; and
engagement of an end of a tube with a port creates a fluidic communication between the port and an unengaged end of the tube.

60. The cartridge module of embodiment 59, wherein:
the ports on the first side of the cartridge communicate with pneumatic channels in the cartridge;
the ports on the second side of the cartridge communicate with fluidic channels in the cartridge; and
the ports are configured to transmit fluid (e.g., a liquid or a gas) into and/or out of the fluidic channels and the pneumatic channels.

61. The cartridge module of any one of embodiments 53 to 60, further comprising a memory device (e.g., EPROM) reader.

62. The cartridge module of any one of embodiments 53 to 61, wherein the cartridge is the cartridge of any one of embodiments 1 to 52.

63. The cartridge module of any one of embodiments 53 to 62, wherein the cartridge receptacle is configured to receive and hold a sample cartridge or a control cartridge.

64. An integrated and automated system for performing a genetic analysis of a sample, comprising:
(a) an isolation module configured to isolate nucleic acid (e.g., DNA) from a sample;
(b) an amplification module configured to amplify one or more selected nucleotide sequences of the isolated nucleic acid to produce amplification products;
(c) a separation and detection module configured to separate and detect the amplification products;
(d) an analysis module configured to analyze the detected amplification products, wherein the analysis module comprises memory and a processor that executes code which identifies an allele of the one amplified nucleotide sequence, or alleles of at least one or all of the plurality of amplified nucleotide sequences;
(e) a cartridge module configured to receive and engage a cartridge; and
(f) a cartridge received by the cartridge module; wherein:
the isolation module and the amplification module are part of the cartridge;
the cartridge comprises chambers that come into fluidic communication with one another via fluidic channels when the cartridge is engaged with the cartridge module; and
for one or more, or al, of the chambers, engagement of the cartridge with the cartridge module creates a fluid flow path comprising a fluidic channel in fluidic communication with a first port of a chamber, the chamber, and a fluidic channel in fluidic communication with a second port of the chamber.

65. The system of embodiment 64, wherein the cartridge further comprises valves (e.g., diaphragm valves) that regulate movement of reagents and/or fluid to and from the chambers via the fluidic channels.

66. The system of embodiment 64 or 65, wherein the isolation module is further configured to extract nucleic acid from the sample and to isolate the extracted nucleic acid by capturing the extracted nucleic acid to a substrate (e.g., magnetically responsive particles).

67. The system of any one of embodiments 64 to 66, wherein the isolation module is further configured to purify the isolated nucleic acid.

68. The system of any one of embodiments 64 to 67, wherein the amplification module is configured to amplify one or more selected nucleotide sequences of the isolated nucleic acid by polymerase chain reaction (PCR).

69. The system of any one of embodiments 64 to 68, wherein the amplification module or another component of the system (e.g., the cartridge module) comprises a heating and cooling device (e.g., a Peltier heating and cooling element) configured to perform thermal cycling for amplifying one or more selected nucleotide sequences of the isolated nucleic acid (e.g., by PCR).

70. The system of embodiment 69, wherein the cartridge and/or the heating and cooling device is configured to move so that a chamber in which one or more selected nucleotide sequences are amplified comes into contact with or becomes adjacent to (e.g., via a thermoconducting element contacting the chamber) the heating and cooling device during thermal cycling.

71. The system of any one of embodiments 64 to 70, wherein the amplification module is configured to amplify one or more selected short tandem repeat (STR) loci of the isolated nucleic acid.

72. The system of embodiment 71, wherein the one or more selected STR loci comprise at least five STR loci utilized in a forensic database (e.g., CODIS).

73. The system of embodiment 72, wherein the one or more selected STR loci comprise all STR loci utilized in CODIS (e.g., CSF1PO, D3S1358, D5S818, D7S820, D8S1179, D13S317, D16S539, D18S51, D21S11, FGA, TH01, TPDX and vWA).

74. The system of any one of embodiments 71 to 73, wherein the one or more selected nucleotide sequences further comprise Penta D, Penta E, and amelogenin.

75. The system of any one of embodiments 64 to 74, wherein the cartridge comprises:
   (a) a chamber comprising a reagent (e.g., a lysis reagent) in a solution or buffer for extracting nucleic acid from a sample, and optionally an anti-foaming reagent;
   (b) a chamber comprising a substrate (e.g., magnetically responsive particles), optionally in a solution or buffer, for isolating extracted nucleic acid;
   (c) one or more (e.g., two) chambers comprising a solution (e.g., a wash solution or buffer) for purifying isolated nucleic acid; and
   (d) a chamber comprising a solution (e.g., water) for diluting amplification products prior to separation of the amplification products.

76. The system of embodiment 75, wherein:
   chamber (a) is configured to receive and/or store waste material; and
   chamber (d) optionally comprises a control in the solution (e.g., a size standard in a lane running a sample, or an allelic ladder (and optionally a size standard) in a lane not running a sample).

77. The system of embodiment 75 or 76, wherein:
   each of chambers (a), (b), (c) and (d) is closed and fluidically isolated prior to engagement of the cartridge with the cartridge module; and
   for each of chambers (a), (b), (c) and (d), engagement of the cartridge with the cartridge module creates a fluid flow path comprising a fluidic channel in fluidic communication with a first port of the chamber, the chamber, and a fluidic channel in fluidic communication with a second port of the chamber.

78. The system of embodiment 77, wherein the first port and the second port of each of chambers (a), (b), (c) and (d) are on substantially the same plane, on the same surface, or at the base or the bottom of the chamber, or any combination thereof.

79. The system of any one of embodiments 64 to 78, wherein the cartridge comprises:
   a chamber configured to receive a sample; and
   a chamber configured to amplify one or more selected nucleotide sequences of isolated nucleic acid (e.g., by PCR).

80. The system of embodiment 79, wherein the sample chamber is further configured to extract nucleic acid from the sample.

81. The system of embodiment 79 or 80, wherein the cartridge further comprises one or more chambers comprising reagents for amplifying the one or more selected nucleotide sequences.

82. The system of embodiment 81, wherein:
   the cartridge comprises two amplification reagent chambers for each amplification reaction chamber;
   one of the two amplification reagent chambers comprises one or more pairs of forward and reverse primers, and the other chamber comprises a polymerase (e.g., a DNA polymerase), nucleotide triphosphates (e.g., deoxyribonucleotide triphosphates), and optionally a buffer and/or a metal salt (e.g., magnesium chloride); and
   the two amplification reagent chambers can be part of a vessel (e.g., two chambers in the cartridge or two chambers of a vial connected to the cartridge) or can be two separate vessels (e.g., two vials connected to the cartridge).

83. The system of embodiment 81 or 82, wherein the reagents for amplifying the one or more selected nucleotide sequences are delivered to the amplification reaction chamber via a channel that does not comprise a valve.

84. The system of any one of embodiments 64 to 83, wherein the separation and detection module is configured to separate the amplification products by electrophoresis (e.g., capillary electrophoresis).

85. The system of any one of embodiments 64 to 84, wherein the separation and detection module comprises:
   one or more heating elements adapted to apply heat to denature the amplification products during separation; &
   a thermal-control device configured to control heating of the amplification products.

86. The system of any one of embodiments 64 to 85, wherein the amplification products are separated in a separation channel (e.g., a capillary) that is part of the cartridge.

87. The system of any one of embodiments 64 to 85, wherein the amplification products are separated in a separation channel (e.g., a capillary) that is not part of the cartridge.

88. The system of embodiment 86 or 87, wherein the amplification products are heated by a denature heater prior to their introduction (e.g., injection) into the separation channel.

89. The system of any one of embodiments 86 to 88, wherein the separation and detection module is further configured to prepare the amplification products for injection into the separation channel by field-amplified stacking or by positioning a bolus of a material (e.g., air) having a different electrical conductivity downstream of the amplification products in a fluidic conduit (e.g., an electrophoresis sample channel) of an electrophoresis assembly.

90. The system of any one of embodiments 64 to 89, wherein one or more, or all, of the fluidic channels are microfluidic channels.

91. The system of any one of embodiments 64 to 90, wherein the cartridge further comprises a readable and/or writable memory device (e.g., an EEPROM memory chip) configured to store, receive and/or transmit information relating to the cartridge (e.g., information relating to the history, a recommended use-by date, the current use (e.g., whether the cartridge is operably engaged with the cartridge module, information input from a user, and/or information generated by the system in operation), the configurations, the conditions, the physical features and/or the chemical features of the cartridge).

92. The system of any one of embodiments 64 to 91, wherein when the cartridge is engaged with the cartridge module, the longitudinal axis of the cartridge is at an angle of about 15-45 degrees, 20-40 degrees or 25-35 degrees, or about 30 degrees, relative to a vertical plane perpendicular to the plane of the surface on which the system rests.

93. The system of any one of embodiments 64 to 92, wherein the cartridge can be configured for a single use or multiple uses.

94. The system of any one of embodiments 64 to 93, wherein the cartridge is the cartridge of any one of embodiments 1 to 52.
95. The system of any one of embodiments 64 to 94, wherein the processor of the analysis module further executes code which determines a likelihood of a match between the source of the nucleic acid and an individual whose genetic profile is stored in a database (e.g., CODIS).
96. The system of any one of embodiments 64 to 95, wherein the processor of the analysis module further executes code which determines a likelihood of a genetic relationship (e.g., kinship) between the source of the nucleic acid and another individual.
97. The system of any one of embodiments 64 to 96, wherein the analysis module is further configured to transfer results of the genetic analysis (e.g., raw data, parsed data, a genetic profile of the source of the nucleic acid, a likelihood of a match between the source of the nucleic acid and an individual, or a likelihood of a genetic relationship between the source of the nucleic acid and another individual, or any combination thereof) to an internal database and/or an external database (e.g., a database used by law enforcement).
98. The system of any one of embodiments 64 to 97, which further comprises a display having a graphical user interface (GUI), wherein the GUI allows a user to perform a genetic analysis of the sample, to control the operation of the system, to see results of the genetic analysis (e.g., an electropherogram), and to handle (e.g., transfer) results of the genetic analysis.
99. The system of any one of embodiments 64 to 98, which is capable of identifying an allele of the one amplified nucleotide sequence, or alleles of at least one or all of the plurality of amplified nucleotide sequences (e.g., for human identification and/or kinship analysis), determining a likelihood of a match between the source of the nucleic acid and an individual, or determining a likelihood of a genetic relationship between the source of the nucleic acid and another individual, or any combination thereof, within about 2 hours, 1.5 hours or 1 hour after commencement of a protocol for performing a genetic analysis of the sample.
100. The system of any one of embodiments 64 to 99, which is capable of performing a genetic analysis (e.g., STR analysis for human identification and/or kinship determination) with a coefficient of variation of no more than about 10%, 5% or 1%, and/or with an accuracy of at least about 90%, 95% or 99%.
101. The system of any one of embodiments 64 to 100, which has a volume of about 10 ft$^3$ or less.
102. A method of performing a genetic analysis of a sample, comprising:
    isolating nucleic acid (e.g., DNA) from a sample;
    amplifying one or more selected nucleotide sequences of the isolated nucleic acid to produce amplification products;
    separating and detecting the amplification products; and
    analyzing the detected amplification products to identify an allele of the one amplified nucleotide sequence, or alleles of at least one or all of the plurality of amplified nucleotide sequences; wherein:
    the method is completed within about two hours;
    the method is performed using an integrated and automated system that comprises a cartridge module configured to receive and engage a cartridge;
    the isolating and the amplifying are performed using a cartridge that comprises chambers that come into fluidic communication with one another via fluidic channels when the cartridge is engaged with the cartridge module; and
    for one or more, or all, of the chambers, engagement of the cartridge with the cartridge module creates a fluid flow path comprising a fluidic channel in fluidic communication with a first port of a chamber, the chamber, and a fluidic channel in fluidic communication with a second port of the chamber.
103. The method of embodiment 102, further comprising:
    extracting nucleic acid from the sample prior to isolating nucleic acid; and
purifying the isolated nucleic acid prior to amplifying one or more selected nucleotide sequences of the isolated nucleic acid.
104. The method of embodiment 103, wherein extracting nucleic acid from the sample is performed with agitation with bubbles of a gas (e.g., air), and/or purifying the isolated nucleic acid (e.g., washing nucleic acid captured to magnetically responsive particles) is performed with agitation with bubbles of a gas (e.g., air).
105. The method of any one of embodiments 102 to 104, further comprising diluting the amplification products prior to separating the amplification products.
106. The method of any one of embodiments 102 to 105, wherein isolating the nucleic acid is performed by capturing the nucleic acid to a substrate.
107. The method of embodiment 106, wherein the capture substrate comprises magnetically responsive particles.
108. The method of embodiment 107, further comprising controlling the amount of nucleic acid isolated by controlling the amount of magnetically responsive particles used.
109. The method of any one of embodiments 102 to 108, wherein amplifying one or more selected nucleotide sequences of the isolated nucleic acid is performed by polymerase chain reaction (PCR).
110. The method of any one of embodiments 102 to 109, wherein amplifying one or more selected nucleotide sequences of the isolated nucleic acid (e.g., by PCR) comprises thermal cycling with the aid of a heating and cooling device (e.g., a Peltier heating and cooling element).
111. The method of any one of embodiments 102 to 110, wherein one or more selected short tandem repeat (STR) loci of the isolated nucleic acid are amplified.
112. The method of embodiment 111, wherein at least five STR loci utilized in a forensic database (e.g., CODIS) are amplified.
113. The method of embodiment 112, wherein all STR loci utilized in CODIS (e.g., CSF1PO, D3S1358, D5S818, D7S820, D8S1179, D13S317, D16S539, D18S51, D21S11, FGA, TH01, TPDX and vWA) are amplified.
114. The method of any one of embodiments 111 to 113, wherein the one or more selected nucleotide sequences that are amplified further comprise Penta D, Penta E, and amelogenin.
115. The method of any one of embodiments 102 to 114, wherein the cartridge comprises:
    (a) a chamber comprising a reagent (e.g., a lysis reagent) in a solution or buffer for extracting nucleic acid from a sample, and optionally an anti-foaming reagent;

(b) a chamber comprising a substrate (e.g., magnetically responsive particles), optionally in a solution or buffer, for isolating extracted nucleic acid;
(c) one or more (e.g., two) chambers comprising a solution (e.g., a wash solution or buffer) for purifying isolated nucleic acid; and
(d) a chamber comprising a solution (e.g., water) for diluting amplification products prior to separation of the amplification products.

116. The method of embodiment 115, wherein:
chamber (a) is configured to receive and/or store waste material; and
chamber (d) optionally further comprises a control in the solution (e.g., a size standard in a lane running a sample, or an allelic ladder (and optionally a size standard) in a lane not running a sample).

117. The method of embodiment 115 or 116, wherein:
each of chambers (a), (b), (c) and (d) is closed and fluidically isolated prior to engagement of the cartridge with the cartridge module; and
for each of chambers (a), (b), (c) and (d), engagement of the cartridge with the cartridge module creates a fluid flow path comprising a fluidic channel in fluidic communication with a first port of the chamber, the chamber, and a fluidic channel in fluidic communication with a second port of the chamber.

118. The method of embodiment 117, wherein the first port and the second port of each of chambers (a), (b), (c) and (d) are on substantially the same plane, on the same surface, or at the base or the bottom of the chamber, or any combination thereof.

119. The method of any one of embodiments 102 to 118, wherein the cartridge comprises:
a chamber configured to receive a sample; and
a chamber configured to amplify one or more selected nucleotide sequences of isolated nucleic acid.

120. The method of embodiment 119, wherein the sample chamber is further configured to extract nucleic acid from the sample.

121. The method of embodiment 119 or 120, wherein the cartridge further comprises one or more chambers comprising reagents for amplifying the one or more selected nucleotide sequences.

122. The method of embodiment 121, wherein:
the cartridge comprises two amplification reagent chambers for each amplification reaction chamber;
one of the two amplification reagent chambers comprises one or more pairs of forward and reverse primers, and the other chamber comprises a polymerase (e.g., a DNA polymerase), nucleotide triphosphates (e.g., deoxyribonucleotide triphosphates), and optionally a buffer and/or a metal salt (e.g., magnesium chloride); and
the two amplification reagent chambers can be part of a vessel (e.g., two chambers in the cartridge or two chambers of a vial connected to the cartridge) or can be two separate vessels (e.g., two vials connected to the cartridge).

123. The method of any one of embodiments 102 to 122, wherein separating the amplification products is performed by electrophoresis (e.g., capillary electrophoresis).

124. The method of any one of embodiments 102 to 123, wherein the amplification products are denatured by applying heat during separation (or prior to and during separation), or by using a chemical denaturant, or both.

125. The method of any one of embodiments 102 to 124, wherein the amplification products are separated in a separation channel (e.g., a capillary) that is part of the cartridge.

126. The method of any one of embodiments 102 to 124, wherein the amplification products are separated in a separation channel (e.g., a capillary) that is not part of the cartridge.

127. The method of any one of embodiments 122 to 126, further comprising preparing the amplification products for introduction (e.g., injection) into a separation channel by field-amplified stacking (FAS), wherein FAS is performed by positioning in an electrophoresis sample channel a diluted mixture comprising the amplification products of lower salt concentration or lower ionic strength between areas comprising an electrophoresis buffer of higher salt concentration or higher ionic strength.

128. The method of any one of embodiments 102 to 127, wherein one or more, or all, of the fluidic channels are micro fluidic channels.

129. The method of any one of embodiments 102 to 128, which is performed using the cartridge of any one of embodiments 1 to 52.

130. The method of any one of embodiments 102 to 129, further comprising determining a likelihood of a match between the source of the nucleic acid and an individual whose genetic profile is stored in a database (e.g., CODIS).

131. The method of any one of embodiments 102 to 130, further comprising determining a likelihood of a genetic relationship (e g, kinship) between the source of the nucleic acid and another individual.

132. The method of any one of embodiments 102 to 131, further comprising transferring results of the genetic analysis (e.g., raw data, parsed data, a genetic profile of the source of the nucleic acid, a likelihood of a match between the source of the nucleic acid and an individual, or a likelihood of a genetic relationship between the source of the nucleic acid and another individual, or any combination thereof) to an internal database and/or an external database (e.g., a database used by law enforcement).

133. The method of any one of embodiments 102 to 132, which is completed within about 1.5 hours or about 1 hour.

134. The method of any one of embodiments 102 to 133, which is performed with a coefficient of variation of no more than about 10%, 5% or 1%, and/or with an accuracy of at least about 90%, 95% or 99%.

135. The method of any one of embodiments 102 to 134, which is performed using the integrated and automated system of any one of embodiments 64 to 101.

136. A method of performing nucleic acid amplification, comprising:
delivering a polynucleotide to a reaction chamber;
delivering a first solution comprising one or more pairs of forward and reverse primers for amplifying one or more selected nucleotide sequences from a first chamber to the reaction chamber;
delivering a second solution comprising a polymerase from a second chamber to the reaction chamber; and
amplifying the one or more selected nucleotide sequences of the polynucleotide;
wherein the first solution or the second solution further comprises nucleotide triphosphates.

137. The method of embodiment 136, wherein the polynucleotide, the first solution and the second solution can be delivered simultaneously or in any order (e.g., the polynucleotide can be delivered to the reaction chamber first, and then the first solution and the second solution can be delivered to the reaction chamber simultaneously or in any order).

138. The method of embodiment 136 or 137, wherein the amount delivered, the rate of delivery and the timing of delivery of each of the first solution and the second solution can be independently controlled (e.g., the first solution and the second solution can be delivered in the same amount or different amounts, at the same rate or different rates, or at the same time or different times, or any combination thereof).

139. The method of any one of embodiments 136 to 138, wherein the polynucleotide comprises DNA (e.g., genomic, isolated or purified DNA) and the polymerase comprises a DNA polymerase (e.g., a Taq polymerase).

140. The method of any one of embodiments 136 to 139, wherein the second solution further comprises nucleotide triphosphates (e.g., deoxyribonucleotide triphosphates).

141. The method of any one of embodiments 136 to 140, wherein the first or second solution (preferably the second solution) further comprises a buffer or a metal salt (e.g., an $M^{+2}$ salt, such as magnesium chloride), or both.

142. The method of any one of embodiments 136 to 141, wherein the one or more pairs of forward and reverse primers are labeled with a dye (e.g., a fluorescent dye), and wherein each of multiple pairs of primers can be labeled with the same dye or different dyes.

143. The method of any one of embodiments 136 to 142, wherein the one or more selected nucleotide sequences comprise one or more selected short tandem repeat (STR) loci.

144. The method of embodiment 143, wherein the one or more selected nucleotide sequences comprise at least five STR loci utilized in a forensic database (e.g., CODIS).

145. The method of embodiment 144, wherein the one or more selected nucleotide sequences comprise all STR loci utilized in CODIS (e.g., CSF1PO, D3S1358, D5S818, D7S820, D8S1179, D13S317, D16S539, D18S51, D21S11, FGA, TH01, TPDX and \TWA).

146. The method of embodiment 144 or 145, wherein the one or more selected nucleotide sequences further comprise Penta D, Penta E, and amelogenin.

147. The method of any one of embodiments 136 to 146, wherein amplifying the one or more selected nucleotide sequences comprises thermal cycling.

148. The method of any one of embodiments 136 to 147, wherein the first chamber and the second chamber are contained in a container (e.g., two chambers in a cartridge) comprising the reaction chamber, are part of a receptacle fluidically connected to a container (e.g., two chambers of a vial removably attached to a cartridge) comprising the reaction chamber, or are separate receptacles fluidically connected to a container (e.g., two vials removably attached to a cartridge) comprising the reaction chamber.

149. The method of embodiment 148, wherein the first chamber and the second chamber are:
(a) two chambers of a vial, wherein each chamber comprises a first movable object (e.g., a plunger or ball) that seals the top of the chamber, and the vial comprises a second movable object (e.g., a ball or plug) or a breakable seal that seals the bottom of each chamber of the vial; or
(b) two vials, wherein each vial comprises a first movable object (e.g., a plunger or ball) that seals the top of the vial and a second movable object (e.g., a ball or plug) or a breakable seal that seals the bottom of the vial.

150. A cartridge comprising:
a first chamber containing a first solution that comprises one or more pairs of forward and reverse primers for amplifying one or more selected nucleotide sequences; and
a second chamber containing a second solution that comprises a polymerase.

151. The cartridge of embodiment 150, wherein the polymerase comprises a DNA polymerase (e.g., a Taq polymerase).

152. The cartridge of embodiment 150 or 151, wherein the first or second solution (preferably the second solution) further comprises nucleotide triphosphates (e.g., deoxyribonucleotide triphosphates).

153. The cartridge of any one of embodiments 150 to 152, wherein the first or second solution (preferably the second solution) further comprises a buffer or a metal salt (e.g., an $M^{+2}$ salt, such as magnesium chloride), or both.

154. The cartridge of any one of embodiments 150 to 153, wherein the one or more pairs of forward and reverse primers are labeled with a dye (e.g., a fluorescent dye), and wherein each of multiple pairs of primers can be labeled with the same dye or different dyes.

155. The cartridge of any one of embodiments 150 to 154, wherein the one or more selected nucleotide sequences comprise one or more selected short tandem repeat (STR) loci.

156. The cartridge of embodiment 155, wherein the one or more selected nucleotide sequences comprise at least five STR loci utilized in a forensic database (e.g., CODIS).

157. The cartridge of embodiment 156, wherein the one or more selected nucleotide sequences comprise all STR loci utilized in CODIS (e.g., CSF1PO, D3S1358, D5S818, D7S820, D8S1179, D13S317, D16S539, D18S51, D21S11, FGA, TH01, TPDX and vWA).

158. The cartridge of embodiment 156 or 157, wherein the one or more selected nucleotide sequences further comprise Penta D, Penta E, and amelogenin.

159. The cartridge of any one of embodiments 150 to 158, wherein the first chamber and the second chamber are part of a receptacle (e.g., two chambers of a vial), or are separate receptacles (e.g., two vials), removably attached to the cartridge.

160. The cartridge of embodiment 159, wherein the first chamber and the second chamber are:
(a) two chambers of a vial, wherein each chamber comprises a first movable object (e.g., a plunger or ball) that seals the top of the chamber, and the vial comprises a second movable object (e.g., a ball or plug) or a breakable seal that seals the bottom of each chamber of the vial; or
(b) two vials, wherein each vial comprises a first movable object (e.g., a plunger or ball) that seals the top of the vial and a second movable object (e.g., a ball or plug) or a breakable seal that seals the bottom of the vial.

161. The cartridge of any one of embodiments 150 to 158, wherein the first chamber and the second chamber are contained in the cartridge.

162. The cartridge of any one of embodiments 150 to 161, wherein the cartridge comprises one or more sets of the first chamber and the second chamber.

163. The cartridge of any one of embodiments 150 to 162, wherein the cartridge comprises one or more reaction chambers for nucleic acid amplification.

164. The cartridge of any one of embodiments 150 to 163, which is part of a kit.

165. The cartridge of any one of embodiments 150 to 164, which is stored at ambient temperature or lower, or at about 4° C. or lower.

166. A kit comprising:
a first chamber containing a first solution that comprises one or more pairs of forward and reverse primers for amplifying one or more selected nucleotide sequences; and
a second chamber containing a second solution that comprises a polymerase.

167. The kit of embodiment 166, wherein the polymerase comprises a DNA polymerase (e.g., a Taq polymerase).

168. The kit of embodiment 166 or 167, wherein the first or second solution (preferably the second solution) further comprises nucleotide triphosphates (e.g., deoxyribonucleotide triphosphates).

169. The kit of any one of embodiments 166 to 168, wherein the first or second solution (preferably the second solution) further comprises a buffer or a metal salt (e.g., an 4+2 salt, such as magnesium chloride), or both.

170. The kit of any one of embodiments 166 to 169, wherein the one or more pairs of forward and reverse primers are labeled with a dye (e.g., a fluorescent dye), and wherein each of multiple pairs of primers can be labeled with the same dye or different dyes.

171. The kit of any one of embodiments 166 to 170, wherein the one or more selected nucleotide sequences comprise one or more selected short tandem repeat (STR) loci.

172. The kit of embodiment 171, wherein the one or more selected nucleotide sequences comprise at least five STR loci utilized in a forensic database (e.g., CODIS).

173. The kit of embodiment 172, wherein the one or more selected nucleotide sequences comprise all STR loci utilized in CODIS (e.g., CSF1PO, D3S1358, D5S818, D7S820, D8S1179, D13S317, D16S539, D18S51, D21S11, FGA, TH01, TPDX and vWA).

174. The kit of embodiment 172 or 173, wherein the one or more selected nucleotide sequences further comprise Penta D, Penta E, and amelogenin.

175. The kit of any one of embodiments 166 to 174, wherein the first chamber and the second chamber are part of a receptacle (e.g., two chambers of a vial) or are separate receptacles (e.g., two vials).

176. The kit of embodiment 175, wherein the first chamber and the second chamber are:
(a) two chambers of a vial, wherein each chamber comprises a first movable object (e.g., a plunger or ball) that seals the top of the chamber, and the vial comprises a second movable object (e.g., a ball or plug) or a breakable seal that seals the bottom of each chamber of the vial; or
(b) two vials, wherein each vial comprises a first movable object (e.g., a plunger or ball) that seals the top of the vial and a second movable object (e.g., a ball or plug) or a breakable seal that seals the bottom of the vial.

177. The kit of embodiment 175 or 176, wherein the first chamber and the second chamber are removably attached to a container (e.g., a cartridge) comprising a reaction chamber for nucleic acid amplification.

178. The kit of any one of embodiments 166 to 174, wherein the first chamber and the second chamber are contained in a container (e.g., a cartridge) comprising a reaction chamber for nucleic acid amplification.

179. The kit of any one of embodiments 166 to 178, which is hermetically sealed or comprises a desiccant, or both.

180. The kit of any one of embodiments 166 to 179, which is stored at ambient temperature or lower, or at about 4° C. or lower.

181. An apparatus comprising:
a first chamber containing a first solution comprising one or more pairs of forward and reverse primers for amplifying one or more selected nucleotide sequences;
a second chamber containing a second solution comprising a polymerase; and
an actuation device configured to actuate delivery of the first solution from the first chamber and the second solution from the second chamber.

182. The apparatus of embodiment 181, wherein the actuation device is further configured to independently control the amount delivered, the rate of delivery and the timing of delivery of each of the first solution and the second solution (e.g., the first solution and the second solution can be delivered in the same amount or different amounts, at the same rate or different rates, or at the same time or different times, or any combination thereof).

183. The apparatus of embodiment 181 or 182, wherein the actuation device is further configured to actuate delivery of the first solution and the second solution so that the first solution and the second solution mix with one another.

184. The apparatus of any one of embodiments 181 to 183, wherein the polymerase comprises a DNA polymerase (e.g., a Taq polymerase).

185. The apparatus of any one of embodiments 181 to 184, wherein the first or second solution (preferably the second solution) further comprises nucleotide triphosphates (e.g., deoxyribonucleotide triphosphates).

186. The apparatus of any one of embodiments 181 to 185, wherein the first or second solution (preferably the second solution) further comprises a buffer or a metal salt (e.g., an $M^{+2}$ salt, such as magnesium chloride), or both.

187. The apparatus of any one of embodiments 181 to 186, wherein the one or more pairs of forward and reverse primers are labeled with a dye (e.g., a fluorescent dye), and wherein each of multiple pairs of primers can be labeled with the same dye or different dyes.

188. The apparatus of any one of embodiments 181 to 187, wherein the one or more selected nucleotide sequences comprise one or more selected short tandem repeat (STR) loci.

189. The apparatus of embodiment 188, wherein the one or more selected nucleotide sequences comprise at least five STR loci utilized in a forensic database (e.g., CODIS).

190. The apparatus of embodiment 189, wherein the one or more selected nucleotide sequences comprise all STR loci utilized in CODIS (e.g., CSF1PO, D3S1358, D5S818, D7S820, D8S1179, D13S317, D16S539, D18S51, D21S11, FGA, TH01, TPDX and vWA).

191. The apparatus of embodiment 189 or 190, wherein the one or more selected nucleotide sequences further comprise Penta D, Penta E, and amelogenin.

192. The apparatus of any one of embodiments 181 to 191, further comprising a cartridge containing a reaction chamber for nucleic acid amplification.

193. The apparatus of embodiment 192, wherein the first chamber and the second chamber are contained in the cartridge.

194. The apparatus of embodiment 192, wherein the first chamber and the second chamber are part of a receptacle (e.g., two chambers of a vial), or are separate receptacles (e.g., two vials), removably attached to the cartridge.

195. The apparatus of embodiment 194, wherein the first chamber and the second chamber are:
   (a) two chambers of a vial, wherein each chamber comprises a first movable object (e.g., a plunger or ball) that seals the top of the chamber, and the vial comprises a second movable object (e.g., a ball or plug) or a breakable seal that seals the bottom of each chamber of the vial; or
   (b) two vials, wherein each vial comprises a first movable object (e.g., a plunger or ball) that seals the top of the vial and a second movable object (e.g., a ball or plug) or a breakable seal that seals the bottom of the vial.

196. The apparatus of embodiment 195, wherein the actuation device comprises an element (e.g., a plunger or pin) configured to depress the first movable object with sufficient force to dislodge the second movable object or to break the breakable seal.

197. The apparatus of any one of embodiments 192 to 196, wherein the cartridge comprises a plurality of reaction chambers for nucleic acid amplification.

198. The apparatus of any one of embodiments 181 to 197, which comprises a plurality of sets of the first chamber and the second chamber.

199. A method of performing nucleic acid amplification, comprising:
   heating a primer mixture comprising one or more pairs of forward and reverse primers for amplifying one or more selected nucleotide sequences, and optionally a polymerase and nucleotide triphosphates, at a temperature substantially equal to or above a selected annealing temperature of an amplification reaction for a period of time;
   if the primer mixture does not comprise a polymerase and nucleotide triphosphates, providing a polymerase and nucleotide triphosphates to the primer mixture;
   providing a polynucleotide to the primer mixture to form a reaction mixture comprising the primers, the polymerase, the nucleotide triphosphates and the polynucleotide; and
   varying the temperature of the reaction mixture to amplify the one or more selected nucleotide sequences of the polynucleotide while heating the reaction mixture at temperatures substantially equal to or above the selected annealing temperature of the reaction until the reaction is completed.

200. The method of embodiment 199, wherein the polymerase, the nucleotide triphosphates, and the polynucleotide can be provided to the primer mixture simultaneously or in any order.

201. The method of embodiment 199 or 200, wherein the selected annealing temperature of the reaction is about 50-65° C. or about 56-62 T.

202. The method of any one of embodiments 199 to 201, wherein the primer mixture is heated at a temperature substantially equal to or above the selected annealing temperature of the reaction for about 0.5-10 minutes (e.g., about 1-5 minutes or about 5-10 minutes).

203. The method of any one of embodiments 199 to 202, wherein the primer mixture is heated at a temperature substantially equal to or above the selected annealing temperature of the amplification reaction in a pre-heating chamber for pre-heating the primer mixture or in a reaction chamber for performing the reaction.

204. The method of embodiment 203, wherein the heated primer mixture is delivered from the pre-heating chamber to a reaction chamber comprising the polynucleotide, or the polynucleotide is delivered to a reaction chamber comprising the heated primer mixture.

205. The method of embodiment 204, wherein the primer mixture is heated in the preheating chamber or the reaction chamber about 1 second to 5 minutes (e.g., about 1 sec, 15 sec, 30 sec, 1 min, 3 min or 5 min) before the polynucleotide is provided to the primer mixture.

206. The method of any one of embodiments 199 to 205, wherein the polynucleotide comprises DNA (e.g., genomic, isolated or purified DNA), the polymerase comprises a DNA polymerase (e.g., a Taq polymerase), and the nucleotide triphosphates comprise deoxyribonucleotide triphosphates.

207. The method of any one of embodiments 199 to 206, wherein the primer mixture or the reaction mixture further comprises a buffer or a metal salt (e.g., an 4+2 salt, such as magnesium chloride), or both.

208. The method of any one of embodiments 199 to 207, wherein the one or more pairs of forward and reverse primers are labeled with a dye (e.g., a fluorescent dye), and wherein each of multiple pairs of primers can be labeled with the same dye or different dyes.

209. The method of any one of embodiments 199 to 208, wherein the one or more selected nucleotide sequences comprise one or more selected short tandem repeat (STR) loci.

210. The method of embodiment 209, wherein the one or more selected nucleotide sequences comprise at least five STR loci utilized in a forensic database (e.g., CODIS).

211. The method of embodiment 210, wherein the one or more selected nucleotide sequences comprise all STR loci utilized in CODIS (e.g., CSF1PO, D3S1358, D5S818, D7S820, D8S1179, D13S317, D16S539, D18S51, D21S11, FGA, TH01, TPDX and vWA).

212. The method of embodiment 210 or 211, wherein the one or more selected nucleotide sequences further comprise Penta D, Penta E, and amelogenin.

213. The method of any one of embodiments 199 to 212, wherein the reagents for performing the amplification reaction can be initially stored in a single vessel (e.g., a chamber in a reaction cartridge comprising a reaction chamber for performing the reaction or a receptacle removably attached to a reaction cartridge), in separate chambers of a container (e.g., two chambers in a reaction cartridge or a two-chamber vial removably attached to a reaction cartridge), or in separate containers (e.g., two vials removably attached to a reaction cartridge).

214. The method of any one of embodiments 199 to 213, wherein the reagents for performing the amplification reaction can be initially stored in liquid form, or in a solid or semi-solid (e.g., dehydrated or lyophilized) form that is later rehydrated.

215. The method of any one of embodiments 199 to 214, wherein the amplification reaction is PCR.

216. A method of hydrating a solid or semi-solid composition, comprising:
   (a) removing gas from a receptacle containing a solid or semi-solid composition comprising one or more reagents;
   (b) providing a hydration solution to the receptacle; and
   (c) optionally repeating steps (a) and (b) at least one more time to produce a mixture in which the composition is substantially dissolved.

217. The method of embodiment 216, wherein removing gas (e.g., air) from the receptacle comprises applying negative pressure to the receptacle.

218. The method of embodiment 216 or 217, further comprising providing a burst of a gas (e.g., air) after an initial amount of the hydration solution is provided to the receptacle in step (b).

219. The method of any one of embodiments 216 to 218, further comprising delivering the mixture to a reaction chamber for performing a reaction (e.g., a nucleic acid amplification reaction, such as PCR).

220. The method of any one of embodiments 216 to 219, wherein the hydration solution substantially completely fills the receptacle (e.g., fills more than about 90%, 95% or 99%, or fills 100%, of the volume of the receptacle).

221. The method of any one of embodiments 216 to 220, wherein the composition is substantially completely dissolved (e.g., at least about 80%, 90%, 95% or 99%, or 100%, of the composition by mass is dissolved).

222. The method of any one of embodiments 216 to 221, wherein the hydration solution comprises water or a buffer.

223. The method of embodiment 222, wherein the hydration solution further comprises a metal salt (e.g., an $M^{+2}$ salt, such as magnesium chloride).

224. The method of any one of embodiments 216 to 223, wherein the composition comprises reagents for performing nucleic acid amplification (e.g., PCR).

225. The method of embodiment 224, wherein the composition comprises one or more pairs of forward and reverse primers for amplifying one or more selected nucleotide sequences, a polymerase (e.g., a DNA polymerase, such as a Taq polymerase), and nucleotide triphosphates (e.g., deoxyribonucleotide triphosphates), and optionally further comprises a buffering agent and/or a metal salt (e.g., an $M^{+2}$ salt, such as magnesium chloride).

226. The method of embodiment 225, wherein the one or more pairs of forward and reverse primers are labeled with a dye (e.g., a fluorescent dye), and wherein each of multiple pairs of primers can be labeled with the same dye or different dyes.

227. The method of embodiment 225 or 226, wherein the one or more selected nucleotide sequences comprise one or more short tandem repeat (STR) loci.

228. The method of embodiment 227, wherein the one or more selected nucleotide sequences comprise at least five STR loci utilized in a forensic database (e.g., CODIS).

229. The method of embodiment 228, wherein the one or more selected nucleotide sequences comprise all STR loci utilized in CODIS (e.g., CSF1PO, D3S1358, D5S818, D7S820, D8S1179, D13S317, D16S539, D18S51, D21S11, FGA, TH01, TPDX and vWA).

230. The method of embodiment 228 or 229, wherein the one or more selected nucleotide sequences further comprise Penta D, Penta E, and amelogenin.

231. The method of any one of embodiments 216 to 230, wherein the solid or semi-solid composition is dry, dehydrated or lyophilized.

232. The method of any one of embodiments 216 to 231, wherein the receptacle is contained in a container (e.g., is a chamber in a cartridge) comprising a reaction chamber for performing a reaction (e.g., PCR), or can be fluidically connected to a container (e.g., a cartridge) comprising a reaction chamber.

233. The method of embodiment 232, wherein the receptacle is a vial comprising a first movable object (e.g., a plunger or ball) that seals the top of the vial and a second movable object (e.g., a ball or plug) or a breakable seal that seals the bottom of the vial.

234. The method of embodiment 233, wherein the first movable object is a plunger configured as a piercable septum.

235. The method of embodiment 234, which is performed using a needle that pierces through the plunger and is fluidically connected to a source of the hydration solution and to a source of negative pressure, and optionally to a source of positive pressure and/or to the external environment.

236. The method of embodiment 232, wherein:
   the receptacle is part of a first container (e.g., a first cartridge) comprising a plurality of receptacles containing a solid or semi-solid composition;
   each of the solid or semi-solid compositions can comprise the same reagent(s) or different reagents; and
   the first container can be fluidically connected to a second container (e.g., a second cartridge) comprising a reaction chamber for performing a reaction (e.g., PCR).

237. The method of any one of embodiments 216 to 236, wherein the method is performed using a device that can be off or on an instrument comprising a container (e.g., a cartridge) that comprises a reaction chamber for performing a reaction (e.g., PCR).

238. A receptacle comprising:
   a solid or semi-solid composition comprising one or more reagents;
   a first movable object that seals the top of the receptacle; and
   an exit port that is sealed by a second movable object or a breakable seal, or is not sealed.

239. The receptacle of embodiment 238, wherein the exit port is located at the bottom of the receptacle.

240. The receptacle of embodiment 238 or 239, wherein the first movable object is configured as a plunger or a ball.

241. The receptacle of any one of embodiments 238 to 240, wherein the second movable object is configured as a ball or a plug.

242. The receptacle of any one of embodiments 238 to 241, wherein the composition is coated or enclosed by one or more layers comprising a metallic material (e.g., aluminum) or a polymeric material, or both.

243. The receptacle of any one of embodiments 238 to 242, wherein the first movable object is configured as a shearing plunger that can shear the composition or cut through the one or more layers coating or enclosing the composition.

244. The receptacle of any one of embodiments 238 to 243, which is configured to receive a solution (e.g., water or a buffer) for hydrating the composition through the top of the receptacle.

245. The receptacle of embodiment 244, wherein the exit port is sealed by a second movable object or a breakable seal.

246. The receptacle of embodiment 244 or 245, wherein the first movable object is a plunger configured as a septum that can be pierced by an object (e.g., a needle) fluidically connected to a source of the hydration solution, and optionally to a source of negative pressure, to a source of positive pressure and/or to the external environment.

247. The receptacle of any one of embodiments 238 to 243, which is configured to receive a solution (e.g., water or a buffer) for hydrating the composition through the exit port.

248. The receptacle of embodiment 247, wherein the exit port is not sealed.

249. The receptacle of embodiment 247 or 248, further comprising one or more vent grooves configured to create a vent path to the external environment as the first movable object moves toward, and optionally contacts, the composition in preparation for hydration of the composition.

250. The receptacle of any one of embodiments 238 to 243, wherein a lower portion of the receptacle is pre-loaded with a solution (e.g., water or a buffer) for hydrating the composition, and wherein a substantially water-impermeable barrier separates the hydration solution from the composition.

251. The receptacle of embodiment 250, wherein the exit port is sealed by a second movable object or a breakable seal.

252. The receptacle of embodiment 250 or 251, wherein the barrier comprises a breakable membrane or film.

253. The receptacle of any one of embodiments 250 to 252, wherein the barrier comprises one or more layers that comprise a metallic material (e.g., aluminum) and/or a polymeric material and coat or enclose the composition, and wherein the coated or enclosed composition optionally contacts a supporting element.

254. The receptacle of embodiment 253, wherein the supporting element comprises a ring that substantially encircles an interior surface of the receptacle.

255. The receptacle of embodiment 253 or 254, wherein the supporting element comprises an 0-ring.

256. The receptacle of embodiment 255, wherein the lower portion and the upper portion of the receptacle are separate components.

257. The receptacle of any one of embodiments 253 to 256, wherein the first movable object is configured as a shearing plunger that can cut through the one or more layers coating or enclosing the composition.

258. The receptacle of any one of embodiments 238 to 257, further comprising one or more vent grooves configured to create a vent path to the external environment as the first movable object moves toward, and optionally contacts, the composition in preparation for hydration of the composition.

259. The receptacle of any one of embodiments 238 to 258, wherein as the first movable object is substantially completely depressed to dispense the composition in hydrated form, the first movable object seals the top of the receptacle.

260. The receptacle of any one of embodiments 238 to 259, wherein the receptacle is configured as a vial.

261. The receptacle of any one of embodiments 238 to 260, wherein the composition comprises reagents for performing nucleic acid amplification (e.g., PCR).

262. The receptacle of embodiment 261, wherein the composition comprises one or more pairs of forward and reverse primers for amplifying one or more selected nucleotide sequences, a polymerase (e.g., a DNA polymerase, such as a Taq polymerase), and nucleotide triphosphates (e.g., deoxyribonucleotide triphosphates), and optionally further comprises a buffering agent and/or a metal salt (e.g., an $M^{+2}$ salt, such as magnesium chloride).

263. The receptacle of embodiment 262, wherein the one or more pairs of forward and reverse primers are labeled with a dye (e.g., a fluorescent dye), and wherein each of multiple pairs of primers can be labeled with the same dye or different dyes.

264. The receptacle of embodiment 262 or 263, wherein the one or more selected nucleotide sequences comprise one or more selected short tandem repeat (STR) loci.

265. The receptacle of embodiment 264, wherein the one or more selected nucleotide sequences comprise at least five STR loci utilized in a forensic database (e.g., CODIS).

266. The receptacle of embodiment 265, wherein the one or more selected nucleotide sequences comprise all STR loci utilized in CODIS (e.g., CSF1PO, D3S1358, D5S818, D7S820, D8S1179, D13S317, D16S539, D18S51, D21S11, FGA, TH01, TPDX and \TWA).

267. The receptacle of embodiment 265 or 266, wherein the one or more selected nucleotide sequences further comprise Penta D, Penta E, and amelogenin.

268. The receptacle of any one of embodiments 238 to 267, wherein the solid or semi-solid composition is dry, dehydrated or lyophilized.

269. The receptacle of any one of embodiments 238 to 268, which is attachable or removably attached to a container (e.g., a cartridge) comprising a reaction chamber for performing a reaction (e.g., a nucleic acid amplification reaction, such as PCR).

270. The receptacle of any one of embodiments 238 to 269, which is part of a kit.

271. The receptacle of embodiment 270, wherein the kit comprises a solution (e.g., water or a buffer) for hydrating the composition.

272. The receptacle of embodiment 270 or 271, wherein the kit comprises the receptacle removably attached to a container (e.g., a cartridge) comprising a reaction chamber for performing a reaction (e.g., PCR).

273. The receptacle of any one of embodiments 270 to 272, wherein the kit is hermetically sealed or comprises a desiccant, or both.

274. A method of performing electrophoresis, comprising: electrophoretically separating polynucleotides through a separation matrix comprising one or more polymers or gels and one or more chemical denaturants in a separation channel while heating the separation matrix at a temperature from about 50° C. to about 90° C.;
wherein the one or more chemical denaturants are selected from the group consisting of acyclic and cyclic amides; acyclic and cyclic ureas; acyclic and cyclic thioureas; nitrogen-containing aromatic compounds; acyclic and cyclic sulfides, sulfoxides and sulfones; acyclic and cyclic ethers; and acyclic and cyclic alcohols.

275. The method of embodiment 274, wherein the separation matrix is heated at a temperature from about 60° C. to about 80° C., or from about 70° C. to about 90° C.

276. The method of embodiment 274 or 275, wherein:
the acyclic and cyclic amides include formamides (e.g., formamide, N-methylformamide, and N,N-dimethylformamide); pyrrolidones (e.g., 2-pyrrolidone, N-methyl-2-pyrrolidone, N-ethyl-2-pyrrolidone, N-hydroxyethyl-2-pyrrolidone, 3-methyl-2-pyrrolidone, 4-methyl-2-pyrrolidone, 5-methyl-2-pyrrolidone, N-methyl-3-methyl-2-pyrrolidone, N-methyl-4-methyl-2-pyrrolidone, N-methyl-5-methyl-2-pyrrolidone, N-ethyl-3-methyl-2-pyrrolidone, N-ethyl-4-methyl-2-pyrrolidone, and N-ethyl-5-methyl-2-pyrrolidone); piperidones (e.g., 2-piperidone, N-methyl-2-piperidone, N-ethyl-2-piperidone, N-hydroxyethyl-2-piperidone, 3-methyl-2-piperidone, 4-methyl-2-piperidone, 5-methyl-2-piperidone, 6-methyl-2-piperidone, N-methyl-3-methyl-2-piperidone, N-methyl-4-methyl-2-piperidone, N-methyl-5-methyl-2-piperidone, N-methyl-6-methyl-2-piperidone, N-ethyl-3-methyl-2-piperidone, N-ethyl-4-methyl-2-piperidone, N-ethyl-5-methyl-2-piperidone, and N-ethyl-6-methyl-2-piperidone); and caprolactams (e.g., c-caprolactam, N-methyl-c-caprolactam, N-ethyl-c-caprolactam, and N-hydroxyethyl-c-caprolactam);
the acyclic and cyclic ureas include urea, N-methylurea, N,N-dimethylurea, N,N'-dimethylurea, tetramethylurea, hydroxyurea, N-methyl-N-hydroxyurea, N-methyl-N-hydroxyurea, N',N'-dimethyl-N-hydroxyurea, N',N'-dimethyl-N-methyl-N-hydroxyurea, methoxyurea, N-methyl-N-methoxyurea, N'-methyl-N-methoxyurea, N',N'-dimethyl-N-methoxyurea, 2-imidazolidone (ethyleneurea), N-methyl-2-imidazolidone, N,N'-dimethyl-2-imidazolidone, trimethyleneurea, N-methyl-trimethyleneurea, and N,N'-dimethyl-trimethyleneurea;
the acyclic and cyclic thioureas include thiourea, N-methylthiourea, N,N-dimethylthiourea, N,N'-dimethylthiourea, tetramethylthiourea, 2-imidazolidinthione (ethylenethiourea), N-methyl-2-imidazolidinethione, N,N'-dimethyl-2-imidazolidinethione, trimethylenethiourea, N-methyl-trimethylenethiourea, and N,N'-dimethyl-trimethylenethiourea;
the nitrogen-containing aromatic compounds include pyridines (e.g., pyridine, 2-aminopyridine, 3-aminopyridine, and 4-aminopyridine), pyrimidines (e.g., pyrimidine, 2-aminopyrimidine, 4-aminopyrimidine, and 5-aminopyrimidine), and pyrazines (e.g., pyrazine and aminopyrazine);
the acyclic and cyclic sulfides, sulfoxides and sulfones include dimethylsulfoxide, sulfolane and sulfolene;
the acyclic and cyclic ethers include dioxanes (e.g., 1,4-dioxane); and
the acyclic and cyclic alcohols include tetrahydro-3-furanol, tetrahydrofurfuryl alcohol (tetrahydrofuran-2-methanol), tetrahydrofuran-3-methanol, 2,5-dihydrofuran-2-methanol, tetrahydro-3-pyranol, tetrahydro-4-pyranol, and tetrahydropyran-2-methanol.

277. The method of any one of embodiments 274 to 276, wherein the one or more chemical denaturants comprise urea, 2-pyrrolidone, N-methyl-2-pyrrolidone (NMP), N-ethyl-2-pyrrolidone (NEP) or tetrahydrofurfuryl alcohol, or any combination thereof.

278. The method of embodiment 277, wherein the one or more chemical denaturants comprise NMP.

279. The method of any one of embodiments 274 to 278, wherein the concentration of each chemical denaturant, or the total concentration of the one or more chemical denaturants, in the separation matrix is about 10-40% or about 15-30% by mass or volume.

280. The method of any one of embodiments 274 to 279, wherein the separation matrix comprises a polyacrylamide (e.g., a linear polyacrylamide (LPA)).

281. The method of any one of embodiments 274 to 280, wherein the separation matrix comprises a self-coating polymer (e.g., V2E) that coats the interior surface of a separation channel (e.g., a capillary).

282. The method of any one of embodiments 274 to 281, wherein the polynucleotides comprise single-stranded polynucleotide (e.g., DNA) fragments.

283. The method of any one of embodiments 274 to 282, wherein the polynucleotides comprise products of nucleic acid amplification (e.g., PCR).

284. The method of any one of embodiments 274 to 283, wherein the polynucleotides are heated to a temperature of about 90-99° C. or 94-98° C., or about 90° C. or 95° C., prior to introduction into the separation channel.

285. The method of any one of embodiments 274 to 284, wherein the electrophoretic separation is completed within about 30 minutes or 20 minutes.

286. An apparatus comprising a base, wherein the base is configured to dampen vibration and shock and comprises:
(a) a top plate;
(b) a bottom plate;
(c) a plurality of taller, more flexible dampening devices; and
(d) a plurality of shorter, stiffer dampening devices;
wherein the taller, more flexible dampening devices are attached to the bottom plate and to the top plate; and
wherein the shorter, stiffer dampening devices are attached to the bottom plate but not to the top plate.

287. The apparatus of embodiment 286, wherein:
the taller dampening devices comprise more flexible metal springs or coils, more flexible elastomeric columns or springs, or more flexible gas springs (e.g., air springs), or any combination thereof; and
the shorter dampening devices comprise stiffer metal springs or coils, stiffer elastomeric columns or springs, or stiffer gas springs (e.g., air springs), or any combination thereof.

288. The apparatus of embodiment 286 or 287, wherein the taller, more flexible dampening devices are configured to attenuate vibration, and the shorter, stiffer dampening devices are configured to attenuate shock.

289. The apparatus of any one of embodiments 286 to 288, wherein the taller dampening devices have a height of about 2-4 inches, and the shorter dampening devices have a height of about 1-3 inches.

290. The apparatus of any one of embodiments 286 to 289, wherein the base further comprises a plurality of pairs of upper constraining elements and lower constraining elements, and wherein the upper constraining elements are attached to the top plate and the lower constraining elements are attached to the bottom plate.
291. The apparatus of embodiment 290, wherein the pairs of upper constraining elements and lower constraining elements are configured to limit the range of horizontal motion.
292. The apparatus of embodiment 290 or 291, wherein the upper constraining elements are substantially cylindrical, and the lower constraining elements have a substantially circular, toroidal shape with a hole in the middle.
293. The apparatus of any one of embodiments 290 to 292, wherein the upper constraining elements are composed of a metallic or polymeric material, and the lower constraining elements are composed of a polymeric material.
294. The apparatus of any one of embodiments 290 to 293, wherein the lower constraining elements have a lower height than the shorter, stiffer dampening devices.
295. The apparatus of any one of embodiments 286 to 294, wherein the base further comprises a plurality of bumpers, and wherein the bumpers are attached to the bottom plate.
296. The apparatus of embodiment 295, wherein the bumpers are configured to absorb shock and to limit the range of vertical motion.
297. The apparatus of embodiment 295 or 296, wherein the bumpers are substantially cylindrical.
298. The apparatus of any one of embodiments 295 to 297, wherein the bumpers are composed of a polymeric material.
299. The apparatus of any one of embodiments 295 to 298, wherein the bumpers have a lower height than the shorter, stiffer dampening devices and a higher height than the lower constraining elements.
300. The apparatus of any one of embodiments 286 to 299, wherein the base further comprises a lining disposed along the edges of the bottom plate, or a lining disposed along the edges of the top plate, or both.
301. The apparatus of any one of embodiments 286 to 300, which further comprises an instrument or system (e.g., an analytical instrument or system) removably attached to the top plate.
302. The apparatus of embodiment 301, wherein the base reduces horizontal motion, vertical motion, rotational motion, vibrational motion or shock, or any combination thereof, that the instrument or system may experience.
303. The apparatus of embodiment 301 or 302, wherein the instrument or system experiences no more than about 10 g's of force when the instrument or system is dropped about 6 inches or less onto a surface (e.g., the ground).
304. The apparatus of any one of embodiments 301 to 303, wherein the instrument or system is capable of performing a function or a protocol (e.g., a processing, a reaction, a separation of analytes, a detection of analytes, an analysis, or a sample-to-answer protocol of a genetic analysis) while in motion (e.g., in a moving vehicle).
305. An apparatus comprising:
an instrument comprising one or more assemblies comprising vibration-sensitive components, wherein a subframe supporting the one or more vibration-sensitive assemblies comprises dampening devices; and
a base of the instrument comprising dampening devices, wherein the instrument comprises the base or is removably attached to the base.
306. The apparatus of embodiment 305, wherein the dampening devices of the subframe supporting the one or more vibration-sensitive assemblies and the dampening devices of the base of the instrument are configured to attenuate vibration and shock that components of the instrument may experience.
307. The apparatus of embodiment 305 or 306, wherein a subframe supporting each vibration-sensitive assembly comprises dampening devices.
308. The apparatus of any one of embodiments 305 to 307, wherein a subframe supporting a plurality of vibration-sensitive assemblies comprises dampening devices.
309. The apparatus of any one of embodiments 305 to 308, wherein the subframe supporting the one or more vibration-sensitive assemblies comprises dampening devices at the base of the subframe.
310. The apparatus of any one of embodiments 305 to 309, wherein the dampening devices of the subframe supporting the one or more vibration-sensitive assemblies comprise metal springs or coils, elastomeric columns or springs, or gas springs (e.g., air springs), or any combination thereof.
311. The apparatus of any one of embodiments 305 to 310, wherein the dampening devices of the base of the instrument comprise metal springs or coils, elastomeric columns or springs, or gas springs (e.g., air springs), or any combination thereof.
312. The apparatus of any one of embodiments 305 to 311, wherein the base of the instrument comprises a plurality of taller, more flexible dampening devices, and a plurality of shorter, stiffer dampening devices.
313. The apparatus of embodiment 312, wherein:
the taller dampening devices comprise more flexible metal springs or coils, more flexible elastomeric columns or springs, or more flexible gas springs (e.g., air springs), or any combination thereof; and
the shorter dampening devices comprise stiffer metal springs or coils, stiffer elastomeric columns or springs, or stiffer gas springs (e.g., air springs), or any combination thereof.
314. The apparatus of embodiment 312 or 313, wherein the base of the instrument is the base of any one of embodiments 284 to 304.
315. The apparatus of any one of embodiments 305 to 314, wherein the instrument comprises a plurality of vibration-sensitive assemblies in close proximity to one another, and wherein such vibration-sensitive assemblies are connected to one another so that they move as a unit in response to motion (e.g., translational or vibrational motion) or shock.
316. The apparatus of any one of embodiments 305 to 315, wherein the one or more vibration-sensitive assemblies comprise:
a separation assembly comprising one or more separation channels (e.g., capillaries) and electrodes; and
a detection assembly comprising a light source (e.g., a laser or a light-emitting diode) and a detector (e.g. a CCD or CMOS camera).

317. The apparatus of embodiment 316, further comprising one or more hard stops configured to prevent the detection assembly or components thereof from bouncing up and from contacting the separation assembly or components thereof.
318. The apparatus of any one of embodiments 305 to 317, wherein the instrument comprises one or more vibrating components, and wherein the one or more vibrating components are flexibly suspended or mounted.
319. The apparatus of embodiment 318, further comprising one or more travel stops configured to limit the travel of the one or more vibrating components.
320. The apparatus of embodiment 318 or 319, wherein the one or more vibrating components comprise one or more pumps.
321. The apparatus of any one of embodiments 305 to 320, wherein the instrument is an analytical instrument.

Example 1

FIGS. 34A-D show examples of a cartridge for processing a sample. FIG. 34A shows a cartridge 3400 having a container 3401 with reagent and processing chambers, as described herein. The cartridge 3400 is configured for use with systems of the invention. The cartridge includes a sample chamber for accepting a sample, such as with the aid of a Q-tip or cotton swab. A thermal conductor 3406 is disposed over a thermocycling chamber (see below) of the cartridge 3400. The thermal conductor 3406 is configured to distribute (or spread) heat from a heating element (e.g., Peltier) to the chambers 3407 of the thermocycler assembly 3405. The thermal conductor can be formed of graphite, graphene, copper, tantalum or aluminum. In some cases, the thermal conductor is formed of a layer of a thermally conductive material. In other cases, the thermal conductor is formed of a plurality of layers, such as a layer of a thermally conductive material (e.g., graphite) adapted to come in thermal communication with a heating element, and a layer of a polymeric material (e.g., polypropylene) adjacent to the layer of the thermally conductive material that is adapted to come in contact with a sample in each chamber 3407 of the thermocycler assembly 3405. For instance, the thermal conductor can include a layer of graphite laminated to a layer of polypropylene. The layer of polypropylene can be adapted to come in contact with a sample in the chamber 3407 during sample processing.

With reference to FIG. 34B, the cartridge 3400 includes a holder or frame 3402 for holding the container 3401. The holder 3402 includes a holding member 3402a for enabling a user to carry the cartridge 3400, such as to insert the cartridge 3400 into a system for processing a sample. With reference to FIG. 34C, the cartridge 3400 includes a layer of deformable material 3403 configured to rest adjacent to the container 3401, and a microfluidic device 3404 having microfluidic channels for transporting samples and reagents to and from chambers of the container 3401, and pneumatic actuation channels for actuating valves of the microfluidic channels of the cartridge 3400. FIG. 34D shows a thermocycler assembly 3405 for performing temperature-regulated processing of a sample, such as PCR. The thermocycler assembly 3405 is configured to be mounted on the microfluidic device 3404, which is configured to be integrated with other components of the cartridge 3400 with the aid of the holder 3402.

Figure 44:
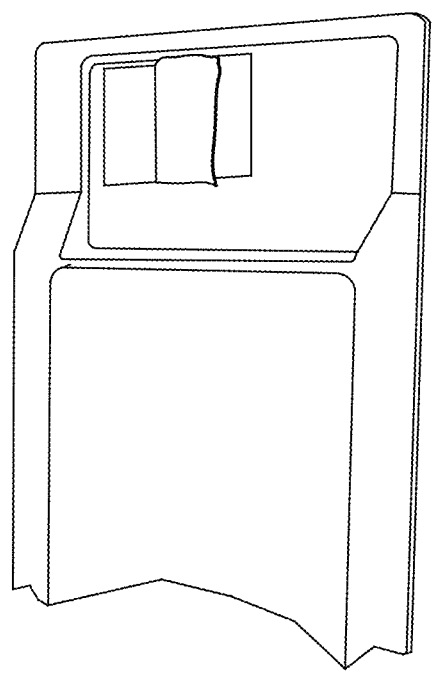
FIG. 44 shows a portion of a cartridge having a thermocycler assembly comprising four reaction chambers and a thermal conductor that has been peeled away to show the four reaction chambers configured to perform amplification (e.g., by PCR) with thermal cycling, in accordance with an embodiment of the invention.

The thermocycler assembly 3405 is a plastic piece that is bolted to an external surface of the microfluidic device 3404. The thermocycler assembly 3405 includes four chambers 3407, with each chamber 3407 having an elongate shape that can have an opening running most of the length of the chamber 3407—i.e., the chamber 3407 can be trough-like. In some cases, the chamber 3407 has a depth of about 0.02 inch (or about 508 microns) and a volume of about 20 microliters. With reference to FIG. 44, the chamber 3407 is covered with the layer of the thermal conductor 3406 that is configured to come in contact with a heating and cooling element (not shown) during sample processing. The heating and cooling element can be external to the cartridge 3400 (see, e.g., thermal cycling heating and cooling device 4200 in FIG. 42). In some cases, a surface of the layer of the thermal conductor is adapted to come in contact with a sample in each chamber of the thermocycler assembly 3405 during sample processing through an opening running most of the length of each chamber.

During sample processing, magnetic-field attractable beads (also "magnetic beads" herein) are directed from the container 3401 and into a reaction chamber 3407 of the thermocycler assembly 3405, where they are immobilized with the aid of a magnetic field provided by a magnetic field source (e.g., magnet, induction coil) adjacent to the chamber 3407. The magnetic field source can be provided in the cartridge, such as, for example, disposed in a compartment between the thermocycler assembly 3405 and the microfluidic device 3404. The compartment can be formed in the thermocycler assembly 3405, and the magnetic field source can be provided in the compartment prior to attaching the thermocycler assembly 3405 to the microfluidic device 3404 (see FIG. 45). An amplification premix is provided to the chamber 3407 and with the beads immobilized in the chamber 3407 the sample is amplified. Following amplification, the amplified sample is directed out of the chamber 3407 and to the container 3401. The beads remain in the chamber 3407 of the thermocycler assembly 3405.

Systems and methods provided herein, including the components of such systems and various routines of such methods, may be combined with or modified by other systems and methods. In some situations, the system 100 described above in the context of FIGS. 1-7, including various components of the system, may be combined or modified by the systems described in U.S. Pat. Pub. 2011/0005932 to Jovanovich et al., which is entirely incorporated herein by reference. For examples, various features of the electrophoresis capillaries of FIG. 5 and the anode cartridge and interface module of FIG. 6 can be combined with, modified by, or elaborated by the teachings of US 2011/0005932.

Example 2

Electrophoretic separation of the PowerPlex®16 allelic ladder (Promega) was performed using the sample-processing and analytical instrument described herein. (The PowerPlex® 16 allelic ladder is an allelic ladder for the loci CSF1PO, D3S1358, D5S818, D7S820, D8S1179, D13S317, D16S539, D18S51, D21S11, FGA, TH01, TPDX, vWA, Penta D, Penta E and amelogenin.) The allelic ladder DNA fragments were labeled with the fluorescein dye. The electrophoresis was performed using an array of capillaries filled with a separation matrix comprising a linear polyacrylamide, a polymer that coats the interior surface of the capillaries, 25% (v/v) N-methyl-2-pyrrolidinone, TAPS, Tris and EDTA. The allelic ladder was injected at 5 kV for 10 seconds, and the electrophoretic separation was performed at 11 kV and 80° C. and completed in about 17 minutes. FIG.

71 shows that the electrophoretic separation at 80° C. using N-methyl-2-pyrrolidinone as a chemical denaturant achieved good resolution of the allelic ladder fragments over a wide range of fragment lengths, as demonstrated by the resolution of the 9.3 and 10 alleles at the TH01 locus which differ by only one base/base pair.

It is understood that, while particular embodiments have been described, various modifications may be made thereto and are contemplated herein. It is also understood that all aspects of the invention are not limited to the specific depictions, configurations or relative proportions set forth herein, which may depend on a variety of conditions and variables. Various modifications in form and detail of the embodiments of the invention will be apparent to a person skilled in the art. It is therefore contemplated that the invention also covers any such modifications, variations and equivalents of the embodiments of the invention described herein.

What is claimed is:

1. A microfluidic device, comprising:
   a reaction chamber;
   a microfluidic channel in fluidic communication with the reaction chamber; and
   a vial comprising:
      a compartment extending between a first end and a second end opposite the first end, wherein the first end is above the second end;
      an exit port at the second end of the compartment and in fluidic communication with the microfluidic channel;
      a first movable stopper sealing the compartment from fluidic communication with an external environment through the first end; and
      a second movable stopper sealing the compartment from fluidic communication with the microfluidic channel through the exit port;
      wherein, in a state of the first movable stopper sealing the compartment and the second movable stopper sealing the compartment, the compartment is configured to hold a fluid composition between the first movable stopper and the second movable stopper; and
      wherein the first movable stopper and the second movable stopper are configured to move relative to each other such that, in response to force applied to the first movable stopper to move the first movable stopper toward the second moveable stopper, the second moveable stopper is actuatable to unseal and place the compartment in fluidic communication with the microfluidic channel through the exit port.

2. A system, comprising:
   the microfluidic device of claim 1; and
   an apparatus, comprising:
      a receptacle configured to receive the microfluidic device; and
      an actuation device configured to apply force to the first movable stopper sufficient to actuate the second movable stopper to unseal and place the compartment in fluidic communication with the microfluidic channel through the exit port.

3. The microfluidic device of claim 1 further comprising a fluid composition disposed in the compartment between the first movable stopper and the second movable stopper.

4. A method of dispensing the fluid composition from the vial in the microfluidic device of claim 3, the method comprising:
   applying force to the first moveable stopper and thereby actuating the second movable stopper to unseal the compartment such that the composition flows from the compartment through the exit port and into the microfluidic channel.

5. The method of claim 4, wherein the force applied to the first movable stopper exerts positive pressure on the second movable stopper, thereby actuating the second movable stopper to unseal the compartment.

6. The method of claim 5, wherein the composition further flows from the microfluidic channel into the reaction chamber.

7. The method of claim 6, wherein the composition comprises one or more reagents for performing nucleic acid amplification.

8. The microfluidic device of claim 1 further comprising a second vial comprising:
   a second compartment extending between a first end and a second end opposite the first end, wherein the first end of the second compartment is above the second end of the second compartment;
   a second exit port at the second end of the second compartment;
   a third movable stopper sealing the second compartment from fluidic communication with the external environment through the first end; and
   a fourth movable stopper sealing the compartment from fluidic communication with the microfluidic channel through the second exit port,
   wherein, in a state of the third movable stopper sealing the second compartment and the fourth movable stopper sealing the second compartment, the second compartment is configured to hold a fluid composition between the third movable stopper and the fourth movable stopper, and
   wherein, in response to force applied to the third movable stopper to move the third movable stopper toward the fourth moveable stopper, the fourth movable stopper is actuatable to unseal and place the second compartment in fluidic communication with the microfluidic channel through the second exit port.

9. A system, comprising:
   the microfluidic device of claim 8; and
   an apparatus, comprising:
      a receptacle configured to receive the microfluidic device; and
      an actuation device configured to apply force to the first movable stopper sufficient to actuate the second movable stopper to unseal and place the first compartment in fluidic communication with the microfluidic channel through the exit port and/or apply force to the third movable stopper sufficient to actuate the fourth movable stopper to unseal and place the second compartment in fluidic communication with the microfluidic channel through the second exit port.

10. The microfluidic device of claim 8 further comprising:
    a fluid composition disposed in the compartment of the vial between the first movable stopper and the second movable stopper; and
    a second fluid composition disposed in the second compartment of the second vial between the third movable stopper and the fourth movable stopper.

11. A method of dispensing (i) the fluid composition from the compartment of the vial and (ii) the second fluid composition from the second compartment of the second vial in the microfluidic device of claim 10, the method comprising:

applying force on the first moveable stopper and thereby actuating the second movable stopper to unseal the compartment such that the composition flows from the compartment through the exit port and into the microfluidic channel; and applying force on the third moveable stopper and thereby actuating the fourth movable stopper to unseal the second compartment such that the second composition flows from the second compartment through the second exit port and into the microfluidic channel.

12. The method of claim 11, wherein the force applied to the first movable stopper exerts positive pressure on the second movable stopper, thereby actuating the second movable stopper to unseal the compartment, and wherein the force applied to the third movable stopper exerts positive pressure on the fourth movable stopper, thereby actuating the fourth movable stopper to unseal the second compartment.

13. The method of claim 12, wherein the composition further flows from the microfluidic channel into the reaction chamber and the second composition further flows from the microfluidic channel into the reaction chamber.

14. The method of claim 13, wherein the composition and second composition each comprise one or more reagents for performing nucleic acid amplification.

15. The microfluidic device of claim 1, wherein the vial is releasably attached to the microfluidic device.

16. The microfluidic device of claim 8, wherein each of the first and second vials is releasably attached to the microfluidic device.

17. The device of claim 7, wherein the composition comprises one or more pairs of forward and reverse primers for amplifying one or more selected nucleotide sequences comprising one or more of selected short tandem repeat (STR) loci; dye-labeled primers; a polymerase and nucleotide triphosphates; buffering agent; or a metal salt.

18. The device of claim 1, wherein the composition comprises an STR allelic ladder; and/or the composition comprises a nucleic acid size standard.

19. The device of claim 1, wherein the second movable stopper remains in the vial after actuation to unseal the compartment.

20. The device of claim 1,
wherein the reaction chamber and the microfluidic channel are formed in a substrate; and
wherein the vial is releasably attached to the substrate.

21. The device of claim 20, wherein the vial is releasably attached at an inlet opening in fluidic communication with the microfluidic channel.

* * * * *